US012686688B2

(12) United States Patent
Huang et al.

(10) Patent No.: US 12,686,688 B2
(45) Date of Patent: Jul. 21, 2026

(54) HETEROCYCLIC PERICONDENSED CDC7 KINASE INHIBITORS FOR THE TREATMENT OF CANCER

(71) Applicant: SCHRÖDINGER, INC., New York, NY (US)

(72) Inventors: Xianhai Huang, Warren, NJ (US); Sayan Mondal, La Jolla, CA (US); Phani Ghanakota, Edison, NJ (US); Nicholas Boyles, Hillsboro, OR (US); Leah Frye, Portland, OR (US); Adam Levinson, Bronx, NY (US); Jeremy Robert Greenwood, Brooklyn, NY (US); Pieter Bos, New York, NY (US); Sathesh Bhat, New York, NY (US); Aleksey Gerasyuto, Flemington, NJ (US); Haifeng Tang, Metuchen, NJ (US)

(73) Assignee: SCHRÖDINGER, INC., NY (US)

( * ) Notice: Subject to any disclaimer, the term of this patent is extended or adjusted under 35 U.S.C. 154(b) by 571 days.

(21) Appl. No.: 18/025,465

(22) PCT Filed: Sep. 8, 2021

(86) PCT No.: PCT/US2021/049415

§ 371 (c)(1),
(2) Date: Mar. 9, 2023

(87) PCT Pub. No.: WO2022/055963

PCT Pub. Date: Mar. 17, 2022

(65) Prior Publication Data

US 2023/0365584 A1 Nov. 16, 2023

Related U.S. Application Data

(60) Provisional application No. 63/076,721, filed on Sep. 10, 2020.

(51) Int. Cl.
*C07D 495/16* (2006.01)
*A61K 45/06* (2006.01)

(52) U.S. Cl.
CPC ............ *C07D 495/16* (2013.01); *A61K 45/06* (2013.01)

(58) Field of Classification Search
CPC .............................. C07D 495/16; A61K 45/06
See application file for complete search history.

(56) References Cited

U.S. PATENT DOCUMENTS

| | | | |
|---|---|---|---|
| 4,939,137 A | 7/1990 | Russell et al. | |
| 7,514,446 B2 | 4/2009 | Davis-Ward et al. | |
| 7,863,289 B2 | 1/2011 | Spevak et al. | |
| 8,026,247 B2 | 9/2011 | Bold et al. | |
| 8,501,756 B2 | 8/2013 | Artman, III et al. | |
| 8,552,002 B2 | 10/2013 | Ding et al. | |
| 8,568,998 B2 | 10/2013 | Mani et al. | |
| 8,815,901 B2 | 8/2014 | Furet et al. | |
| 8,912,204 B2 | 12/2014 | Ibrahim et al. | |
| 9,260,437 B2 | 2/2016 | Ibrahim et al. | |
| 9,273,051 B2 | 3/2016 | Chen et al. | |
| 2007/0191344 A1 | 8/2007 | Choidas et al. | |
| 2009/0247559 A1 | 10/2009 | Brown et al. | |
| 2013/0029925 A1 | 1/2013 | Vandier et al. | |
| 2014/0121231 A1 | 5/2014 | Bolin et al. | |
| 2015/0018336 A1 | 1/2015 | Chen et al. | |
| 2016/0163999 A1 | 6/2016 | Kim et al. | |
| 2017/0117491 A1 | 4/2017 | Sasada et al. | |
| 2017/0244043 A1 | 8/2017 | Kim et al. | |
| 2017/0294489 A1 | 10/2017 | Lim et al. | |
| 2018/0047912 A1 | 2/2018 | Kwong et al. | |
| 2018/0159043 A1 | 6/2018 | Fukuzaki et al. | |
| 2019/0214577 A1 | 7/2019 | Pan et al. | |
| 2019/0233451 A1 | 8/2019 | Ji et al. | |
| 2019/0278176 A1 | 9/2019 | Baek et al. | |
| 2019/0312209 A1 | 10/2019 | Jeon et al. | |
| 2019/0330226 A1 | 10/2019 | Lindsley et al. | |
| 2020/0055867 A1* | 2/2020 | Zhang | C07D 495/04 |
| 2020/0194694 A1 | 6/2020 | Han et al. | |
| 2021/0111353 A1 | 4/2021 | Choi et al. | |

FOREIGN PATENT DOCUMENTS

| | | |
|---|---|---|
| CN | 101965351 A | 2/2011 |
| CN | 103951676 A | 7/2014 |
| CN | 105777666 A | 7/2016 |
| CN | 104478900 B | 5/2017 |
| CN | 104610178 B | 1/2018 |
| CN | 108218887 A | 6/2018 |

(Continued)

OTHER PUBLICATIONS

Kurasawa, J. Med. Chem. 2020, 63, 1084-1104 (Year: 2020).*
Amit, M., et al. "Upregulation of RET induces perineurial invasion of pancreatic adenocarcinoma." Oncogene 36.23 (2017): 3232-3239.
Andreucci et al., "Targeting the receptor tyrosine kinase RET in combination with aromatase inhibitors in ER positive breast cancer xenografts" Oncotarget, 2017, p. 80543-80553, vol. 7.
Bhinge, Kaustubh, et al. "EGFR mediates activation of RET in lung adenocarcinoma with neuroendocrine differentiation characterized by ASCL1 expression." Oncotarget 8. 16 (2017): 27155.

(Continued)

*Primary Examiner* — Andrew D Kosar
*Assistant Examiner* — Phillip Matthew Rzeczycki
(74) *Attorney, Agent, or Firm* — Barnes & Thornburg LLP; Steven M. Sturlis; William Boudreaux

(57) ABSTRACT

The present application relates to compounds of Formula (I), as defined herein, and pharmaceutically acceptable salts thereof. The present application also describes pharmaceutical composition comprising a compound of Formula (I), and pharmaceutically acceptable salts thereof, and methods of using the compounds and compositions for inhibiting kinase activity, and for treating cancer.

20 Claims, No Drawings

(56) References Cited

FOREIGN PATENT DOCUMENTS

| | | | |
|---|---|---|---|
| CN | 110117290 | A | 8/2019 |
| CN | 112457326 | B | 2/2022 |
| CN | 111057048 | B | 3/2022 |
| EP | 2097419 | A1 | 9/2009 |
| EP | 2540728 | B1 | 4/2019 |
| EP | 3229290 | B1 | 5/2024 |
| WO | 1999067238 | A2 | 12/1999 |
| WO | 2000023451 | A1 | 4/2000 |
| WO | 2004001058 | A2 | 12/2003 |
| WO | 2004065351 | A1 | 8/2004 |
| WO | 2004113330 | A1 | 12/2004 |
| WO | 2005014537 | A2 | 2/2005 |
| WO | 2005037843 | A1 | 4/2005 |
| WO | 2005082841 | A1 | 9/2005 |
| WO | 2005121138 | A2 | 12/2005 |
| WO | 2006014135 | A1 | 2/2006 |
| WO | 2006102097 | A2 | 9/2006 |
| WO | 2007000246 | A1 | 1/2007 |
| WO | 2007000248 | A1 | 1/2007 |
| WO | 2007002325 | A1 | 1/2007 |
| WO | 2007002433 | A1 | 1/2007 |
| WO | 2007047604 | A2 | 4/2007 |
| WO | 2007070201 | A1 | 6/2007 |
| WO | 2007084451 | A1 | 7/2007 |
| WO | 2007084455 | A1 | 7/2007 |
| WO | 2007110344 | A1 | 10/2007 |
| WO | 2007143523 | A2 | 12/2007 |
| WO | 2008070908 | A1 | 6/2008 |
| WO | 2008079903 | A1 | 7/2008 |
| WO | 2008079906 | A1 | 7/2008 |
| WO | 2008079909 | A1 | 7/2008 |
| WO | 2008080001 | A2 | 7/2008 |
| WO | 2008080015 | A2 | 7/2008 |
| WO | 2009007748 | A2 | 1/2009 |
| WO | 2009012283 | A1 | 1/2009 |
| WO | 2009014637 | A2 | 1/2009 |
| WO | 2009071480 | A2 | 6/2009 |
| WO | 2009071890 | A1 | 6/2009 |
| WO | 2009071895 | A1 | 6/2009 |
| WO | 2009086264 | A1 | 7/2009 |
| WO | 2009118411 | A2 | 10/2009 |
| WO | 2009143018 | A2 | 11/2009 |
| WO | 2009143024 | A2 | 11/2009 |
| WO | 2009152083 | A1 | 12/2009 |
| WO | 2010031816 | A1 | 3/2010 |
| WO | 2010056631 | A1 | 5/2010 |
| WO | 2010077530 | A1 | 7/2010 |
| WO | 2010088414 | A2 | 8/2010 |
| WO | 2010101302 | A1 | 9/2010 |
| WO | 2010111527 | A1 | 9/2010 |
| WO | 2010145998 | A1 | 12/2010 |
| WO | 2011025859 | A1 | 3/2011 |
| WO | 2011043994 | A1 | 4/2011 |
| WO | 2011092120 | A1 | 8/2011 |
| WO | 2011102399 | A1 | 8/2011 |
| WO | 2011117145 | A2 | 9/2011 |
| WO | 2011123419 | A1 | 10/2011 |
| WO | 2012013271 | A1 | 2/2012 |
| WO | 2012041987 | A1 | 4/2012 |
| WO | 2012101029 | A1 | 8/2012 |
| WO | 2012101032 | A1 | 8/2012 |
| WO | 2012109075 | A1 | 8/2012 |
| WO | 2012113774 | A1 | 8/2012 |
| WO | 2012121992 | A1 | 9/2012 |
| WO | 2012139930 | A1 | 10/2012 |
| WO | 2012143248 | A1 | 10/2012 |
| WO | 2012152763 | A1 | 11/2012 |
| WO | 2012169605 | A1 | 12/2012 |
| WO | 2013000994 | A1 | 1/2013 |
| WO | 2013014039 | A1 | 1/2013 |
| WO | 2013050446 | A1 | 4/2013 |
| WO | 2013050448 | A1 | 4/2013 |
| WO | 2013102059 | A1 | 7/2013 |
| WO | 2013138413 | A1 | 9/2013 |
| WO | 2013152269 | A1 | 10/2013 |
| WO | 2013177241 | A1 | 11/2013 |
| WO | 2014011900 | A2 | 1/2014 |
| WO | 2014019908 | A2 | 2/2014 |
| WO | 2014024750 | A1 | 2/2014 |
| WO | 2014055548 | A1 | 4/2014 |
| WO | 2014071031 | A1 | 5/2014 |
| WO | 2014072220 | A1 | 5/2014 |
| WO | 2014083567 | A2 | 6/2014 |
| WO | 2014092083 | A1 | 6/2014 |
| WO | WO-2014139324 | A1 * | 9/2014 ............. A61P 31/18 |
| WO | 2014160521 | A1 | 10/2014 |
| WO | 2014184069 | A1 | 11/2014 |
| WO | 2014194127 | A1 | 12/2014 |
| WO | 2014196585 | A1 | 12/2014 |
| WO | 2015017528 | A1 | 2/2015 |
| WO | 2015017533 | A1 | 2/2015 |
| WO | 2015057873 | A1 | 4/2015 |
| WO | 2015058129 | A1 | 4/2015 |
| WO | 2015061572 | A1 | 4/2015 |
| WO | 2015108992 | A1 | 7/2015 |
| WO | 2015112806 | A2 | 7/2015 |
| WO | 2015161274 | A1 | 10/2015 |
| WO | 2015161277 | A1 | 10/2015 |
| WO | 2015191666 | A2 | 12/2015 |
| WO | 2015191667 | A1 | 12/2015 |
| WO | 2016011141 | A1 | 1/2016 |
| WO | 2016011144 | A1 | 1/2016 |
| WO | 2016011147 | A1 | 1/2016 |
| WO | 2016022569 | A1 | 2/2016 |
| WO | 2016057713 | A1 | 4/2016 |
| WO | 2016075224 | A1 | 5/2016 |
| WO | 2016081450 | A1 | 5/2016 |
| WO | 2016113668 | A1 | 7/2016 |
| WO | 2017197240 | A1 | 11/2017 |
| WO | 2018108109 | A1 | 6/2018 |
| WO | 2018129205 | A1 | 7/2018 |
| WO | 2018138039 | A1 | 8/2018 |
| WO | 2018153326 | A1 | 8/2018 |
| WO | 2018161831 | A1 | 9/2018 |
| WO | 2018181054 | A1 | 10/2018 |
| WO | 2018181056 | A1 | 10/2018 |
| WO | 2018197257 | A1 | 11/2018 |
| WO | 2018217439 | A1 | 11/2018 |
| WO | 2019013311 | A1 | 1/2019 |
| WO | 2019052933 | A1 | 3/2019 |
| WO | 2019120085 | A1 | 6/2019 |
| WO | 2019120177 | A1 | 6/2019 |
| WO | 2019161320 | A1 | 8/2019 |
| WO | 2019195565 | A1 | 10/2019 |
| WO | 2019231226 | A1 | 12/2019 |
| WO | 2020202978 | A1 | 10/2020 |
| WO | 2021/113492 | A1 | 6/2021 |
| WO | 2021252661 | A1 | 12/2021 |
| WO | 2022195011 | A1 | 9/2022 |
| WO | 2022195462 | A1 | 9/2022 |
| WO | 2022198062 | A2 | 9/2022 |
| WO | WO 2022/197898 | A1 | 9/2022 |
| WO | 2022214031 | A1 | 10/2022 |
| WO | 2022228547 | A1 | 11/2022 |
| WO | 2022269508 | A1 | 12/2022 |
| WO | 2023011533 | A1 | 2/2023 |
| WO | 2023133284 | A2 | 7/2023 |

OTHER PUBLICATIONS

Blom, Karl F., et al. "Preparative LC-MS Purification: Improved Compound-Specific Method Optimization." Journal of Combinatorial Chemistry 6.6 (2004): 874-883.

Chang, Hyun, et al. "EGF induced RET inhibitor resistance in CCDC6-RET lung cancer cells." Yonsei Medical Journal 58.1 (2017): 9-18.

Cheng, An Ning, et al. "Increased Cdc7 expression is a marker of oral squamous cell carcinoma and overexpression of Cdc7 contributes to the resistance to DNA-damaging agents." Cancer letters 337.2 (2013): 218-225.

Cho, Won-Ho, et al. "CDC7 kinase phosphorylates serine residues adjacent to acidic amino acids in the minichromosome maintenance

(56) References Cited

OTHER PUBLICATIONS 2 protein." Proceedings of the National Academy of Sciences 103.31 (2006): 11521-11526.
Choschzick, Matthias, et al. "Overexpression of cell division cycle 7 homolog is associated with gene amplification frequency in breast cancer." Human pathology 41.3 (2010): 358-365.
Datta, Arindam, et al. "p53 gain-of-function mutations increase Cdc7-dependent replication initiation." EMBO reports 18.11 (2017): 2030-2050.
Ding K et al., "Artemin, a Member of the Glial Cell Line-derived Neurotrophic Factor Family of Ligands, is HER2-regulated and Mediates Acquired Trastuzumab Resistance by Promoting Cancer Stem Cell-like Behavior in Mammary Carcinoma Cells" J Biol Chem Jun. 6, 2014, p. 16057-71, vol. 289, No. 23.
Gao L, et al., "Neurotrophic Factor Artemin Promotes Invasiveness and Neurotrophic Function of Pancreatic Adenocarcinoma In Vivo and In Vitro" Pancreas Jan. 2015, p. 134-143, vol. 44.
Hanahan, Douglas, et al. "Hallmarks of cancer: the next generation." cell 144.5 (2011): 646-674.
Hezam K et al., "Artemin promotes oncogenicity, metastasis and drug resistance in cancer cells", Rev Neurosci, Jan. 26, 2018, vol. 29, 93-98.
Hou, Xueqing et al. "Dissecting Trichalcogenasumanenes: TT-Bowl to Planar, Invertible Curvature, and Chiral Polycycles." Chemistry—A European Journal (2017), 23(57), 14375-14383.
Hou, Xueqing et al. "Opening two benzene rings on trichalcogenasumanenes toward high performance organic optical-limiting materials." Chemical Communications (2018), 54(78), 10981-10984.
Jiang, Wei, et al. "Mammalian Cdc7-Dbf4 protein kinase complex is essential for initiation of DNA replication." The EMBO journal 18.20 (1999): 5703-5713.
Kato, Shumei, et al. "RET aberrations in diverse cancers: next-generation sequencing of 4,871 patients." Clinical Cancer Research 23.8 (2017): 1988-1997.
Kim, Samuel W., Peter Goedegebuure, and William E. Gillanders. "Mammaglobin-A is a target for breast cancer vaccination." Oncoimmunology 5.2 (2016): e1069940.
Kübler, Hubert, et al. "Self-adjuvanted mRNA vaccination in advanced prostate cancer patients: a first-in-man phase I/IIa study." Journal for immunotherapy of cancer 3.1 (2015): 1-14.
Kulkarni, Anjana A., et al. "Cdc7 kinase is a predictor of survival and a novel therapeutic target in epithelial ovarian carcinoma." Clinical Cancer Research 15.7 (2009): 2417-2425.
Li, Xuexiang et al. "Ring Reconstruction on a Trichalcogenasumanene Buckybowl: A Facile Approach to Donor-Acceptor-Type [5-6-7] Fused Planar Polyheterocycles." Angewandte Chemie, International Edition (2015), 54(1), 267-271.
Lopez-Delisle, Lucille, et al. "Activated ALK signals through the ERK-ETV5-RET pathway to drive neuroblastoma oncogenesis." Oncogene 37.11 (2018): 1417-1429.
Masai, Hisao, et al. "Phosphorylation of MCM4 by Cdc7 Kinase Facilitates its Interaction with Cdc45 on the Chromatin" Journal of Biological Chemistry 281.51 (2006): 39249-39261.
McGranahan, Nicholas, et al., "Clonal heterogeneity and tumor evolution: past, present, and the future." Cell 168.4 (2017): 613-628.
Nelson-Taylor, Sarah K., et al. "Resistance to RET-inhibition in RET-rearranged NSCLC is mediated by reactivation of RAS/MAPK signaling." Molecular cancer therapeutics 16.8 (2017): 1623-1633.
Ott, Patrick A., et al. "An immunogenic personal neoantigen vaccine for patients with melanoma." Nature 547.7662 (2017): 217-221.
Pétursson, Sigthór, "Protecting groups in carbohydrate chemistry." Journal of chemical education 74.11 (1997): 1297.
Rausch et al. "mRNA vaccine CV9103 and CV9104 for the treatment of prostate cancer", Human Vaccin Immunother, 2014 p. 3146-52, vol. 10, No. 11.
Sahin, Ugur, et al. "Personalized RNA mutanome vaccines mobilize poly-specific therapeutic immunity against cancer." Nature 547. 7662 (2017): 222-226.
Sun, Yantao et al. "Trichalcogenasumanene ortho-Quinones: Synthesis, Properties, and Transformation into Various Heteropolycycles." Angewandte Chemie, International Edition (2017), 56(43), 13470-13474.
Tang, Zhenya, et al. "Coexistent genetic alterations involving ALK, RET, ROS1 or MET in 15 cases of lung adenocarcinoma." Modern Pathology 31.2 (2018): 307-312.
Yamada, et al., "Regulation and roles of Cdc7 kinase under replication stress", Cell Cycle, 2014 pp. 1859-1866, vol. 13.
Yu, Craig et al., "Air-Stable Benzo[c]thiophene Diimide n-Type TT-Electron Core." Organic Letters (2019), 21(12), 4448-4453.
Zeng, Q., et al. "The relationship between over-expression of glial cell-derived neurotrophic factor and its RET receptor with progression and prognosis of human pancreatic cancer." Journal of International Medical Research 36.4 (2008): 656-664.
International Search Report dated May 23, 2022, prepared in International Application No. PCT/US2022/020712.
International Preliminary Report on Patentability dated Sep. 12, 2023, prepared in International Application No. PCT/US2022/020712.
International Search Report dated Mar. 12, 2021, prepared in International Application No. PCT/US2020/063081.
International Preliminary Report on Patentability dated May 17, 2022, prepared in International Application No. PCT/US2020/063081.
International Search Report dated Nov. 15, 2021, prepared in International Application No. PCT/US2021/049415.
International Preliminary Report on Patentability dated Mar. 7, 2023, prepared in International Application No. PCT/US2021/049415.
Russell, Ronald et al. "Thiophene systems. 11. The synthesis of novel thieno[4,3,2-de]tricyclic ring systems." Journal of Heterocyclic Chemistry (1990), 27(6), 1761-70.
Im, Jun-Sub, et al.,. "ATR-dependent activation of p38 MAP kinase is responsible for apoptotic cell death in cells depleted of Cdc7." Journal of Biological Chemistry 283.37 (2008): 25171-25177.
Irie, Takayuki et al: "CDC7 kinase inhibitors: a survey of recent patent literature (2017-2022)", Expert Opinion on Therapeutic Patents, vol. 33, No. 7-8 (Nov. 6, 2023), p. 493-501.
Kurasawa, Osamu, et al. "2-Aminomethylthieno [3, 2-d] pyrimidin-4 (3H)-ones bearing 3-methylpyrazole hinge binding moiety: Highly potent, selective, and time-dependent inhibitors of Cdc7 kinase." Bioorganic & Medicinal Chemistry 25.14 (2017): 3658-3670.
Kurasawa, Osamu, et al. "Discovery of a novel, highly potent, and selective Thieno [3, 2-d] pyrimidinone-based Cdc7 inhibitor with a quinuclidine moiety (TAK-931) as an orally active investigational antitumor agent." Journal of Medicinal Chemistry 63.3 (2020): 1084-1104.
Kurasawa, Osamu, et al. "Identification of a new class of potent Cdc7 inhibitors designed by putative pharmacophore model: Synthesis and biological evaluation of 2, 3-dihydrothieno [3, 2-d] pyrimidin-4 (1H)-ones." Bioorganic & Medicinal Chemistry 25.7 (2017): 2133-2147.
Louis, David N., et al. "The 2016 World Health Organization classification of tumors of the central nervous system: a summary." Acta neuropathologica 131 (2016): 803-820.
Montagnoli, Alessia, et al. "Cdc7 inhibition reveals a p53-dependent replication checkpoint that is defective in cancer cells." Cancer research 64.19 (2004): 7110-7116.
Mulligan, Lois M. "RET revisited: expanding the oncogenic portfolio." Nature Reviews Cancer 14.3 (2014): 173-186.

* cited by examiner

HETEROCYCLIC PERICONDENSED CDC7 KINASE INHIBITORS FOR THE TREATMENT OF CANCER

CROSS REFERENCE TO RELATED APPLICATION

This application claims the benefit of U.S. Patent Application No. 63/076,721 filed on Sep. 10, 2020, which is incorporated herein by reference in its entirety.

TECHNICAL FIELD

This present application relates to tricyclic, and other multi-cyclic compounds, that are useful for treating proliferative disorders such as cancer.

BACKGROUND

Cancer is characterized by aberrant cell growth and proliferation. Genomic instability is a hallmark of cancer cells, with high rates of mutation and genomic rearrangements leading to aggressive and therapy-resistant tumors. See Hanahan and Weinberg, Cell, 144, pp. 646-674 (2011) and McGranahan and Swanton, Cell 168, pp. 613-628 (2017). Dysregulation of DNA replication contributes to genomic instability and tumorigenesis. Eukaryotic cells divide by a directed, highly regulated step-wise process known as the cell cycle. DNA replication is an essential part of the highly-regulated, step-wise cell cycle, and this tight regulation ensures that DNA replication occurs only once during S-phase, and occurs with high-fidelity.

During the late G1-to-S phase, CDC7 kinase (also known as DDK) is activated by binding to its regulatory protein, DBF4 (ASK in eukaryotes), which then phosphorylates chromatin loaded minichromosome maintenance (MCM) 2, 4 and 6 proteins at multiple phosphorylation sites to initiate DNA synthesis. See Jiang, et al., EMBO J., 18, pp. 5703-5713 (1999), Cho, et al., Proc. Natl. Acad. Sci. U.S.A., 103, pp. 11521-11526 (2006) and Masai, et al., J Biol Chem., 281, pp. 39249-39261 (2006). CDC7 kinase plays important roles in the maintenance of DNA replication forks and DNA damage response pathways. See Yamada, et al., Cell Cycle 13, pp. 1859-1866 (2014).

CDC7 is a highly conserved serine/threonine kinase from yeast to humans. Knockdown of CDC7 was shown to cause cell death in cancer cells, but not in normal cells, in which p53-dependent pathways arrest the cell cycle in G1 phase. The apoptotic response induced in cancer cells by CDC7 depletion is not mediated by p53, but rather by p38 MAPK. See Montagnoli, et al., Cancer Res., 64, pp. 7110-7116 (2004) and Im and Lee, J. Biol. Chem., 283, pp. 25171-25177 (2008). In addition, CDC7 up-regulation has been correlated with poor prognosis in various cancer types. See, e.g., Kulkarni, et al., Clin. Cancer Res., 15, pp. 2417-2425 (2009); Choschzick, et al., Hum. Pathol., 41, pp. 358-365 (2010); Datta, et al., EMBO Rep., 18, pp. 2030-2050 (2017); Cheng, et al., Cancer Lett., 337, 218-225 (2013).

SUMMARY

It has now been found that certain fused compounds are inhibitors of CDC7 kinase, and are useful for treating diseases such as proliferative diseases such as cancers.

Accordingly, provided herein is a compound of the Formula (I):

(I)

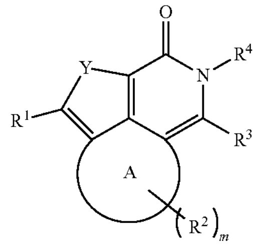

or a pharmaceutically acceptable salt thereof, wherein $R^1$, $R^2$, $R^3$, $R^4$, $R^A$, $R^B$, $R^C$, $R^D$, $R^E$, $R^F$, $R^G$, Y, m, p, and Ring A, are as defined herein.

Also provided herein is a pharmaceutical composition comprising a compound of Formula (I), or a pharmaceutically acceptable salt thereof, and at least one pharmaceutically acceptable excipient.

Also provided herein is a method of inhibiting mammalian cell proliferation, in vitro or in vivo, comprising contacting a cell with an effective amount of a compound of Formula (I) or a pharmaceutically acceptable salt thereof, or a pharmaceutical composition thereof as defined herein.

Also provided herein is a method of inhibiting CDC7 kinase activity in a mammalian cell, in vitro or in vivo, comprising contacting a cell with an effective amount of a compound of Formula (I) or a pharmaceutically acceptable salt thereof, or a pharmaceutical composition thereof as defined herein.

Also provided herein is a method of treating cancer in a subject in need of such treatment, comprising administering to the subject an effective amount of a compound of Formula (I), or a pharmaceutically acceptable salt thereof, or a pharmaceutical composition thereof as defined herein.

Also provided herein is a method of treating a CDC7-associated disease or disorder in a subject in need of such treatment, comprising administering to the subject an effective amount of a compound of Formula (I), or a pharmaceutically acceptable salt thereof, or a pharmaceutical composition thereof as defined herein.

Also provided herein is a method of treating cancer and/or inhibiting metastasis associated with a particular cancer in a subject in need of such treatment, comprising administering to the subject an effective amount of a compound of Formula (I), or a pharmaceutically acceptable salt thereof or a pharmaceutical composition thereof as defined herein.

Also provided herein is a compound of Formula (I), or a pharmaceutically acceptable salt thereof, or a pharmaceutical composition thereof as defined herein for use in the treatment of cancer.

Also provided herein is a compound of Formula (I), or a pharmaceutically acceptable salt thereof, or a pharmaceutical composition thereof as defined herein for use in the treatment of a CDC7-associated disease or disorder.

Also provided herein is a compound of Formula (I), or a pharmaceutically acceptable salt thereof or a pharmaceutical composition thereof as defined herein for use in the treatment of cancer and/or inhibiting metastasis associated with a particular cancer.

Also provided herein is a compound of Formula (I), or a pharmaceutically acceptable salt thereof for use in the inhibition of CDC7 kinase activity.

Also provided herein is a compound of Formula (I), or a pharmaceutically acceptable salt thereof or a pharmaceutical composition thereof as defined herein, for use in the treatment of a CDC7-associated disease or disorder.

Also provided herein is a compound of Formula (I), or a pharmaceutically acceptable salt thereof, as defined herein in the manufacture of a medicament for the treatment of cancer and/or inhibiting metastasis associated with a particular cancer.

Also provided herein is a compound of Formula (I), or a pharmaceutically acceptable salt thereof, defined herein in the manufacture of a medicament for the inhibition of CDC7 kinase activity.

Also provided herein is a compound of Formula (I), or a pharmaceutically acceptable salt thereof, as defined herein, in the manufacture of a medicament for the treatment of a CDC7-associated disease or disorder.

Also provided are methods of treating an individual with a CDC7-associated cancer that include administering a compound of Formula (I), or a pharmaceutically acceptable salt thereof, before, during, or after administration of other anticancer drug(s) (e.g., a first CDC7 kinase inhibitor or another kinase inhibitor).

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Definitions

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified.

The term "precursor," as used herein is a first compound that is reacted in one or more chemical transformations to provide a second compound, the first compound being the precursor of the second compound.

The term "tautomer," as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. An example of a tautomeric forms includes the following example:

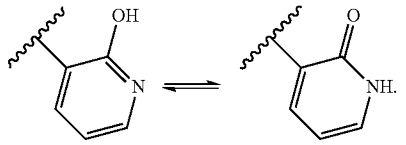 [SMILES: *c1cccnc1O ; *c1ccc[nH]c1=O]

It will be appreciated that certain compounds provided herein may contain one or more centers of asymmetry and may therefore be prepared and isolated in a mixture of isomers such as a racemic mixture, or in an enantiomerically pure form.

The term "halo" refers to one of the halogens, group 17 of the periodic table. In particular the term refers to fluorine, chlorine, bromine and iodine. Preferably, the term refers to fluorine or chlorine.

The term "C0-C6 alkyl" refers to a linear or branched saturated hydrocarbon chain containing 0, 1, 2, 3, 4, 5 or 6 carbon atoms, for example, methyl, ethyl, n-propyl, iso-propyl, n-butyl, sec-butyl, tert-butyl, n-pentyl and n-hexyl. A "C0" alkyl group, as used herein, refers to a bond, e.g., R—(C0 alkyl)-R' refers to R—R'.

The term "C1-C6 haloalkyl" refers to a C1-C6 alkyl group, as defined herein, substituted with at least one halogen atom independently chosen at each occurrence, for example fluorine, chlorine, bromine and iodine. The halogen atom may be present at any position on the alkyl group. For example, C1-C6 haloalkyl may refer to chloromethyl, fluoromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "C1-C6 alkoxy" refers to a C1-C6 alkyl group which is attached to a molecule via oxygen. This includes moieties where the alkyl part may be linear or branched, such as methoxy, ethoxy, n-propoxy, iso-propoxy, n-butoxy, sec-butoxy, tert-butoxy, n-pentoxy and n-hexoxy.

As used herein, the term "cyano" refers to a —CN radical.

As used herein, the term "hydroxyl" refers to an —OH radical.

The term "C1-C6 hydroxyalkyl" refers to a C1-C6 alkyl group, as defined herein, substituted with one or more hydroxyl radical(s). The hydroxyl radical(s) may be present at any position on the hydrocarbon chain. For example, C1-C6 hydroxyalkyl may refer to hydroxymethyl, hydroxyethyl (e.g., 1-hydroxyethyl or 2-hydroxyethyl), and 2-hydroxyisopropyl.

The term "C1-C6 alkoxyalkyl" refers to a C1-C6 alkyl group which is substituted with one or more C1-C6 alkoxy groups, as defined herein, wherein the alkoxy group(s) are attached to the alkyl group via an oxygen. This includes moieties where the alkyl part of the C1-C6 alkyl or the C1-C6 alkoxy may be independently linear or branched, such as methoxyethyl, ethoxyethyl, or 1,3 dimethoxypropyl.

As used herein, the term "amino" refers to a $—NH_2$ radical.

As used herein, the term "aryl" refers to a 6-10 all carbon mono- or bicyclic group wherein at least one ring in the system is aromatic. Non-limiting examples of aryl groups include phenyl, naphthyl, tetrahydronaphthyl.

As used herein, the term "heteroaryl" refers to a 5-10 membered mono- or bicyclic group wherein at least one ring in the system is aromatic; and wherein one or more carbon atoms in at least one ring in the system is/are replaced with an heteroatom independently selected from N, O, and S. Non-limiting examples of heteroaryl groups include furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine.

As used herein, the term "cycloalkyl" refers to a saturated or partially unsaturated mono- or bicyclic carbon group having 3 to 10 carbon atoms. Bicyclic cycloalkyl groups include fused, spiro, and bridged ring systems. Non-limiting examples of cycloalkyl groups include cyclopropyl, cyclohexyl, spiro[2.3]hexyl, and bicyclo[1.1.1]pentyl.

The term "heterocyclyl" refers to a saturated or partially unsaturated hydrocarbon monocyclic or bicyclic ring system, having 3 to 10 ring atoms, that is not aromatic, having at least one heteroatom within the ring selected from N, O and S. Bicyclic heterocyclyl groups include fused, spiro, and bridged ring systems. The heterocyclyl group may be denoted as, for example, a "5 to 10 membered heterocyclyl group," which is a ring system containing 5, 6, 7, 8, 9 or 10 atoms at least one being a heteroatom. For example there may be 1, 2 or 3 heteroatoms, optionally 1 or 2. A heterocycle may further contain one or more carbonyl or thiocarbonyl functionalities, so as to make the definition include oxo-systems and thio-systems such as lactams, lactones, cyclic imides, cyclic thioimides and cyclic carbamates. The heterocyclyl group may be bonded to the rest of the molecule through any carbon atom or through a heteroatom such as nitrogen. Exemplary heterocyclyl groups include, but are not limited to 1,3-dioxolane, 1,4-dioxolane, maleimide, succinimide, dioxopiperazine, hydantoin, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, azetidine, oxetane, and 2-azaspiro[3.3]heptanyl.

As used herein, the term "geminal" refers to substituent atoms or groups attached to the same atom in a molecule.

As used herein, the term "vicinal" refers to substituent atoms or groups attached to adjacent atoms in a molecule. The stereochemical relationship between the substituent atoms or groups can be cis, trans, undefined, or unresolved.

As used herein, the term "oxo" refers to an "═O" group attached to a carbon atom.

As used herein, the symbol ∿ depicts the point of attachment of an atom or moiety to the indicated atom or group in the remainder of the molecule.

The compounds of Formula (I) (e.g., any one of Formulas (Ia), (Ib), (Ic), and (Id)) include pharmaceutically acceptable salts thereof. In addition, the compounds of Formula (I) (e.g., any one of Formulas (Ia), (Ib), (Ic), and (Id)) also include other salts of such compounds which are not necessarily pharmaceutically acceptable salts, and which may be useful as intermediates for preparing and/or purifying compounds of Formula (I) (e.g., any one of Formulas (Ia), (Ib), (Ic), and (Id)) and/or for separating enantiomers of compounds of Formula (I) (e.g., any one of Formulas (Ia), (Ib), (Ic), and (Id)). Non-limiting examples of pharmaceutically acceptable salts of compounds of Formula (I) (e.g., any one of Formulas (Ia), (Ib), (Ic), and (Id)) include trifluoroacetic acid and hydrochloride salts.

It will further be appreciated that the compounds of Formula (I) (e.g., any one of Formulas (Ia), (Ib), (Ic), and (Id)) or their salts may be isolated in the form of solvates, and accordingly that any such solvate is included within the scope of the present invention. For example, compounds of Formula (I) (e.g., any one of Formulas (Ia), (Ib), (Ic), and (Id)) and salts thereof can exist in unsolvated as well as solvated forms with pharmaceutically acceptable solvents such as water, ethanol, and the like.

In some embodiments, the compounds of Formula (I) (e.g., any one of Formulas (Ia), (Ib), (Ic), and (Id)) include the compounds of Examples 1-65 and stereoisomers and pharmaceutically acceptable salts and solvates thereof. In some embodiments, the compounds of Examples 1-65 are in the free base form. In some embodiments, the compounds of Examples 1-65 are in the salt form.

In some embodiments, the compounds of Formula (I) (e.g., any one of Formulas (Ia), (Ib), (Ic), and (Id)) are prepared as pharmaceutically acceptable salts. In some embodiments, the pharmaceutically acceptable salt is an acid addition salt of the compound. Pharmaceutically salts acceptable salts can be obtained by reacting a compound with inorganic acids such as hydrohalic acid (e.g., hydrochloric acid or hydrobromic acid), sulfuric acid, nitric acid and phosphoric acid. Pharmaceutically acceptable salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutically acceptable salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C1-C7 alkylamine, cyclohexylamine, triethanolamine, ethylenediamine, and salts with amino acids such as arginine and lysine.

The term "pharmaceutically acceptable" indicates that the compound, or salt or composition thereof is compatible chemically and/or toxicologically with the other ingredients comprising a formulation and/or the subject being treated therewith.

Protecting groups can be a temporary substituent which protects a potentially reactive functional group from undesired chemical transformations. The choice of the particular protecting group employed is well within the skill of one of ordinary skill in the art. A number of considerations can determine the choice of protecting group including, but not limited to, the functional group being protected, other functionality present in the molecule, reaction conditions at each step of the synthetic sequence, other protecting groups present in the molecule, functional group tolerance to conditions required to remove the protecting group, and reaction conditions for the thermal decomposition of the compounds provided herein. The field of protecting group chemistry has been reviewed (Greene, T. W.; Wuts, P. G. M. *Protective Groups in Organic Synthesis,* 2.sup.nd ed.; Wiley: New York, 1991).

A nitrogen protecting group can be any temporary substituent which protects an amine moiety from undesired chemical transformations. Examples of moieties formed when such protecting groups are bonded to an amine include, but are not limited to allylamine, benzylamines (e.g., benzylamine, p-methoxybenzylamine, 2,4-dimethoxybenzylamine, and tritylamine), acetylamide, trichloroacetammide, trifluoroacetamide, pent-4-enamide, phthalimides, carbamates (e.g., methyl carbamate, t-butyl carbamate, benzyl carbamate, allyl carbamates, 2,2,2-trichloroethyl carbamate, and 9-fluorenylmethyl carbamate), imines, and sulfonamides (e.g., benzene sulfonamide, p-toluenesulfonamide, and p-nitrobenzenesulfonamide).

An oxygen protecting group can be any temporary substituent which protects a hydroxyl moiety from undesired chemical transformations. Examples of moieties formed when such protecting groups are bonded to a hydroxyl include, but are not limited to esters (e.g., acetyl, t-butyl carbonyl, and benzoyl), benzyl (e.g., benzyl, p-methoxybenzyl, and 2,4-dimethoxybenzyl, and trityl), carbonates (e.g., methyl carbonate, allyl carbonate, 2,2,2-trichloroethyl carbonate and benzyl carbonate) ketals, and acetals, and ethers.

Compounds provided herein may also contain unnatural proportions of atomic isotopes at one or more of the atoms that constitute such compounds. That is, an atom, in particular when mentioned in relation to a compound according to Formula (I) (e.g., any one of Formulas (Ia), (Ib), (Ic), and (Id)), comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof; unless expressly noted otherwise. For example, in deuteroalkyl and deuteroalkoxy groups, where one or more hydrogen atoms are specifically replaced with deuterium ($^{2}H$). As some of the aforementioned isotopes are radioactive, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

The ability of test compounds to act as CDC7 inhibitors may be demonstrated by the biological and computational assays described herein. $IC_{50}$ values are shown in Tables A-B.

In some embodiments, the compounds provided herein exhibit brain and/or central nervous system (CNS) penetrance. Such compounds are capable of crossing the blood brain barrier and inhibiting CDC7 kinase activity in the brain and/or other CNS structures. In some embodiments, the compounds provided herein are capable of crossing the blood brain barrier in a therapeutically effective amount. For example, treatment of a subject with cancer (e.g., a CDC7-associated cancer such as a CDC7-associated brain or CNS cancer) can include administration (e.g., oral administration) of the compound to the subject. In some such embodiments, the compounds provided herein are useful for treating a primary brain tumor or metastatic brain tumor. For example, a CDC7-associated primary brain tumor or metastatic brain tumor.

In some embodiments, the compounds of Formula (I) (e.g., any one of Formulas (Ia), (Ib), (Ic), and (Id)), or a pharmaceutically acceptable salt thereof, exhibit one or more of high GI absorption, low clearance, and low potential for drug-drug interactions.

Compounds of Formula (I) (e.g., any one of Formulas (Ia), (Ib), (Ic), and (Id)), or a pharmaceutically acceptable salt thereof, are useful for treating diseases and disorders which can be treated with a CDC7 kinase inhibitor, such as CDC7-associated cancers, including hematological cancers and solid tumors.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the term "subject" refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented.

In some embodiments, the subject has been identified or diagnosed as having a cancer with a dysregulation of a CDC7 gene, a CDC7 protein, or expression or activity, or level of any of the same (a CDC7-associated cancer) (e.g., as determined using a regulatory agency-approved, e.g., FDA-approved, assay or kit). In some embodiments, the subject has a tumor that is positive for a dysregulation of a CDC7 gene, a CDC7 protein, or expression or activity, or level of any of the same (e.g., as determined using a regulatory agency-approved assay or kit). The subject can be a subject with a tumor(s) that is positive for a dysregulation of a CDC7 gene, a CDC7 protein, or expression or activity, or level of any of the same (e.g., identified as positive using a regulatory agency-approved, e.g., FDA-approved, assay or kit). The subject can be a subject whose tumors have a dysregulation of a CDC7 gene, a CDC7 protein, or expression or activity, or a level of the same (e.g., where the tumor is identified as such using a regulatory agency-approved, e.g., FDA-approved, kit or assay). In some embodiments, the subject is suspected of having a CDC7-associated cancer. In some embodiments, the subject has a clinical record indicating that the subject has a tumor that has a dysregulation of a CDC7 gene, a CDC7 protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a CDC7 gene, a CDC7 protein, or expression or activity, or level of any of the same (a CDC7-associated cancer).

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula (I) (e.g., any one of Formulas (Ia), (Ib), (Ic), and (Id)), or a pharmaceutically acceptable salt thereof are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "CDC7-associated cancer" as used herein refers to cancers associated with or having a dysregulation of a CDC7 gene, a CDC7 kinase (also called herein CDC7 kinase protein), or the expression or activity or level of any (e.g., one or more) of the same (e.g., any of the types of dysregulation of a CDC7 gene, a CDC7 kinase, a CDC7 kinase domain, or the expression or activity or level of any of the same, as described herein). Non-limiting examples of a CDC7-associated cancer are described herein.

The phrase "dysregulation of a CDC7 gene, a CDC7 kinase, or the expression or activity or level of any of the same" refers to a genetic mutation (e.g., a chromosomal translocation that results in the expression of a fusion protein including a CDC7 kinase domain and a fusion partner, a mutation in a CDC7 gene that results in the expression of a CDC7 protein that includes a deletion of at least one amino acid as compared to a wild-type CDC7 protein, a mutation in a CDC7 gene that results in the expression of a CDC7 protein with one or more point mutations as compared to a wild-type CDC7 protein, a mutation in a CDC7 gene that results in the expression of a CDC7 protein with at least one inserted amino acid as compared to a wild-type CDC7 protein, a gene duplication that results in an increased level of CDC7 protein in a cell, or a mutation in a regulatory sequence (e.g., a promoter and/or enhancer) that results in an increased level of CDC7 protein in a cell), an alternative spliced version of a CDC7 mRNA that results in a CDC7 protein having a deletion of at least one amino acid in the CDC7 protein as compared to the wild-type CDC7 protein), or increased expression (e.g., increased levels) of a wild-type CDC7 kinase in a mammalian cell due to aberrant cell signaling and/or dysregulated autocrine/paracrine signaling (e.g., as compared to a control non-cancerous cell). As another example, a dysregulation of a CDC7 gene, a CDC7 protein, or expression or activity, or level of any of the same, can be a mutation in a CDC7 gene that encodes a CDC7 protein that is constitutively active or has increased activity as compared to a protein encoded by a CDC7 gene that does not include the mutation. As a further example, an increased copy number of the CDC7 gene can result in overexpression of CDC7 kinase. For example, a dysregulation of a CDC7 gene, a CDC7 protein, or expression or activity, or level of any of the same, can be the result of a gene or chromosome translocation which results in the expression of a fusion protein that contains a first portion of CDC7 that includes a functional kinase domain, and a second portion of a partner protein (i.e., that is not CDC7). In some examples, dysregulation of a CDC7 gene, a CDC7 protein, or expression or activity or level of any of the same can be a result of a gene translocation of one CDC7 gene with another non-CDC7 gene.

The term "wild-type" describes a nucleic acid (e.g., a CDC7 gene or a CDC7 mRNA) or protein (e.g., a CDC7 protein) that is found in a subject that does not have a CDC7-associated disease, e.g., a CDC7-associated cancer (and optionally also does not have an increased risk of developing a CDC7-associated disease and/or is not suspected of having a CDC7-associated disease), or is found in a cell or tissue from a subject that does not have a CDC7-associated disease, e.g., a CDC7-associated cancer (and optionally also does not have an increased risk of developing a CDC7-associated disease and/or is not suspected of having a CDC7-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein are compounds of Formula (I):

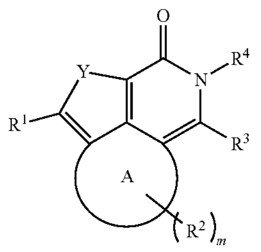

or a pharmaceutically acceptable salt thereof, wherein:

$R^1$ is a 5-10 membered heteroaryl, optionally substituted with 1-3 substituents independently selected from the group consisting of C1-C6 alkyl, amino, halogen, hydroxy, cyano, C1-C6 haloalkyl, C1-C6 alkoxy, and C3-C6 cycloalkyl;

Y is —S— or —S(=O)—;

Ring A is a C5-C7 cycloalkyl or 5-7 membered heterocyclyl;

each $R^2$ is independently selected from the group consisting of hydrogen, halogen, hydroxy, cyano, C1-C6 haloalkyl, C1-C6 hydroxyalkyl, C1-C6 alkoxy, —$NR^BR^C$, C1-C6 alkoxyalkyl, —C(=O)NH-5-10 membered heteroaryl, 4-6 membered heterocyclyl, 5-10 membered heteroaryl, C1-C6 alkyl optionally substituted with 1-3 independently selected $R^A$, and C3-C6 cycloalkyl optionally substituted with hydroxyl; or two $R^2$ together with the atom to which they are attached, join together to form an oxo group; a C3-C6 cycloalkyl optionally substituted with 1-3 substituents independently selected from halogen, cyano, C1-C6 alkyl, and C1-C6 alkoxy; or a 3-6 membered heterocyclyl optionally substituted with 1-3 substituents independently selected from halogen, cyano, C1-C6 alkyl, and C1-C6 alkoxy;

$R^3$ is selected from hydrogen and C0-C6 alkyl optionally substituted with 1-4 substituents independently selected from:

(i) hydroxyl;

(ii) cyano;

(iii) halogen;

(iv) C3-C6 cycloalkoxy;

(v) C(═O)OR$^F$;

(vi) C1-C6 alkoxy;

(vii) 4-10 membered heterocyclyloxy optionally substituted with 1-3 independently selected halogens;

(viii) —NR$^B$R$^C$;

(ix) C3-C6 cycloalkyl optionally substituted with 1-3 groups independently selected from hydroxyl, cyano, halogen, C1-C6 alkoxy, C1-C6 haloalkoxy, —NR$^B$R$^C$, 3-6 membered heterocyclyloxy, and 3-6 membered heterocyclyl optionally substituted with 1-3 C1-C6 alkoxy;

(x) 3 to 10 membered heterocyclyl optionally substituted with 1-4 substituents independently selected from halogen, hydroxyl, C1-C6 hydroxyalkyl, C1-C6 alkoxy, C1-C6 haloalkyl, —NR$^B$R$^C$, C1-C6 alkyl optionally substituted with 1-3 substituents independently selected from halogen, C1-C6 alkoxy, and C3-C6 cycloalkoxy, and C3-C6 cycloalkyl optionally substituted with halogen or hydroxyl;

(xi) 5-6 membered heteroaryl optionally substituted with 1-3 substituents independently selected from cyano, hydroxyl, C1-C6 alkyl, C1-C6 alkoxy, C3-C6 cycloalkyl optionally substituted with 1-2 substituents independently selected from cyano and hydroxyl; and 4-10 membered heterocyclyl optionally substituted with 1-3 independently selected R$^A$; and (xii) —C(═O)—X; wherein X is —NR$^B$R$^C$, C1-C6 alkyl, 5-6 membered heteroaryl, —NH-5-6 membered heteroaryl, —OR$^E$, or 3-6 membered heterocyclyl optionally substituted with hydroxyl;

each R$^A$ and R$^E$ are independently halogen, cyano, hydroxyl, C1-C6 alkoxy, C1-C6 alkyl, C1-C6 haloalkyl, C1-C6 hydroxyalkyl, C1-C6 alkylamino, 4-6 membered heterocyclyl, or C3-C6 cycloalkyl;

each R$^B$ and R$^C$ are independently hydrogen, C1-C6 alkyl, C1-C6 haloalkyl, —C(═O)—C1-C6 alkyl, —(C1-C6 alkylene)$_p$-C3-C8 cycloalkyl optionally substituted with C1-C6 alkyl, cyano, halogen, hydroxyl, or C3-C6 cycloalkyl; 3 to 6 membered heterocyclyl optionally substituted with C1-C6 alkyl; —C(═O)O—C1-C6 alkyl; or benzyl optionally substituted with C1-C6 alkoxy; or R$^B$ and R$^C$ together with the atom to which they are attached, join together to form a 4-10 membered heterocyclyl optionally substituted with 1-3 substituents independently selected from halogen, hydroxyl, cyano, C1-C6 alkyl, —NR$^F$R$^G$, C3-C6 cycloalkoxy, C1-C6 haloalkoxy, and C1-C6 alkoxy;

each p is independently 0 or 1;

m is 0, 1, 2, 3, or 4;

$R^4$ is hydrogen or C1-C6 alkyl;

R$^D$ is hydrogen, C1-C6 haloalkyl, C1-C6 alkyl optionally substituted with 1-3 independently selected R$^E$, C3-C6 cycloalkyl optionally substituted with 1-3 independently selected R$^E$, 4-10 membered heterocyclyl optionally substituted with 1-3 independently selected R$^E$, C6-C10 aryl, or 5-10 membered heteroaryl optionally substituted with 1-3 independently selected R$^E$; and each R$^F$ and R$^G$ are independently hydrogen or C1-C6 alkyl.

In some embodiments, Y is —S—. In some embodiments, Y is —S(═O)—.

In some embodiments, Ring A is a 5-7 membered heterocyclyl. In some embodiments, Ring A is a 6-7 membered monocyclic heterocyclyl. In some embodiments, Ring A includes one oxygen atom. In some embodiments, Ring A includes one nitrogen atom. In some embodiments, Ring A includes one oxygen atom and one nitrogen atoms. In some embodiments, Ring A is a 6-membered heterocyclyl comprising one oxygen atom bonded to the 5-membered ring containing Y. In some embodiments, Ring A is a 7-membered heterocyclyl comprising one oxygen atom bonded to the 5-membered ring containing Y. In some embodiments, Ring A is tetrahydrofuran, tetrahydropyran, or oxepan.

In some embodiments, Ring A is a C5-C7 cycloalkyl. In some embodiments, Ring A is a monocyclic C5-C7 cycloalkyl such as cyclopentyl, cyclohexyl, or cycloheptyl.

In some embodiments, $R^1$ is a 5-10 membered heteroaryl, optionally substituted with 1-3 substituents independently selected from the group consisting of C1-C6 alkyl, amino, halogen, hydroxyl, cyano, C1-C6 haloalkyl, C1-C6 alkoxy, and C3-C6 cycloalkyl. In some embodiments, $R^1$ is a 5-10 membered heteroaryl, substituted with 1-3 substituents independently selected from the group consisting of C1-C6 alkyl, amino, halogen, hydroxyl, cyano, C1-C6 haloalkyl, C1-C6 alkoxy, and C3-C6 cycloalkyl.

In some embodiments, $R^1$ is a 5-6 membered heteroaryl, optionally substituted with 1-3 substituents independently selected from the group consisting of C1-C6 alkyl, amino, halogen, hydroxy, cyano, C1-C6 haloalkyl, C1-C6 alkoxy, and C3-C6 cycloalkyl. In some embodiments, $R^1$ is a 5-6 membered heteroaryl, substituted with 1-3 substituents independently selected from the group consisting of C1-C6 alkyl, amino, halogen, hydroxy, cyano, C1-C6 haloalkyl, C1-C6 alkoxy, and C3-C6 cycloalkyl.

In some embodiments, $R^1$ is pyrazole, pyridine, or pyrimidine; each substituted with 1-3 substituents independently selected from the group consisting of C1-C6 alkyl, amino, halogen, hydroxy, cyano, C1-C6 haloalkyl, C1-C6 alkoxy, and C3-C6 cycloalkyl. In some embodiments, $R^1$ is pyrazole, pyridine, or pyrimidine; each substituted with one substituent selected from the group consisting of C1-C6 alkyl, amino, halogen, hydroxy, cyano, C1-C6 haloalkyl, C1-C6 alkoxy, and C3-C6 cycloalkyl.

In some embodiments, $R^1$ is pyrazole, pyridine, or pyrimidine; each substituted with C1-C6 alkyl, such as methyl, ethyl, n-propyl, or isopropyl. In some embodiments, $R^1$ is pyrazole substituted with methyl. In some embodiments, $R^1$ is

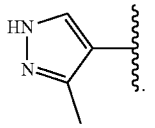

In some embodiments, $R^1$ is pyridine or pyrimidine; each substituted with methyl. In some embodiments, $R^1$ is

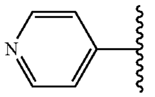 or 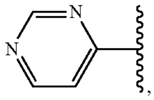, each substituted with methyl.

In some embodiments, $R^1$ is an unsubstituted 5-10 membered heteroaryl. In some embodiments, $R^1$ is an unsubstituted 5-6 membered heteroaryl. In some embodiments, $R^1$ is pyrazole. In some embodiments, $R^1$ is

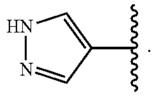.

In some embodiments, $R^1$ is pyridine. In some embodiments, $R^1$ is

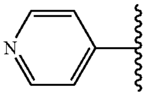.

In some embodiments, $R^1$ is pyrimidine. In some embodiments, $R^1$ is

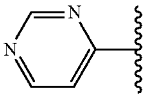.

In some embodiments, each $R^2$ is independently selected from the group consisting of halogen, hydroxy, cyano, C1-C6 haloalkyl, C1-C6 hydroxyalkyl, C1-C6 alkoxy, —$NR^BR^C$, C1-C6 alkoxyalkyl, —C(═O)NH-5-10 membered heteroaryl, 4-6 membered heterocyclyl, 5-10 membered heteroaryl, C1-C6 alkyl optionally substituted with 1-3 independently selected $R^A$, and C3-C6 cycloalkyl optionally substituted with hydroxyl.

In some embodiments, each $R^2$ is independently —C(═O)NH-5-10 membered heteroaryl. In some embodiments, each $R^2$ is independently —C(═O)NH-5-membered heteroaryl. In some embodiments, each $R^2$ is independently —C(═O)NH-6-membered heteroaryl. In some embodiments, each $R^2$ is independently —C(═O)NH-10 membered heteroaryl. In some embodiments, the heteroaryl group is selected from furan, thiophene, pyrrole, oxazole, 1,2,3-oxadiazole, 1,2,4-oxadiazole, thiazole, 1,2,3-thiadiazole, 1,2,4-thiadiazole, imidazole, isoxazole, isothiazole, thiadiazole, pyridine, pyridazine, pyrimidine, and pyrazine.

In some embodiments, each $R^2$ is independently 4-6 membered heterocyclyl. In some embodiments, the 4-6 membered heterocyclyl is connected to Formula (I) via a carbon atom. In some embodiments, the 4-6 membered heterocyclyl is connected to Formula (I) via a nitrogen atom. In some embodiments, each $R^2$ is independently selected from morpholine, piperidine, piperazine, pyrrolidine, pyrrolidone, 4-piperidone, azetidine, and oxetane.

In some embodiments, each $R^2$ is independently 5-10 membered heteroaryl. In some embodiments, each $R^2$ is independently a 5-membered heteroaryl. In some embodiments, each $R^2$ is independently a 6-membered heteroaryl. In some embodiments, each $R^2$ is selected from furan, thiophene, pyrrole, oxazole, 1,2,3-oxadiazole, 1,2,4-oxadiazole, thiazole, 1,2,3-thiadiazole, 1,2,4-thiadiazole, imidazole, isoxazole, isothiazole, thiadiazole, pyridine, pyridazine, pyrimidine, and pyrazine.

In some embodiments, each $R^2$ is independently C3-C6 cycloalkyl optionally substituted with hydroxyl. In some embodiments, each $R^2$ is independently C3-C6 cycloalkyl substituted with hydroxyl. In some embodiments, each $R^2$ is independently C3-C6 cycloalkyl.

In some embodiments, each $R^2$ is independently C1-C6 alkyl optionally substituted with 1-3 independently selected $R^A$. In some embodiments, each $R^2$ is independently C1-C6 alkyl substituted with 1-3 independently selected $R^A$. In some embodiments, each $R^2$ is independently C1-C6 alkyl substituted with one $R^A$. In some embodiments, each $R^2$ is independently C1-C6 alkyl substituted with 2 or 3 independently selected $R^A$.

In some embodiments, each $R^A$ is independently selected from the group consisting of halogen, cyano, hydroxyl, C1-C6 alkyl, C1-C6 haloalkyl, C1-C6 hydroxyalkyl, C1-C6 alkoxy, C1-C6 alkylamino, 4-6 membered heterocyclyl, and C3-C6 cycloalkyl. In some embodiments, each $R^A$ is independently selected from the group consisting of halogen, cyano, hydroxyl, C1-C3 alkoxy, C1-C3 alkyl, C1-C3 haloalkyl, C1-C3 hydroxyalkyl, C1-C3 alkylamino, 4-6 membered heterocyclyl, and C3-C6 cycloalkyl. In some embodiments, each $R^A$ is independently selected from the group consisting of fluoro, methyl, methoxy, trifluoromethyl, hydroxymethyl, or hydroxyethyl.

In some embodiments, each $R^2$ is independently unsubstituted C1-C6 alkyl, such as methyl, ethyl, n-propyl, or isopropyl. In some embodiments, each $R^2$ is methyl.

In some embodiments, each $R^2$ is independently selected from the group consisting of halogen, hydroxy, cyano, C1-C6 haloalkyl, C1-C6 hydroxyalkyl, C1-C6 alkoxy, —$NR^BR^C$, and C1-C6 alkoxyalkyl.

In some embodiments, each $R^2$ is independently halogen. In some embodiments, each $R^2$ is fluoro.

In some embodiments, each $R^2$ is independently selected from hydroxy, cyano, C1-C6 haloalkyl, C1-C6 hydroxyalkyl, C1-C6 alkoxy, and C1-C6 alkoxyalkyl.

In some embodiments, each $R^2$ is independently —$NR^BR^C$, as defined herein.

In some embodiments, two $R^2$ together with the atom to which they are attached, join together to form an oxo group; a C3-C6 cycloalkyl optionally substituted with 1-3 substituents independently selected from halogen, cyano, C1-C6 alkyl, and C1-C6 alkoxy; or a 3-6 membered heterocyclyl optionally substituted with 1-3 substituents independently selected from halogen, cyano, C1-C6 alkyl, and C1-C6 alkoxy.

In some embodiments, two $R^2$ together with the atom to which they are attached, join together to form an oxo group.

In some embodiments, two $R^2$ together with the atom to which they are attached, join together to form a C3-C6 cycloalkyl optionally substituted with 1-3 substituents independently selected from halogen, cyano, C1-C6 alkyl, and C1-C6 alkoxy. In some embodiments, two $R^2$ together with the atom to which they are attached, join together to form an unsubstituted C3-C6 cycloalkyl.

In some embodiments, two $R^2$ together with the atom to which they are attached, join together to form a 3-6 membered heterocyclyl optionally substituted with 1-3 substituents independently selected from halogen, cyano, C1-C6 alkyl, and C1-C6 alkoxy. In some embodiments, two $R^2$ together with the atom to which they are attached, join together to form an unsubstituted 3-6 membered heterocyclyl.

In some embodiments, m is 1. In some embodiments, m is 2. In some embodiments, m is 3. In some embodiments, m is 4.

In some embodiments, m is 0.

In some embodiments, m is 1 and $R^2$ is unsubstituted C1-C6 alkyl, such as methyl, ethyl, n-propyl, or isopropyl. In some embodiments, m is 1 and $R^2$ is methyl.

In some embodiments, m is 1 and $R^2$ is halogen. In some embodiments, m is 1 and $R^2$ is fluoro.

In some embodiments, m is 2 and each $R^2$ is independently unsubstituted C1-C6 alkyl. In some embodiments, m is 2 and each $R^2$ is methyl.

In some embodiments, m is 2 and each $R^2$ is independently halogen. In some embodiments, m is 2 and each $R^2$ is fluoro.

In some embodiments, m is 2 and the $R^2$ groups are geminal. In some embodiments, the $R^2$ groups are geminal dimethyl. In some embodiments, the $R^2$ groups are geminal difluoro.

In some embodiments, $R^3$ is selected from hydrogen and C0-C6 alkyl optionally substituted with 1-4 substituents independently selected from (i)-(xii):

(i) hydroxyl;
(ii) cyano;
(iii) halogen;
(iv) C3-C6 cycloalkoxy;
(v) C(=O)$OR^F$;
(vi) C1-C6 alkoxy;
(vii) 4-10 membered heterocyclyloxy optionally substituted with 1-3 independently selected halogens;
(viii) —$NR^BR^C$;
(ix) C3-C6 cycloalkyl optionally substituted with 1-3 groups independently selected from hydroxyl, cyano, halogen, C1-C6 alkoxy, C1-C6 haloalkoxy, —$NR^BR^C$, 3-6 membered heterocyclyloxy, and 3-6 membered heterocyclyl optionally substituted with 1-3 C1-C6 alkoxy;
(x) 3 to 10 membered heterocyclyl optionally substituted with 1-4 substituents independently selected from halogen, hydroxyl, C1-C6 hydroxyalkyl, C1-C6 alkoxy, C1-C6 haloalkyl, —$NR^BR^C$, C1-C6 alkyl optionally substituted with 1-3 substituents independently selected from halogen, C1-C6 alkoxy, and C3-C6 cycloalkoxy, and C3-C6 cycloalkyl optionally substituted with halogen or hydroxyl;
(xi) 5-6 membered heteroaryl optionally substituted with 1-3 substituents independently selected from cyano, hydroxyl, C1-C6 alkyl, C1-C6 alkoxy, C3-C6 cycloalkyl optionally substituted with 1-2 substituents independently selected from cyano and hydroxyl; and 4-10 membered heterocyclyl optionally substituted with 1-3 independently selected $R^A$; and
(xii) —C(=O)—X; wherein X is —$NR^BR^C$, C1-C6 alkyl, 5-6 membered heteroaryl, —NH-5-6 membered heteroaryl, —$OR^E$, or 3-6 membered heterocyclyl optionally substituted with hydroxyl;

In some embodiments, $R^3$ is hydrogen.

In some embodiments, $R^3$ is an unsubstituted C1-C6 alkyl.

In some embodiments, $R^3$ is a substituted C0-C6 alkyl. In some embodiments, $R^3$ is a C0-C6 alkyl with one substituent selected from (i)-(xii). In some embodiments, $R^3$ is a C0-C6 alkyl with two substituents independently selected from (i)-(xii). In some embodiments, $R^3$ is a C0-C6 alkyl with three substituents independently selected from (i)-(xii). In some embodiments, $R^3$ is a C0-C6 alkyl with four substituents independently selected from (i)-(xii).

In some embodiments, $R^3$ is C0-C6 alkyl optionally substituted with 1-3 substituents independently selected from hydroxyl, cyano, C1-C6 alkoxy, C3-C6 cycloalkoxy and C3-C6 cycloalkyl optionally substituted with 1-3 groups independently selected from hydroxyl, cyano, halogen, C1-C6 alkoxy, C1-C6 haloalkoxy, —$NR^BR^C$, 3-6 membered heterocyclyloxy, and 3-6 membered heterocyclyl optionally substituted with 1-3 C1-C6 alkoxy. In some embodiments, $R^3$ is C0-C6 alkyl optionally substituted with 1-3 substituents independently selected from hydroxyl, cyano, C1-C6 alkoxy, C3-C6 cycloalkoxy and C3-C6 cycloalkyl optionally substituted with hydroxyl, cyano, halogen, C1-C6 alkoxy, C1-C6 haloalkoxy, —$NR^BR^C$, 3-6 membered heterocyclyloxy, and 3-6 membered heterocyclyl optionally substituted with 1-3 C1-C6 alkoxy. In some embodiments, $R^3$ is C0-C6 alkyl optionally substituted with 1 or 2 substituents independently selected from hydroxyl, cyano, C1-C6 alkoxy, C3-C6 cycloalkoxy and C3-C6 cycloalkyl optionally substituted with hydroxyl.

In some embodiments, $R^3$ is C0-C6 alkyl optionally substituted with 1-3 substituents independently selected from hydroxyl, C1-C6 alkoxy, C3-C6 cycloalkoxy, and C3-C6 cycloalkyl optionally substituted with hydroxyl. In some embodiments, $R^3$ is C0-C6 alkyl optionally substituted with 1 or 2 substituents independently selected from hydroxyl, C1-C6 alkoxy, C3-C6 cycloalkoxy, and C3-C6 cycloalkyl optionally substituted with hydroxyl. In some embodiments, $R^3$ is C0-C6 alkyl optionally substituted with 1 or 2 substituents independently selected from hydroxyl, C1-C6 alkoxy, C3-C6 cycloalkoxy, and C3-C6 cycloalkyl substituted with hydroxyl.

In some embodiments, $R^3$ is unsubstituted C1-C6 alkyl, such as methyl, ethyl, n-propyl, or isopropyl. In some embodiments, $R^3$ is methyl.

In some embodiments, $R^3$ is C0-C6 alkyl substituted with hydroxyl. In some embodiments, $R^3$ is hydroxymethyl, 1-hydroxyethyl, 2-hydroxyethyl, 2-hydroxy-2-propyl, 1-hydroxypropyl, 2-hydroxypropyl, or 3-hydroxypropyl. In some embodiments, $R^3$ is

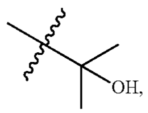 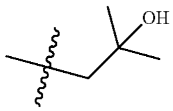 , 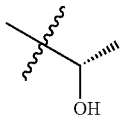 ,

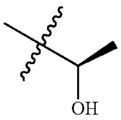 , 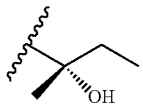 , or 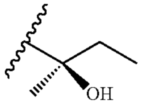 .

In some embodiments, $R^3$ is C0-C6 alkyl substituted with C3-C6 cycloalkyl optionally substituted with hydroxyl. In some embodiments, $R^3$ is C0-C1 alkyl substituted with C3-C6 cycloalkyl substituted with hydroxyl. In some embodiments, $R^3$ is

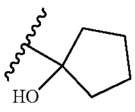 .

In some embodiments, $R^3$ is C1-C6 alkyl substituted with hydroxyl and C3-C6 cycloalkyl. In some embodiments, $R^3$ is methyl or ethyl; each substituted with hydroxyl and one C3-C6 cycloalkyl. In some embodiments, $R^3$ is

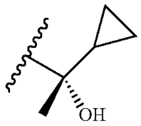

or

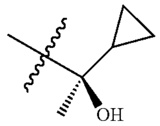

.

In some embodiments, $R^3$ is C1-C6 alkyl substituted with C3-C6 cycloalkoxy. In some embodiments, $R^3$ is methyl or ethyl; each substituted with C3-C6 cycloalkoxy. In some embodiments, $R^3$ is

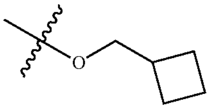

.

In some embodiments, $R^3$ is C1-C6 alkyl substituted with one or two C1-C6 alkoxy. In some embodiments, $R^3$ is ethyl or n-propyl; each substituted with one or two C1-C2 alkoxy. In some embodiments, $R^3$ is

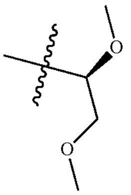

or

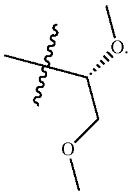

.

In some embodiments, $R^3$ is C1-C6 alkyl substituted with C(=O)—O—$X^1$. In some embodiments, $X^1$ is C1-C6 alkyl, such as methyl, ethyl, n-propyl, or isopropyl. In some embodiments, $R^3$ is methyl or ethyl; each substituted with C(=O)—OMe or C(=O)—OEt. In some embodiments, $R^3$ is

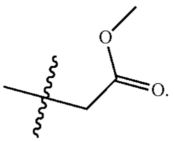 [SMILES: *CC(=O)OC]

.

In some embodiments, $R^3$ is C1-C6 alkyl substituted with 1-3 substituents independently selected from hydroxyl, C1-C6 alkoxy and 3 to 10 membered heterocyclyl, wherein the 3 to 10 membered heterocyclyl is optionally substituted with 1-3 substituents selected from C1-C6 alkyl, hydroxyl, and halogen. In some embodiments, $R^3$ is C1-C6 alkyl substituted with 1-3 groups independently selected from 3 to 10 membered heterocyclyl, wherein the 3 to 10 membered heterocyclyl is optionally substituted with 1-3 substituents selected from C1-C6 alkyl, hydroxyl, and halogen. In some embodiments, $R^3$ is C1-C6 alkyl substituted with a 3 to 10 membered heterocyclyl. In some embodiments, $R^3$ is C1-C6 alkyl substituted with a 3 to 10 membered heterocyclyl substituted with hydroxyl. In some embodiments, $R^3$ is C1-C6 alkyl substituted with a 3 to 10 membered heterocyclyl substituted with halogen. In some embodiments, $R^3$ is C1-C6 alkyl substituted with a 3 to 10 membered heterocyclyl substituted with methyl. In some embodiments, the C1-C6 alkyl is a methyl, ethyl, n-propyl, or isopropyl. In some embodiments, the 3 to 10 membered heterocyclyl is a 4-6 membered heterocyclyl. In some embodiments, the heterocyclyl group comprises one or two nitrogen atoms. In some embodiments, the heterocyclyl group is connected to the alkyl group of $R^3$ via a carbon atom. In some embodiments, the heterocyclyl group is connected to the alkyl group of $R^3$ via a nitrogen atom.

In some embodiments, $R^3$ is C1-C6 alkyl substituted with azetidine, pyrrolidine, pyrrolidinone, or piperidine; each optionally substituted with 1-3 substituents independently selected from C1-C6 alkyl, hydroxyl, and halogen. In some embodiments, $R^3$ is C1-C6 alkyl substituted with azetidine, pyrrolidine, pyrrolidinone, or piperidine; each substituted with 2 substituents independently selected from C1-C6 alkyl, hydroxyl, or halogen. In some embodiments, $R^3$ is C1-C6 alkyl substituted with azetidine, pyrrolidine, pyrrolidinone, or piperidine; each substituted with C1-C6 alkyl, hydroxyl, or halogen. In some embodiments, $R^3$ is C1-C6 alkyl substituted with azetidine, pyrrolidine, pyrrolidinone, or piperidine.

In some embodiments, $R^3$ is C1-C3 alkyl substituted with azetidine. In some embodiments, $R^3$ is C1-C3 alkyl substituted with azetidine substituted with methyl, fluoro, or hydroxyl. In some embodiments, $R^3$ is C1-C3 alkyl substituted with pyrrolidine. In some embodiments, $R^3$ is C1-C3 alkyl substituted with pyrrolidine substituted with hydroxyl, methyl, or 1 or 2 fluoros. In some embodiments, $R^3$ is C1-C3 alkyl substituted with pyrrolidinone. In some embodiments, $R^3$ is C1-C3 alkyl substituted with pyrrolidinone substituted with methyl or 1 or 2 fluoros. In some embodiments, $R^3$ is C1-C3 alkyl substituted with piperidine.

In some embodiments, $R^3$ is:

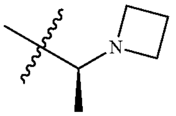

,

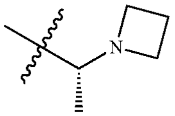

,

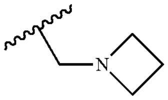

,

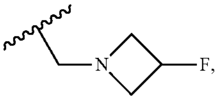

,

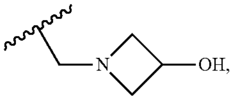

,

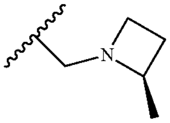

, or

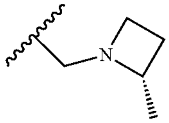

.

In some embodiments, $R^3$ is:

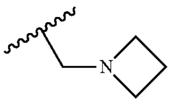

,

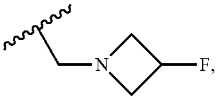

,

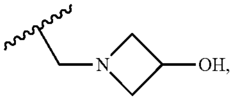

,

-continued

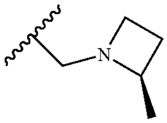

, or

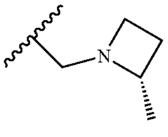

.

In some embodiments, $R^3$ is

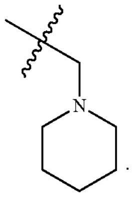 [SMILES: *CN1CCCCC1]

.

In some embodiments, $R^3$ is

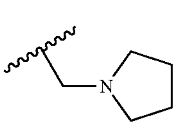

,

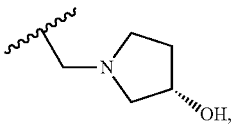

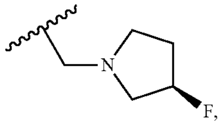

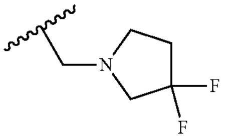

, or

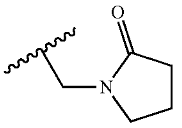

.

In some embodiments, $R^3$ is

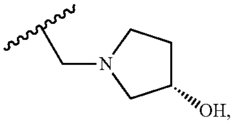

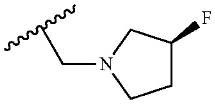

,

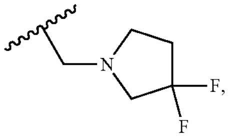

or

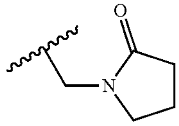

.

In some embodiments, $R^3$ is C0-C6 alkyl substituted with —$NR^BR^C$. In some embodiments, $R^B$ and $R^C$ are each independently hydrogen, C1-C6 alkyl, C3-C6 cycloalkyl, C(=O)—C1-C6 alkyl, C(=O)—O—C1-C6 alkyl or benzyl substituted with C1-C6 alkoxy. In some embodiments, $R^B$ and $R^C$ are each independently hydrogen, C1-C6 alkyl, C3-C6 cycloalkyl, or C(=O)—C1-C6 alkyl.

In some embodiments, $R^B$ and $R^C$ together with the atom to which they are attached, join together to form a 4-10 membered heterocyclyl optionally substituted with 1-3 substituents independently selected from halogen, hydroxyl, cyano, C1-C6 alkyl, —$NR^FR^G$, C3-C6 cycloalkoxy, C1-C6 haloalkoxy, and C1-C6 alkoxy. In some embodiments, the 4-10 membered heterocyclyl is a bicyclic fused heterocyclyl, such as a [5,5], [5,6], or [6,6] fused ring system.

In some embodiments, $R^3$ is

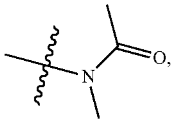

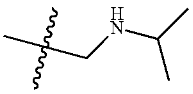

, or

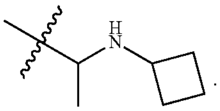

.

In some embodiments, $R^3$ is C0-C6 alkyl substituted with $NH_2$. In some embodiments, $R^3$ is $NH_2$ (i.e., when the C0-C6 alkyl is a C0 alkyl).

In some embodiments, each $R^F$ and $R^G$ are independently hydrogen or C1-C6 alkyl. In some embodiments, each $R^F$ and $R^G$ are the same. In some embodiments, each $R^F$ and $R^G$ are different. In some embodiments, one of $R^F$ and $R^G$ is hydrogen and the other of $R^F$ and $R^G$C1-C6 alkyl.

In some embodiments, $R^3$ is —C(=O)—$X^2$, wherein $X^2$ is C1-C6 alkyl or 3-6 membered heterocyclyl optionally substituted with hydroxyl. In some embodiments, the 3-6 membered heterocyclyl is azetidine, morpholine, or pyrrolidine.

In some embodiments, $R^3$ is C1-C6 alkyl substituted with 1-3 substituents independently selected from cyano, hydroxyl, halogen, and C1-C6 alkoxy. In some embodiments, $R^3$ is C1-C2 alkyl substituted with 1 or 2 substituents independently selected from cyano, hydroxyl, halogen, and C1-C2 alkoxy. In some embodiments, $R^3$ is C1-C6 alkyl substituted with cyano. In some embodiments, $R^3$ is

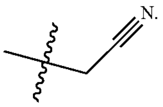 [SMILES: *CC#N]

In some embodiments, $R^3$ is C1-C6 alkyl substituted with 1-3 substituents independently selected from hydroxyl, C1-C6 alkoxy, and 5-6 membered heteroaryl. In some embodiments, $R^3$ is C1-C3 alkyl substituted with 1 or 2 substituents independently selected from hydroxyl, C1-C3 alkoxy, and 5-6 membered heteroaryl. In some embodiments, the 5-6 membered heteroaryl is optionally substituted with 1-3 substituents independently selected from cyano, hydroxyl, C1-C6 alkyl, and C1-C6 alkoxy. In some embodiments, the 5-6 membered heteroaryl is substituted with 1-3 substituents independently selected from cyano, hydroxyl, C1-C6 alkyl, and C1-C6 alkoxy. In some embodiments, the 5-6 membered heteroaryl is substituted with 1 or 2 substituents independently selected from cyano, hydroxyl, C1-C3 alkyl, and C1-C3 alkoxy. In some embodiments, the 5-6 membered heteroaryl is imidazole, pyrazole, or triazole.

In some embodiments, the 5-6 membered heteroaryl is pyrazole substituted with cyano. In some embodiments, $R^3$ is

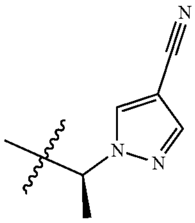 or 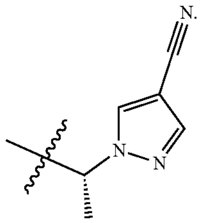

In some embodiments, the 5-6 membered heteroaryl is pyrazole. In some embodiments, $R^3$ is

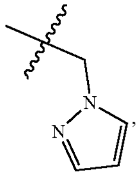 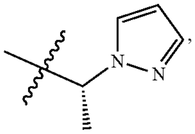 or 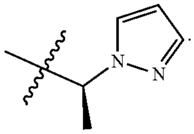

In some embodiments, $R^3$ is

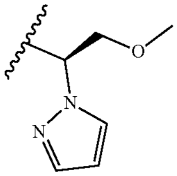 or 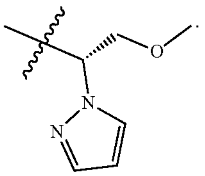

In some embodiments, the 5-6 membered heteroaryl is imidazole. In some embodiments, $R^3$ is

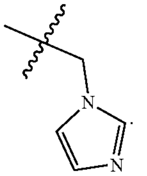 [SMILES: *Cn1ccnc1]

In some embodiments, the 5-6 membered heteroaryl is triazole. In some embodiments, $R^3$ is

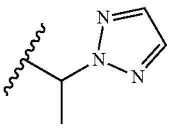 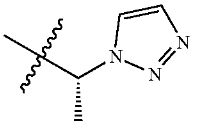 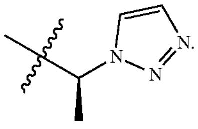

In some embodiments, $R^3$ is C1-C6 alkyl substituted with unsubstituted 5-6 membered heteroaryl. In some embodiments, the 5-6 membered heteroaryl is imidazole. In some embodiments, the 5-6 membered heteroaryl is triazole. In some embodiments, the 5-6 membered heteroaryl is

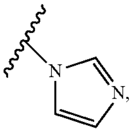 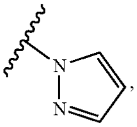 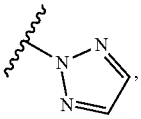

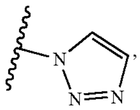 or 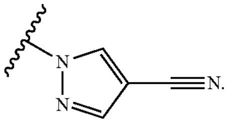

In some embodiments, each p is 0. In some embodiments, each p is 1. In some embodiments, there are two occurrences of p and one p is 1 and the other p is 0.

In some embodiments, $R^4$ is C1-C6 alkyl, such as methyl, ethyl, n-propyl, or isopropyl. In some embodiments, $R^4$ is methyl. In some embodiments, $R^4$ is hydrogen.

In some embodiments, the compound of Formula (I) is a compound of Formula (Ia):

(Ia)

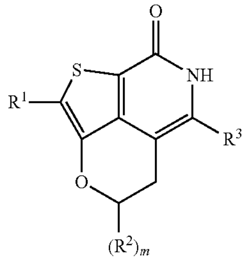

or a pharmaceutically acceptable salt thereof, wherein:

$R^1$ is a 5 or 6 membered heteroaryl group, optionally substituted with C1-C6 alkyl; and $R^2$ is independently selected from halogen and C1-C6 alkyl, and m is 1 or 2.

In some embodiments, the compound of Formula (I) is a compound of Formula (Ib):

(Ib)

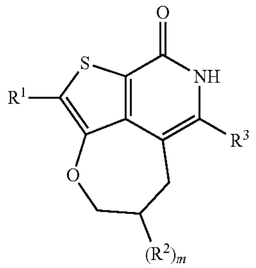

or a pharmaceutically acceptable salt thereof, wherein:

$R^1$ is a 5 or 6 membered heteroaryl group, optionally substituted with C1-C6 alkyl; and $R^2$ is independently selected from halogen and C1-C6 alkyl, and m is 1 or 2.

In some embodiments, m is 2 and $R^2$ is geminal difluoro. In some embodiments, m is 2 and $R^2$ is geminal dimethyl. In some embodiments, m is 1 and $R^2$ is fluoro. In some embodiments, m is 1 and $R^2$ is methyl.

In some embodiments, the compound of Formula (I) is a compound of Formula (Ic):

(Ic)

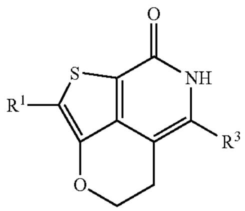 or (Id)

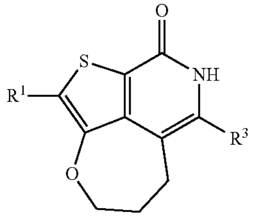

or a pharmaceutically acceptable salt of either of the foregoing.

In some embodiments, $R^1$ is pyrazole, pyridine, or pyrimidine; each substituted with C1-C6 alkyl, such as methyl, ethyl, n-propyl, or isopropyl. In some embodiments, $R^1$ is pyrazole substituted with methyl. In some embodiments, $R^1$ is pyridine substituted with methyl. In some embodiments, $R^1$ is pyrimidine substituted with methyl.

In some embodiments, $R^1$ is pyrazole, pyridine, or pyrimidine. In some embodiments, $R^1$ is

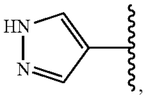, 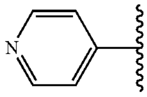, or 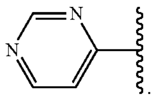.

In some embodiments, $R^3$ is C1-C6 alkyl optionally substituted with 1-3 substituents independently selected from hydroxyl, C1-C6 alkoxy, C3-C6 cycloalkoxy, and C3-C6 cycloalkyl optionally substituted with hydroxyl. In some embodiments, $R^3$ is C1-C6 alkyl substituted with 1-3 substituents independently selected from hydroxyl, C1-C6 alkoxy, C3-C6 cycloalkoxy, and C3-C6 cycloalkyl optionally substituted with hydroxyl. In some embodiments, $R^3$ is C1-C6 alkyl substituted with hydroxyl, C1-C6 alkoxy, C3-C6 cycloalkoxy, or C3-C6 cycloalkyl optionally substituted with hydroxyl.

In some embodiments, $R^3$ is unsubstituted C1-C6 alkyl. In some embodiments, $R^3$ is methyl, ethyl, n-propyl, or isopropyl. In some embodiments, $R^3$ is methyl.

In some embodiments, $R^3$ is C1-C6 alkyl substituted with hydroxyl. In some embodiments, $R^3$ is

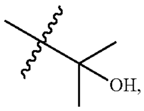, 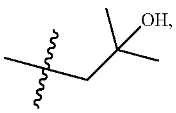, 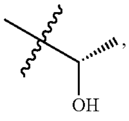,

-continued

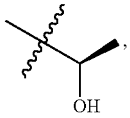, 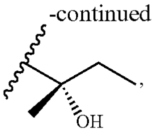, or 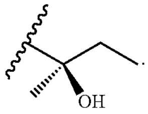.

In some embodiments, $R^3$ is C0-C6 alkyl substituted with C3-C6 cycloalkyl optionally substituted with hydroxyl. In some embodiments, $R^3$ is C1-C6 alkyl substituted with C3-C6 cycloalkyl substituted with hydroxyl. In some embodiments, $R^3$ is methyl substituted with C3-C6 cycloalkyl substituted with hydroxyl. In some embodiments, $R^3$ is

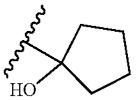 [SMILES: *C1(O)CCCC1]

(i.e., when the C0-C6 alkyl is a C0 alkyl).

In some embodiments, $R^3$ is C1-C6 alkyl substituted with one hydroxyl and one C3-C6 cycloalkyl. In some embodiments, $R^3$ is methyl or ethyl; each substituted with one hydroxyl and one C3-C6 cycloalkyl. In some embodiments, $R^3$ is methyl or ethyl; each substituted with one hydroxyl and cyclopropyl or cyclobutyl. In some embodiments, $R^3$ is

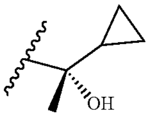 or 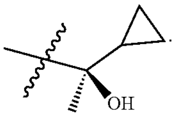.

In some embodiments, $R^3$ is C1-C6 alkyl substituted with C3-C6 cycloalkoxy. In some embodiments, $R^3$ is

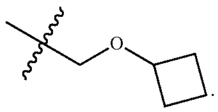 [SMILES: *COC1CCC1].

In some embodiments, $R^3$ is C1-C6 alkyl substituted with one or two C1-C6 alkoxy. In some embodiments, $R^3$ is methyl, ethyl, or n-propyl; each substituted with one or two C1-C6 alkoxy. In some embodiments, $R^3$ is methyl, ethyl, or n-propyl; each substituted with one or two methoxy. In some embodiments, $R^3$ is

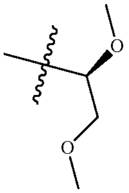 or 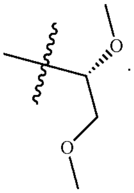.

In some embodiments, $R^3$ is C1-C6 alkyl substituted with C(=O)—O—$X^1$. In some embodiments, $X^1$ is C1-C6 alkyl. In some embodiments, $R^3$ is

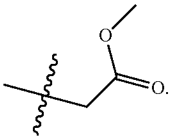 [SMILES: *CC(=O)OC]

In some embodiments, $R^3$ is C1-C6 alkyl substituted with 1-3 3 to 10 membered heterocyclyl, wherein the 3 to 10 membered heterocyclyl is optionally substituted with 1-3 substituents selected from C1-C6 alkyl, hydroxyl, and halogen. In some embodiments, $R^3$ is C1-C6 alkyl substituted with 3 to 10 membered heterocyclyl. In some embodiments, $R^3$ is C1-C6 alkyl substituted with 3 to 10 membered heterocyclyl substituted with hydroxyl. In some embodiments, $R^3$ is C1-C6 alkyl substituted with 3 to 10 membered heterocyclyl substituted with halogen. In some embodiments, $R^3$ is C1-C6 alkyl substituted with 3 to 10 membered heterocyclyl substituted with methyl.

In some embodiments, $R^3$ is C1-C6 alkyl substituted with azetidine, pyrrolidine, or piperidine; each optionally substituted with C1-C6 alkyl, hydroxyl or halogen.

In some embodiments, $R^3$ is C1-C6 alkyl substituted with azetidine substituted with 1-3 substituents independently selected from C1-C6 alkyl, hydroxyl and halogen. In some embodiments, $R^3$ is C1-C6 alkyl substituted with unsubstituted azetidine. In some embodiments, $R^3$ is:

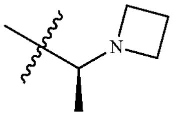 , 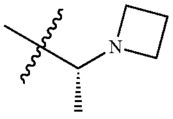 , 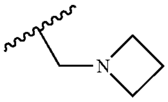 ,

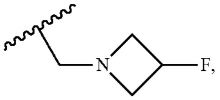 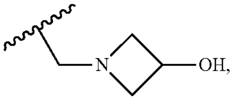

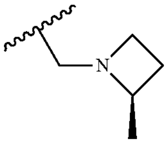 , or 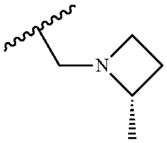 .

In some embodiments, $R^3$ is C1-C6 alkyl substituted with unsubstituted piperidine. In some embodiments, $R^3$ is

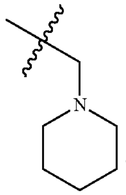 .

In some embodiments, $R^3$ is C1-C6 alkyl substituted with pyrrolidine substituted with 1-3 substituents independently selected from hydroxyl and halogen. In some embodiments, $R^3$ is C1-C6 alkyl substituted with unsubstituted pyrrolidine. In some embodiments, $R^3$ is

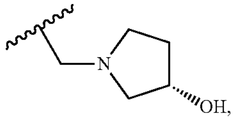 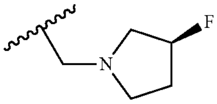 ,

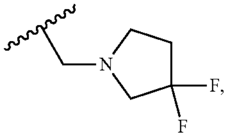 or 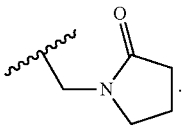 .

In some embodiments, R is C0-C6 alkyl substituted with —$NR^BR^C$. In some embodiments, $R^B$ and $R^C$ are each independently hydrogen, C1-C6 alkyl, C3-C6 cycloalkyl, or C(═O)—C1-C6 alkyl. In some embodiments, $R^3$ is

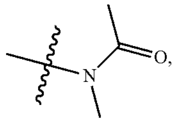 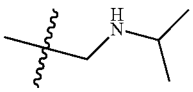 , or

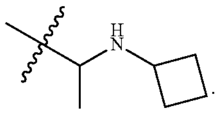 .

In some embodiments, $R^3$ is C0-C6 alkyl substituted with $NH_2$. In some embodiments, $R^3$ is $NH_2$.

In some embodiments, $R^3$ is C1-C6 alkyl substituted with cyano. In some embodiments, $R^3$ is

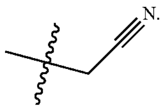 [SMILES: *CC#N]

In some embodiments, $R^3$ is C1-C6 alkyl substituted with 1-3 substituents independently selected from C1-C6 alkoxy and 5-6 membered heteroaryl.

In some embodiments, the 5-6 membered heteroaryl is optionally substituted with 1-3 substituents independently selected from cyano, hydroxyl, C1-C6 alkyl, and C1-C6 alkoxy.

In some embodiments, the 5-6 membered heteroaryl is imidazole, pyrazole or triazole.

In some embodiments, the 5-6 membered heteroaryl is unsubstituted pyrazole. In some embodiments, $R^3$ is

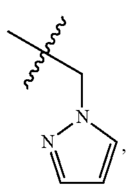 , 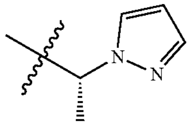 , or 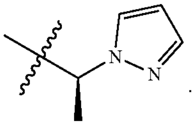 .

In some embodiments, $R^3$ is

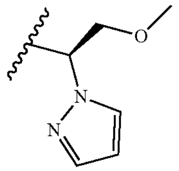

or

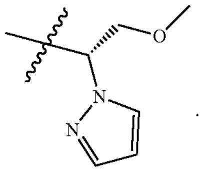

.

In some embodiments, the 5-6 membered heteroaryl is pyrazole substituted with cyano. In some embodiments, $R^3$ is

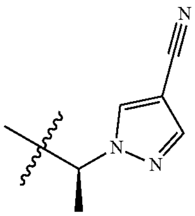

or

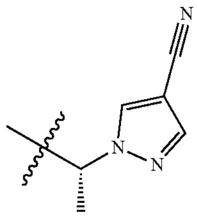

.

In some embodiments, the 5-6 membered heteroaryl is unsubstituted imidazole. In some embodiments, $R^3$ is

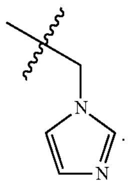

In some embodiments, the 5-6 membered heteroaryl is unsubstituted triazole. In some embodiments, $R^3$ is

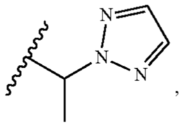

,

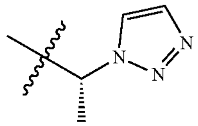

, or

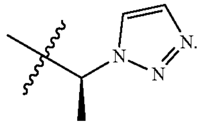

In some embodiments, the compound is a compound selected from Table 1, or a pharmaceutically acceptable salt thereof.

TABLE 1

| Cmpd No. | Structure | Name |
|---|---|---|
| 1. | 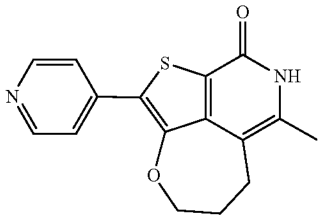 [SMILES: Cc1[nH]c(=O)c2sc(-c3ccncc3)c3c2c1CCCO3] | 5-methyl-1-(pyridin-4-yl)-4,6,7,8-tetrahydro-3H-9-oxa-2-thia-4-azabenzo[cd]azulen-3-one; Scheme |
| 2. | 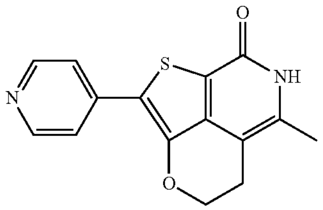 [SMILES: Cc1[nH]c(=O)c2sc(-c3ccncc3)c3c2c1CCO3] | 6-methyl-2-(pyridin-4-yl)-5,7-dihydro-3-oxa-1-thia-7-azaacenaphthylen-8(4H)-one |
| 3. | 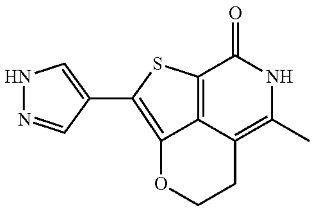 [SMILES: Cc1[nH]c(=O)c2sc(-c3cn[nH]c3)c3c2c1CCO3] | 6-methyl-2-(1H-pyrazol-4-yl)-5,7-dihydro-3-oxa-1-thia-7-azaacenaphthylen-8(4H)-one |
| 4. | 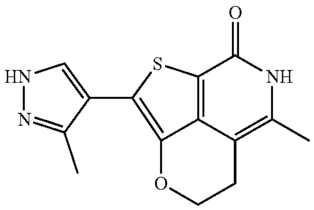 [SMILES: Cc1n[nH]cc1-c1sc2c(=O)[nH]c(C)c3c2c1OCC3] | 6-methyl-2-(3-methyl-1H-pyrazol-4-yl)-5,7-dihydro-3-oxa-1-thia-7-azaacenaphthylen-8(4H)-one |

TABLE 1-continued

| Cmpd No. | Structure | Name |
|---|---|---|
| 5. | 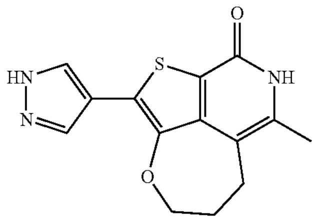 [SMILES: Cc1[nH]c(=O)c2sc(-c3cn[nH]c3)c3c2c1CCCO3] | 5-methyl-1-(1H-pyrazol-4-yl)-4,6,7,8-tetrahydro-3H-9-oxa-2-thia-4-azabenzo[cd]azulen-3-one |
| 6. | 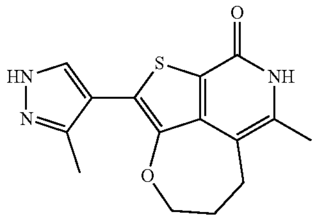 [SMILES: Cc1n[nH]cc1-c1sc2c(=O)[nH]c(C)c3c2c1OCCC3] | 5-methyl-1-(3-methyl-1H-pyrazol-4-yl)-4,6,7,8-tetrahydro-3H-9-oxa-2-thia-4-azabenzo[cd]azulen-3-one |
| 7. | 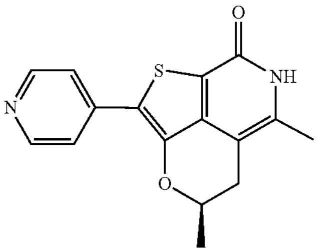 [SMILES: Cc1[nH]c(=O)c2sc(-c3ccncc3)c3c2c1C[C@@H](C)O3] | (R)-4,6-dimethyl-2-(pyridin-4-yl)-5,7-dihydro-3-oxa-1-thia-7-azaacenaphthylen-8(4H)-one |
| 8. | 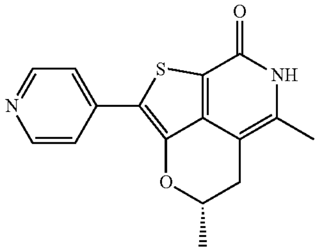 [SMILES: Cc1[nH]c(=O)c2sc(-c3ccncc3)c3c2c1C[C@H](C)O3] | (S)-4,6-dimethyl-2-(pyridin-4-yl)-5,7-dihydro-3-oxa-1-thia-7-azaacenaphthylen-8(4H)-one |
| 9. | 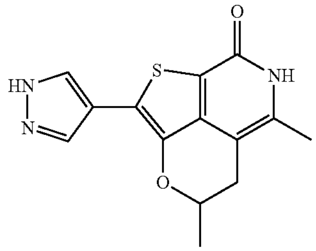 [SMILES: Cc1[nH]c(=O)c2sc(-c3cn[nH]c3)c3c2c1CC(C)O3] | 4,6-dimethyl-2-(1H-pyrazol-4-yl)-5,7-dihydro-3-oxa-1-thia-7-azaacenaphthylen-8(4H)-one |
| 10. | 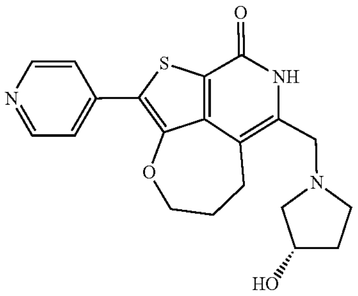 [SMILES: O=c1[nH]c(CN2CC[C@H](O)C2)c2c3c(c(-c4ccncc4)sc13)OCCC2] | (S)-5-((3-hydroxypyrrolidin-1-yl)methyl)-1-(pyridin-4-yl)-4,6,7,8-tetrahydro-3H-9-oxa-2-thia-4-azabenzo[cd]azulen-3-one |

TABLE 1-continued

| Cmpd No. | Structure | Name |
| --- | --- | --- |
| 11. | 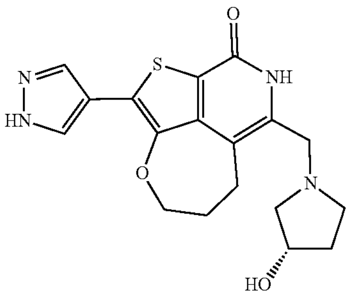 [SMILES: O=c1[nH]c(CN2CC[C@H](O)C2)c2c3c(c(-c4cn[nH]c4)sc13)OCCC2] | (S)-5-((3-hydroxypyrrolidin-1-yl)methyl)-1-(1H-pyrazol-4-yl)-4,6,7,8-tetrahydro-3H-9-oxa-2-thia-4-azabenzo[cd]azulen-3-one |
| 12. | 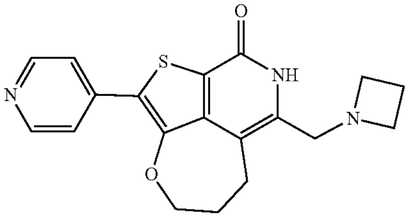 [SMILES: O=c1[nH]c(CN2CCC2)c2c3c(c(-c4ccncc4)sc13)OCCC2] | 5-(azetidin-1-ylmethyl)-1-(pyridin-4-yl)-4,6,7,8-tetrahydro-3H-9-oxa-2-thia-4-azabenzo[cd]azulen-3-one |
| 13. | 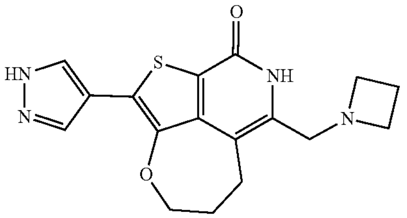 [SMILES: O=c1[nH]c(CN2CCC2)c2c3c(c(-c4cn[nH]c4)sc13)OCCC2] | 5-(azetidin-1-ylmethyl)-1-(1H-pyrazol-4-yl)-4,6,7,8-tetrahydro-3H-9-oxa-2-thia-4-azabenzo[cd]azulen-3-one |
| 14. | 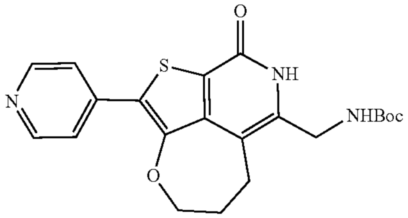 [SMILES: CC(C)(C)OC(=O)NCc1[nH]c(=O)c2sc(-c3ccncc3)c3c2c1CCCO3] | Tert-butyl ((3-oxo-1-(pyridin-4-yl)-4,6,7,8-tetrahydro-3H-9-oxa-2-thia-4-azabenzo[cd]azulen-5-yl)methyl)carbamate |
| 15. | 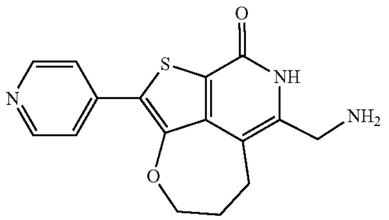 [SMILES: NCc1[nH]c(=O)c2sc(-c3ccncc3)c3c2c1CCCO3] | 5-(aminomethyl)-1-(pyridin-4-yl)-4,6,7,8-tetrahydro-3H-9-oxa-2-thia-4-azabenzo[cd]azulen-3-one |
| 16. | 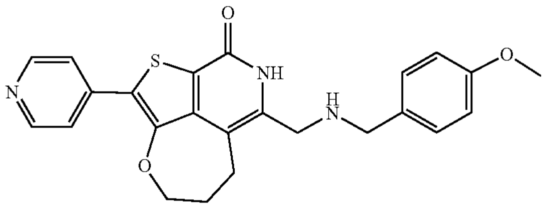 [SMILES: COc1ccc(CNCc2[nH]c(=O)c3sc(-c4ccncc4)c4c3c2CCCO4)cc1] | 5-(((4-methoxybenzyl)amino)methyl)-1-(pyridin-4-yl)-4,6,7,8-tetrahydro-3H-9-oxa-2-thia-4-azabenzo[cd]azulen-3-one |

TABLE 1-continued

| Cmpd No. | Structure | Name |
|---|---|---|
| 17. | 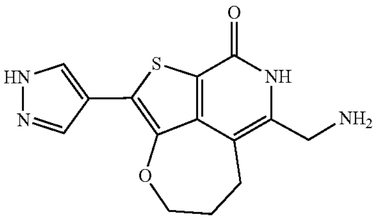 [SMILES: NCc1[nH]c(=O)c2sc(-c3cn[nH]c3)c3c2c1CCCO3] | 7-(aminomethyl)-2-(1H-pyrazol-4-yl)-12-oxa-3-thia-6-azatricyclo[6.4.1.04,13]trideca-1,4(13),7-trien-5-one |
| 18. | 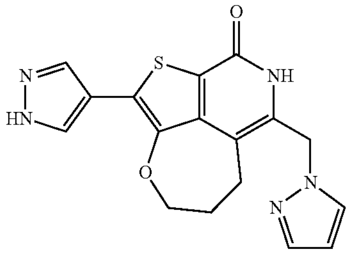 [SMILES: O=c1[nH]c(Cn2cccn2)c2c3c(c(-c4cn[nH]c4)sc13)OCCC2] | 2-(1H-pyrazol-4-yl)-7-(pyrazol-1-ylmethyl)-12-oxa-3-thia-6-azatricyclo[6.4.1.0$^{4,13}$] trideca-1,4(13),7-trien-5-one |
| 19. | 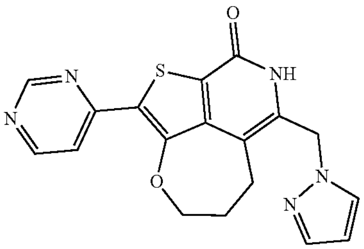 [SMILES: O=c1[nH]c(Cn2cccn2)c2c3c(c(-c4ccncn4)sc13)OCCC2] | 7-(pyrazol-1-ylmethyl)-2-pyrimidin-4-yl-12-oxa-3-thia-6-azatricyclo[6.4.1.04,13]trideca-1,4(13),7-trien-5-one |
| 20. | 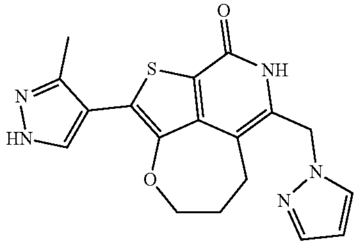 [SMILES: Cc1n[nH]cc1-c1sc2c(=O)[nH]c(Cn3cccn3)c3c2c1OCCC3] | 2-(3-methyl-1H-pyrazol-4-yl)-7-(pyrazol-1-ylmethyl)-12-oxa-3-thia-6-azatricyclo [6.4.1.0$^{4,13}$]trideca-1,4(13),7-trien-5-one |
| 21. | 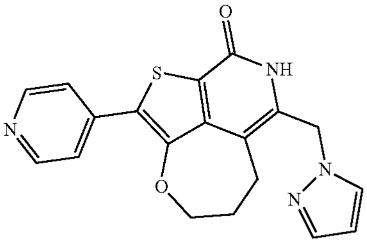 [SMILES: O=c1[nH]c(Cn2cccn2)c2c3c(c(-c4ccncc4)sc13)OCCC2] | 7-(pyrazol-1-ylmethyl)-2-(4-pyridyl)-12-oxa-3-thia-6-azatricyclo[6.4.1.0$^{4,13}$]trideca-1,4(13),7-trien-5-one |
| 22. | 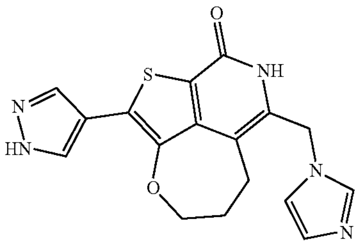 [SMILES: O=c1[nH]c(Cn2ccnc2)c2c3c(c(-c4cn[nH]c4)sc13)OCCC2] | 7-(imidazol-1-ylmethyl)-2-(1H-pyrazol-4-yl)-12-oxa-3-thia-6-azatricyclo[6.4.1.0$^{4,13}$] trideca-1,4(13),7-trien-5-one |

TABLE 1-continued

| Cmpd No. | Structure | Name |
|---|---|---|
| 23. | 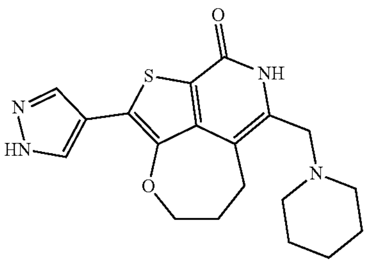 [SMILES: O=c1[nH]c(CN2CCCCC2)c2c3c(c(-c4cn[nH]c4)sc13)OCCC2] | 5-(piperidin-1-ylmethyl)-1-(1H-pyrazol-4-yl)-4,6,7,8-tetrahydro-3H-9-oxa-2-thia-4-azabenzo[cd]azulen-3-one |
| 24. | 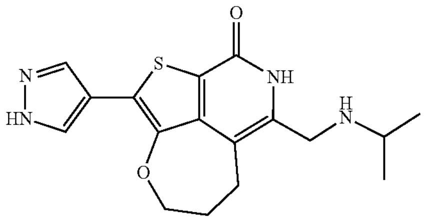 [SMILES: CC(C)NCc1[nH]c(=O)c2sc(-c3cn[nH]c3)c3c2c1CCCO3] | 5-((isopropylamino)methyl)-1-(1H-pyrazol-4-yl)-4,6,7,8-tetrahydro-3H-9-oxa-2-thia-4-azabenzo[cd]azulen-3-one |
| 25. | 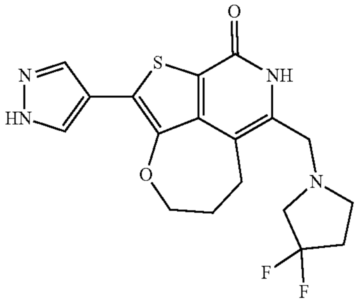 [SMILES: O=c1[nH]c(CN2CCC(F)(F)C2)c2c3c(c(-c4cn[nH]c4)sc13)OCCC2] | 7-[(3,3-difluoropyrrolidin-1-yl)methyl]-2-(1H-pyrazol-4-yl)-12-oxa-3-thia-6-azatricyclo[6.4.1.0$^{4,13}$]trideca-1,4(13),7-trien-5-one |
| 26. | 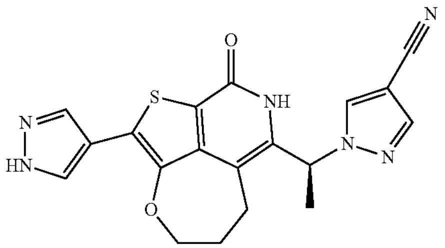 [SMILES: C[C@@H](c1[nH]c(=O)c2sc(-c3cn[nH]c3)c3c2c1CCCO3)n1cc(C#N)cn1] | (S)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile |
| 27. | 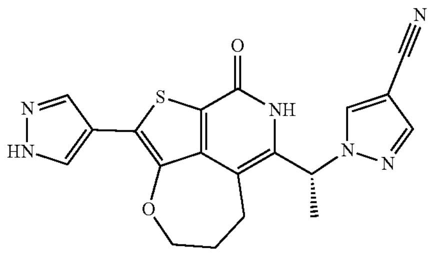 [SMILES: C[C@H](c1[nH]c(=O)c2sc(-c3cn[nH]c3)c3c2c1CCCO3)n1cc(C#N)cn1] | (R)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile |
| 28. | 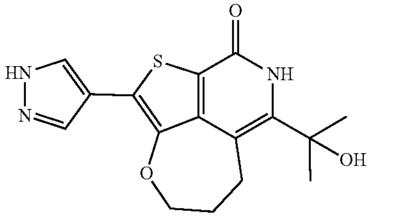 [SMILES: CC(C)(O)c1[nH]c(=O)c2sc(-c3cn[nH]c3)c3c2c1CCCO3] | 5-(2-hydroxypropan-2-yl)-1-(1H-pyrazol-4-yl)-4,6,7,8-tetrahydro-3H-9-oxa-2-thia-4-azabenzo[cd]azulen-3-one |

TABLE 1-continued

| Cmpd No. | Structure | Name |
|---|---|---|
| 29. | 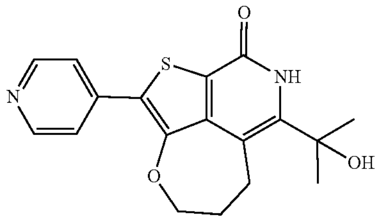 [SMILES: CC(C)(O)c1[nH]c(=O)c2sc(-c3ccncc3)c3c2c1CCCO3] | 5-(2-hydroxypropan-2-yl)-1-(pyridin-4-yl)-4,6,7,8-tetrahydro-3H-9-oxa-2-thia-4-azabenzo[cd]azulen-3-one |
| 30. | 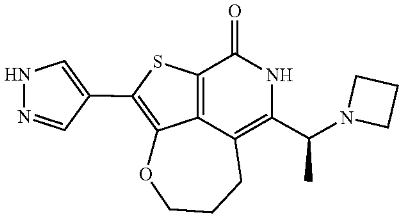 [SMILES: C[C@@H](c1[nH]c(=O)c2sc(-c3cn[nH]c3)c3c2c1CCCO3)N1CCC1] | (S)-5-(1-(azetidin-1-yl)ethyl)-1-(1H-pyrazol-4-yl)-4,6,7,8-tetrahydro-3H-9-oxa-2-thia-4-azabenzo[cd]azulen-3-one |
| 31. | 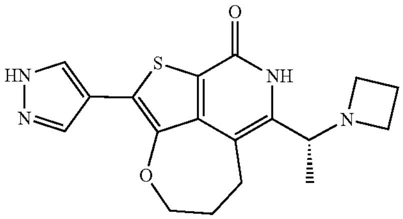 [SMILES: C[C@H](c1[nH]c(=O)c2sc(-c3cn[nH]c3)c3c2c1CCCO3)N1CCC1] | (R)-5-(1-(azetidin-1-yl)ethyl)-1-(1H-pyrazol-4-yl)-4,6,7,8-tetrahydro-3H-9-oxa-2-thia-4-azabenzo[cd]azulen-3-one |
| 32. | 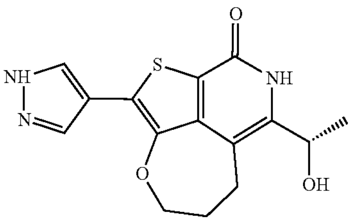 [SMILES: C[C@H](O)c1[nH]c(=O)c2sc(-c3cn[nH]c3)c3c2c1CCCO3] | (S)-5-(1-hydroxyethyl)-1-(1H-pyrazol-4-yl)-4,6,7,8-tetrahydro-3H-9-oxa-2-thia-4-azabenzo[cd]azulen-3-one |
| 33. | 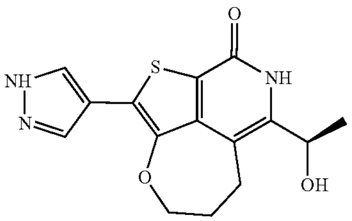 [SMILES: C[C@@H](O)c1[nH]c(=O)c2sc(-c3cn[nH]c3)c3c2c1CCCO3] | (R)-5-(1-hydroxyethyl)-1-(1H-pyrazol-4-yl)-4,6,7,8-tetrahydro-3H-9-oxa-2-thia-4-azabenzo[cd]azulen-3-one |
| 34. | 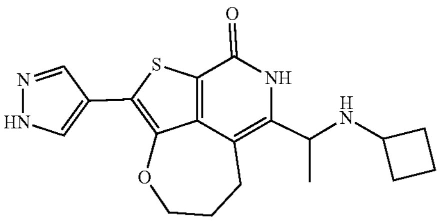 [SMILES: CC(NC1CCC1)c1[nH]c(=O)c2sc(-c3cn[nH]c3)c3c2c1CCCO3] | 5-(1-(cyclobutylamino)ethyl)-1-(1H-pyrazol-4-yl)-4,6,7,8-tetrahydro-3H-9-oxa-2-thia-4-azabenzo[cd]azulen-3-one |

TABLE 1-continued

| Cmpd No. | Structure | Name |
|---|---|---|
| 35. | 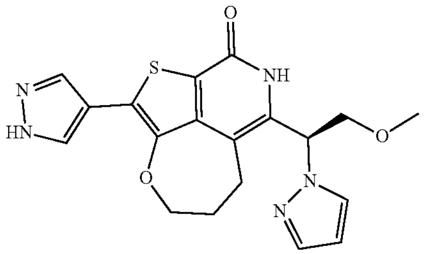 [SMILES: COC[C@H](c1[nH]c(=O)c2sc(-c3cn[nH]c3)c3c2c1CCCO3)n1cccn1] | (S)-5-(2-methoxy-1-(1H-pyrazol-1-yl)ethyl)-1-(1H-pyrazol-4-yl)-4,67,8-tetrahydro-3H-9-oxa-2-thia-4-azabenzo[cd]azulen-3-one |
| 36. | 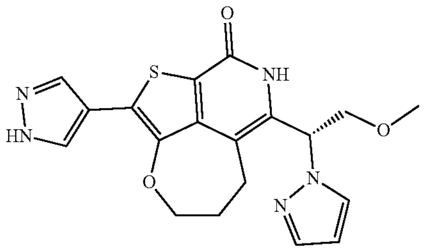 [SMILES: COC[C@@H](c1[nH]c(=O)c2sc(-c3cn[nH]c3)c3c2c1CCCO3)n1cccn1] | (R)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one |
| 37. | 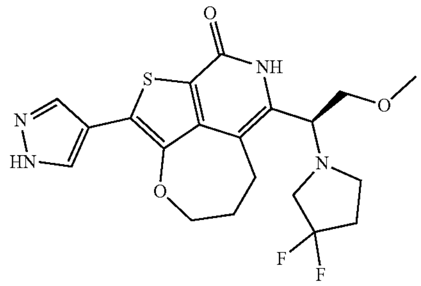 [SMILES: COC[C@H](c1[nH]c(=O)c2sc(-c3cn[nH]c3)c3c2c1CCCO3)N1CCC(F)(F)C1] | (S)-5-(1-(3,3-difluoropyrrolidin-1-yl)-2-methoxyethyl)-1-(1H-pyrazol-4-yl)-4,6,7,8-tetrahydro-3H-9-oxa-2-thia-4-azabenzo[cd]azulen-3-one |
| 38. | 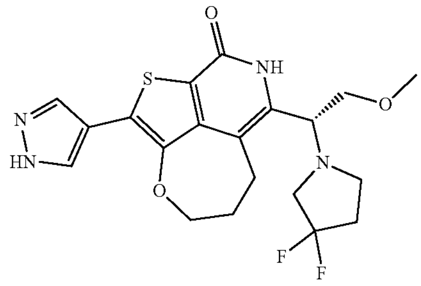 [SMILES: COC[C@@H](c1[nH]c(=O)c2sc(-c3cn[nH]c3)c3c2c1CCCO3)N1CCC(F)(F)C1] | (R)-5-(1-(3,3-difluoropyrrolidin-1-yl)-2-methoxyethyl)-1-(1H-pyrazol-4-yl)-4,6,7,8-tetrahydro-3H-9-oxa-2-thia-4-azabenzo[cd]azulen-3-one |
| 39. | 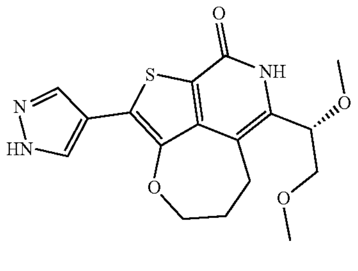 [SMILES: COC[C@@H](OC)c1[nH]c(=O)c2sc(-c3cn[nH]c3)c3c2c1CCCO3] | (S)-5-(1,2-dimethoxyethyl)-1-(1H-pyrazol-4-yl)-4,6,7,8-tetrahydro-3H-9-oxa-2-thia-4-azabenzo[cd]azulen-3-one |

TABLE 1-continued

| Cmpd No. | Structure | Name |
|---|---|---|
| 40. | 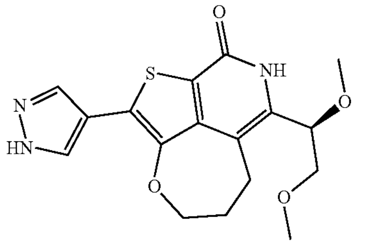 [SMILES: COC[C@H](OC)c1[nH]c(=O)c2sc(-c3cn[nH]c3)c3c2c1CCCO3] | (S)-5-(1,2-dimethoxyethyl)-1-(1H-pyrazol-4-yl)-4,6,7,8-tetrahydro-3H-9-oxa-2-thia-4-azabenzo[cd]azulen-3-one |
| 41. | 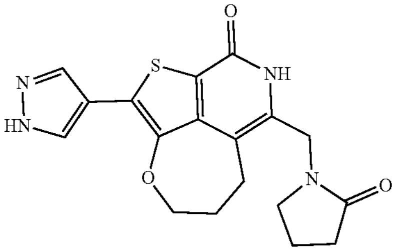 [SMILES: O=C1CCCN1Cc1[nH]c(=O)c2sc(-c3cn[nH]c3)c3c2c1CCCO3] | 5-((2-oxopyrrolidin-1-yl)methyl)-1-(1H-pyrazol-4-yl)-4,6,7,8-tetrahydro-3H-9-oxa-2-thia-4-azabenzo[cd]azulen-3-one |
| 42. | 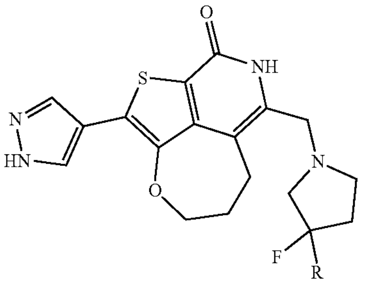 | 5-((3,3-difluoropyrrolidin-1-yl)methyl)-1-(1H-pyrazol-4-yl)-4,6,7,8-tetrahydro-3H-9-oxa-2-thia-4-azabenzo[cd]azulen-3-one |
| 43. | 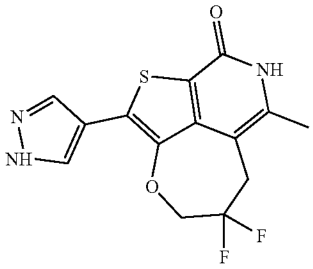 [SMILES: Cc1[nH]c(=O)c2sc(-c3cn[nH]c3)c3c2c1CC(F)(F)CO3] | 10,10-difluoro-7-methyl-2-(1H-pyrazol-4-yl)-12-oxa-3-thia-6-azatricyclo[6.4.1.$0^{4,13}$]trideca-1,4(13),7-trien-5-one |
| 44. | 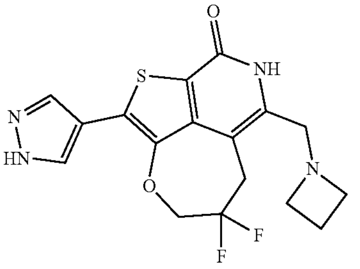 [SMILES: O=c1[nH]c(CN2CCC2)c2c3c(c(-c4cn[nH]c4)sc13)OCC(F)(F)C2] | 7-(azetidin-1-ylmethyl)-10,10-difluoro-2-(1H-pyrazol-4-yl)-12-oxa-3-thia-6-azatricyclo [6.4.1.$0^{4,13}$]trideca-1,4(13),7-trien-5-one |

TABLE 1-continued

| Cmpd No. | Structure | Name |
|---|---|---|
| 45. | 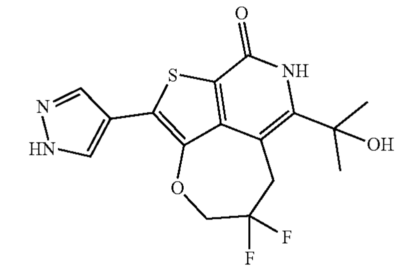 [SMILES: CC(C)(O)c1[nH]c(=O)c2sc(-c3cn[nH]c3)c3c2c1CC(F)(F)CO3] | 10,10-difluoro-7-(1-hydroxy-1-methyl-ethyl)-2-(1H-pyrazol-4-yl)-12-oxa-3-thia-6-aza tricyclo [6.4.1.$0^{4,13}$]trideca-1,4(13),7-trien-5-one |
| 46. | 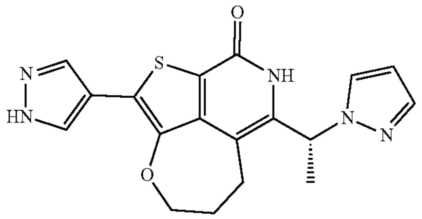 [SMILES: C[C@H](c1[nH]c(=O)c2sc(-c3cn[nH]c3)c3c2c1CCCO3)n1cccn1] | (R)-2-(1H-pyrazol-4-yl)-7-(1-pyrazol-1-ylethyl)-12-oxa-3-thia-6-azatricyclo[6.4.1.04,13]trideca-1,4(13),7-trien-5-one |
| 47. | 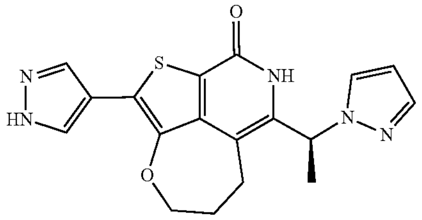 [SMILES: C[C@@H](c1[nH]c(=O)c2sc(-c3cn[nH]c3)c3c2c1CCCO3)n1cccn1] | (S)-2-(1H-pyrazol-4-yl)-7-(1-pyrazol-1-ylethyl)-12-oxa-3-thia-6-azatricyclo[6.4.1.$0^{4,13}$]trideca-1,4(13),7-trien-5-one |
| 48. | 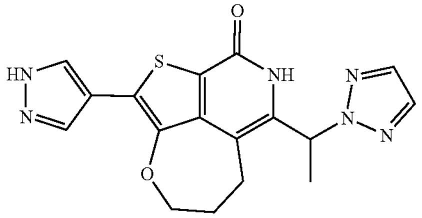 [SMILES: CC(c1[nH]c(=O)c2sc(-c3cn[nH]c3)c3c2c1CCCO3)n1nccn1] | 2-(1H-pyrazol-4-yl)-7-[1-(triazol-2-yl)ethyl]-12-oxa-3-thia-6-azatricyclo[6.4.1.$0^{4,13}$]trideca-1,4(13),7-trien-5-one |
| 49. | 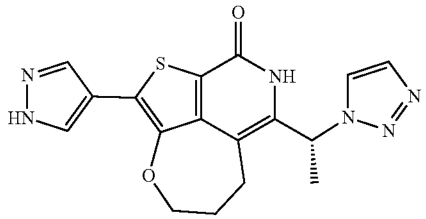 [SMILES: C[C@H](c1[nH]c(=O)c2sc(-c3cn[nH]c3)c3c2c1CCCO3)n1ccnn1] | (R)-5-(-(1H-1,2,3-triazol-1-yl)ethyl)-1-(1H-pyrazol-4-yl)-4,6,7,8-tetrahydro-3H-9-oxa-2-thia-4-azabenzo[cd]azulen-3-one |
| 50. | 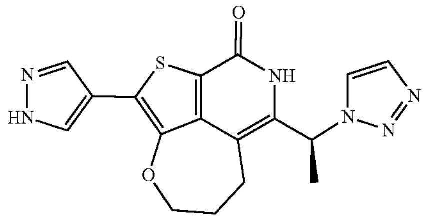 [SMILES: C[C@@H](c1[nH]c(=O)c2sc(-c3cn[nH]c3)c3c2c1CCCO3)n1ccnn1] | (S)-5-(1-(1H-1,2,3-triazol-1-yl)ethyl)-1-(1H-pyrazol-4-yl)-4,6,7,8-tetrahydro-3H-9-oxa-2-thia-4-azabenzo[cd]azulen-3-one |

TABLE 1-continued

| Cmpd No. | Structure | Name |
|---|---|---|
| 51. | 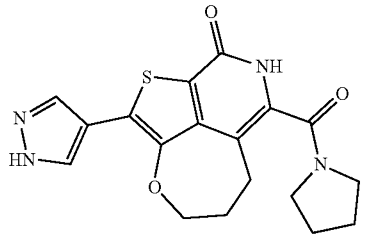 [SMILES: O=C(c1[nH]c(=O)c2sc(-c3cn[nH]c3)c3c2c1CCCO3)N1CCCC1] | 2-(1H-pyrazol-4-yl)-7-(pyrrolidine-1-carbonyl)-12-oxa-3-thia-6-azatricyclo[6.4.1.0$^{4,13}$]-trideca-1,4(13),7-trien-5-one |
| 52. | 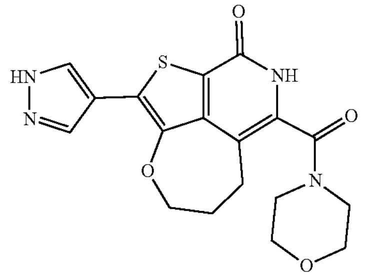 [SMILES: O=C(c1[nH]c(=O)c2sc(-c3cn[nH]c3)c3c2c1CCCO3)N1CCOCC1] | 7-(morpholine-4-carbonyl)-2-(1H-pyrazol-4-yl)-12-oxa-3-thia-6-azatricyclo[6.4.1.0$^{4,13}$]-trideca-1,4(13),7-trien-5-one |
| 53. | 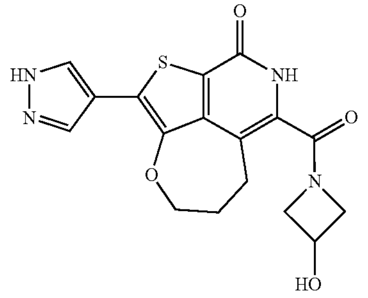 | 5-(3-hydroxyazetidine-1-carbonyl)-1-(1H-pyrazol-4-yl)-4,6,7,8-tetrahydro-3H-9-oxa-2-thia-4-azabenzo[cd]azulen-3-one |
| 54. | 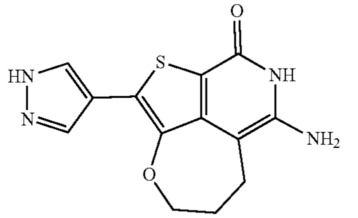 [SMILES: Nc1[nH]c(=O)c2sc(-c3cn[nH]c3)c3c2c1CCCO3] | 7-amino-2-(1H-pyrazol-4-yl)-12-oxa-3-thia-6-azatricyclo[6.4.1.0$^{4,13}$]trideca-1,4(13),7-trien-5-one |
| 55. | 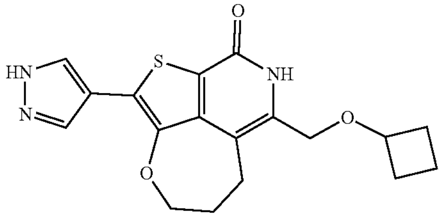 [SMILES: O=c1[nH]c(COC2CCC2)c2c3c(c(-c4cn[nH]c4)sc13)OCCC2] | 5-(cyclobutoxymethyl)-1-(1H-pyrazol-4-yl)-4,6,7,8-tetrahydro-3H-9-oxa-2-thia-4-azaben-zo[cd]azulen-3-one |
| 56. | 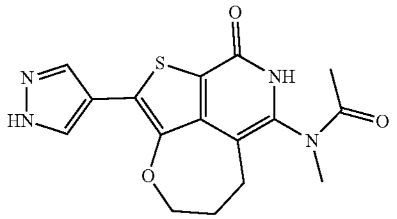 [SMILES: CC(=O)N(C)c1[nH]c(=O)c2sc(-c3cn[nH]c3)c3c2c1CCCO3] | N-methyl-N-(3-oxo-1-(1H-pyrazol-4-yl)-4,6,7,8-tetrahydro-3H-9-oxa-2-thia-4-azabenzo[cd]azulen-5-yl)acetamide |

TABLE 1-continued

| Cmpd No. | Structure | Name |
|---|---|---|
| 57. | 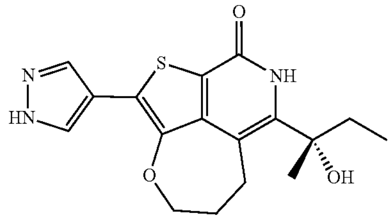 [SMILES: CC[C@](C)(O)c1[nH]c(=O)c2sc(-c3cn[nH]c3)c3c2c1CCCO3] | (S)-5-(2-hydroxybutan-2-yl)-1-(1H-pyrazol-4-yl)-4,6,7,8-tetrahydro-3H-9-oxa-2-thia-4-azabenzo[cd]azulen-3-one |
| 58. | 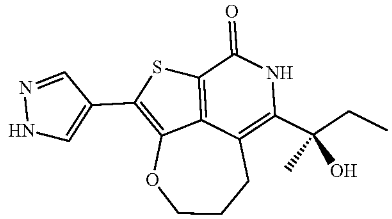 [SMILES: CC[C@@](C)(O)c1[nH]c(=O)c2sc(-c3cn[nH]c3)c3c2c1CCCO3] | (R)-5-(2-hydroxybutan-2-yl)-1-(1H-pyrazol-4-yl)-4,6,7,8-tetrahydro-3H-9-oxa-2-thia-4-azabenzo[cd]azulen-3-one |
| 59. | 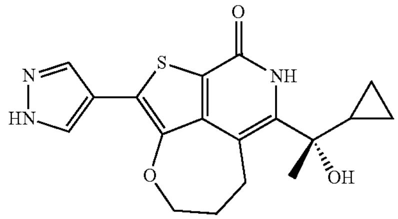 [SMILES: C[C@@](O)(c1[nH]c(=O)c2sc(-c3cn[nH]c3)c3c2c1CCCO3)C1CC1] | (S)-5-(1-cyclopropyl-1-hydroxyethyl)-1-(1H-pyrazol-4-yl)-4,6,7,8-tetrahydro-3H-9-oxa-2-thia-4-azabenzo[cd]azulen-3-one |
| 60. | 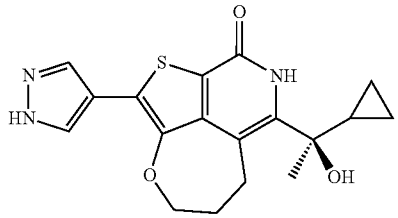 [SMILES: C[C@](O)(c1[nH]c(=O)c2sc(-c3cn[nH]c3)c3c2c1CCCO3)C1CC1] | (R)-5-(1-cyclopropyl-1-hydroxyethyl)-1-(1H-pyrazol-4-yl)-4,6,7,8-tetrahydro-3H-9-oxa-2-thia-4-azabenzo[cd]azulen-3-one |
| 61. | 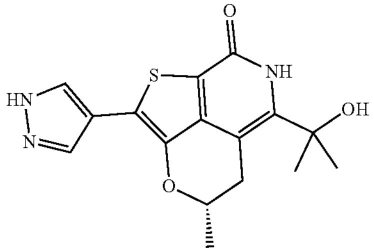 [SMILES: C[C@H]1Cc2c(C(C)(C)O)[nH]c(=O)c3sc(-c4cn[nH]c4)c(c23)O1] | (S)-6-(2-hydroxypropan-2-yl)-4-methyl-2-(1H-pyrazol-4-yl)-5,7-dihydro-3-oxa-1-thia-7-azaacenaphthylen-8(4H)-one |
| 62. | 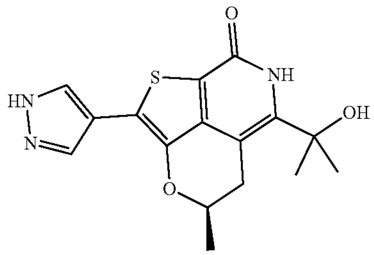 [SMILES: C[C@@H]1Cc2c(C(C)(C)O)[nH]c(=O)c3sc(-c4cn[nH]c4)c(c23)O1] | (R)-6-(2-hydroxypropan-2-yl)-4-methyl-2-(1H-pyrazol-4-yl)-5,7-dihydro-3-oxa-1-thia-7-azaacenaphthylen-8(4H)-one |

TABLE 1-continued

| Cmpd No. | Structure | Name |
|---|---|---|
| 63. | 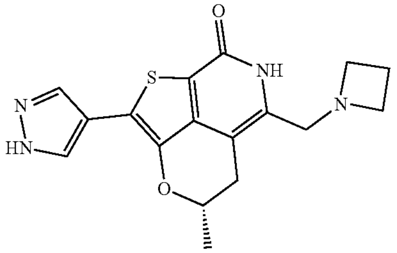 [SMILES: C[C@H]1Cc2c(CN3CCC3)[nH]c(=O)c3sc(-c4cn[nH]c4)c(c23)O1] | (S)-6-(azetidin-1-ylmethyl)-4-methyl-2-(1H-pyrazol-4-yl)-5,7-dihydro-3-oxa-1-thia-7-azaacenaphthylen-8(4H)-one |
| 64. | 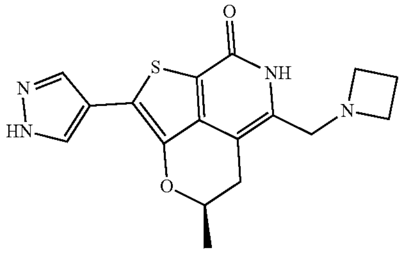 [SMILES: C[C@@H]1Cc2c(CN3CCC3)[nH]c(=O)c3sc(-c4cn[nH]c4)c(c23)O1] | (R)-6-(azetidin-1-ylmethyl)-4-methyl-2-(1H-pyrazol-4-yl)-5,7-dihydro-3-oxa-1-thia-7-azaacenaphthylen-8(4H)-one |
| 65. | 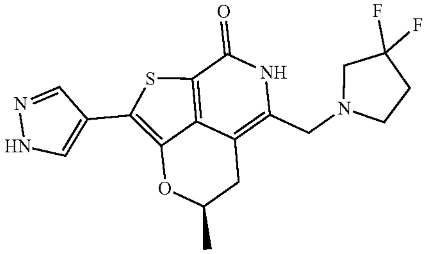 [SMILES: C[C@@H]1Cc2c(CN3CCC(F)(F)C3)[nH]c(=O)c3sc(-c4cn[nH]c4)c(c23)O1] | (R)-6-((3,3-difluoropyrrolidin-1-yl)methyl)-4-methyl-2-(1H-pyrazol-4-yl)-5,7-dihydro-3-oxa-1-thia-7-azaacenaphthylen-8(4H)-one |
| 66. | 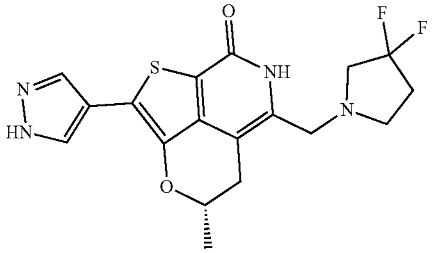 [SMILES: C[C@H]1Cc2c(CN3CCC(F)(F)C3)[nH]c(=O)c3sc(-c4cn[nH]c4)c(c23)O1] | (S)-6-((3,3-difluoropyrrolidin-1-yl)methyl)-4-methyl-2-(1H-pyrazol-4-yl)-5,7-dihydro-3-oxa-1-thia-7-azaacenaphthylen-8(4H)-one |
| 67. | 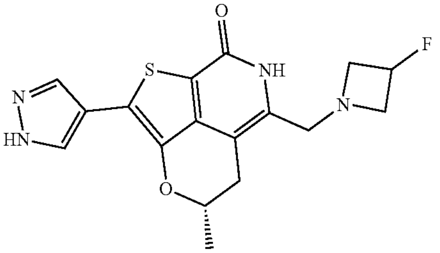 [SMILES: C[C@H]1Cc2c(CN3CC(F)C3)[nH]c(=O)c3sc(-c4cn[nH]c4)c(c23)O1] | (R)-6-((3-fluoroazetidin-1-yl)methyl)-4-methyl-2-(1H-pyrazol-4-yl)-5,7-dihydro-3-oxa-1-thia-7-azaacenaphthylen-8(4H)-one |
| 68. | 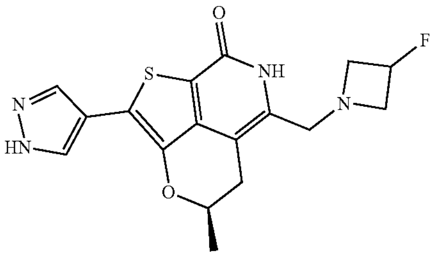 [SMILES: C[C@@H]1Cc2c(CN3CC(F)C3)[nH]c(=O)c3sc(-c4cn[nH]c4)c(c23)O1] | (S)-6-((3-fluroazetidin-1-yl)methyl)-4-methyl-2-(1H-pyrazol-4-yl)-5,7-dihydro-3-oxa-1-thia-7-azaacenaphthylen-8(4H)-one |

TABLE 1-continued

| Cmpd No. | Structure | Name |
|---|---|---|
| 69. | 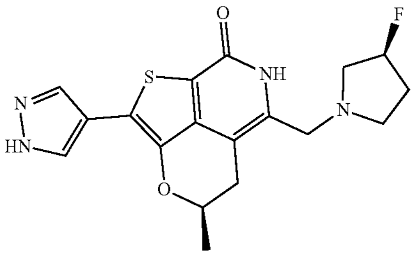 [SMILES: C[C@@H]1Cc2c(CN3CC[C@H](F)C3)[nH]c(=O)c3sc(-c4cn[nH]c4)c(c23)O1] | (S)-6-(((S)-3-fluoropyrrolidin-1-yl)methyl)-4-methyl-2-(1H-pyrazol-4-yl)-5,7-dihydro-3-oxa-1-thia-7-azaacenaphthylen-8(4H)-one |
| 70. | 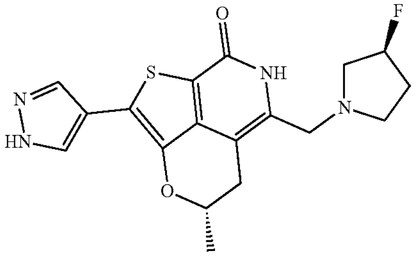 [SMILES: C[C@H]1Cc2c(CN3CC[C@H](F)C3)[nH]c(=O)c3sc(-c4cn[nH]c4)c(c23)O1] | (R)-6-(((S)-3-fluoropyrrolidin-1-yl)methyl)-4-methyl-2-(1H-pyrazol-4-yl)-5,7-dihydro-3-oxa-1-thia-7-azaacenaphthylen-8(4H)-one |
| 71. | 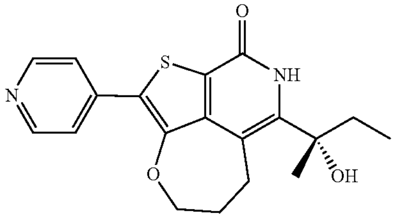 [SMILES: CC[C@](C)(O)c1[nH]c(=O)c2sc(-c3ccncc3)c3c2c1CCCO3] | (S)-5-(2-hydroxybutan-2-yl)-1-(pyridin-4-yl)-4,6,7,8-tetrahydro-3H-9-oxa-2-thia-4-azabenzo[cd]azulen-3-one |
| 72. | 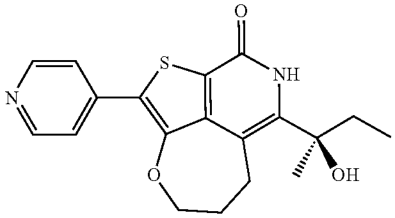 [SMILES: CC[C@@](C)(O)c1[nH]c(=O)c2sc(-c3ccncc3)c3c2c1CCCO3] | (R)-5-(2-hydroxybutan-2-yl)-1-(pyridin-4-yl)-4,6,7,8-tetrahydro-3H-9-oxa-2-thia-4-azabenzo[cd]azulen-3-one |
| 73. | 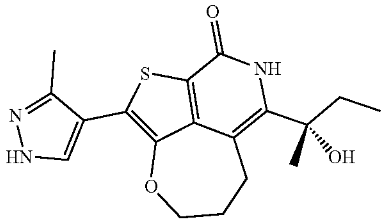 [SMILES: CC[C@](C)(O)c1[nH]c(=O)c2sc(-c3c[nH]nc3C)c3c2c1CCCO3] | (S)-5-(2-hydroxybutan-2-yl)-1-(3-methyl-1H-pyrazol-4-yl)-4,6,7,8-tetrahydro-3H-9-oxa-2-thia-4-azabenzo[cd]azulen-3-one |
| 74. | 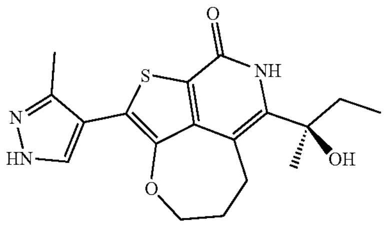 [SMILES: CC[C@@](C)(O)c1[nH]c(=O)c2sc(-c3c[nH]nc3C)c3c2c1CCCO3] | (R)-5-(2-hydroxybutan-2-yl)-1-(3-methyl-1H-pyrazol-4-yl)-4,6,7,8-tetrahydro-3H-9-oxa-2-thia-4-azabenzo[cd]azulen-3-one |

TABLE 1-continued

| Cmpd No. | Structure | Name |
| --- | --- | --- |
| 75. | 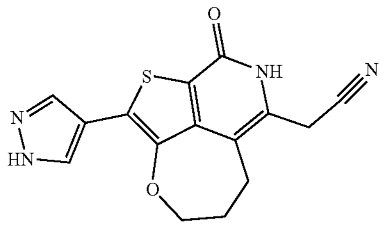 [SMILES: N#CCc1[nH]c(=O)c2sc(-c3cn[nH]c3)c3c2c1CCCO3] | 2-(3-oxo-1-(1H-pyrazol-4-yl)-4,6,7,8-tetrahydro-3H-9-oxa-2-thia-4-azabenzo[cd]azulen-5-yl)acetonitrile |
| 76. | 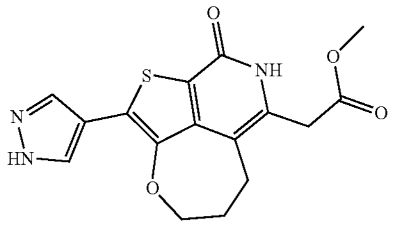 [SMILES: COC(=O)Cc1[nH]c(=O)c2sc(-c3cn[nH]c3)c3c2c1CCCO3] | methyl 2-(3-oxo-1-(1H-pyrazol-4-yl)-4,6,7,8-tetrahydro-3H-9-oxa-2-thia-4-azabenzo[cd]azulen-5-yl)acetate |
| 77. | 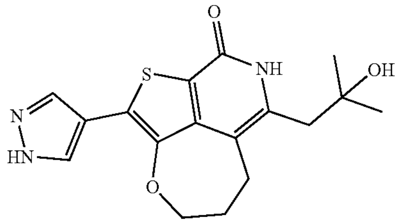 [SMILES: CC(C)(O)Cc1[nH]c(=O)c2sc(-c3cn[nH]c3)c3c2c1CCCO3] | 5-(2-hydroxy-2-methylpropyl)-1-(1H-pyrazol-4-yl)-4,6,7,8-tetrahydro-3H-9-oxa-2-thia-4-azabenzo[cd]azulen-3-one |
| 78. | 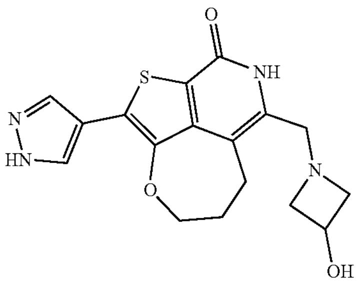 [SMILES: O=c1[nH]c(CN2CC(O)C2)c2c3c(c(-c4cn[nH]c4)sc13)OCCC2] | 7-[(3-hydroxyazetidin-1-yl)methyl]-2-(1H-pyrazol-4-yl)-12-oxa-3-thia-6-azatricyclo [6.4.1.$0^{4,13}$]trideca-1,4(13),7-trien-5-one |
| 79. | 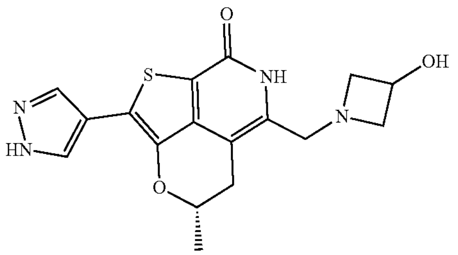 [SMILES: C[C@H]1Cc2c(CN3CC(O)C3)[nH]c(=O)c3sc(-c4cn[nH]c4)c(c23)O1] | (S)-6-((3-hydroxyazetidin-1-yl)methyl)-4-methyl-2-(1H-pyrazol-4-yl)-5,7-dihydro-3-oxa-1-thia-7-azaacenaphthylen-8(4H)-one |
| 80. | 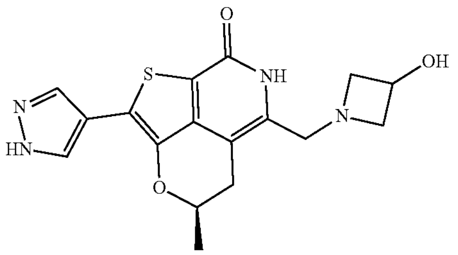 [SMILES: C[C@@H]1Cc2c(CN3CC(O)C3)[nH]c(=O)c3sc(-c4cn[nH]c4)c(c23)O1] | (R)-6-((3-hydroxyazetidin-1-yl)methyl)-4-methyl-2-(1H-pyrazol-4-yl)-5,7-dihydro-3-oxa-1-thia-7-azaacenaphthylen-8(4H)-one |

TABLE 1-continued

| Cmpd No. | Structure | Name |
|---|---|---|
| 81. | 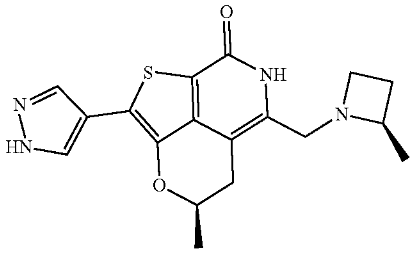 [SMILES: C[C@@H]1Cc2c(CN3CC[C@H]3C)[nH]c(=O)c3sc(-c4cn[nH]c4)c(c23)O1] | (R)-4-methyl-6-(((R)-2-methylazetidin-1-yl)methyl)-2-(1H-pyrazol-4-yl)-5,7-dihydro-3-oxa-1-thia-7-azaacenaphthylen-8(4H)-one |
| 82. | 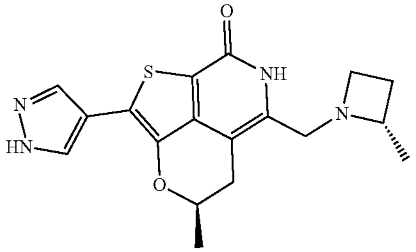 [SMILES: C[C@@H]1Cc2c(CN3CC[C@@H]3C)[nH]c(=O)c3sc(-c4cn[nH]c4)c(c23)O1] | (R)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one |
| 83. | 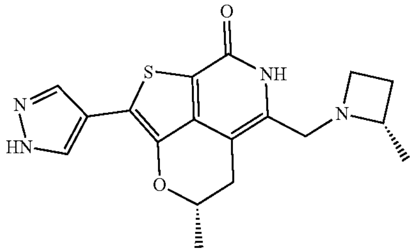 [SMILES: C[C@H]1Cc2c(CN3CC[C@@H]3C)[nH]c(=O)c3sc(-c4cn[nH]c4)c(c23)O1] | (S)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one |
| 84. | 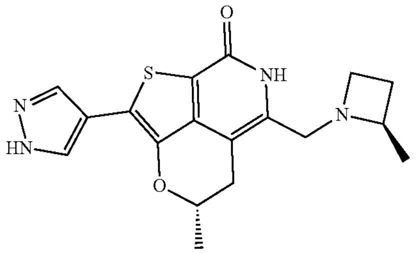 [SMILES: C[C@@H]1CCN1Cc1[nH]c(=O)c2sc(-c3cn[nH]c3)c3c2c1C[C@H](C)O3] | (S)-4-methyl-6-(((R)-2-methylazetidin-1-yl)methyl)-2-(1H-pyrazol-4-yl)-5,7-dihydro-3-oxa-1-thia-7-azaacenaphthylen-8(4H)-one |
| 85. | 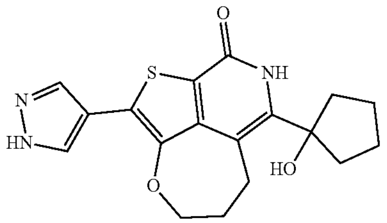 [SMILES: O=c1[nH]c(C2(O)CCCC2)c2c3c(c(-c4cn[nH]c4)sc13)OCCC2] | 5-(1-hydroxycyclopentyl)-1-(1H-pyrazol-4-yl)-4,6,7,8-tetrahydro-3H-9-oxa-2-thia-4-azabenzo[cd]azulen-3-one |

Processes of Preparation

For illustrative purposes, general methods for preparing the compounds are provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Provided herein is a method of making a compound of Formula (I), comprising forming the pyridone ring by reacting a Formula (I) precursor comprising a moiety of Formula (I-iA):

(I-iA)

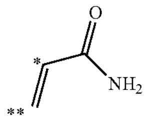

wherein the carbon atom closest to * and the carbon atom closest to ** are each ring members of the Formula (I) thiophene; and the carbon atom closest to * is bonded to the sulfur ring member of the Formula (I) thiophene;

with a compound of Formula (int-1)

(int-1)

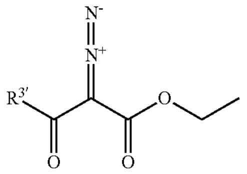

wherein R is an unsubstituted C1-C6 alkyl;

to form a Formula (I) precursor comprising a moiety of Formula (I-iA')

(I-iA')

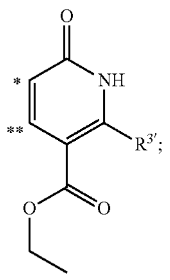

and reacting the moiety of Formula (I-iA') in the precursor comprising the moiety of Formula (I-iA') to form the

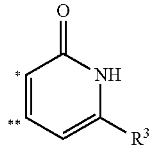

moiety of the compound of Formula (I).

In some embodiments, reacting the Formula (I) first precursor comprising the moiety of Formula (I-iA) is performed in the presence of a catalyst. In some embodiments, the catalyst is a rhodium catalyst. In some embodiments, the catalyst is a rhodium (II) catalyst. In some embodiments, the rhodium catalyst is selected from $Rh_2(OAc)_4$, $Rh_2(Oct)_4$, and $(C_5(CH_3)_5RhCl)_2Cl_2$. In some embodiments, the rhodium catalyst is $(C_5(CH_3)_5RhCl)_2Cl_2$. In some embodiments, reacting the Formula (I) first precursor comprising the moiety of Formula (I-iA) is performed in the presence of a base. In some embodiments, the base is an acetate base. In some embodiments, the base is cesium acetate.

In some embodiments, reacting the moiety of Formula (I-iA') in the precursor comprising the moiety of Formula (I-iA') to form the

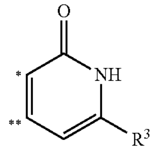

moiety of the compound of Formula (I) comprises one or more chemical transformations that convert $R^{3'}$ to $R^3$ (e.g., 1, 2, 3, 4, 5, 6, 7, or 8 chemical transformations). For example, bromination of a methyl group with subsequent displacement of the bromine with a nucleophile such as an amine.

Also provided herein is a method of making a compound of Formula (I), comprising forming the pyridone ring by reacting a Formula (I) precursor comprising a moiety of Formula (I-iB):

(I-iB)

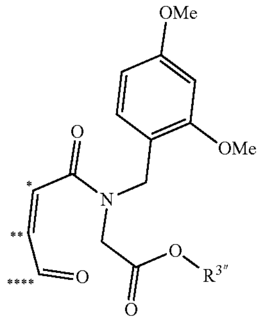

wherein $R^{3''}$ is an unsubstituted C1-C6 alkyl;

the carbon atom closest to * and the carbon atom closest to ** are each ring members of the Formula (I) thiophene, the carbon atom closest to * is bonded to the sulfur ring member of the Formula (I) thiophene, and the carbon atom closest to **** is a ring member of the pyridone ring in the compound of Formula (I);

in the presence of a base to form a Formula (I) precursor comprising a moiety of Formula (I-iB')

(I-iB')

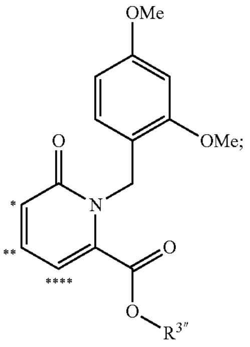

and reacting the moiety of Formula (I-iB') in the precursor comprising the moiety of Formula (I-iB') to form the

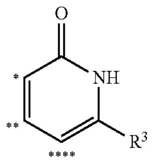

moiety of the compound of Formula (I).

In some embodiments, the base is a hydride base. In some embodiments, the base is sodium hydride or potassium hydride. In some embodiments, the base is sodium hydride.

In some embodiments, reacting the Formula (I) precursor comprising the moiety of Formula (I-iB') to form the

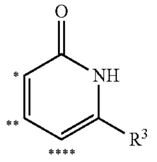

moiety of the compound of Formula (I) comprises removing the 2,4-dimethoxybenzyl group from the ring nitrogen of the moiety of Formula (I-iB'), then converting $R^{3''}$ to $R^3$. In some embodiments, reacting the Formula (I) precursor comprising the moiety of Formula (I-iB') to form the

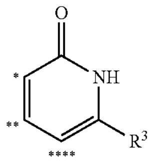

moiety of the compound of Formula (I) comprises converting $R^{3''}$ to $R^3$, then removing the 2,4-dimethoxybenzyl group from the ring nitrogen. In some embodiments, converting $R^{3''}$ to $R^3$ comprises one or more chemical transformations (e.g., 1, 2, 3, 4, 5, 6, 7, or 8 chemical transformations). In some embodiments (when converting $R^{3''}$ to $R^3$ comprises two or more chemical transformations), reacting the moiety of Formula (I-iB') to form the

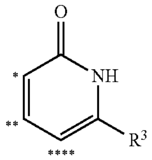

moiety of the compound of Formula (I) comprises (i) performing at least one but less than all of the two or more chemical transformations required to convert $R^{3''}$ to $R^3$, (ii) removing the 2,4-dimethoxybenzyl group from the ring nitrogen, then (iii) performing the remaining chemical transformations required to convert $R^{3''}$ to $R^3$.

In some embodiments of the methods of making the compound of Formula (I), the compound of Formula (I) is a compound of Formula (I')

(I')

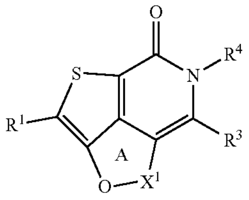

wherein $R^1$, $R^2$, $R^3$, and $R^4$ are as defined herein;

$X^1$ is (i) methylene optionally substituted with 0, 1, or 2 $R^2$; or (ii) C2-C3 alkylene optionally substituted with m $R^2$, and wherein all carbon atoms of the C2-C3 alkylene are ring members of Ring A; and the method further comprises reacting a precursor comprising a moiety of Formula (I-iiA):

(I-iiA)

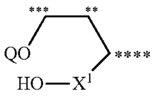

wherein the carbon atom closest to ** is the ring member of the thiophene that is (i) not directly bonded to the sulfur ring member of the thiophene and (ii) is also a ring member of the pyridone ring in the compound of Formula (I');

the carbon atom closest to *** is the ring member of the thiophene that is (i) not directly bonded to the sulfur ring member of the thiophene and (ii) is not a ring member of the pyridone ring in the compound of Formula (I');

the carbon atom closest to **** is a ring member of the pyridone ring in the compound of Formula (I');

Q is H or methyl;

$X^1$ is (i) methylene optionally substituted with 0, 1, or 2 $R^2$; or (ii) C2-C3 alkylene optionally substituted with m $R^2$, and wherein all carbon atoms of the C2-C3 alkylene are ring members of Ring A;

with an acid to form the

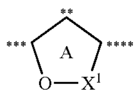

moiety of the compound of Formula (I').

In some embodiments, Q is hydrogen. In some embodiments, Q is methyl.

In some embodiments, the acid is selected from HCl and HBr. In some embodiments, the acid is aqueous. In some of these embodiments, Q is methyl. In some embodiments, the acid is aqueous HCl. In some embodiments, the acid is aqueous HBr. In some embodiments, the acid is about 48% aqueous HBr.

In some embodiments, the acid is trimethylsilyl triflate. In some of these embodiments, Q is hydrogen.

In some embodiments, $X^1$ is propylene and m is 0. In some embodiments, $X^1$ is ethylene, m is 1, and $R^2$ is methyl.

In some embodiments of the methods of making the compound of Formula (I), the compound of Formula (I) is a compound of Formula (I")

(I")

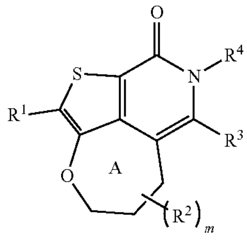

wherein $R^1$, $R^2$, $R^3$, $R^4$, and m are as defined herein;

and the method further comprises reacting a precursor comprising a moiety of Formula (I-iiB):

(I-iiB)

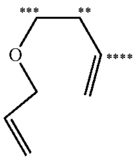

wherein the carbon atom closest to ** is the ring member of the thiophene that is (i) not directly bonded to the sulfur ring member of the thiophene and (ii) is also a ring member of the pyridone ring in the compound of Formula (I");

the carbon atom closest to *** is the ring member of the thiophene that is (i) not directly bonded to the sulfur ring member of the thiophene and (ii) is not a ring member of the pyridone ring in the compound of Formula (I");

the carbon atom closest to **** is a ring member of the pyridone ring;

in the presence of a ruthenium catalyst to form a precursor comprising a moiety of Formula (I-iiB');

(I'-iiB')

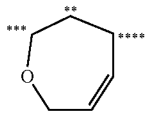

and reacting the moiety of Formula (I-iiB') of the precursor comprising the moiety of Formula (I-iiB') to form the

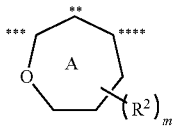

moiety of Formula (I").

In some embodiments, the ruthenium catalyst is a ruthenium carbene complex. In some embodiments, the ruthenium carbene complex is selected from benzylidene-bis (tricyclohexylphosphino)-dichlororuthenium and 1,3-bis-(2, 4,6-trimethylphenyl)-2-imidazolidinylidene]dichloro (phenylmethylene)(tricyclohexylphosphino)ruthenium, dichloro(o-isopropoxyphenylmethylene)(tricyclohexylphosphine)ruthenium(II), and [1,3-bis-(2,4,6-trimethylphenyl)-2-imidazolidinylidene]dichloro(o-isopropoxyphenylmethylene)ruthenium. In some embodiments, the ruthenium carbene complex is [1,3-bis-(2,4,6-trimethylphenyl)-2-imidazolidinylidene]dichloro(o-isopropoxyphenylmethylene)ruthenium.

In some embodiments, reacting the moiety of Formula (I-iiB') of the precursor comprising the moiety of Formula (I-iiB') to form the

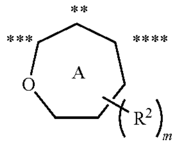

moiety of Formula (I") comprises oxidizing the Ring A double bond, reducing the Ring A double bond, or performing an addition (e.g., an addition of HBr or $Br_2$) across the Ring A double bond. In some embodiments, reacting the moiety of Formula (I-iiB') of the precursor comprising the moiety of Formula (I-iiB') to form the

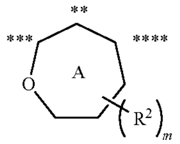

moiety of Formula (I") further comprises reacting the product of oxidation, reduction, or addition of the Ring A double bond in one or more chemical transformations to form the compound of Formula (I").

In some embodiments of Embodiment 2, the compound of Formula (I) is a compound of Formula (I'")

(I'''')

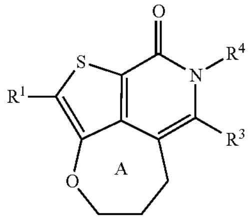

wherein $R^1$, $R^3$, and $R^4$ are as defined herein;

and the method further comprises reacting a precursor comprising a moiety of Formula (I-iiC):

(I-iiC)

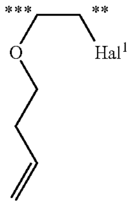

wherein the carbon atom closest to ** is the ring member of the thiophene that is (i) not directly bonded to the sulfur ring member of the thiophene and (ii) is also a ring member of the pyridone ring in the compound of Formula (I''');

the carbon atom closest to *** is the ring member of the thiophene that is (i) not directly bonded to the sulfur ring member of the thiophene and (ii) is not a ring member of the pyridone ring in the compound of Formula (I'''); and $Hal^1$ is selected from chloro, bromo, and iodo;

in the presence of a catalyst to form a precursor comprising a moiety of Formula (I-iiC')

(I-iiC')

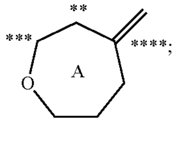

and reacting the precursor comprising the moiety of Formula (I-iiC') to form a precursor comprising a moiety of Formula (I-iiC'')

(I-iiC'')

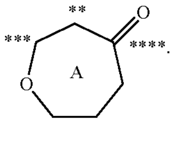

In some embodiments, the precursor comprising the moiety of Formula (I-iiC'') is the Formula (I) precursor comprising the moiety of Formula (I-iB).

In some embodiments, the catalyst is a palladium catalyst. In some embodiments, the palladium catalyst is tetrakistriphenylphosphine palladium(0).

In some embodiments, reacting the precursor comprising the moiety of Formula (I-iiC) is performed in the presence of a base. In some embodiments, the base is a carbonate base. In some embodiments, the carbonate base is sodium carbonate, potassium carbonate, or cesium carbonate. In some embodiments, the carbonate base is potassium carbonate.

In some embodiments, Hal is chloro. In some embodiments, Hal is bromo. In some embodiments, Hal is iodo.

In any of the foregoing embodiments of the methods of making the compound of Formula (I), (I'), (I''), and (I'''), the method further comprises reacting a precursor comprising a moiety of Formula (I-iiiA):

$Z^1$—***** (I-iiiA)

wherein the carbon atom adjacent to ***** in the moiety of Formula (I-iiiA) is the ring member of the Formula (I), (I'), (I''), or (I''') thiophene that is bonded to the sulfur ring member and not bonded to the carbon corresponding to the carbonyl of the pyridone ring in Formula (I), (I'), (I''), or (I''');

with a compound of formula $Z^2$—$R^1$;

wherein one of $Z^1$ and $Z^2$ is $Hal^2$ and the other of $Z^1$ and $Z^2$ is M;

$Hal^2$ is selected from the group consisting of: iodo, bromo, chloro, and trifluoromethanesulfonate;

M is selected from the group consisting of: tributylstannyl, trimethylstannyl, —$B(OH)_2$,

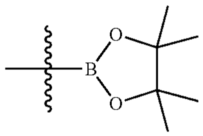

,

—MgCl, —MgBr, —MgI, —ZnCl, —ZnBr, and —ZnI; and wherein $R^1$ is as defined herein; to form the $R^1$—***** moiety of the compound of Formula (I), (I'), (I''), or (I''').

In some embodiments, $Z^1$ is $Hal^2$ and $Z^2$ is M. In some embodiments, $Z^1$ is M and $Z^2$ is $Hal^2$.

In some embodiments, the reaction of the precursor comprising the moiety of Formula (I-iiiA) with the compound of formula $Z^2$—$R^1$ is performed in the presence of a catalyst, a base or salt, and an optional ligand.

In some embodiments, the catalyst is a palladium catalyst. In some embodiments, the palladium catalyst is selected from the group consisting of: tetrakis(triphenylphosphine) palladium(0), (1,1'-bis(diphenylphosphino)ferrocene)palladium(II) dichloride, (1,1'-bis(diphenylphosphino)ferrocene) palladium(II) dichloride-dichloromethane complex, palladium (II) acetate, and tris(dibenzylideneacetone)dipalladium(0). In some embodiments, the palladium catalyst is (1,1'-bis(diphenylphosphino)ferrocene)palladium(II) dichloride or (1,1'-bis(diphenylphosphino)ferrocene)palladium(II) dichloride-dichloromethane complex. In some embodiments, the palladium catalyst is (1,1'-bis(diphenylphosphino)ferrocene)palladium(II) dichloride.

In some embodiments, the ligand is selected from the group consisting of: tricyclohexylphosphine, 2-dicyclohexylphosphino-2',4',6'-triisopropylbiphenyl, tri-t-butylphosphine, triisopropylbiphenyl (t-Bu X-Phos), dicyclohexyl-[2-(2,4,6-triisopropylphenyl)phenyl]phosphane, and rac-2-(Ditert-butylphosphino)-1,1'-binaphthyl. For example, the ligand is 2-dicyclohexylphosphino-2',4',6'-triisopropylbiphenyl.

In some embodiments, the salt or base is selected from the group consisting of copper (I) iodide, cesium carbonate, sodium carbonate, potassium carbonate, sodium hydrogen carbonate, and cesium fluoride. For example, the salt or base is sodium carbonate.

In some embodiments, the reaction of the precursor comprising the moiety of Formula (I-iiiA) with the compound of formula $Z^2$—$R^1$ is performed at a temperature of about 40° C. to about 130° C. For example, the reaction of the precursor comprising the moiety of Formula (I-iiiA) with the compound of formula $Z^2$—$R^1$ is performed at a temperature of about 50° C. to about 130° C., about 60° C. to about 130° C., 70° C. to about 130° C., about 80° C. to about 130° C., 90° C. to about 130° C., about 100° C. to about 130° C., about 110° C. to about 130° C., about 120° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 60° C. to about 120° C., about 70° C. to about 110° C., about 80° C. to about 100° C., about 50° C., about 60° C., about 70° C., about 80° C., about 90° C., about 100° C., about 120° C., and about 130° C.

In some embodiments, when any moiety of a precursor that is reacted comprises one or more N—H and/or O—H bonds, at least one hydrogen of the one or more N—H and/or O—H bonds is optionally replaced with a protecting group (e.g., tert-butoxycarbonyl).

It is understood that in any of the embodiments herein, no particular order of steps is implied or excluded unless otherwise stated or unless a particular sequence of steps is chemically infeasible. Further, unless otherwise stated or unless chemically infeasible, any precursor can serve as an intermediate in the formation of any other precursor.

In a non-limiting exemplary embodiment, the precursor comprising the moiety of Formula (I-iA) is a precursor to the precursor comprising the moiety of Formula (I-iA'); which can be a precursor to the precursor comprising the moiety of Formula (I-iiA); which can be a precursor to the precursor comprising the moiety of Formula (I-iiiA). In another non-limiting example, the precursor comprising the moiety of Formula (I-iiA) can be a precursor to the precursor comprising the moiety of Formula (I-iA), which is a precursor to the precursor comprising the moiety of Formula (I-iA'); which can be a precursor to the precursor comprising the moiety of Formula (I-iiiA). In another non-limiting example, the precursor comprising the moiety of Formula (I-iiiA) can be a precursor to the precursor comprising the moiety of Formula (I-iA), which is a precursor to the precursor comprising the moiety of Formula (I-iA'); which can be a precursor to the precursor comprising the moiety of Formula (I-iiA). Further precursor relationships are within the purview of one of ordinary skill in the art.

Methods of Treatment

Provided herein is a method of treating cancer (e.g., a CDC7-associated cancer) in a subject in need of such treatment, the method comprising administering to the subject a therapeutically effective amount of a compound of Formula (I) (e.g., any one of Formulas (Ia), (Ib), (Ic), and (Id)), or a pharmaceutically acceptable salt thereof or a pharmaceutical composition thereof. For example, provided herein are methods for treating a CDC7-associated cancer in a subject in need of such treatment, the method comprising a) detecting a dysregulation of a CDC7 gene, a CDC7 kinase, or the expression or activity or level of any of the same in a sample from the subject; and b) administering a therapeutically effective amount of a compound of Formula (I) (e.g., any one of Formulas (Ia), (Ib), (Ic), and (Id)), or a pharmaceutically acceptable salt thereof. In some embodiments, the dysregulation of a CDC7 gene, a CDC7 kinase, or the expression or activity or level of any of the same includes one or more fusion proteins.

In some embodiments of any of the methods or uses described herein, the cancer (e.g., CDC7-associated cancer) is a hematological cancer. In some embodiments of any of the methods or uses described herein, the cancer (e.g., CDC7-associated cancer) is a solid tumor. In some embodiments of any of the methods or uses described herein, the cancer (e.g., CDC7-associated cancer) is a lung cancer (e.g., small cell lung carcinoma or non-small cell lung carcinoma), thyroid cancer (e.g., papillary thyroid cancer, medullary thyroid cancer (e.g., sporadic medullary thyroid cancer or hereditary medullary thyroid cancer), differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., CDC7-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, CDC7 inoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and uCDC7er, unknown primary carcinoma, uCDC7hral cancer, uterine cancer, uterine sarcoma, vaginal cancer, vulvar cancer, and Wilms' tumor.

In some embodiments, a hematological cancer (e.g., hematological cancers that are CDC7-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a CDC7-associated cancer) is AML or CMML.

In some embodiments, the cancer (e.g., the CDC7-associated cancer) is a solid tumor. Examples of solid tumors (e.g., solid tumors that are CDC7-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the subject is a human.

Compounds of Formula (I) (e.g., any one of Formulas (Ia), (Ib), (Ic), and (Id)) and pharmaceutically acceptable salts and solvates thereof are also useful for treating a CDC7-associated cancer.

Accordingly, also provided herein is a method for treating a subject diagnosed with or identified as having a CDC7-associated cancer, e.g., any of the exemplary CDC7-associated cancers disclosed herein, comprising administering to the subject a therapeutically effective amount of a compound of Formula (I) (e.g., any one of Formulas (Ia), (Ib), (Ic), and (Id)), or a pharmaceutically acceptable salt thereof, or a pharmaceutical composition thereof as defined herein. In some embodiments, a compound of Formula (I) (e.g., any one of Formulas (Ia), (Ib), (Ic), and (Id)) is selected from Examples 1-65.

Dysregulation of a CDC7 kinase, a CDC7 gene, or the expression or activity or level of any (e.g., one or more) of the same can contribute to tumorigenesis. For example, a fusion protein can have increased kinase activity as compared to a wild-type CDC7 protein, increased expression (e.g., increased levels) of a wild-type CDC7 kinase in a mammalian cell can occur due to aberrant cell signaling and/or dysregulated autocrine/paracrine signaling (e.g., as compared to a control non-cancerous cell), CDC7 mRNA splice variants may also result in dysregulation of CDC7.

In some embodiments, the compounds provided herein exhibit brain and/or central nervous system (CNS) penetrance. Such compounds are capable of crossing the blood brain barrier and inhibiting CDC7 kinase activity in the brain and/or other CNS structures. In some embodiments, the compounds provided herein are capable of crossing the blood brain barrier in an effective amount. For example, treatment of a subject with cancer (e.g., a CDC7-associated cancer such as a CDC7-associated brain or CNS cancer) can include administration (e.g., oral administration) of the compound to the subject. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the subject has previously been treated with another anticancer agent, e.g., another CDC7 inhibitor (e.g., a compound that is not a compound of General Formula (I)) or a multi-kinase inhibitor. In some embodiments, the brain tumor is a metastatic brain tumor. In some embodiments, the subject has previously been treated with another anticancer agent, e.g., another CDC7 inhibitor (e.g., a compound that is not a compound of Formula (I)) or a multi-kinase inhibitor.

In some embodiments of any of the methods or uses described herein, an assay used to determine whether the subject has a dysregulation of a CDC7 gene, or a CDC7 kinase, or expression or activity or level of any of the same, using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a CDC7 gene, a CDC7 kinase, or expression or activity or levels of any of the same. In some embodiments, the sample is a biological sample or a biopsy sample (e.g., a paraffin-embedded biopsy sample) from the subject. In some embodiments, the subject is a subject suspected of having a CDC7-associated cancer, a subject having one or more symptoms of a CDC7-associated cancer, and/or a subject that has an increased risk of developing a CDC7-associated cancer).

In some embodiments, dysregulation of a CDC7 gene, a CDC7 kinase, or the expression or activity or level of any of the same can be identified using a liquid biopsy (variously referred to as a fluid biopsy or fluid phase biopsy). Liquid biopsy methods can be used to detect total tumor burden and/or the dysregulation of a CDC7 gene, a CDC7 kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a CDC7 gene, a CDC7 kinase, or the expression or activity or level of any of the same. In some embodiments, liquid biopsies can be used to detect the presence of dysregulation of a CDC7 gene, a CDC7 kinase, or the expression or activity or level of any of the same at an earlier stage than traditional methods. In some embodiments, the biological sample to be used in a liquid biopsy can include, blood, plasma, urine, cerebrospinal fluid, saliva, sputum, bronchoalveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a CDC7 gene, a CDC7 kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a CDC7 gene, a CDC7 kinase, or the expression or activity or level of any of the same). Liquid biopsies can be used to detect dysregulation of a CDC7 gene, a CDC7 kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a dysregulation of a CDC7 gene, a CDC7 kinase, or the expression or activity or level of any of the same identified using a liquid biopsy is also present in a cancer cell that is present in the subject (e.g., in a tumor). In some embodiments, any of the types of dysregulation of a CDC7 gene, a CDC7 kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a CDC7 gene, a CDC7 kinase, or the expression or activity or level of any of the same in the subject can indicate that the subject will be responsive to a treatment that includes administration of a compound of Formula (I) (e.g., any one of Formulas (Ia), (Ib), (Ic), and (Id)), or a pharmaceutically acceptable salt thereof.

Liquid biopsies can be performed at multiple times during a course of diagnosis, a course of monitoring, and/or a course of treatment to determine one or more clinically relevant parameters including, without limitation, progression of the disease and/or efficacy of a treatment. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable). In some embodiments, a treatment to be administered to a subject can include a compound of Formula (I) (e.g., any one of Formulas (Ia), (Ib), (Ic), and (Id)), or a pharmaceutically acceptable salt thereof.

In some embodiments, the efficacy of a compound of Formula (I) (e.g., any one of Formulas (Ia), (Ib), (Ic), and (Id)), or a pharmaceutically acceptable salt thereof, can be determined by assessing the allele frequency of a dysregulation of a CDC7 gene in cfDNA obtained from a subject at different time points, e.g., cfDNA obtained from the subject at a first time point and cfDNA obtained from the subject at a second time point, where at least one dose of a compound of Formula (I) (e.g., any one of Formulas (Ia), (Ib), (Ic), and (Id)), or a pharmaceutically acceptable salt thereof, is administered to the subject between the first and second time points. Some embodiments of these methods can further include administering to the subject at least one dose of the compound of Formula (I) (e.g., any one of Formulas (Ia), (Ib), (Ic), and (Id)), or a pharmaceutically acceptable salt thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a CDC7 gene in the cfDNA obtained from the subject at the second time point as compared to the allele frequency (AF) of the dysregulation of a CDC7 gene in the cfDNA obtained from the subject at the first time point indicates that the compound of Formula (I) (e.g., any one of Formulas (Ia), (Ib), (Ic), and (Id)), or a pharmaceutically acceptable salt thereof, was effective in the subject. In some embodiments, the AF is reduced such that the level is below the detection limit of the instrument. Alternatively, an increase in the allele frequency (AF) of the dysregulation of a CDC7 gene in the cfDNA obtained from the subject at the second time point as compared to the allele frequency (AF) of the dysregulation of a CDC7 gene in the cfDNA obtained from the subject at the first time point indicates that the compound of Formula (I) (e.g., any one of Formulas (Ia), (Ib), (Ic), and (Id)), or a pharmaceutically acceptable salt thereof, was not effective in the subject. Some embodiments of these methods can further include, administering additional doses of a compound of Formula (I) (e.g., any one of Formulas (Ia), (Ib), (Ic), and (Id)), or a pharmaceutically acceptable salt thereof, to a subject in which a compound of Formula (I) (e.g., any one of Formulas (Ia), (Ib), (Ic), and (Id)), or a pharmaceutically acceptable salt thereof, was determined to be effective. Some embodiments of these methods can further include, administering a different treatment (e.g., a treatment that does not include the administration of a compound of Formula (I) (e.g., any one of Formulas (Ia), (Ib), (Ic), and (Id)), or a pharmaceutically acceptable salt thereof, as a monotherapy) to a subject in which a compound of Formula (I) (e.g., any one of Formulas (Ia), (Ib), (Ic), and (Id)), or a pharmaceutically acceptable salt thereof, was determined not to be effective.

In some embodiments, the CDC7-associated cancer is a high microsatellite instability (MSI-H) cancer. In other embodiments, the CDC7-associated cancer is not a high microsatellite instability (MSI-H) cancer. In some embodiments, the MSI-H status is determined by detection of repetitive DNA sequences selected from the group consisting of: mononucleotide repeat markers, dinucleotide repeat markers, quasimonomorphic markers, or a combination of any of the foregoing.

In some embodiments, a tumor associated with the cancer comprises a phenotype selected from the group consisting of: chromosome instability (CIN), a spindle checkpoint assembly defect, a mitosis defect, a Gl/S checkpoint defect, and combinations thereof. In some embodiments, a tumor associated with the cancer comprises a Wnt signaling pathway mutation. In some embodiments, the Wnt signaling pathway mutation is selected from the group consisting of: an Adenomatous polyposis coli (APC) gene mutation, a FAT1 mutation, a FAT4 mutation, or a combination of any of the foregoing.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the subject can be previously identified as having a cancer having a dysregulated CDC7 gene (e.g., any of the examples of a dysregulated CDC7 gene described herein). In some embodiments of these methods, a subject can have been previously diagnosed as having any of the types of cancer described herein. In some embodiments of these methods, the subject can have one or more metastases (e.g., one or more brain metastases).

In some of the above embodiments, the cfDNA comprises ctDNA such as CDC7-associated ctDNA. For example, the cfDNA is ctDNA such as CDC7-associated ctDNA. In some embodiments, at least some portion of cfDNA is determined to be CDC7-associated ctDNA, for example, a sequenced and/or quantified amount of the total cfDNA is determined to have a CDC7 fusion and/or overexpression of CDC7.

In the field of medical oncology it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula (I) (e.g., any one of Formulas (Ia), (Ib), (Ic), and (Id)), or a pharmaceutically acceptable salt thereof therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula (I) (e.g., any one of Formulas (Ia), (Ib), (Ic), and (Id)), or a pharmaceutically acceptable salt thereof, can be used prior to administration of an additional therapeutic agent or additional therapy. For example, a subject in need thereof can be administered one or more doses of a compound of Formula (I) (e.g., any one of Formulas (Ia), (Ib), (Ic), and (Id)), or a pharmaceutically acceptable salt thereof for a period of time and then undergo at least partial resection of the tumor. In some embodiments, the treatment with one or more doses of a compound of Formula (I) (e.g., any one of Formulas (Ia), (Ib), (Ic), and (Id)), or a pharmaceutically acceptable salt thereof reduces the size of the tumor (e.g., the tumor burden) prior to the at least partial resection of the tumor. In some embodiments, a subject in need thereof can be administered one or more doses of a compound of Formula (I) (e.g., any one of Formulas (Ia), (Ib), (Ic), and (Id)), or a pharmaceutically acceptable salt thereof for a period of time and under one or more rounds of radiation therapy. In some embodiments, the treatment with one or more doses of a compound of Formula (I) (e.g., any one of Formulas (Ia), (Ib), (Ic), and (Id)), or a pharmaceutically acceptable salt thereof reduces the size of the tumor (e.g., the tumor burden) prior to the one or more rounds of radiation therapy.

In some embodiments, a subject has a cancer (e.g., a locally advanced or metastatic tumor) that is refractory or intolerant to standard therapy (e.g., administration of a chemotherapeutic agent, such as a first CDC7 inhibitor or a multikinase inhibitor, immunotherapy, or radiation (e.g., radioactive iodine)). In some embodiments, a subject has a cancer (e.g., a locally advanced or metastatic tumor) that is refractory or intolerant to prior therapy (e.g., administration of a chemotherapeutic agent, such as a first CDC7 inhibitor or a multikinase inhibitor, immunotherapy, or radiation (e.g., radioactive iodine)). In some embodiments, a subject has a cancer (e.g., a locally advanced or metastatic tumor) that has no standard therapy. In some embodiments, a subject is CDC7-kinase inhibitor naïve. For example, the subject is naïve to treatment with a selective CDC7-kinase inhibitor. In some embodiments, a subject is not CDC7-kinase inhibitor naïve.

In some embodiments, a subject has undergone prior therapy. In some embodiments, a subject having NSCLC (e.g., a CDC7-associated NSCLC) has received treatment with a platinum-based chemotherapy, PD-1/PDL1 immunotherapy, or both prior to treatment with a compound of Formula (I) (e.g., any one of Formulas (Ia), (Ib), (Ic), and (Id)), or a pharmaceutically acceptable salt thereof. In some embodiments, a subject having a thyroid cancer (e.g., a CDC7-associated thyroid cancer) has received treatment with one or more of sorafenib, lenvatinib, and radioactive iodine prior to treatment with a compound of Formula (I) (e.g., any one of Formulas (Ia), (Ib), (Ic), and (Id)), or a pharmaceutically acceptable salt thereof. In some embodiments, a subject having a colorectal cancer (e.g., a CDC7-associated colorectal cancer) has received treatment with a fluoropyrimidine-based chemotherapy, with or without ant-VEGF-directed therapy or anti-EGFR-directed therapy, prior to treatment with a compound of Formula (I) (e.g., any one of Formulas (Ia), (Ib), (Ic), and (Id)), or a pharmaceutically acceptable salt thereof. In some embodiments, a subject having a pancreatic cancer (e.g., a CDC7-associated pancreatic cancer) has received treatment with one or more of a fluoropyrimidine-based chemotherapy, a gemcitabine-based chemotherapy, and a S-1 chemotherapy prior to treatment with a compound of Formula (I) (e.g., any one of Formulas (Ia), (Ib), (Ic), and (Id)), or a pharmaceutically acceptable salt thereof. In some embodiments, a subject having a breast cancer (e.g., a CDC7-associated breast cancer) has received treatment with one or more of anthracycline, taxane, HER2-directed therapy, and hormonal therapy prior to treatment with a compound of Formula (I) (e.g., any one of Formulas (Ia), (Ib), (Ic), and (Id)), or a pharmaceutically acceptable salt thereof. In some embodiments, a subject having a MTC (e.g., a CDC7-associated MTC cancer) has received treatment with one or more of caboxantinib and vandetanib prior to treatment with a compound of Formula (I) (e.g., any one of Formulas (Ia), (Ib), (Ic), and (Id)), or a pharmaceutically acceptable salt thereof.

In some embodiments of any of the methods described herein, the compound of Formula (I) (e.g., any one of Formulas (Ia), (Ib), (Ic), and (Id)), or a pharmaceutically acceptable salt thereof, is administered in combination with an effective amount of at least one additional therapeutic agent selected from one or more additional therapies or therapeutic (e.g., chemotherapeutic) agents.

Non-limiting examples of additional therapeutic agents include: other CDC7-targeted therapeutic agents (i.e. a first or second CDC7 kinase inhibitor), other kinase inhibitors (e.g., receptor tyrosine kinase-targeted therapeutic agents (e.g., Trk inhibitors or EGFR inhibitors)), signal transduction pathway inhibitors, checkpoint inhibitors, modulators of the apoptosis pathway (e.g., obataclax); cytotoxic chemotherapeutics, angiogenesis-targeted therapies, immune-targeted agents, including immunotherapy, and radiotherapy.

In some embodiments, the other CDC7-targeted therapeutic is a multikinase inhibitor exhibiting CDC7 inhibition activity. In some embodiments, the other CDC7-targeted therapeutic inhibitor is selective for a CDC7 kinase. Exemplary CDC7 kinase inhibitors can exhibit inhibition activity ($IC_{50}$) against a CDC7 kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a CDC7 kinase inhibitors can exhibit inhibition activity ($IC_{50}$) against a CDC7 kinase of less than about 25 nM, less than about 10 nM, less than about 5 nM, or less than about 1 nM as measured in an assay as provided herein.

Non-limiting examples of kinase-targeted therapeutic agents (e.g., a first CDC7 inhibitor or a second CDC7 inhibitor) include TAK931, SRA141, and PHA-767491.

Non-limiting examples of multi-kinase inhibitors include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl)piperazine-1-carbothioamide); apatinib (YN968D1) (N-[4-(1-cyanocyclopentyl)phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide);

dovitinib (TK1258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene)methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy]phenyl}amino)-4-pyrimidinyl]amino}benzenesulfonamide); foCDC7inib (XL880, EXEL-2880, GSK1363089, GSK089) (N1'-[3-fluoro-4-[[6-methoxy-7-(3-morpholinopropoxy)-4-quinolyl]oxy]phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methyoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl)phenyl]benzamide); PP242 (torkinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorafenib (BAY 73-4506, stivarga) (4-[4-({[4-Chloro-3-(trifluoromethyl)phenyl]carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b]pyridin-7-yl]oxy}phenyl)-N'-(4-fluorophenyl)-1,1-cyclopropanedicarboxamide); sorafenib (BAY 43-9006) (4-[4-[[[[4-chloro-3-(trifluoromethyl)phenyl]amino]carbonyl]amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); BPR1K871 (1-(3-chlorophenyl)-3-(5-(2-((7-(3-(dimethylamino)propoxy)quinazolin-4-yl)amino)ethyl)thiazol-2-yl)urea); CLM3 (1-phenethyl-N-(1-phenylethyl)-1H-pyrazolo[3,4-d]pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl)phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl)phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl)phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl)(5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a CDC7 antibody (Y078) linked to a derivative of the cytotoxic agent maytansine); Y078-DM4 (an antibody drug conjugate composed of a CDC7 antibody (Y078) linked to a derivative of the cytotoxic agent maytansine); ITRI-305 (DON5 TB, DIB003599); BLU-667 ((1S,4R)-N-((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide); BLU6864; DS-5010; GSK3179106; GSK3352589; NMS-E668; TAS0286/HM05; TPX0046; and N-(3-(2-(dimethylamino)ethoxy)-5-(trifluoromethyl)phenyl)-2-(4-(4-ethoxy-6-oxo-1,6-dihydropyridin-3-yl)-2-fluorophenyl)acetamide.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, VM-902A, TPX-0005, TSR-011, GNF-4256, N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea, AZ623, AZ64, (S)-5-Chloro-N2-(1-(5-fluoropyridin-2-yl)ethyl)-N4-(5-isopropoxy-1H-pyrazol-3-yl)pyrimidine-2,4-diamine, AZD7451, CEP-751, CT327, sunitinib, GNF-8625, and (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol.

Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), RO5185426 (Hofmann-LaRoche), and GSK2118436 (GlaxoSmithKline). Additional examples of a BRAF inhibitor are known in the art.

In some embodiments, the receptor tyrosine kinase inhibitor is an epidermal growth factor receptor typrosine kinase inhibitor (EGFR). For example, EGFR inhibitors can include osimertinib (merelectinib, Tagrisso®), erlotinib (Tarceva®), gefitinib (Iressa®), cetuximab (Erbitux®), necitumumab (Portrazza®), neratinib (Nerlynx®), lapatinib (Tykerb®), panitumumab (Vectibix®), and vandetanib (Caprelsa®).

In some embodiments, signal transduction pathway inhibitors include Ras-Raf-MEK-ERK pathway inhibitors (e.g., binimetinib, selumetinib, encorafenib, sorafenib, trametinib, and vemurafenib), PI3K-Akt-mTOR-S6K pathway inhibitors (e.g., everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3] benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

In some embodiments, an additional therapy or therapeutic agent can include a histidyl-tRNA synthetase (HRS) polypeptide or an expressible nucleotide that encodes the HRS polypeptide.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™) inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is *bacillus* Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; WO 2016/075224; WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its CDC7 receptor tyrosine kinase have been correlated with cancer proliferation and metastasis. See, e.g., Zeng, et al. J. Int. Med. Res. (2008) 36(4): 656-64.

Accordingly, also provided herein are methods for inhibiting, preventing, aiding in the prevention, or decreasing the symptoms of metastasis of a cancer in a subject in need thereof, the method comprising administering to the subject an effective amount of a compound of Formula (I) (e.g., any one of Formulas (Ia), (Ib), (Ic), and (Id)), or a pharmaceutically acceptable salt thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., *Pancreas* 2015 January; 44:134-143; Ding K et al., *J Biol Chem* 2014 Jun. 6; 289:16057-71; and Amit M et al., *Oncogene* 2017 Jun. 8; 36:3232-3239. In some embodiments, the cancer is a CDC7-associated cancer. In some embodiments, the compound of Formula (I) (e.g., any one of Formulas (Ia), (Ib), (Ic), and (Id)), or a pharmaceutically acceptable salt thereof is used in combination with an additional therapy or another therapeutic agent, including a chemotherapeutic agent, such as a kinase inhibitor. For example, a first or second CDC7 kinase inhibitor. In some embodiments, the additional therapeutic agent is crizotinib. In some embodiments, the additional therapeutic agent is osimertinib. In some embodiments, the subject has been administered one or more doses of a compound of Formula (I) (e.g., any one of Formulas (Ia), (Ib), (Ic), and (Id)), or a pharmaceutically acceptable salt thereof, prior to administration of the pharmaceutical composition. In some embodiments, the cancer is a lung cancer (e.g., a CDC7-associated lung cancer). In some embodiments, the additional therapeutic agent is a PARP inhibitor (e.g., olaparib). In some embodiments, the additional therapeutic agent is an ATR inhibitor (e.g., ceralasertib). In some embodiments, the additional therapeutic agent is a Weel inhibitor (e.g., AZD-1775). In some embodiments, the additional therapeutic agent is an EGFR inhibitor (e.g., lapatinib).

The term "metastasis" is an art known term and means the formation of an additional tumor (e.g., a solid tumor) at a site distant from a primary tumor in a subject, where the additional tumor includes the same or similar cancer cells as the primary tumor.

Also provided are methods of decreasing the risk of developing a metastasis or an additional metastasis in a subject having a CDC7-associated cancer that include: selecting, identifying, or diagnosing a subject as having a CDC7-associated cancer, and administering an effective amount of a compound of Formula (I) (e.g., any one of Formulas (Ia), (Ib), (Ic), and (Id)), or a pharmaceutically acceptable salt thereof to the subject selected, identified, or diagnosed as having a CDC7-associated cancer. Also provided are methods of decreasing the risk of developing a metastasis or an additional metastasis in a subject having a CDC7-associated cancer that includes administering an effective amount of a compound of Formula (I) (e.g., any one of Formulas (Ia), (Ib), (Ic), and (Id)), or a pharmaceutically acceptable salt thereof to a subject having a CDC7-associated cancer. The decrease in the risk of developing a metastasis or an additional metastasis in a subject having a CDC7-associated cancer can be compared to the risk of developing a metastasis or an additional metastasis in the subject prior to treatment, or as compared to a subject or a population of subjects having a similar or the same CDC7- associated cancer that has received no treatment or a different treatment. In some embodiments, the additional therapeutic agent is crizotinib. In some embodiments, the additional therapeutic agent is osimertinib. In some embodiments, the subject has been administered one or more doses of a compound of Formula (I) (e.g., any one of Formulas (Ia), (Ib), (Ic), and (Id)), or a pharmaceutically acceptable salt thereof, prior to administration of the pharmaceutical composition. In some embodiments, the cancer is a lung cancer (e.g., a CDC7-associated lung cancer).

The phrase "risk of developing a metastasis" means the risk that a subject having a primary tumor will develop an additional tumor (e.g., a solid tumor) at a site distant from a primary tumor in a subject over a set period of time, where the additional tumor includes the same or similar cancer cells as the primary tumor. Methods for reducing the risk of developing a metastasis in a subject having a cancer are described herein.

The phrase "risk of developing additional metastases" means the risk that a subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Treatment of a subject having a cancer with a multi-kinase inhibitor (MKI) or target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) can result in dysregulation of a CDC7 gene, a CDC7 kinase, or the expression or activity or level of the same in the cancer, and/or resistance to a CDC7 inhibitor. See, e.g., Bhinge et al., *Oncotarget* 8:27155-27165, 2017; Chang et al., *Yonsei Med. J.* 58:9-18, 2017; and Lopez-Delisle et al., doi: 10.1038/s41388-017-0039-5, *Oncogene* 2018.

Treatment of a subject having a cancer with a CDC7 inhibitor in combination with a multi-kinase inhibitor or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) can have increased therapeutic efficacy as compared to treatment of the same subject or a similar subject with the CDC7 inhibitor as a monotherapy, or the multi-kinase inhibitor or the target-specific kinase inhibitor as a monotherapy. See, e.g., Tang et al., doi: 10.1038/modpathol.2017.109, *Mod. Pathol.* 2017; Andreucci et al., *Oncotarget* 7:80543-80553, 2017; Nelson-Taylor et al., *Mol. Cancer Ther.* 16:1623-1633, 2017; and Kato et al., *Clin. Cancer Res.* 23:1988-1997, 2017.

Provided herein are methods of treating a subject having a cancer (e.g., any of the cancers described herein) and previously administered a multi-kinase inhibitor (MKI) or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) that include: administering to the subject (i) an effective dose of a compound of Formula (I) (e.g., any one of Formulas (Ia), (Ib), (Ic), and (Id)), or a pharmaceutically acceptable salt thereof as a monotherapy, or (ii) an effective dose of a compound of Formula (I) (e.g., any one of Formulas (Ta), (Ib), (Ic), and (Id)), or a pharmaceutically acceptable salt thereof, and an effective dose of the previously administered MKI or the previously administered target-specific kinase inhibitor.

Provided herein are methods of treating a subject having a cancer (e.g., any of the cancers described herein) previously administered a MKI or a target specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) that include: identifying a subject having a cancer cell that has a dysregulation of a CDC7 gene, a CDC7 kinase, or the expression or activity or level of the same; and administering to the identified subject (i) an effective dose of a compound of Formula (I) (e.g., any one of Formulas (Ia), (Ib), (Ic), and (Id)), or a pharmaceutically acceptable salt thereof as a monotherapy, or (ii) an effective dose of a compound of Formula (I) (e.g., any one of Formulas (Ia), (Ib), (Ic), and (Id)), or a pharmaceutically acceptable salt thereof, and an effective dose of the previously administered MKI or the previously administered target-specific kinase inhibitor.

Provided herein are methods of treating a subject having a cancer (e.g., any of the cancers described herein) that include: administering to a subject an effective amount of a MKI or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) for a first period of time; after the period of time, identifying a subject having a cancer cell that has a dysregulation of a CDC7 gene, a CDC7 kinase, or the expression or activity or level of the same; and administering to the identified subject (i) an effective dose of a compound of Formula (I) (e.g., any one of Formulas (Ia), (Ib), (Ic), and (Id)), or a pharmaceutically acceptable salt thereof as a monotherapy, or (ii) an effective dose of a compound of Formula (I) (e.g., any one of Formulas (Ia), (Ib), (Ic), and (Id)), or a pharmaceutically acceptable salt thereof, and an effective dose of the previously administered MKI or the previously administered target-specific kinase inhibitor.

Also provided is a method for inhibiting CDC7 kinase activity in a mammalian cell, comprising contacting the mammalian cell with a compound of Formula (I) (e.g., any one of Formulas (Ia), (Ib), (Ic), and (Id)). In some embodiments, the contacting is in vitro. In some embodiments, the contacting is in vivo. In some embodiments, the contacting is in vivo, wherein the method comprises administering an effective amount of a compound of Formula (I) (e.g., any one of Formulas (Ia), (Ib), (Ic), and (Id)), or a pharmaceutically acceptable salt thereof to a subject having a mammalian cell having CDC7 kinase activity. In some embodiments, the mammalian cell is a mammalian cancer cell. In some embodiments, the mammalian cancer cell is any cancer as described herein. In some embodiments, the mammalian cancer cell is a CDC7-associated mammalian cancer cell.

Also provided is a method for inhibiting CDC7 kinase activity in a mammalian mammalian cell, comprising contacting the mammalian cell with a compound of Formula (I) (e.g., any one of Formulas (Ia), (Ib), (Ic), and (Id)). In some embodiments, the contacting is in vitro. In some embodiments, the contacting is in vivo. In some embodiments, the contacting is in vivo, wherein the method comprises administering an effective amount of a compound of Formula (I)

(e.g., any one of Formulas (Ia), (Ib), (Ic), and (Id)), or a pharmaceutically acceptable salt thereof to a mammal having a mammalian cell having CDC7 kinase activity. In some embodiments, the mammalian cell is a mammalian cancer cell. In some embodiments, the mammalian cancer cell is any cancer as described herein. In some embodiments, the mammalian cancer cell is a CDC7-associated mammalian cancer cell.

As used herein, the term "contacting" refers to the bringing together of indicated moieties in an in vitro system or an in vivo system. For example, "contacting" a CDC7 kinase with a compound provided herein includes the administration of a compound provided herein to a subject, such as a human, having a CDC7 kinase, as well as, for example, introducing a compound provided herein into a sample containing a mammalian cellular or purified preparation containing the CDC7 kinase.

Also provided herein is a method of inhibiting mammalian cell proliferation, in vitro or in vivo, the method comprising contacting a mammalian cell with an effective amount of a compound of Formula (I) (e.g., any one of Formulas (Ia), (Ib), (Ic), and (Id)), or a pharmaceutically acceptable salt thereof, or a pharmaceutical composition thereof as defined herein.

A "CDC7 kinase inhibitor" as defined herein includes any compound exhibiting CDC7 inhibition activity. In some embodiments, a CDC7 kinase inhibitor is selective for a CDC7 kinase. Exemplary CDC7 kinase inhibitors can exhibit inhibition activity ($IC_{50}$) against a CDC7 kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a CDC7 kinase inhibitor can exhibit inhibition activity ($IC_{50}$) against a CDC7 kinase of less than about 25 nM, less than about 10 nM, less than about 5 nM, or less than about 1 nM as measured in an assay as provided herein.

As used herein, a "first CDC7 kinase inhibitor" or "first CDC7 inhibitor" is a CDC7 kinase inhibitor as defined herein, but which does not include a compound of Formula (I) (e.g., any one of Formulas (Ia), (Ib), (Ic), and (Id)), or a pharmaceutically acceptable salt thereof as defined herein. As used herein, a "second CDC7 kinase inhibitor" or a "second CDC7 inhibitor" is a CDC7 kinase inhibitor as defined herein, but which does not include a compound of Formula (I) (e.g., any one of Formulas (Ia), (Ib), (Ic), and (Id)), or a pharmaceutically acceptable salt thereof as defined herein. When both a first and a second CDC7 inhibitor are present in a method provided herein, the first and second CDC7 kinase inhibitor are different.

Exemplary first and second CDC7 kinase inhibitors are described herein. In some embodiments, a first or second CDC7 kinase inhibitor can be selected from the group consisting of TAK931, SRA141, and PHA-767491.

The phrase "effective amount" means an amount of compound that, when administered to a subject in need of such treatment, is sufficient to (i) treat a CDC7-associated disease or disorder (such as a CDC7-associated cancer), (ii) attenuate, ameliorate, or eliminate one or more symptoms of the particular disease, condition, or disorder, or (iii) delay the onset of one or more symptoms of the particular disease, condition, or disorder described herein. The amount of a compound of Formula (I) (e.g., any one of Formulas (Ia), (Ib), (Ic), and (Id)), or a pharmaceutically acceptable salt thereof that will correspond to such an amount will vary depending upon factors such as the particular compound, disease condition and its severity, the identity (e.g., weight) of the subject in need of treatment, but can nevertheless be routinely determined by one skilled in the art.

When employed as pharmaceuticals, compounds of Formula (I) (e.g., any one of Formulas (Ia), (Ib), (Ic), and (Id)), including pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula (I) (e.g., any one of Formulas (Ia), (Ib), (Ic), and (Id)) or pharmaceutically acceptable salt thereof, in combination with one or more pharmaceutically acceptable excipients. For example, a pharmaceutical composition prepared using a compound of Formula (I) (e.g., any one of Formulas (Ia), (Ib), (Ic), and (Id)) or a pharmaceutically acceptable salt thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula (I) (e.g., any one of Formulas (Ia), (Ib), (Ic), and (Id)) or a pharmaceutically acceptable salt thereof with a pharmaceutically acceptable carrier. Pharmaceutical compositions containing a compound of Formula (I) (e.g., any one of Formulas (Ia), (Tb), (Ic), and (Id)) or a pharmaceutically acceptable salt thereof as the active ingredient can be prepared by intimately mixing the compound of Formula (I) (e.g., any one of Formulas (Ia), (Ib), (Ic), and (Id)), or a pharmaceutically acceptable salt thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

The compositions comprising a compound of Formula (I) (e.g., any one of Formulas (Ia), (Ib), (Ic), and (Id)) or a pharmaceutically acceptable salt thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other subjects, each unit containing a predetermined quantity of active material (i.e., a compound of Formula (I) (e.g., any one of Formulas (Ia), (Ib), (Ic), and (Id)) or a pharmaceutically acceptable salt thereof) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain about 10 mg, about 20 mg, about 80 mg, or about 160 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The daily dosage of the compound of Formula (I) (e.g., any one of Formulas (Ia), (Ib), (Ic), and (Id)) or a pharmaceutically acceptable salt thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the subject to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula (I) (e.g., any one of Formulas (Ia), (Ib), (Ic), and (Id)) or a pharmaceutically acceptable salt thereof can be administered on a regimen of 1 to 4 times per day or in a single daily dose.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

In some embodiments, the compounds provided herein can be administered in an amount of about 10 mg twice a day (BID), 20 mg BID, about 40 mg BID, about 60 mg BID, about 80 mg BID, about 120 mg BID, about 160 mg BID, and about 240 mg BID. In some embodiments, each dose is administered at least six hours after the previous dose. In some embodiments, each dose is administered at least twelve hours after the previous dose.

In some embodiments, a compound of Formula (I) (e.g., any one of Formulas (Ia), (Ib), (Ic), and (Id)), or a pharmaceutically acceptable salt thereof exhibits pH dependent solubility at lower pH values. Accordingly, subjects also receiving proton pump inhibitors (PPIs) and/or antacids may need to adjust the dosage of the compound of Formula (I) (e.g., any one of Formulas (Ia), (Ib), (Ic), and (Id)), or a pharmaceutically acceptable salt thereof (e.g., increase the dose of the compound of Formula (I) (e.g., any one of Formulas (Ia), (Tb), (Ic), and (Id)), or a pharmaceutically acceptable salt thereof). In some embodiments, the isoform of cytochrome P450 (CYP) that metabolizes a compound of Formula (I) (e.g., any one of Formulas (Ta), (Tb), (Ic), and (Id)), or a pharmaceutically acceptable salt thereof, is CYP3A4. Accordingly, subjects also receiving agents that inhibit or induce CYP3A4 may need to adjust the dosage of the compound of Formula (I) (e.g., any one of Formulas (Ia), (Ib), (Ic), and (Id)), or a pharmaceutically acceptable salt thereof (e.g., increase the dose of the compound of Formula (I) (e.g., any one of Formulas (Ia), (Ib), (Ic), and (Id)), or a pharmaceutically acceptable salt thereof, in the case of a CYP3A4 inducer or decrease the dose of the compound of Formula (I) (e.g., any one of Formulas (Ta), (Ib), (Ic), and (Id)), or a pharmaceutically acceptable salt thereof, in the case of a CYP3A4 inhibitor).

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of CDC7-associated diseases or disorders, such as cancer, which include one or more containers containing a pharmaceutical composition comprising an effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

Materials and Methods

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry,* $1^{st}$ Ed., Oxford University Press, 2000; *March's Advanced Organic Chemistry: Reactions, Mechanisms, and Structure,* $5^{th}$ Ed., Wiley-Interscience Publication, 2001; and Peturssion, S. et al., "*Protecting Groups in Carbohydrate Chemistry,*" *J. Chem. Educ.,* 74(11), 1297 (1997).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), normal phase silica chromatography, and supercritical fluid chromatography (SFC).

All solvents and reagents were obtained from commercial sources and used without further purification unless indicated otherwise. Anhydrous solvents were purchased and used as supplied. Reactions were monitored by thin-layer chromatography (TLC), visualizing with a UV lamp (254 nm) and $KMnO_4$ stain. NMR spectra were obtained on a Bruker Neo 400M spectrometer operating at 400 MHz. Chemical shifts are reported in parts per million (6) from the tetramethysilane resonance in the indicated solvent. LC-Mass spectra were taken with Agilent 1260-6125B single quadrupole mass spectrometer using a Welch Biomate column (C18, 2.7 um, 4.6*50 mm) or waters H-Class SQD2 system. The detection was by DAD (254 nm and 210 nm and 280 nm). Chiral HPLC was performed on the Waters acquity UPC2 system under base-containing on Daicel chiralpak AD-H (5 um, 4.6*250 mm), Daicel chiralpak OD-H (5 um, 4.6*250 mm), Daicel chiralpak IG-3 (3 um, 4.6*150 mm), Chiral Technologies Europe AD-3 (3 um, 3.0*150 mm) and Trefoil™ Technology Trefoil™ AMY1 (2.5 um, 3.0*150 mm). The detection was by DAD (254 nm). Preparative HPLC was performed on GILSON Trilution LC system using a Welch XB-C18 column (5 um, 21.2*150 mm). Flash chromatography was carried out on Biotage Isolera Prime system using Welch WelFlash flash columns (40-63 um). The compounds synthesized are all with purity ≥95% unless otherwise specified.

Abbreviations

*=an indication that the amount of the solvent or reagent preceding the "*" is used in the technique for a number of times equal to the number following the "*".

° C.=degrees Celsius $^1$H NMR=proton nuclear magnetic resonance spectrum

AcOH=acetic acid $Boc_2O$=tert-butoxycarbonyl anhydride con.=concentrated d=doublet DCM=dichloromethane DIAD=diisopropylazodicarboxylate DIPEA=N,N-diisopropylethylamine DMF=N,N-dimethylformamide EA=ethyl acetate ESI=electrospray ionization g=gram(s)

h=hour(s)

HATU=(1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium HPLC=high-performance liquid chromatography LCMS=liquid chromatograph-mass spectrum M=mass m/z=mass-to-charge ratio MeCN=acetonitrile MeOH=methanol MeONa=sodium methoxide mg=milligram(s)

mL=milliliter mmol=millimole(s)

mol=mole(s)

MS=mass spectrum

NBS=N-bromosuccinimide obsd.=observed $PCy_3$=tricyclohexylphosphine $Pd(AcO)_2$=palladium (II) acetate $Pd(dppf)Cl_2$=(1,1'-Bis(diphenylphosphino)ferrocene)palladium(II) dichloride PE=petroleum ether ppm=parts per million PTSA=para-toluenesulfonic acid rt=room temperature s=singlet t=triplet TBAF=tetrabutylammonium fluoride TFA=trifluoroacetic acid THF=tetrahydrofuran TLC=thin-layer chromatography Trixiephos=rac-2-(Di-tert-butylphosphino)-1,1'-binaphthyl

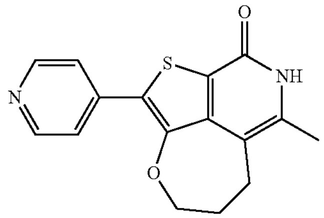 [SMILES: Cc1[nH]c(=O)c2sc(-c3ccncc3)c3c2c1CCCO3]

Step A: 4-methoxythiophene-2-carboxylic acid

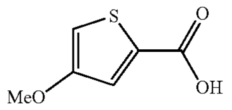

To a solution of freshly prepared NaOMe (250 mL, 1 M, 2.2 eq.) in MeOH was added methyl 4-bromothiophene-2-carboxylate (26 g, 117.6 mmol, 1 eq) and NMP (30 mL) at 0° C. under $N_2$. The reaction was heated to 100° C. and CuI (2.2 g, 11.8 mmol, 0.1 eq.) was added. Then the mixture was kept stirring at 100° C. overnight. After most of methyl 4-methoxythiophene-2-carboxylate was consumed, the reaction was cooled to 50° C. and $H_2O$ was added followed by another 1 h of continuous stirring. The mixture was cooled to room temperature, concentrated down and extracted with $Et_2O$ to remove unreacted starting material. The pH of aqueous layer was adjusted to 6-7 and extracted again with EA. Solvent was removed under vacuum to afford crude compound 4-methoxythiophene-2-carboxylic acid (18.0 g) as yellow oil which was used in the next step without further purification.

Step B: 4-methoxythiophene-2-carboxamide

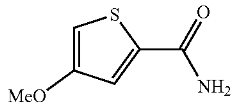

To a mixture of crude compound 4-methoxythiophene-2-carboxylic acid (18.0 g, 113.9 mmol, 1 eq.) in DCM (250 mL) was added DIPEA (73.7 g, 570.0 mmol, 5.0 eq.), HATU (56.4 g, 148.2 mmol, 1.3 eq.). After stirring at rt. for 10 min, anhydrous $NH_4Cl$ (12.2 g, 228.0 mmol, 2 eq.) was added and kept stirring at 38° C. overnight. Reaction was quenched with $H_2O$ and extracted with DCM. The organic layer was separated, concentrated and purified by flash chromatography eluting with 0-30% EA in PE to afford 4-methoxythiophene-2-carboxamide (17 g) as a white solid. MS obsd. ($ESI^+$): m/z 157.8 $[(M+H)^+]$.

Step C: ethyl 3-methoxy-5-methyl-7-oxo-6,7-dihydrothieno[2,3-c]pyridine-4-carboxylate

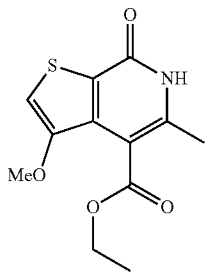 [SMILES: CCOC(=O)c1c(C)[nH]c(=O)c2scc(OC)c12]

To a solution of 4-methoxythiophene-2-carboxamide (300 mg, 1.9 mmol, 1.0 eq) in DCE (4 mL) was added CsOAc (183 mg, 0.950 mmol, 0.5 eq) and $(C_5(CH_3)_5RhCl)_2Cl_2$ (23.5 mg, 2%) under $N_2$. The mixture was stirred at room temperature for 5 min then ethyl 2-diazo-3-oxobutanoate (0.4 mL, 2.85 mmol, 1.50 eq) was added dropwise under $N_2$. After stirring at room temperature for 30 min the reaction was heated to 100° C. overnight. Upon completion, the mixture cooled to rt., diluted with DCM, filtered through a pad of celite, and washed with DCM. The filtrate was concentrated down and purified by flash column eluting 0-50% EA in PE to afford ethyl 3-methoxy-5-methyl-7-oxo-6,7-dihydrothieno[2,3-c]pyridine-4-carboxylate (116 mg) as a yellow solid. MS obsd. ($ESI^+$): m/z 268.1 $[(M+H)^+]$.

Step D: ethyl 7-chloro-3-methoxy-5-methylthieno[2,3-c]pyridine-4-carboxylate

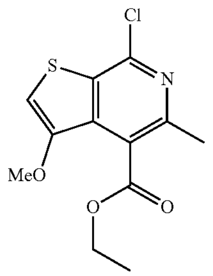 [SMILES: CCOC(=O)c1c(C)nc(Cl)c2scc(OC)c12]

Ethyl 3-methoxy-5-methyl-7-oxo-6,7-dihydrothieno[2,3-c]pyridine-4-carboxylate (30 mg, 0.11 mmol, 1.0 eq) was dissolved in $POCl_3$ (2 mL) under $N_2$ and kept stirring at 105° C. overnight. Reaction was quenched with MeOH, filtered and purified with reversed phase column (MeOH/$H_2O$=55%) to afford ethyl 7-chloro-3-methoxy-5-methylthieno[2,3-c]pyridine-4-carboxylate (20 mg) as a white solid. MS obsd. ($ESI^+$): m/z 286 $[(M+H)^+]$.

Step F: (7-chloro-3-methoxy-5-methylthieno[2,3-c]pyridin-4-yl)methanol

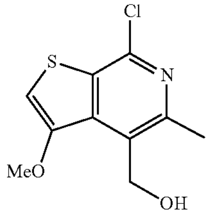

To a mixture of ethyl 7-chloro-3-methoxy-5-methylthieno[2,3-c]pyridine-4-carboxylate (100 mg, 0.35 mmol, 1.0 eq) in dry THF (10 mL) was added LAH (1 mL, 1M in THF, 2.00 eq) dropwise at −78° C. under $N_2$. The reaction was immediately heated to 50° C. and kept stirring for 40 min. The reaction was quenched with iced water (5 drops) at −78° C. and sodium-potassium tartrate solution (5 mL) was added while stirring. The mixture was filtered, diluted with $H_2O$, extracted with DCM. The organic layer was separated, dried with anhydrous $Na_2SO_4$, concentrated down and purified with flash column eluting 0-40% EA in PE to afford (7-chloro-3-methoxy-5-methylthieno[2,3-c]pyridin-4-yl)methanol (25 mg) as a white solid. MS obsd. ($ESI^+$): m/z 244 $[(M+H)^+]$.

Step G: 7-chloro-3-methoxy-5-methylthieno[2,3-c]pyridine-4-carbaldehyde

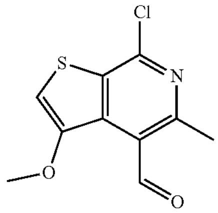

To a mixture of (7-chloro-3-methoxy-5-methylthieno[2,3-c]pyridin-4-yl)methanol (5 mg, 0.021 mmol, 1.0 eq) in DCM (10 mL) was added DMP (17.4 mg, 0.041 mmol, 2.00 eq). The reaction was kept stirring and slowly warmed to room temperature for 2 h. Reaction was quenched with sodium thiosulfate solution (2 mL). The mixture was filtered, diluted with $H_2O$, extracted with EA, and dried with anhydrous sodium sulfate. The organic layer was concentrated down and purified by prep-TLC (EA/PE=20%) to afford 7-chloro-3-methoxy-5-methylthieno[2,3-c]pyridine-4-carbaldehyde (3 mg) as a white solid. MS obsd. ($ESI^+$): m/z 242 $[(M+H)^+]$.

Step H: (E)-ethyl 3-(7-chloro-3-methoxy-5-methylthieno[2,3-c]pyridin-4-yl)acrylate

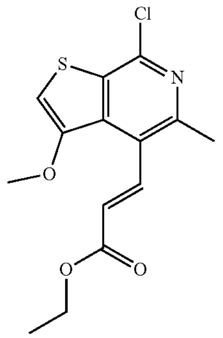

Triethyl phosphonoacetate (51.0 mg, 0.23 mmol, 1.1 eq) was added dropwise to a mixture of t-BuOK (27.8 mg, 0.25 mmol, 1.2 eq) in dry THF (2 mL) at −5° C. and then stirred for 30 min. A solution of 7-chloro-3-methoxy-5-methylthieno[2,3-c]pyridine-4-carbaldehyde (50 mg, 0.21 mmol, 1.0 eq) in another 2 mL of dry THF was added dropwise and stirred at −5° C. for 30 min. Upon completion the reaction mixture was poured into iced water, extracted with EA and the organic layer was washed with $NaHCO_3$, brine, dried with anhydrous sodium sulfate, concentrated and purified by flash column (EA in PE=30%) to afford (E)-ethyl 3-(7-chloro-3-methoxy-5-methylthieno[2,3-c]pyridin-4-yl)acrylate (20 mg) as a green solid. MS obsd. ($ESI^+$): m/z 312 $[(M+H)^+]$.

Step I: 3-(7-chloro-3-methoxy-5-methylthieno[2,3-c]pyridin-4-yl)propan-1-ol

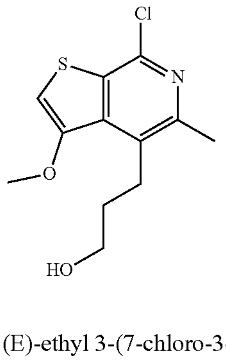

To a mixture of (E)-ethyl 3-(7-chloro-3-methoxy-5-methylthieno[2,3-c]pyridin-4-yl)acrylate (86 mg, 0.28 mmol, 1 eq) in PEG 400 (5 mL) was added $NaBH_4$ (100 mg, 2.45 mmol, 9.0 eq). The reaction mixture was heated to 80° C. and stirred for 2 h. The reaction was quenched with 1N HCl followed by extraction with EA. The organic layer was separated, dried with anhydrous sodium sulfate, concentrated down and purified by prep-TLC (EA/PE=1:1) to afford 3-(7-chloro-3-methoxy-5-methylthieno[2,3-c]pyridin-4-yl)propan-1-ol (45 mg) as a white solid. MS obsd. ($ESI^+$): m/z 272 $[(M+H)^+]$.

Step J: 3-chloro-5-methyl-7,8-dihydro-6H-9-oxa-2-thia-4-azabenzo[cd]azulene

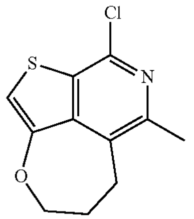

3-(7-chloro-3-methoxy-5-methylthieno[2,3-c]pyridin-4-yl)propan-1-ol (30 mg, 0.11 mmol, 1.0 eq) was added into 48% HBr aqueous solution (3 mL) and kept stirring at 50° C. overnight. Reaction was quenched with $NaHCO_3$ saturated aqueous solution to adjust pH to 6-7. The mixture was extracted with EA, dried with anhydrous sodium sulfate, concentrated down and purified by prep-TLC (EA/PE=1:1) to afford 3-chloro-5-methyl-7,8-dihydro-6H-9-oxa-2-thia-4-azabenzo[cd]azulene (15 mg) as a white solid. MS obsd. ($ESI^+$): m/z 239.95 $[(M+H)^+]$.

Step K: 5-methyl-4,6,7,8-tetrahydro-3H-9-oxa-2-thia-4-azabenzo[cd]azulen-3-one

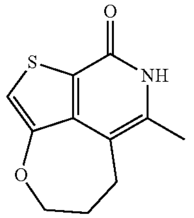

To a mixture of 3-chloro-5-methyl-7,8-dihydro-6H-9-oxa-2-thia-4-azabenzo[cd]azulene (56 mg, 0.23 mmol, 1.0 eq) in 80% AcOH aqueous solution (5 mL) was added $NH_4OAc$ (200 mg, 2.60 mmol, 11.1 eq). The reaction was sealed in autoclave and heated to 210° C. for 40 min. Upon completion the reaction was cooled to rt. and poured into iced water (10 mL), extracted with EA (4*20 mL). The organic layer was washed with $NaHCO_3$, brine, dried with anhydrous sodium sulfate, concentrated down and purified by prep-TLC (EA/PE=50%) to afford 5-methyl-4,6,7,8-tetrahydro-3H-9-oxa-2-thia-4-azabenzo[cd]azulen-3-one (30 mg) as a white solid. MS obsd. ($ESI^+$): m/z 221.8 $[(M+H)^+]$.

Step L: 1-bromo-5-methyl-4,6,7,8-tetrahydro-3H-9-oxa-2-thia-4-azabenzo[cd]azulen-3-one

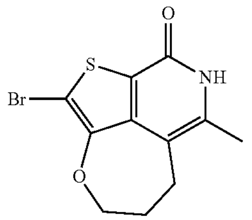 [SMILES: Cc1[nH]c(=O)c2sc(Br)c3c2c1CCCO3]

To a mixture of 5-methyl-4,6,7,8-tetrahydro-3H-9-oxa-2-thia-4-azabenzo[cd]azulen-3-one (10 mg, 0.045 mmol, 1.0 eq) in AcOH:DCM (1:1) (15 mL) was added NBS (6.4 mg, 0.036 mmol, 0.80 eq) in AcOH:DCM (1:1) (5 mL) at −2° C. and the reaction was kept stirring at −2° C. for 24 h. The mixture was poured into ice-water, extracted with EA and the organic layer was washed with $NaHCO_3$, dried with anhydrous sodium sulfate, concentrated down and purified by prep-TLC (EA/PE=50%) to afford 1-bromo-5-methyl-4,6,7,8-tetrahydro-3H-9-oxa-2-thia-4-azabenzo[cd]azulen-3-one (3 mg) as a yellow solid. MS obsd. ($ESI^+$): m/z 299.8 [$(M+H)^+$].

Step M: 5-methyl-1-(pyridin-4-yl)-4,6,7,8-tetrahydro-3H-9-oxa-2-thia-4-azabenzo[cd]azulen-3-one

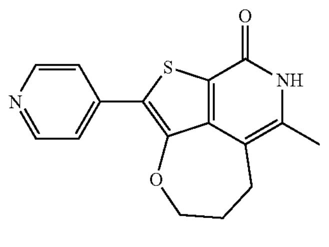 [SMILES: Cc1[nH]c(=O)c2sc(-c3ccncc3)c3c2c1CCCO3]

1-bromo-5-methyl-4,6,7,8-tetrahydro-3H-9-oxa-2-thia-4-azabenzo[cd]azulen-3-one (10 mg, 0.033 mmol, 1.0 eq), pyridin-4-ylboronic acid (25.0 mg, 0.20 mmol, 6.00 eq), pd(dppf)$Cl_2$ (5.0 mg, 0.007 mmol, 0.20 eq), $K_2CO_3$ (27.7 mg, 0.20 mmol, 6.00 eq) were dissolved in dioxane:$H_2O$ (1:1) (5 mL) and degassed by bubbling $N_2$ for 5 min. Then the reaction was sealed in a tube and kept stirring at 95° C. for 3 h. It was filtered and purified by prep-HPLC to afford 5-methyl-1-(pyridin-4-yl)-4,6,7,8-tetrahydro-3H-9-oxa-2-thia-4-azabenzo[cd]azulen-3-one (5.0 mg) as a white solid. MS obsd. ($ESI^+$): m/z 298.8 [$(M+H)^+$]. $^1H$ NMR (400 MHz, $CDCl_3$) δ ppm: 10.29 (s, 1H), 8.65 (s, 2H), 7.76 (s, 2H), 4.28-4.45 (m, 2H), 3.04-2.88 (m, 2H), 2.37 (s, 3H), 2.24-2.31 (m, 2H).

Example 2: 6-methyl-2-(pyridin-4-yl)-5,7-dihydro-3-oxa-1-thia-7-azaacenaphthylen-8(4H)-one

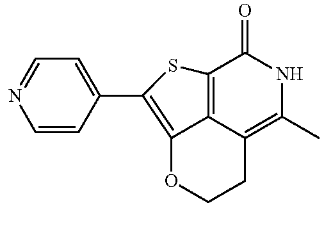 [SMILES: Cc1[nH]c(=O)c2sc(-c3ccncc3)c3c2c1CCO3]

Step A: 7-chloro-3-methoxy-4-(2-methoxyvinyl)-5-methylthieno[2,3-c]pyridine

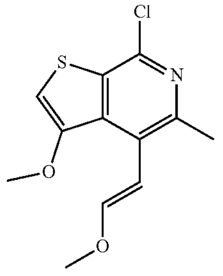

To a mixture of t-BuOK (3.3 g, 29.8 mmol, 2.4 eq) in dry THF (30 mL) was added (methoxymethylene)triphenylphosphane (9.36 g, 27.3 mmol, 2.2 eq) at −5° C. and stirred for 30 min. A solution of 7-chloro-3-methoxy-5-methylthieno[2,3-c]pyridine-4-carbaldehyde (3.0 g, 12.4 mmol, 1.0 eq) in another 5 mL of dry THF was added dropwise and stirred at −5° C. for 30 min. Upon completion the reaction mixture was poured into iced water, extracted with EA and the organic layer was washed with sat. $NaHCO_3$ aqueous solution, brine, dried with anhydrous sodium sulfate, concentrated and purified by flash column (0-15% EA in PE) to afford 7-chloro-3-methoxy-4-(2-methoxyvinyl)-5-methylthieno[2,3-c]pyridine (1.8 g) as a yellow solid. MS obsd. ($ESI^+$): m/z 270 [$(M+H)^+$].

Step B: 2-(7-chloro-3-methoxy-5-methylthieno[2,3-c]pyridin-4-yl)acetaldehyde

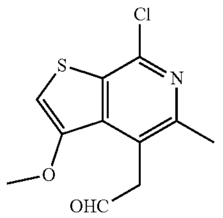

7-chloro-3-methoxy-4-(2-methoxyvinyl)-5-methylthieno[2,3-c]pyridine (1.0 g, 3.70 mmol, 1.0 eq) was added into 48% HBr aqueous solution (5 mL) and kept stirring at 70° C. for 2 h. LCMS showed the reaction was complete and it was quenched with $NaHCO_3$ saturated aqueous solution to adjust pH to 6-7. The mixture was extracted with EA, dried with anhydrous sodium sulfate, concentrated down and purified by flash chromatography eluting 0-40% EA in PE to afford 2-(7-chloro-3-methoxy-5-methylthieno[2,3-c]pyridin-4-yl)acetaldehyde (550 mg) as a yellow solid. MS obsd. ($ESI^+$): m/z 256 [$(M+H)^+$].

Step C: 2-(7-chloro-3-methoxy-5-methylthieno[2,3-c]pyridin-4-yl)ethanol

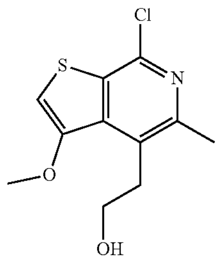

To a mixture of 2-(7-chloro-3-methoxy-5-methylthieno[2,3-c]pyridin-4-yl)acetaldehyde (550 mg, 2.15 mmol, 1.0 eq) in MeOH (20 mL) was added $NaBH_4$ (163.3 mg, 4.30 mmol, 2.0 eq) at 0° C. The reaction mixture was slowly warmed up to RT and kept stirring for 40 min. LCMS showed the reaction was complete. The mixture was filtered and extracted with EA. The organic layer was separated, dried with anhydrous sodium sulfate, concentrated down and purified with flash column (EA in PE=50%) to afford 2-(7-chloro-3-methoxy-5-methylthieno[2,3-c]pyridin-4-yl) ethanol (530 mg) as a yellow solid. MS obsd. ($ESI^+$): m/z 258 $[(M+H)^+]$.

Step D: 8-chloro-6-methyl-4,5-dihydro-3-oxa-1-thia-7-azaacenaphthylene

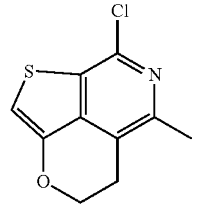

2-(7-chloro-3-methoxy-5-methylthieno[2,3-c]pyridin-4-yl)ethanol (530 mg, 2.05 mmol, 1.0 eq) was added into 48% HBr aqueous solution (5 mL) and kept stirring at 70° C. for 18 h. LCMS showed the reaction was complete and it was quenched with $NaHCO_3$ saturated aqueous solution to adjust pH to 6-7. The mixture was extracted with EA, dried with anhydrous sodium sulfate, concentrated down and purified by flash chromatography eluting 0-20% EA in PE to afford 8-chloro-6-methyl-4,5-dihydro-3-oxa-1-thia-7-azaacenaphthylene (450 mg) as a yellow solid. MS obsd. ($ESI^+$): m/z 226 $[(M+H)^+]$.

Step E: 6-methyl-5,7-dihydro-3-oxa-1-thia-7-azaacenaphthylen-8(4H)-one

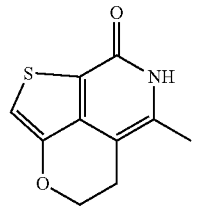

To a mixture of 8-chloro-6-methyl-4,5-dihydro-3-oxa-1-thia-7-azaacenaphthylene (40 mg, 0.18 mmol, 1.0 eq) in 80% AcOH aqueous solution (5 mL) was added $NH_4OAc$ (126.2 mg, 1.78 mmol, 10.0 eq). The reaction was sealed in an autoclave and heated to 210° C. for 1.5 h. Upon completion the reaction was cooled to RT, poured into iced water and extracted with. The organic layer was washed with $NaHCO_3$, brine, dried with anhydrous sodium sulfate, concentrated down and purified by Prep-TLC (EA/PE=50%) to afford 6-methyl-5,7-dihydro-3-oxa-1-thia-7-azaacenaphthylen-8(4H)-one (30 mg) as a yellow solid. MS obsd. ($ESI^+$): m/z 208 $[(M+H)^+]$.

Step F: 2-bromo-6-methyl-5,7-dihydro-3-oxa-1-thia-7-azaacenaphthylen-8(4H)-one

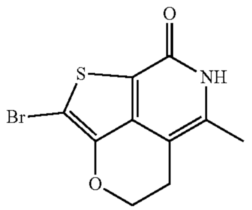

To a solution of 6-methyl-5,7-dihydro-3-oxa-1-thia-7-azaacenaphthylen-8(4H)-one (50 mg, 0.24 mmol, 1 eq) in DCM/MeOH (5 mL, 1:1) was added $CaCO_3$ (96 mg, 1 mmol, 4 eq) and $BTMABr_3$ (96 mg, 0.24 mmol, 1 eq). The tube was covered in aluminum foil to avoid light and kept stirring at −5° C. for 1 h. LCMS showed the reaction was complete but containing some di-brominated by-product. The mixture was quenched with $Na_2SO_3$ powder and filtered. The organic filtrate was concentrated and purified with Prep-HPLC which resulted in 2-bromo-6-methyl-5,7-dihydro-3-oxa-1-thia-7-azaacenaphthylen-8(4H)-one (17 mg) as a white crystal. MS obsd. ($ESI^+$): m/z 286.0, 288.0 $[(M+H)^+]$.

Step G: 6-methyl-2-(pyridin-4-yl)-5,7-dihydro-3-oxa-1-thia-7-azaacenaphthylen-8(4H)-one

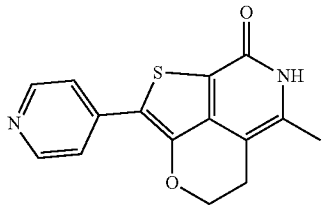 [SMILES: Cc1[nH]c(=O)c2sc(-c3ccncc3)c3c2c1CCO3]

To a solution of 2-bromo-6-methyl-5,7-dihydro-3-oxa-1-thia-7-azaacenaphthylen-8(4H)-one (16 mg, 0.05 mmol, 1 eq) in dioxane/$H_2O$ (2 mL, 3:1) was added $Na_2CO_3$ (18 mg, 0.17 mmol, 3 eq), $Pd(dppf)Cl_2$ (8 mg, 0.01 mmol, 0.2 eq) and pyridin-4-ylboronic acid (14 mg, 0.11 mmol, 2 eq). The mixture was degassed by bubbling N2 for 10 min. The reaction was then sealed in a tube and heated to 105° C. for 1 h with microwave. LCMS showed the reaction was complete and the resulting mixture was filtered and purified with prep-HPLC to give 6-methyl-2-(pyridin-4-yl)-5,7-dihydro-3-oxa-1-thia-7-azaacenaphthylen-8(4H)-one (1.5 mg) as a white solid. MS obsd. ($ESI^+$): m/z 285.1 [$(M+H)^+$]. $^1H$ NMR (400 MHz, DMSO) δ 11.55 (s, 1H), 8.62 (dd, J=4.6, 1.6 Hz, 2H), 7.75 (dd, J=4.6, 1.7 Hz, 2H), 4.48 (t, J=5.6 Hz, 2H), 2.83 (t, J=5.4 Hz, 1H), 2.21 (s, 3H).

The following compounds were prepared in a similar manner as that illustrated in Example 2 from corresponding bromide through Suzuki reaction.

| Ex. No. | Structure | Name | MS obsd. ($ESI^+$): m/z [$(M + H)^+$] |
|---|---|---|---|
| 3 | 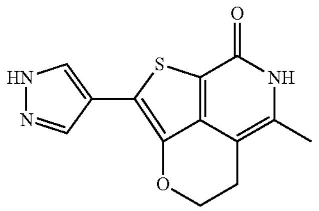 [SMILES: Cc1[nH]c(=O)c2sc(-c3cn[nH]c3)c3c2c1CCO3] | 6-methyl-2-(1H-pyrazol-4-yl)-5,7-dihydro-3-oxa-1-thia-7-azaacenaphthylen-8(4H)-one | 274 |
| 4 | 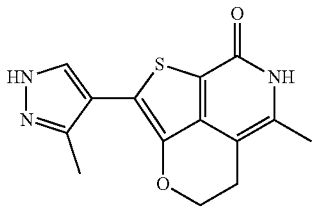 [SMILES: Cc1n[nH]cc1-c1sc2c(=O)[nH]c(C)c3c2c1OCC3] | 6-methyl-2-(3-methyl-1H-pyrazol-4-yl)-5,7-dihydro-3-oxa-1-thia-7-azaacenaphthylen-8(4H)-one | 288 |
| 5 | 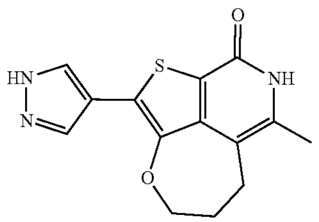 [SMILES: Cc1[nH]c(=O)c2sc(-c3cn[nH]c3)c3c2c1CCCO3] | 5-methyl-1-(1H-pyrazol-4-yl)-4,6,7,8-tetrahydro-3H-9-oxa-2-thia-4-azabenzo[cd]azulen-3-one | 288 |
| 6 | 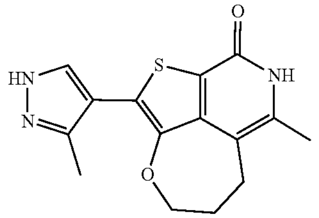 [SMILES: Cc1n[nH]cc1-c1sc2c(=O)[nH]c(C)c3c2c1OCCC3] | 5-methyl-1-(3-methyl-1H-pyrazol-4-yl)-4,6,7,8-tetrahydro-3H-9-oxa-2-thia-4-azabenzo[cd]azulen-3-one | 302 |

Example 7: (R)-4,6-dimethyl-2-(pyridin-4-yl)-5,7-dihydro-3-oxa-1-thia-7-azaacenaphthylen-8(4H)-one

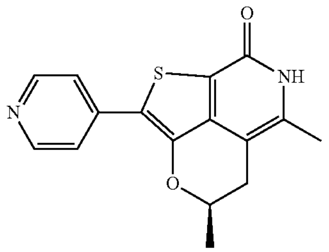 [SMILES: Cc1[nH]c(=O)c2sc(-c3ccncc3)c3c2c1C[C@@H](C)O3]

Example 8: (S)-4,6-dimethyl-2-(pyridin-4-yl)-5,7-dihydro-3-oxa-1-thia-7-azaacenaphthylen-8(4H)-one

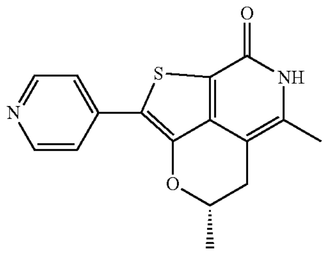 [SMILES: Cc1[nH]c(=O)c2sc(-c3ccncc3)c3c2c1C[C@H](C)O3]

Step A: 7-chloro-3-methoxy-4-(2-methoxyvinyl)-5-methylthieno[2,3-c]pyridine

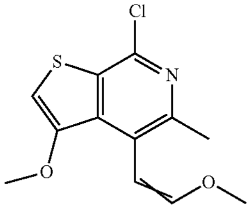

The solution of (methoxymethyl)triphenylphosphonium bromide (3.85 g, 10 mmol, 0.1 eq) in dry THF (100 mL) was degassed and refilled with $N_2$ for three times at −78° C. Then a solution of t-BuOK (11 mL, 1.0 M, 11 mmol, 2.2 eq) in THF was added dropwise over 30 min. Then this mixture was stirred at −78° C. for 0.5 hour. Then 7-chloro-3-methoxy-5-methylthieno[2,3-c]pyridine-4-carbaldehyde (1.2 g, 5 mmol, 1 eq) was added in one portion. The mixture was stirred at 0° C. for 3 h and warmed up to 25° C. for another 3 h. Upon completion, saturated $NH_4Cl$ solution and EtOAc were added at 0° C. The resulting mixture was extracted with EtOAc. The combined organic layers were dried over anhydrous $Na_2SO_4$, filtered and concentrated in vacuum. The crude product was purified by silica gel column chromatography (eluted with PE:EtOAc=1:1) to give 7-chloro-3-methoxy-4-(2-methoxyvinyl)-5-methylthieno[2,3-c]pyridine (807 mg) as a yellow solid. MS obsd. ($ESI^+$): m/z 270.0 $[(M+H)^+]$.

Step B: 2-(7-chloro-3-hydroxy-5-methylthieno[2,3-c]pyridin-4-yl)acetaldehyde

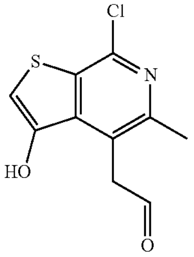

7-chloro-3-methoxy-4-(2-methoxyvinyl)-5-methylthieno[2,3-c]pyridine (807 mg, 3 mmol, 1 eq) was dissolved in 40% HBr aqueous solution (20 mL) and stirred at 70° C. for 16 h. Upon completion, the mixture was concentrated in vacuum. The crude product was recrystallized with PE:EtOAc=1:1 to give 2-(7-chloro-3-hydroxy-5-methylthieno[2,3-c]pyridin-4-yl)acetaldehyde (482 mg) as a yellow solid. MS obsd. ($ESI^+$): m/z 242.0 $[(M+H)^+]$.

Step C: 7-chloro-4-(2-hydroxypropyl)-5-methylthieno[2,3-c]pyridin-3-ol

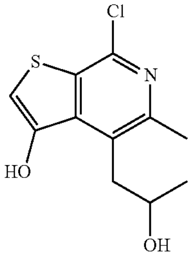 [SMILES: Cc1nc(Cl)c2scc(O)c2c1CC(C)O]

The solution of 2-(7-chloro-3-hydroxy-5-methylthieno[2,3-c]pyridin-4-yl)acetaldehyde (482 mg, 2 mmol, 1 eq) in dry THF (100 mL) at 0° C. was degassed and refilled with $N_2$ for three times. Then a solution of $CH_3MgBr$ (2.7 mL, 3.0 M, 8 mmol, 4 eq) in THF was added in one portion. Then the mixture was stirred at 0° C. for 1 h. Upon completion, saturated $NH_4Cl$ solution and EtOAc were added successively at 0° C. The resulting mixture was extracted with EtOAc. The combined organic layers were dried over anhydrous $Na_2SO_4$, filtered and concentrated in vacuum. The crude product was purified by silica gel column chromatography (eluted with PE:EtOAc=1:1) to give 7-chloro-4-(2-hydroxypropyl)-5-methylthieno[2,3-c]pyridin-3-ol (206 mg) as a yellow solid. MS obsd. ($ESI^+$): m/z 257.8 $[(M+H)^+]$.

Step D: 8-chloro-4,6-dimethyl-4,5-dihydro-3-oxa-1-thia-7-azaacenaphthylene

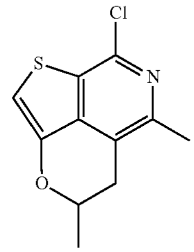

To a solution of 7-chloro-4-(2-hydroxypropyl)-5-methylthieno[2,3-c]pyridin-3-ol (206 mg, 0.8 mmol, 1 eq) in dry DCM (50 mL) at 0° C. was added TMSOTf (5 mL) dropwise over 3 min. Then this mixture was stirred at 40° C. for 16 h. Upon completion, the mixture was concentrated in vacuum. The residue was diluted with $H_2O$, basified with saturated $NaHCO_3$ solution (pH=8) at 0° C. The resulting mixture was extracted with EtOAc. The combined organic phase was dried over anhydrous $Na_2SO_4$, filtered and concentrated in vacuum. The crude product was purified by silica gel column chromatography (eluted with PE:EtOAc=1:1) to give 8-chloro-4,6-dimethyl-4,5-dihydro-3-oxa-1-thia-7-azaacenaphthylene (143 mg) as a yellow solid. MS obsd. ($ESI^+$): m/z 239.8 [$(M+H)^+$].

Step E: 4,6-dimethyl-5,7-dihydro-3-oxa-1-thia-7-azaacenaphthylen-8(4H)-one

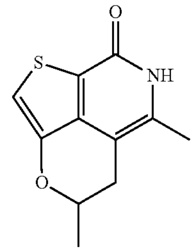

To a solution of 8-chloro-4,6-dimethyl-4,5-dihydro-3-oxa-1-thia-7-azaacenaphthylene (143 mg, 0.6 mmol, 1 eq) in AcOH (10 mL) was added one drop of water and $NH_4OAc$ (231 mg, 3 mmol, 5 eq) successively at room temperature. Then this mixture was stirred at 200° C. for 0.5 h. Upon completion, the mixture was cooled to RT and concentrated in vacuum. The residue was diluted with $H_2O$, basified with 30 wt % $NH_4OH$ aqueous solution (pH=8) at 0° C. The resulting mixture was extracted with DCM:MeOH=1:1. The combined organic phase was dried over anhydrous $Na_2SO_4$, filtered and concentrated in vacuum to give 4,6-dimethyl-5,7-dihydro-3-oxa-1-thia-7-azaacenaphthylen-8(4H)-one (119 mg) as a yellow solid. MS obsd. ($ESI^+$): m/z 221.8 [$(M+H)^+$].

Step F: 2-bromo-4,6-dimethyl-5,7-dihydro-3-oxa-1-thia-7-azaacenaphthylen-8(4H)-one

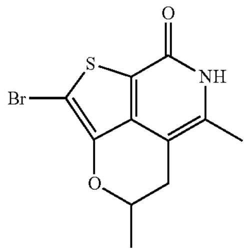 [SMILES: Cc1[nH]c(=O)c2sc(Br)c3c2c1CC(C)O3]

To a solution of 4,6-dimethyl-5,7-dihydro-3-oxa-1-thia-7-azaacenaphthylen-8(4H)-one (119 mg, 0.54 mmol, 1 eq) in DCM:MeOH=1:1 (24 mL) was added $BTMABr_3$ (210 mg, 0.54 mmol, 1 eq) small portions at 0° C. in a tube covered with aluminum foil to avoid light. Then this mixture was stirred at 25° C. under dark for 16 h. Upon completion, the mixture was diluted with $H_2O$, quenched with saturated of $Na_2SO_3$ solution at 0° C. The resulting mixture was extracted with DCM:MeOH=1:1. The combined organic phase was dried over anhydrous $Na_2SO_4$, filtered and concentrated in vacuum. The crude product was recrystallized with PE:EtOAc=1:2 to give 2-bromo-4,6-dimethyl-5,7-dihydro-3-oxa-1-thia-7-azaacenaphthylen-8(4H)-one (120 mg) as a yellow solid. MS obsd. ($ESI^+$): m/z 300.8 [$(M+H)^+$].

Step G: 4,6-dimethyl-2-(pyridin-4-yl)-5,7-dihydro-3-oxa-1-thia-7-azaacenaphthylen-8(4H)-one

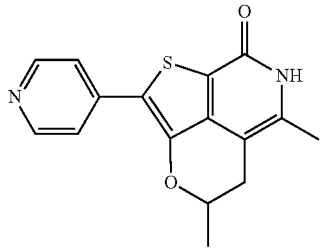 [SMILES: Cc1[nH]c(=O)c2sc(-c3ccncc3)c3c2c1CC(C)O3]

The mixture of 2-bromo-6,6-dimethyl-4,5,6,7-tetrahydro-8H-3-oxa-1-thia-5a,7-diazaacenaphthylen-8-one (30 mg, 0.1 mmol, 1 eq), (pyridin-4-ylboronic acid (24.4 mg, 0.2 mmol, 2 eq), $Pd(dppf)Cl_2$ (7.3 mg, 0.01 mmol, 0.1 eq), sodium carbonate (31.8 mg, 0.03 mmol, 3 eq) in 1,4-dioxane/$H_2O$=5/1 (4 mL) was degassed and refilled with $N_2$ for three times. Then the mixture was heated to 110° C. with microwave and kept stirring for 1 h. The resulting mixture was cooled to room temperature, diluted with DCM/MeOH=10/1, filtered through celite, concentrated in vacuum. The residue was purified by Prep-HPLC (eluted with MeCN in water from 0% to 30, 0.5% FA in water) to give 4,6-dimethyl-2-(pyridin-4-yl)-5,7-dihydro-3-oxa-1-thia-7-azaacenaphthylen-8(4H)-one (5.7 mg, 0.0191 mmol) as a yellow solid. MS obsd. ($ESI^+$): m/z 298.8 [$(M+H)^+$]. $^1H$ NMR (400 MHz, DMSO-d6) δ ppm: 11.53 (s, 1H), 8.62 (d, J=6.1 Hz, 2H), 7.76 (d, J=6.1 Hz, 2H), 4.36-4.58 (m, 1H), 2.94 (dd, J=15.9, 2.8 Hz, 1H), 2.55-2.67 (m, 1H), 2.19 (s, 3H), 1.54 (d, J=6.2 Hz, 3H). Racemic 4,6-dimethyl-2-

(pyridin-4-yl)-5,7-dihydro-3-oxa-1-thia-7-azaacenaphthylen-8(4H)-one was resolved with chiral SFC to give enantiomeric pure (R)-4,6-dimethyl-2-(pyridin-4-yl)-5,7-dihydro-3-oxa-1-thia-7-azaacenaphthylen-8(4H)-one and (S)-4,6-dimethyl-2-(pyridin-4-yl)-5,7-dihydro-3-oxa-1-thia-7-azaacenaphthylen-8(4H)-one. The absolute stereochemistry was randomly assigned for these two compounds.

Example 9: 4,6-dimethyl-2-(1H-pyrazol-4-yl)-5,7-dihydro-3-oxa-1-thia-7-azaacenaphthylen-8(4H)-one

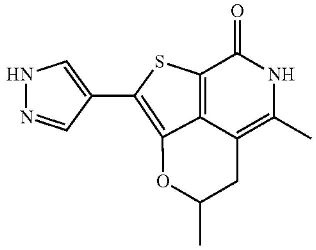 [SMILES: Cc1[nH]c(=O)c2sc(-c3cn[nH]c3)c3c2c1CC(C)O3]

Example 9 was prepared in a similar manner as that illustrated in Examples 7 and 8 from corresponding bromide through Suzuki reaction. MS obsd. (ESI+): m/z [(M+H)+] 288.

Example 10: (S)-5-((3-hydroxypyrrolidin-1-yl)methyl)-1-(pyridin-4-yl)-4,6,7,8-tetrahydro-3H-9-oxa-2-thia-4-azabenzo[cd]azulen-3-one

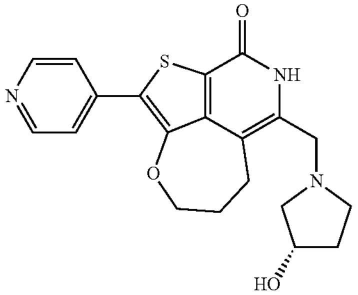 [SMILES: O=c1[nH]c(CN2CC[C@H](O)C2)c2c3c(c(-c4ccncc4)sc13)OCCC2]

Step A: 2-bromo-7-(bromomethyl)-12-oxa-3-thia-6-azatricyclo[6.4.1.$0^{4,13}$]trideca-1,4(13),7-trien-5-one

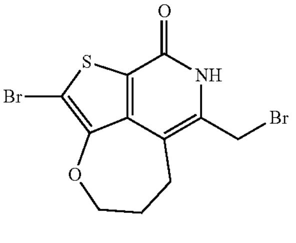 [SMILES: O=c1[nH]c(CBr)c2c3c(c(Br)sc13)OCCC2]

To a solution of 7-methyl-12-oxa-3-thia-6-azatricyclo[6.4.1.$0^{4,13}$]trideca-1,4(13),7-trien-5-one (100 mg, 452 umol, 1 eq) in Chloroform (15 mL, 99.8%, ACS Reagent) was added bromine (722 mg, 4.52 mmol, 231.5 uL, 10 eq) at 0° C. The mixture was allowed to warm to room temperature and stirred for 16 h. Upon completion, the resulting mixture was diluted with ice/water, quenched with saturated $Na_2SO_3$ at 0° C. (pH=8). The reaction was stirred at 0° C. for 10 min. The mixture was extracted with DCM. The combined organic solution containing crude 2-bromo-7-(bromomethyl)-12-oxa-3-thia-6-azatricyclo[6.4.1.$0^{4,13}$]trideca-1,4(13),7-trien-5-one (173.3 mg) (in DCM and Chloroform) was used in the next step without further purification due to the product's instability. MS obsd. ($ESI^+$): m/z 377.8 [$(M+H)^+$].

Step B: 2-bromo-7-(bromomethyl)-12-oxa-3-thia-6-azatricyclo[6.4.1.$0^{4,13}$]trideca-1,4(13),7-trien-5-one

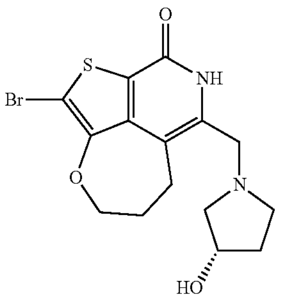 [SMILES: O=c1[nH]c(CN2CC[C@H](O)C2)c2c3c(c(Br)sc13)OCCC2]

To a solution of (S)-pyrrolidin-3-ol (362.2 mg, 4.16 mmol, 10 eq) in DCM (10 mL) was added a solution of 2-bromo-7-(bromomethyl)-12-oxa-3-thia-6-azatricyclo[6.4.1.$0^{4,13}$]trideca-1,4(13),7-trien-5-one (157.5 mg, 0.41 mmol, 52.5 mL) in DCM at 0° C. Then the mixture was stirred at 25° C. for 16 h. Upon completion, the mixture was diluted with water, extracted with DCM. The combined organic phase was dried over anhydrous $Na_2SO_4$, filtered and concentrated in vacuum. The crude product was purified by Prep-HPLC (eluted with MeCN in water from 0% to 30%, 0.5% FA in water) to give (S)-1-bromo-5-((3-hydroxypyrrolidin-1-yl)methyl)-4,6,7,8-tetrahydro-3H-9-oxa-2-thia-4-azabenzo[cd]azulen-3-one (60 mg) as a yellow solid. MS obsd. ($ESI^+$): m/z 385.0 [$(M+H)^+$].

Step C: (S)-5-((3-hydroxypyrrolidin-1-yl)methyl)-1-(pyridin-4-yl)-4,6,7,8-tetrahydro-3H-9-oxa-2-thia-4-azabenzo[cd]azulen-3-one

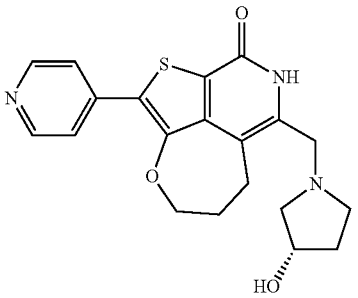 [SMILES: O=c1[nH]c(CN2CC[C@H](O)C2)c2c3c(c(-c4ccncc4)sc13)OCCC2]

The mixture of (S)-1-bromo-5-((3-hydroxypyrrolidin-1-yl)methyl)-4,6,7,8-tetrahydro-3H-9-oxa-2-thia-4-azabenzo[cd]azulen-3-one (63 mg, 164 umol), pyridin-4-ylboronic acid (60.4 mg, 491.5 umol, 3 eq), sodium carbonate (86.82 mg, 819 umol, 3 eq), X-Phos (23.4 mg, 49.2 umol, 0.3 eq), $Pd(dppf)Cl_2$ (36.0 mg, 49.2 umol, 0.3 eq) in 12 mL 1,4-dioxane/$H_2O$=5/1 was purged with argon 3 times. Then it was stirred at 105° C. under M.W. for 2.5 h. Upon completion, the resulting mixture was cooled to room temperature, concentrated in vacuum. The crude product was purified by silica Prep-TLC (eluted with DCM:MeOH=10:1) to give the crude product which was further purified by Prep-HPLC (eluted with MeCN in water from 0% to 30%, 0.5% FA in water) to give (S)-5-((3-hydroxypyrrolidin-1-yl)methyl)-1-(pyridin-4-yl)-4,6,7,8-tetrahydro-3H-9-oxa-2-thia-4-azabenzo[cd]azulen-3-one (7.5 mg) as a yellow solid. MS obsd. ($ESI^+$): m/z 354.2 [$(M+H)^+$]. $^1H$ NMR (400 MHz, MeOD) δ ppm: 8.57 (dd, J=4.7, 1.6 Hz, 2H), 8.33 (s, 1H), 7.89 (dd, J=4.7, 1.6 Hz, 2H), 4.42-4.49 (m, 2H), 4.38-4.40 (m, 1H), 3.75 (s, 2H), 3.03-3.10 (m, 2H), 2.89-2.98 (m, 1H), 2.83 (dd, J=10.0, 5.5 Hz, 1H), 2.69 (dd, J=10.0, 2.5 Hz, 1H), 2.57 (td, J=8.7, 6.0 Hz, 1H), 2.16-2.33 (m, 3H), 1.75-1.82 (m, 1H).

Example 11: (S)-5-((3-hydroxypyrrolidin-1-yl)methyl)-1-(1H-pyrazol-4-yl)-4,6,7,8-tetrahydro-3H-9-oxa-2-thia-4-azabenzo[cd]azulen-3-one

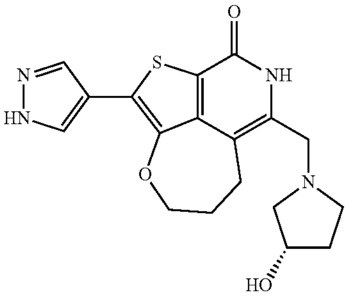 [SMILES: O=c1[nH]c(CN2CC[C@H](O)C2)c2c3c(c(-c4cn[nH]c4)sc13)OCCC2]

To a suspension of (S)-1-bromo-5-((3-hydroxypyrrolidin-1-yl)methyl)-4,6,7,8-tetrahydro-3H-9-oxa-2-thia-4-azabenzo[cd]azulen-3-one (56 mg, 0.15 mmol, 1 eq) in dioxane (10 mL) was added pyrazole-4-boronic acid (32.6 mg, 0.29 mmol, 2 eq), potassium carbonate (80.6 mg, 0.58 mmol, 4 eq), $Pd(dppf)Cl_2$ (27.8 mg, 0.038 mmol, 0.26 eq) and water (2 mL). The mixture was degassed for 2 min with $N_2$. The mixture was stirred at 105° C. for 1 h under microwave. LCMS showed the reaction was complete. It was diluted with water and DCM. The organic layer was concentrated, diluted with MeOH and purified by Prep-HPLC to give (S)-5-((3-hydroxypyrrolidin-1-yl)methyl)-1-(1H-pyrazol-4-yl)-4,6,7,8-tetrahydro-3H-9-oxa-2-thia-4-azabenzo[cd]azulen-3-one (5.6 mg) as a yellow solid. MS obsd. ($ESI^+$): m/z 373.20 [$(M+H)^+$]. $^1H$ NMR (400 MHz, MeOD) δ 8.20 (s, 1H), 8.03 (s, 2H), 4.42 (ddd, J=16.4, 8.4, 4.2 Hz, 3H), 3.86 (d, J=14.7 Hz, 2H), 3.05 (dd, J=7.1, 5.1 Hz, 3H), 2.95 (dd, J=10.5, 5.3 Hz, 1H), 2.86-2.67 (m, 2H), 2.28-2.16 (m, 3H), 1.84 (dt, J=13.3, 5.5 Hz, 1H).

Example 12: 5-(azetidin-1-ylmethyl)-1-(pyridin-4-yl)-4,6,7,8-tetrahydro-3H-9-oxa-2-thia-4-azabenzo[cd]azulen-3-one

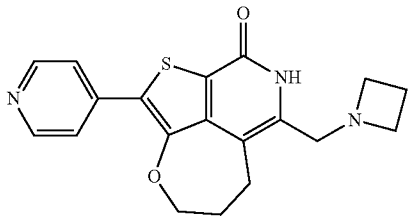 [SMILES: O=c1[nH]c(CN2CCC2)c2c3c(c(-c4ccncc4)sc13)OCCC2]

Example 13: 5-(azetidin-1-ylmethyl)-1-(1H-pyrazol-4-yl)-4,6,7,8-tetrahydro-3H-9-oxa-2-thia-4-azabenzo[cd]azulen-3-one

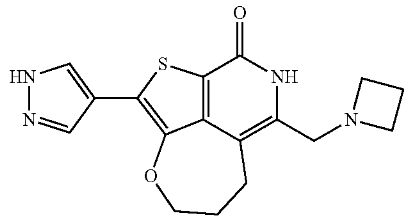 [SMILES: O=c1[nH]c(CN2CCC2)c2c3c(c(-c4cn[nH]c4)sc13)OCCC2]

Examples 12 and 13 were prepared in a similar manner as that illustrated in Example 10 from corresponding bromide through Suzuki reaction. Example 12: MS obsd. ($ESI^+$): m/z [$(M+H)^+$] 354. Example 13 MS obsd. ($ESI^+$): m/z [$(M+H)^+$] 343.

Example 14: tert-butyl ((3-oxo-1-(pyridin-4-yl)-4,6,7,8-tetrahydro-3H-9-oxa-2-thia-4-azabenzo[cd]azulen-5-yl)methyl)carbamate

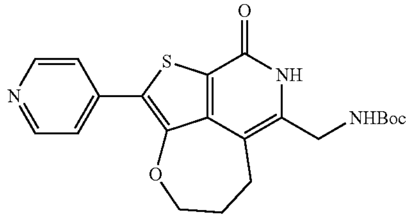 [SMILES: CC(C)(C)OC(=O)NCc1[nH]c(=O)c2sc(-c3ccncc3)c3c2c1CCCO3]

Step A: Tert-butyl ((1-bromo-3-oxo-4,6,7,8-tetrahydro-3H-9-oxa-2-thia-4-azabenzo[cd]azulen-5-yl)methyl)carbamate

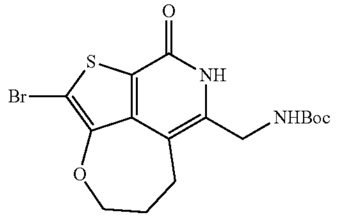 [SMILES: CC(C)(C)OC(=O)NCc1[nH]c(=O)c2sc(Br)c3c2c1CCCO3]

To a solution of ammonium hydroxide (900 mg, 28%, 25.7 mmol, 40 eq) in acetonitrile (10 mL) was added a solution of 2-bromo-7-(bromomethyl)-12-oxa-3-thia-6-azatricyclo[6.4.1.0$^{4,13}$]trideca-1,4(13),7-trien-5-one (240 mg, 0.63 mmol, 1 eq) in $CHCl_3$ and DCM at 0° C. The mixture was then allowed to warm to room temperature and stirred for 16 h. Di-tert-butyl dicarbonate (2.76 g, 12.66 mmol, 20 eq) was added to the reaction. Then the mixture was stirred at room temperature for another 3 h. Upon completion, the resulting mixture was diluted with water, extracted with DCM. The combined organic phase was dried over anhydrous $Na_2SO_4$, filtered and concentrated under vacuum. The crude product was purified by silica gel column chromatography (eluted with PE:EtOAc=3:1) to give tert-butyl N-[(2-bromo-5-oxo-12-oxa-3-thia-6-azatricyclo[6.4.1.0$^{4,13}$]trideca-1,4(13),7-trien-7-yl)methyl]carbamate (55 mg) as a yellow solid. MS obsd. ($ESI^+$): m/z 414.8 [$(M+H)^+$].

Step B: Tert-butyl ((3-oxo-1-(pyridin-4-yl)-4,6,7,8-tetrahydro-3H-9-oxa-2-thia-4-azabenzo[cd]azulen-5-yl)methyl)carbamate

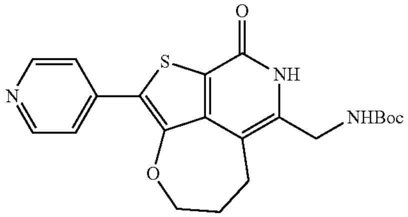 [SMILES: CC(C)(C)OC(=O)NCc1[nH]c(=O)c2sc(-c3ccncc3)c3c2c1CCCO3]

The mixture of tert-butyl N-[(2-bromo-5-oxo-12-oxa-3-thia-6-azatricyclo[6.4.1.0$^{4,13}$]trideca-1,4(13),7-trien-7-yl)methyl]carbamate (55 mg, 0.1 mmol, 1 eq), pyridin-4-ylboronic acid (37.4 mg, 0.3 mmol, 3 eq), sodium carbonate (53.28 mg, 0.5 mmol, 5 eq), X-Phos (14.36 mg, 0.3 mmol, 0.3 eq), $Pd(dppf)Cl_2$ (22.1 mg, 0.03 mmol, 0.3 eq) in 1,4-dioxane/$H_2O$=5/1 (12 mL) was purged with argon for 3 times. Then the reaction was stirred at 105° C. under M.W. for 2.5 h. Upon completion, the resulting mixture was cooled to room temperature and concentrated under vacuum. The residue was purified by silica Prep-TLC (eluted with DCM: MeOH=15:1) to give crude product which was further purified by Prep-HPLC (eluted with MeCN in water from 0% to 30%, 0.5% FA in water) to give tert-butyl ((3-oxo-1-(pyridin-4-yl)-4,6,7,8-tetrahydro-3H-9-oxa-2-thia-4-azabenzo[cd]azulen-5-yl)methyl)carbamate (15 mg) as a yellow solid. MS obsd. ($ESI^+$): m/z 354.2 [$(M+H)^+$]. $^1$H NMR (400 MHz, DMSO) S ppm: 11.23 (s, 1H), 8.63 (dd, J=4.6, 1.6 Hz, 2H), 7.77 (dd, J=4.6, 1.6 Hz, 2H), 7.19 (s, 1H), 4.39 (t, J=5.8 Hz, 2H), 4.13 (d, J=5.4 Hz, 2H), 2.91-3.02 (m, 2H), 2.12-2.18 (m, 2H), 1.37 (s, 9H).

Example 15: 5-(aminomethyl)-1-(pyridin-4-yl)-4,6,7,8-tetrahydro-3H-9-oxa-2-thia-4-azabenzo[cd]azulen-3-one;hydrochloride

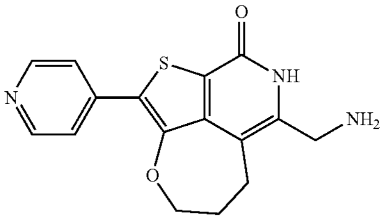 [SMILES: NCc1[nH]c(=O)c2sc(-c3ccncc3)c3c2c1CCCO3]

To a solution of tert-butyl ((3-oxo-1-(pyridin-4-yl)-4,6,7,8-tetrahydro-3H-9-oxa-2-thia-4-azabenzo[cd]azulen-5-yl)methyl)carbamate (15 mg, 0.036 mmol, 1 eq) in DCM (10 mL) was added a solution of hydrogen chloride (4 M, 2 mL) in 1,4-dioxane at 0° C. The mixture was then stirred at room temperature for 3 h. Upon completion, the resulting mixture was concentrated under vacuum and the resulting mixture was dissolved in water, washed with DCM. The aqueous layer was freeze-dried to give 5-(aminomethyl)-1-(pyridin-4-yl)-4,6,7,8-tetrahydro-3H-9-oxa-2-thia-4-azabenzo[cd]azulen-3-one hydrochloride (12 mg, 0.0342 mol) as a yellow solid. MS obsd. ($ESI^+$): m/z 314.0 [$(M+H)^+$]. $^1$H NMR (400 MHz, MeOD) δ ppm: 8.73 (s, 2H), 8.36 (d, J=5.5 Hz, 2H), 4.54-4.62 (m, 2H), 4.24 (s, 2H), 3.15 (dd, J=7.2, 4.9 Hz, 2H), 2.37 (dt, J=11.5, 5.8 Hz, 2H).

Example 16: 5-(((4-methoxybenzyl)amino)methyl)-1-(pyridin-4-yl)-4,6,7,8-tetrahydro-3H-9-oxa-2-thia-4-azabenzo[cd]azulen-3-one

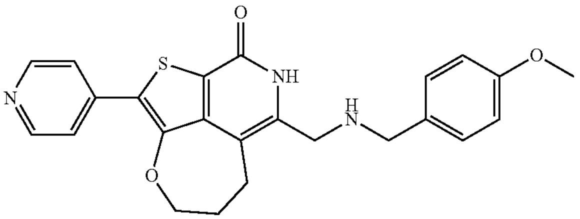 [SMILES: COc1ccc(CNCc2[nH]c(=O)c3sc(-c4ccncc4)c4c3c2CCCO4)cc1]

Step A: 1-bromo-5-(((4-methoxybenzyl)amino)methyl)-4,6,7,8-tetrahydro-3H-9-oxa-2-thia-4-azabenzo[cd]azulen-3-one

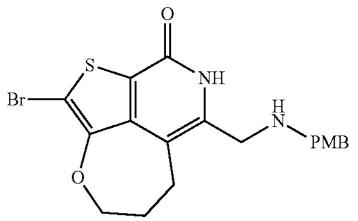

A solution of 1-bromo-5-(bromomethyl)-4,6,7,8-tetrahydro-3H-9-oxa-2-thia-4-azabenzo[cd]azulen-3-one in $CHCl_3$ (30 ml) and DCM (60 ml) from previous step was added to (4-methoxyphenyl)methanamine (211 mg, 1.54 mmol, 2.0 eq). The mixture was stirred at 25° C. for 16 h. LCMS showed the reaction was complete. Then the mixture was concentrated in vacuum and purified by flash chromatography column (DCM:MeOH=100:3) to give 1-bromo-5-(((4-methoxybenzyl)amino)methyl)-4,6,7,8-tetrahydro-3H-9-oxa-2-thia-4-azabenzo[cd]azulen-3-one (130 mg) as a yellow oil. MS obsd. ($ESI^+$): m/z 434.8, 436.8 $[(M+H)^+]$.

Step B: Tert-butyl ((1-bromo-3-oxo-4,6,7,8-tetrahydro-3H-9-oxa-2-thia-4-azabenzo[cd]azulen-5-yl)methyl)(4-methoxybenzyl)carbamate

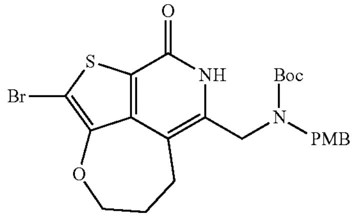

To a solution of 1-bromo-5-(((4-methoxybenzyl)amino)methyl)-4,6,7,8-tetrahydro-3H-9-oxa-2-thia-4-azabenzo[cd]azulen-3-one (120 mg, 0.28 mmol, 1.0 eq) in DCM (5 ml) was added TEA (41.9 mg, 0.41 mmol, 1.5 eq) and $(Boc)_2O$ (90.5 mg, 0.41 mmol, 1.5 eq). The mixture was stirred at 25° C. for 16 h. LCMS showed the reaction was complete. Then the mixture was concentrated in vacuum and purified by flash chromatography column to give tert-butyl ((1-bromo-3-oxo-4,6,7,8-tetrahydro-3H-9-oxa-2-thia-4-azabenzo[cd]azulen-5-yl)methyl)(4-methoxybenzyl)carbamate (70 mg) as a white solid. MS obsd. ($ESI^+$): m/z 535.0, 537.0 $[(M+H)^+]$.

Step C: Tert-butyl (4-methoxybenzyl)((3-oxo-1-(pyridin-4-yl)-4,6,7,8-tetrahydro-3H-9-oxa-2-thia-4-azabenzo[cd]azulen-5-yl)methyl)carbamate

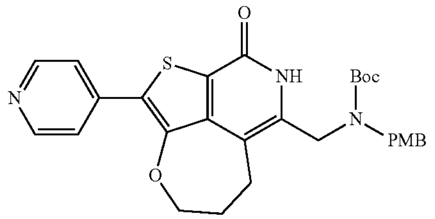

To a solution of tert-butyl ((1-bromo-3-oxo-4,6,7,8-tetrahydro-3H-9-oxa-2-thia-4-azabenzo[cd]azulen-5-yl)methyl)(4-methoxybenzyl)carbamate (70 mg, 0.13 mmol, 1.0 eq) in dioxane/$H_2O$=10:1 (11 ml) was added pyridin-4-ylboronic acid (32 mg, 0.26 mmol, 2.0 eq) and $K_2CO_3$ (54 mg, 0.39 mmol, 3.0 eq). The mixture was degassed with $N_2$ for 3 times. Then $Pd(dppf)Cl_2$ (29 mg, 0.039 mmol, 0.3 eq) was added to the mixture. The mixture was stirred at 80° C. for 1 h under microwave irradiation. LCMS showed the reaction was complete. Then water was added to the mixture and extracted with EA. The combine organic layer was dried over anhydrous $Na_2SO_4$ and concentrated in vacuum. The residue was purified by prep-TLC to give tert-butyl (4-methoxybenzyl)((3-oxo-1-(pyridin-4-yl)-4,6,7,8-tetrahydro-3H-9-oxa-2-thia-4-azabenzo[cd]azulen-5-yl)methyl)carbamate (50 mg) as a yellow solid. MS obsd. ($ESI^+$): m/z 534.1 $[(M+H)^+]$.

Step D: 5-(((4-methoxybenzyl)amino)methyl)-1-(pyridin-4-yl)-4,6,7,8-tetrahydro-3H-9-oxa-2-thia-4-azabenzo[cd]azulen-3-one

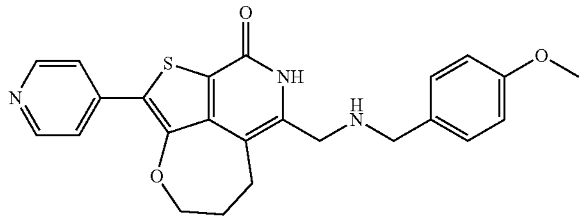 [SMILES: COc1ccc(CNCc2[nH]c(=O)c3sc(-c4ccncc4)c4c3c2CCCO4)cc1]

To a solution of tert-butyl (4-methoxybenzyl)((3-oxo-1-(pyridin-4-yl)-4,6,7,8-tetrahydro-3H-9-oxa-2-thia-4-azabenzo[cd]azulen-5-yl)methyl)carbamate (50 mg, 0.094 mmol, 1.0 eq) in MeOH (5 mL) was added 4M HCl/dioxane (2 mL). The mixture was stirred at 25° C. for 16 h. LCMS showed the reaction was complete. Then the mixture was concentrated in vacuum and purified by Prep-HPLC to give 5-(((4-methoxybenzyl)amino)methyl)-1-(pyridin-4-yl)-4,6,7,8-tetrahydro-3H-9-oxa-2-thia-4-azabenzo[cd]azulen-3-one (16.8 mg) as a white solid. MS obsd. ($ESI^+$): m/z 434.0 $[(M+H)^+]$. $^1H$ NMR (400 MHz, DMSO) δ 8.63 (dd, J=4.6, 1.6 Hz, 2H), 8.19 (s, 1H), 7.77 (dd, J=4.6, 1.6 Hz, 2H), 7.25 (d, J=8.6 Hz, 2H), 6.87 (d, J=8.6 Hz, 2H), 4.41-4.34 (m, 2H), 3.72 (s, 3H), 3.64 (d, J=11.2 Hz, 4H), 2.83 (dd, J=7.2, 4.9 Hz, 2H), 2.13 (dd, J=11.9, 5.8 Hz, 2H).

Example 17: 7-(aminomethyl)-2-(1H-pyrazol-4-yl)-12-oxa-3-thia-6-azatricyclo[6.4.1.04,13]trideca-1,4(13),7-trien-5-one

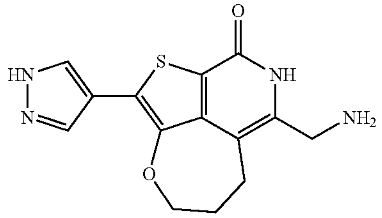 [SMILES: NCc1[nH]c(=O)c2sc(-c3cn[nH]c3)c3c2c1CCCO3]

Example 17 was prepared in a similar manner as that illustrated in Example 15. MS obsd. ($ESI^+$): m/z $[(M+H)^+]$ 303.

The following compounds were prepared in a similar manner as that illustrated in Example 10.

| Ex. No. | Structure | Name | MS obsd. (ESI+): m/z [(M + H)+] |
|---|---|---|---|
| 18 | 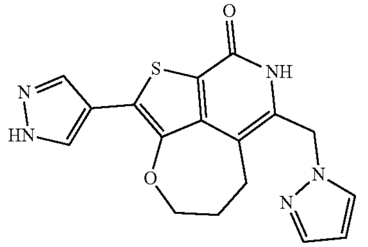 [SMILES: O=c1[nH]c(Cn2cccn2)c2c3c(c(-c4cn[nH]c4)sc13)OCCC2] | 2-(1H-pyrazol-4-yl)-7-(pyrazol-1-ylmethyl)-12-oxa-3-thia-6-azatricyclo[6.4.1.04,13]trideca-1,4(13),7-trien-5-one | 354 |
| 19 | 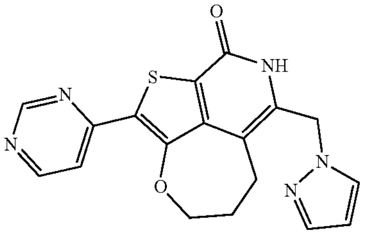 [SMILES: O=c1[nH]c(Cn2cccn2)c2c3c(c(-c4ccncn4)sc13)OCCC2] | 7-(pyrazol-1-ylmethyl)-2-pyrimidin-4-yl-12-oxa-3-thia-6-azatricyclo[6.4.1.$0^{4,13}$]trideca-1,4(13),7-trien-5-one | 366 |
| 20 | 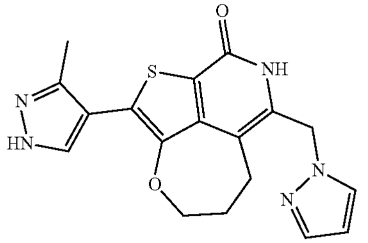 [SMILES: Cc1n[nH]cc1-c1sc2c(=O)[nH]c(Cn3cccn3)c3c2c1OCCC3] | 2-(3-methyl-1H-pyrazol-4-yl)-7-(pyrazol-1-ylmethyl)-12-oxa-3-thia-6-azatricyclo [6.4.1.$0^{4,13}$]trideca-1,4(13),7-trien-5-one | 368 |
| 21 | 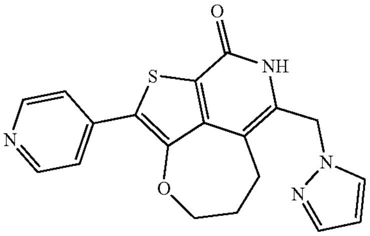 [SMILES: O=c1[nH]c(Cn2cccn2)c2c3c(c(-c4ccncc4)sc13)OCCC2] | 7-(pyrazol-1-ylmethyl)-2-(4-pyridyl)-12-oxa-3-thia-6-azatricyclo[6.4.1.$0^{4,13}$]trideca-1,4(13),7-trien-5-one | 365 |
| 22 | 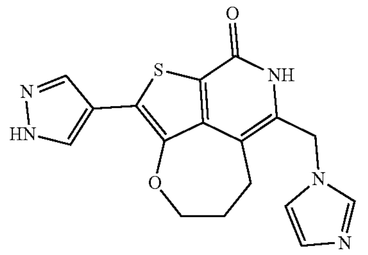 [SMILES: O=c1[nH]c(Cn2ccnc2)c2c3c(c(-c4cn[nH]c4)sc13)OCCC2] | 7-(imidazol-1-ylmethyl)-2-(1H-pyrazol-4-yl)-12-oxa-3-thia-6-azatricyclo[6.4.1.$0^{4,13}$]trideca-1,4(13),7-trien-5-one | 354 |
| 23 | 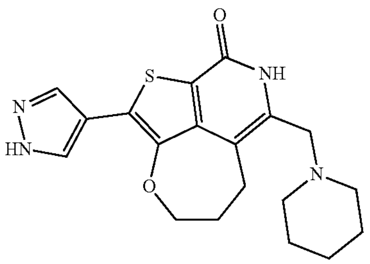 [SMILES: O=c1[nH]c(CN2CCCCC2)c2c3c(c(-c4cn[nH]c4)sc13)OCCC2] | 5-(piperidin-1-ylmethyl)-1-(1H-pyrazol-4-yl)-4,6,7,8-tetrahydro-3H-9-oxa-2-thia-4-azabenzo[cd]azulen-3-one | 371 |

-continued

| Ex. No. | Structure | Name | MS obsd. (ESI$^+$): m/z [(M + H)$^+$] |
| --- | --- | --- | --- |
| 24 | 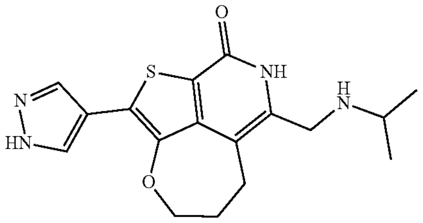 [SMILES: CC(C)NCc1[nH]c(=O)c2sc(-c3cn[nH]c3)c3c2c1CCCO3] | 5-((isopropylamino)methyl)-1-(1H-pyrazol-4-yl)-4,6,7,8-tetrahydro-3H-9-oxa-2-thia-4-azabenzo[cd]azulen-3-one | 345 |
| 25 | 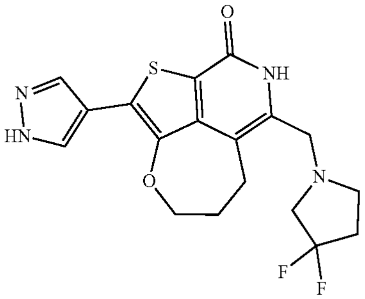 [SMILES: O=c1[nH]c(CN2CCC(F)(F)C2)c2c3c(c(-c4cn[nH]c4)sc13)OCCC2] | 7-[(3,3-difluoropyrrolidin-1-yl)methyl]-2-(1H-pyrazol-4-yl)-12-oxa-13-thia-6-azatricyclo [6.4.1.0$^{4,13}$]trideca-1,4(13),7-trien-5-one | 393 |

Example 26: (S)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile

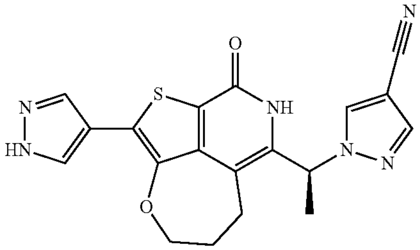 [SMILES: C[C@@H](c1[nH]c(=O)c2sc(-c3cn[nH]c3)c3c2c1CCCO3)n1cc(C#N)cn1]

Example 27: (R)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile

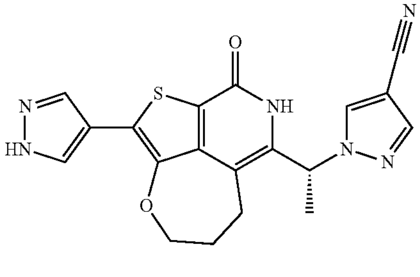 [SMILES: C[C@H](c1[nH]c(=O)c2sc(-c3cn[nH]c3)c3c2c1CCCO3)n1cc(C#N)cn1]

Step A: 1-bromo-5-(1-hydroxyethyl)-4,6,7,8-tetrahydro-3H-9-oxa-2-thia-4-azabenzo[cd]azulen-3-one

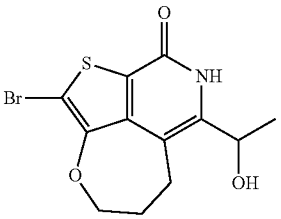 [SMILES: CC(O)c1[nH]c(=O)c2sc(Br)c3c2c1CCCO3]

To a solution of 1-bromo-3-oxo-4,6,7,8-tetrahydro-3H-9-oxa-2-thia-4-azabenzo[cd]azulene-5-carbaldehyde (170 mg, 0.54 mmol) in THF (20 mL) was added $CH_3MgBr$ (5.4 mL, 5.4 mmol, 1M) dropwise at 0° C. The mixture was stirred at 0° C. for 1 h. The reaction was quenched by saturated $NH_4Cl$ solution and extracted by EtOAc. The organic layer was dried over anhydrous sodium sulfate and concentrated in vacuum to give 1-bromo-5-(1-hydroxyethyl)-4,6,7,8-tetrahydro-3H-9-oxa-2-thia-4-azabenzo[cd]azulen-3-one (166 mg) as a yellow solid which was used in the next step without further purification. MS obsd. (ESI$^+$): m/z 332.3 [(M+H)$^+$].

Step B: 1-bromo-5-(1-chloroethyl)-4,6,7,8-tetrahydro-3H-9-oxa-2-thia-4-azabenzo[cd]azulen-3-one

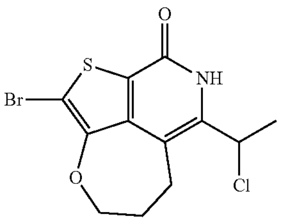 [SMILES: CC(Cl)c1[nH]c(=O)c2sc(Br)c3c2c1CCCO3]

To a solution of 1-bromo-5-(1-hydroxyethyl)-4,6,7,8-tetrahydro-3H-9-oxa-2-thia-4-azabenzo[cd]azulen-3-one (160 mg, 0.49 mmol) in DCM (15 mL) was added $SOCl_2$ (577 mg, 4.9 mmol) at 0° C. The mixture was stirred at 25° C. for 2 h. The mixture was concentrated in vacuum to give 1-bromo-5-(1-chloroethyl)-4,6,7,8-tetrahydro-3H-9-oxa-2-thia-4-azabenzo[cd]azulen-3-one (150 mg) as a yellow solid which was used in the next step without further purification. MS obsd. ($ESI^+$): m/z 348.3 [$(M+H)^+$], 350.3 [$(M+2+H)^+$].

Step C: 1-(1-(1-bromo-3-oxo-4,6,7,8-tetrahydro-3H-9-oxa-2-thia-4-azabenzo[cd]azulen-5-yl)ethyl)-1H-pyrazole-4-carbonitrile

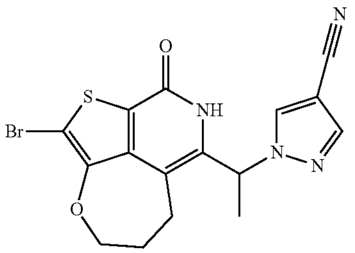 [SMILES: CC(c1[nH]c(=O)c2sc(Br)c3c2c1CCCO3)n1cc(C#N)cn1]

To a solution of 1-bromo-5-(1-chloroethyl)-4,6,7,8-tetrahydro-3H-9-oxa-2-thia-4-azabenzo[cd]azulen-3-one (150 mg, 0.43 mmol) in MeCN (20 mL) was added 1H-pyrazole-4-carbonitrile (400 mg, 4.30 mmol). The mixture was stirred at 80° C. for 16 h. The mixture was concentrated in vacuum, the residue was purified by flash column chromatography (eluted with DCM:MeOH=20:1) at first and then purified by reverse phase chromatography (eluted with MeCN in water from 0% to 40%, 0.5% FA in water) to give 1-(1-(1-bromo-3-oxo-4,6,7,8-tetrahydro-3H-9-oxa-2-thia-4-azabenzo[cd]azulen-5-yl)ethyl)-1H-pyrazole-4-carbonitrile (106 mg) as a white solid. MS obsd. ($ESI^+$): m/z 407.4 [$(M+H)^+$].

Step D: 1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile

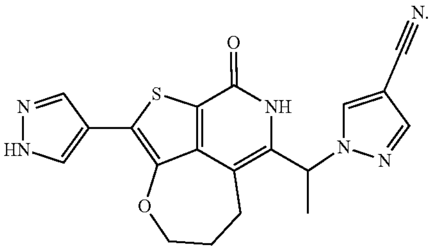 [SMILES: CC(c1[nH]c(=O)c2sc(-c3cn[nH]c3)c3c2c1CCCO3)n1cc(C#N)cn1]

To a solution of 1-(1-(1-bromo-3-oxo-4,6,7,8-tetrahydro-3H-9-oxa-2-thia-4-azabenzo[cd]azulen-5-yl)ethyl)-1H-pyrazole-4-carbonitrile (20 mg, 49.4 umol) 1,4-dioxane: $H_2O$=5:1 (3.6 mL) was added sodium carbonate (16 mg, 148.0 umol), cyclopentyl(diphenyl)phosphane;dichloropalladium;iron (Pd(dppf)$Cl_2$-DCM) (8 mg, 9.9 umol), 4-(4,4,5,5-tetramethyl-1,3,2-dioxaborolan-2-yl)-1H-pyrazole (19 mg, 98.7 umol) and dicyclohexyl-[2-(2,4,6-triisopropylphenyl)phenyl]phosphane (7 mg, 14.8 umol). The suspension was degassed with $N_2$ for 10 min. Then the mixture was sealed in a tube and heated to 105° C. with microwave for 1.5 h under $N_2$. Upon the completion, the mixture was added $H_2O$ and extracted by ethyl acetate. The organic layer was dried and concentrated in vacuum. The crude was purified by silica Prep-TLC (eluted with DCM:MeOH=20:1) at first and then purified by Prep-HPLC (eluted with MeCN in water from 0% to 45%, 0.1% FA in water) to give 1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile (2 mg) as a white solid. MS obsd. ($ESI^+$): m/z 393.1 [$(M+H)^+$]. $^1$H NMR (400 MHz) δ ppm: 13.20 (s, 1H), 10.97 (s, 1H), 8.73 (s, 1H), 8.23-7.79 (m, 3H), 5.96 (q, J=6.6 Hz, 1H), 4.32 (dt, J=11.9, 5.8 Hz, 2H), 3.01 (dd, J=12.8, 5.9 Hz, 2H), 2.15-2.09 (m, 2H), 1.89 (d, J=6.9 Hz, 3H).

1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile (35 mg) were separated by chiral HPLC (Column: AD-H, Column size: 0.46 cm I.D.×15 cm L, Injection: 2 ul, Mobile phase: HEP:ETOH (0.1% DEA)=60:40, Flow rate: 0.5 ml, Wave length: UV 254 nm, Temperature 25° C., Sample solution in ETOH) to give (S)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile (5.8 mg) as a white solid. MS obsd. ($ESI^+$): m/z 393.1 [$(M+H)^+$]. $^1$H NMR (400 MHz, DMSO) δ ppm: 13.17 (s, 1H), 10.95 (s, 1H), 8.73 (s, 1H), 8.01 (d, J=81.1 Hz, 3H), 5.95 (q, J=6.9 Hz, 1H), 4.37-4.27 (m, 2H), 3.01 (dd, J=12.9, 6.0 Hz, 2H), 2.16-2.07 (m, 2H), 1.89 (d, J=7.0 Hz, 3H) and (R)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile (3.8 mg). MS obsd. ($ESI^+$): m/z 393.1 [$(M+H)^+$]. $^1$H NMR (400 MHz, DMSO) δ ppm: δ 13.18 (s, 1H), 10.96 (s, 1H), 8.73 (s, 1H), 8.25-7.82 (m, 3H), 5.95 (q, J=6.9 Hz, 1H), 4.38-4.28 (m, 2H), 3.01 (dd, J=12.8, 6.0 Hz, 2H), 2.17-2.07 (m, 2H), 1.89 (d, J=7.0 Hz, 3H). The absolute stereochemistry was randomly assigned for these two compounds.

Example 28: 5-(2-hydroxypropan-2-yl)-1-(1H-pyrazol-4-yl)-4,6,7,8-tetrahydro-3H-9-oxa-2-thia-4-azabenzo[cd]azulen-3-one

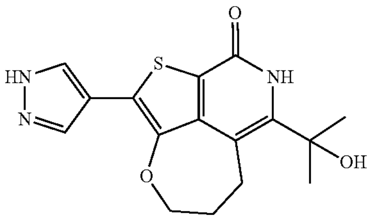 [SMILES: CC(C)(O)c1[nH]c(=O)c2sc(-c3cn[nH]c3)c3c2c1CCCO3]

Step A: 5-acetyl-1-bromo-4,6,7,8-tetrahydro-3H-9-oxa-2-thia-4-azabenzo[cd]azulen-3-one

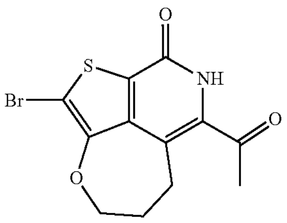

To a solution of 1-bromo-5-(1-hydroxyethyl)-4,6,7,8-tetrahydro-3H-9-oxa-2-thia-4-azabenzo[cd]azulen-3-one (340 mg, 1.03 mmol) in DCM (10 mL) was added Dess-Martin Periodinane (1.31 g, 3.09 mmol) in portions at 0° C. Then the mixture was stirred at 25° C. for 3 h. Upon the completion, the mixture was diluted with water (30 mL), quenched with saturated $Na_2S203$ (30 mL), extracted with DCM (30 mL×3). The combined organic phase was washed with saturated $NaHCO_3$ and brine, dried over anhydrous $Na_2SO_4$, filtered and concentrated in vacuum. The crude product was purified by silica gel column chromotography (eluted with DCM:$^i$PrOH=10:1) to give 7-acetyl-2-bromo-12-oxa-3-thia-6-azatricyclo[6.4.1.$0^{4,13}$]trideca-1,4(13),7-trien-5-one (210 mg) as a white solid. MS obsd. ($ESI^+$): m/z 328.0 $[(M+H)^+]$.

Step B: 5-acetyl-1-(1-((2-(trimethylsilyl)ethoxy)methyl)-1H-pyrazol-4-yl)-4,6,7,8-tetrahydro-3H-9-oxa-2-thia-4-azabenzo[cd]azulen-3-one

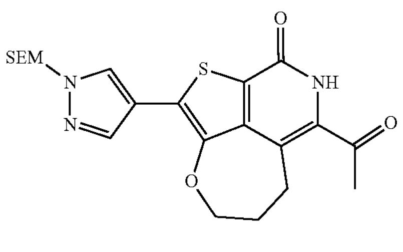 [SMILES: CC(=O)c1[nH]c(=O)c2sc(-c3cnn(COCC[Si](C)(C)C)c3)c3c2c1CCCO3]

The mixture of 5-acetyl-1-bromo-4,6,7,8-tetrahydro-3H-9-oxa-2-thia-4-azabenzo[cd]azulen-3-one (63 mg, 192.1 umol), 4-(4,4,5,5-tetramethyl-1,3,2-dioxaborolan-2-yl)-1-((2-(trimethylsilyl)ethoxy)methyl)-1H-pyrazole (125 mg, 384.1 umol), sodium carbonate (61 mg, 576.2 umol), Xphos (28 mg, 57.6 umol), $Pd(dppf)Cl_2$ (42 mg, 57.6 umol) in 1,4-dioxane:$H_2O$=5:1 (12 mL) was purged with argon 3 times. Then it was stirred at 105° C. under M.W. for 1 h. Upon the completion, the resulting mixture was cooled to room temperature, concentrated in vacuum. The crude product was purified by silica gel column chromatography (eluted with DCM:MeOH=10:1) to give 7-acetyl-2-[1-(2-trimethylsilylethoxymethyl)pyrazol-4-yl]-12-oxa-3-thia-6-azatricyclo[6.4.1.$0^{4,13}$]trideca-1,4(13),7-trien-5-one (21 mg) as a white solid. MS obsd. ($ESI^+$): m/z 446.2 $[(M+H)^+]$.

Step C: 5-(2-hydroxypropan-2-yl)-1-(1-((2-(trimethylsilyl)ethoxy)methyl)-1H-pyrazol-4-yl)-4,6,7,8-tetrahydro-3H-9-oxa-2-thia-4-azabenzo[cd]azulen-3-one

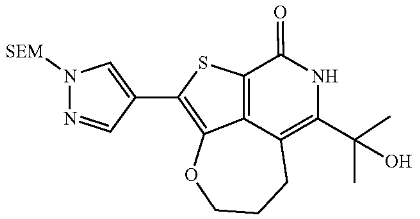 [SMILES: CC(C)(O)c1[nH]c(=O)c2sc(-c3cnn(COCC[Si](C)(C)C)c3)c3c2c1CCCO3]

To a solution of 5-acetyl-1-(1-((2-(trimethylsilyl)ethoxy)methyl)-1H-pyrazol-4-yl)-4,6,7,8-tetrahydro-3H-9-oxa-2-thia-4-azabenzo[cd]azulen-3-one (60 mg, 134.6 umol) in THF (15 mL) was added methylmagnesium bromide (3 M in ethyl ether, 2.69 mmol, 0.90 mL) at 0° C. After addition, the mixture was warmed to rt and stirred for 2 h. Upon the completion, the resulting mixture was quenched with saturated $NH_4Cl$ at 0° C. The reaction was extracted with EtOAc. The combined organic solution was dried, concentrated, and purified by silica gel column chromatography (eluted with DCM:MeOH=10:1) to give 7-(1-hydroxy-1-methyl-ethyl)-2-[1-(2-trimethylsilylethoxymethyl)pyrazol-4-yl]-12-oxa-3-thia-6-azatricyclo[6.4.1.$0^{4,13}$]trideca-1,4(13),7-trien-5-one (33 mg) as a colorless liquid. MS obsd. ($ESI^+$): m/z 462.2 $[(M+H)^+]$.

Step D: 5-(2-hydroxypropan-2-yl)-1-(1H-pyrazol-4-yl)-4,6,7,8-tetrahydro-3H-9-oxa-2-thia-4-azabenzo[cd]azulen-3-one

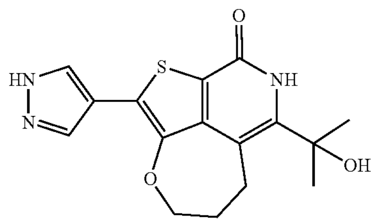 [SMILES: CC(C)(O)c1[nH]c(=O)c2sc(-c3cn[nH]c3)c3c2c1CCCO3]

To a solution of 5-(2-hydroxypropan-2-yl)-1-(1-((2-(trimethylsilyl)ethoxy)methyl)-1H-pyrazol-4-yl)-4,6,7,8-tetrahydro-3H-9-oxa-2-thia-4-azabenzo[cd]azulen-3-one (45 mg, 97.5 umol) in DCM (5 mL) was added TFA (2 mL) at 0° C. The solution was stirred at room temperature for 1 h. Upon the completion, the mixture was concentrated and diluted with MeOH. PH was adjusted to about 7 with 30% $NH_4OH$ solution. It was purified by Prep-HPLC to give 7-(1-hydroxy-1-methyl-ethyl)-2-(1H-pyrazol-4-yl)-12-oxa-3-thia-6-azatricyclo[6.4.1.$0^{4,13}$]trideca-1,4(13),7-trien-5-one (11.2 mg) as a white solid. MS obsd. ($ESI^+$): m/z 331.9 $[(M+H)^+]$. $^1H$ NMR (400 MHz, DMSO) δ ppm: 13.18 (s, 1H), 9.73 (s, 1H), 8.19 (s, 1H), 7.90 (s, 1H), 6.12 (s, 1H), 4.30 (t, J=6.8 Hz, 2H), 3.10-2.91 (m, 2H), 2.20-1.98 (m, 2H), 1.56 (s, 6H).

Example 29: 5-(2-hydroxypropan-2-yl)-1-(pyridin-4-yl)-4,6,7,8-tetrahydro-3H-9-oxa-2-thia-4-azabenzo[cd]azulen-3-one

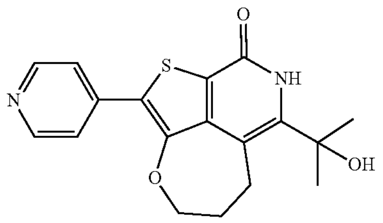 [SMILES: CC(C)(O)c1[nH]c(=O)c2sc(-c3ccncc3)c3c2c1CCCO3]

Example 29 was prepared in a similar manner as that illustrated in Example 28 from corresponding bromide through Suzuki reaction. MS obsd. ($ESI^+$): m/z $[(M+H)^+]$ 343.

Example 30: (S)-5-(1-(azetidin-1-yl)ethyl)-1-(1H-pyrazol-4-yl)-4,6,7,8-tetrahydro-3H-9-oxa-2-thia-4-azabenzo[cd]azulen-3-one

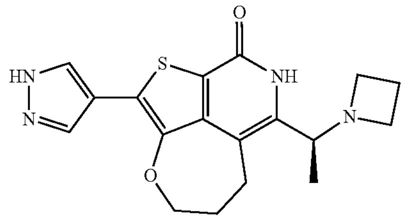 [SMILES: C[C@@H](c1[nH]c(=O)c2sc(-c3cn[nH]c3)c3c2c1CCCO3)N1CCC1]

Example 31: (R)-5-(1-(azetidin-1-yl)ethyl)-1-(1H-pyrazol-4-yl)-4,6,7,8-tetrahydro-3H-9-oxa-2-thia-4-azabenzo[cd]azulen-3-one

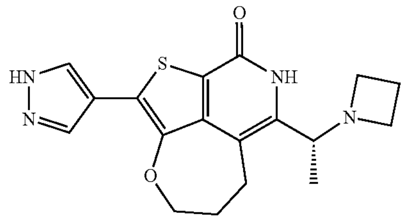 [SMILES: C[C@H](c1[nH]c(=O)c2sc(-c3cn[nH]c3)c3c2c1CCCO3)N1CCC1]

Step A: 5-(1-hydroxyethyl)-1-(1-trityl-1H-pyrazol-4-yl)-4,6,7,8-tetrahydro-3H-9-oxa-2-thia-4-azabenzo[cd]azulen-3-one

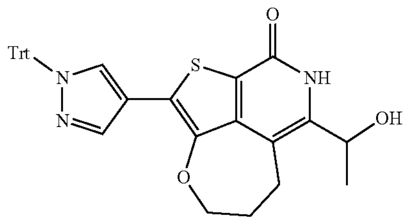

The mixture of 1-bromo-5-(1-hydroxyethyl)-4,6,7,8-tetrahydro-3H-9-oxa-2-thia-4-azabenzo[cd]azulen-3-one (30 mg, 90.8 umol), 4-(4,4,5,5-tetramethyl-1,3,2-dioxaborolan-2-yl)-1-trityl-1H-pyrazole (79 mg, 181.7 umol, 2 eq), sodium carbonate (39 mg, 363.4 umol, 4 eq), Xphos (13 mg, 27.3 umol), Pd(dppf)$Cl_2$ (20 mg, 27.3 umol) in 1,4-dioxane: $H_2O$=5:1 (6 mL) was purged with argon 3 times. Then it was stirred at 105° C. under M.W. for 1 h. Upon the completion, the resulting mixture was cooled to room temperature, concentrated in vacuum. The crude product was purified by silica gel column chromatography (eluted with DCM: MeOH=10:1) to give 7-(1-hydroxyethyl)-2-(1-tritylpyrazol-4-yl)-12-oxa-3-thia-6-azatricyclo[6.4.1.$0^{4,13}$]trideca-1,4(13),7-trien-5-one (34.7 mg) as a yellow solid. MS obsd. ($ESI^+$): m/z 560.2 $[(M+H)^+]$.

Step B: 5-acetyl-1-(1-trityl-1H-pyrazol-4-yl)-4,6,7,8-tetrahydro-3H-9-oxa-2-thia-4-azabenzo[cd]azulen-3-one

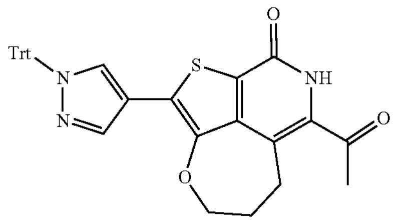

To a solution of 7-(1-hydroxyethyl)-2-(1-tritylpyrazol-4-yl)-12-oxa-3-thia-6-azatricyclo[6.4.1.$0^{4,13}$]trideca-1,4(13),7-trien-5-one (100 mg, 178.7 umol) in DCM (10 mL) was added Dess-Martin Periodinane (151.57 mg, 357.4 umol) in portions at 0° C. Then the mixture was stirred at 25° C. for 2 h. Upon the completion, the mixture was diluted with water, quenched with saturated $Na_2S203$, extracted with DCM. The combined organic phase was washed with saturated $NaHCO_3$ and brine, dried over anhydrous $Na_2SO_4$, filtered and concentrated in vacuum. The crude product was purified by silica Prep-TLC (DCM:$^i$PrOH=10:1) to give 7-acetyl-2-(1-tritylpyrazol-4-yl)-12-oxa-3-thia-6-azatricyclo[6.4.1.$0^{4,13}$]trideca-1,4(13),7-trien-5-one (63 mg) as a yellow solid. MS obsd. ($ESI^+$): m/z 559.2 $[(M+H)^+]$.

Step C: 5-(1-(azetidin-1-yl)ethyl)-1-(1-trityl-1H-pyrazol-4-yl)-4,6,7,8-tetrahydro-3H-9-oxa-2-thia-4-azabenzo[cd]azulen-3-one

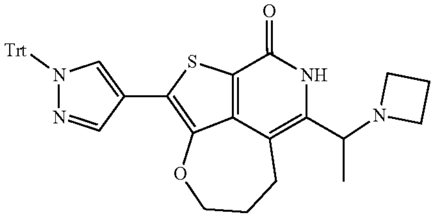

To a suspension of 7-acetyl-2-(1-tritylpyrazol-4-yl)-12-oxa-3-thia-6-azatricyclo[6.4.1.$0^{4,13}$]trideca-1,4(13),7-trien-5-one (65 mg, 116.6 umol) in MeOH (20 mL) was added acetic acid (14 mg, 233.1 umol, 2 eq), azetidine (67 mg, 1.17 mmol) and sodium cyanoborohydride (22 mg, 349.7 umol) followed. The mixture was stirred at rt for 2 h. Upon the completion, the mixture was concentrated, diluted with water and extracted with DCM. The organic layers were combined, washed with brine, dried over anhydrous sodium sulfate, filtered and the filtrate was concentrated in vacuum. The residue was purified by silica Prep-TLC (eluted with DCM:MeOH=10:1) to give 7-[1-(azetidin-1-yl)ethyl]-2-(1-tritylpyrazol-4-yl)-12-oxa-3-thia-6-azatricyclo[6.4.1.$0^{4,13}$]trideca-1,4(13),7-trien-5-one (55 mg) as a white solid. MS obsd. ($ESI^+$): m/z 599.2 [$(M+H)^+$].

Step D: 5-(1-(azetidin-1-yl)ethyl)-1-(1H-pyrazol-4-yl)-4,6,7,8-tetrahydro-3H-9-oxa-2-thia-4-azabenzo[cd]azulen-3-one

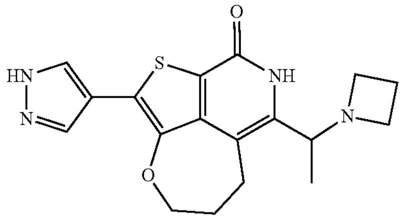 [SMILES: CC(c1[nH]c(=O)c2sc(-c3cn[nH]c3)c3c2c1CCCO3)N1CCC1]

To a solution of 7-[1-(azetidin-1-yl)ethyl]-2-(1-tritylpyrazol-4-yl)-12-oxa-3-thia-6-azatricyclo[6.4.1.$0^{4,13}$]trideca-1,4(13),7-trien-5-one (55 mg, 91.9 umol) in DCM (5 mL) was added TFA (2 mL) at 0° C. The solution was stirred at room temperature for 1 h. Upon the completion, the mixture was concentrated and diluted with MeOH. PH was adjusted to about 8 with 30% $NH_4OH$ solution. It was purified by Prep-HPLC to give 7-[1-(azetidin-1-yl)ethyl]-2-(1H-pyrazol-4-yl)-12-oxa-3-thia-6-azatricyclo[6.4.1.$0^{4,13}$]trideca-1,4(13),7-trien-5-one (18 mg) as a light yellow solid. MS obsd. ($ESI^+$): m/z 357.2 [$(M+H)^+$]. $^1H$ NMR (400 MHz, MeOD) δ ppm: 8.19-8.09 (m, 1H), 8.05 (s, 2H), 4.40 (d, J=6.3 Hz, 2H), 4.21-4.03 (m, 1H), 3.64-3.45 (m, 4H), 3.21-3.06 (m, 1H), 3.06-2.94 (m, 1H), 2.34-2.14 (m, 4H), 1.30 (d, J=6.6 Hz, 3H). 7-[1-(azetidin-1-yl)ethyl]-2-(1H-pyrazol-4-yl)-12-oxa-3-thia-6-azatricyclo[6.4.1.$0^{4,13}$]trideca-1,4(13),7-trien-5-one underwent SFC chiral resolution to give (S)-5-(1-(azetidin-1-yl)ethyl)-1-(1H-pyrazol-4-yl)-4,6,7,8-tetrahydro-3H-9-oxa-2-thia-4-azabenzo[cd]azulen-3-one and (R)-5-(1-(azetidin-1-yl)ethyl)-1-(1H-pyrazol-4-yl)-4,6,7,8-tetrahydro-3H-9-oxa-2-thia-4-azabenzo[cd]azulen-3-one. The absolute stereochemistry was randomly assigned for these two compounds.

Examples 32 and 33 were prepared using intermediates from Example 30 and through chiral resolution.

| Ex. No. | Structure | Name | MS obsd. ($ESI^+$): m/z [$(M + H)^+$] |
|---|---|---|---|
| 32 | 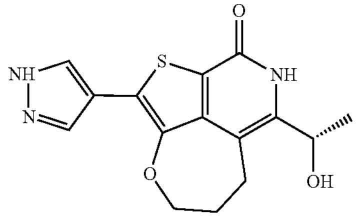 [SMILES: C[C@H](O)c1[nH]c(=O)c2sc(-c3cn[nH]c3)c3c2c1CCCO3] | (S)-5-(1-hydroxyethyl)-1-(1H-pyrazol-4-yl)-4,6,7,8-tetrahydro-3H-9-oxa-2-thia-4-azabenzo[cd]azulen-3-one# | 318 |
| 33 | 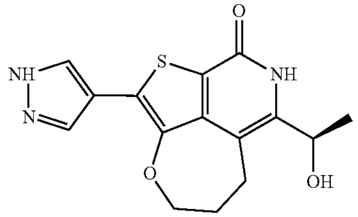 [SMILES: C[C@@H](O)c1[nH]c(=O)c2sc(-c3cn[nH]c3)c3c2c1CCCO3] | (R)-5-(1-hydroxyethyl)-1-(1H-pyrazol-4-yl)-4,6,7,8-tetrahydro-3H-9-oxa-2-thia-4-azabenzo[cd]azulen-3-one# | 318 |

#The absolute stereochemistry was randomly assigned.

Example 34: (5-(1-(cyclobutylamino)ethyl)-1-(1H-pyrazol-4-yl)-4,6,7,8-tetrahydro-3H-9-oxa-2-thia-4-azabenzo[cd]azulen-3-one

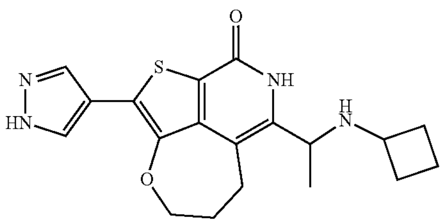 [SMILES: CC(NC1CCC1)c1[nH]c(=O)c2sc(-c3cn[nH]c3)c3c2c1CCCO3]

Example 34 was prepared in a similar manner as that illustrated in Example 30. MS obsd. ($ESI^+$): m/z $[(M+H)^+]$ 371.

Example 35: (S)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one

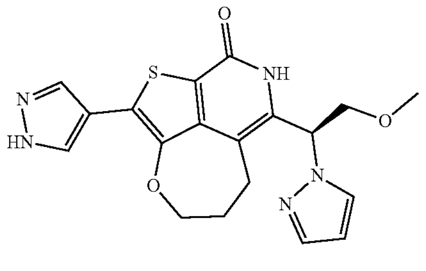 [SMILES: COC[C@H](c1[nH]c(=O)c2sc(-c3cn[nH]c3)c3c2c1CCCO3)n1cccn1]

Example 36: (R)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one

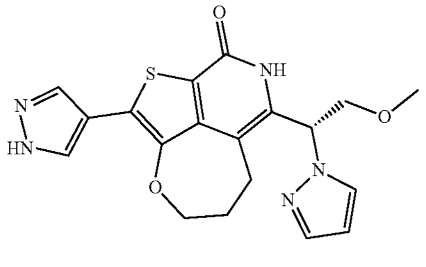 [SMILES: COC[C@@H](c1[nH]c(=O)c2sc(-c3cn[nH]c3)c3c2c1CCCO3)n1cccn1]

Step A: 1-bromo-5-(oxiran-2-yl)-4,6,7,8-tetrahydro-3H-9-oxa-2-thia-4-azabenzo[cd]azulen-3-one

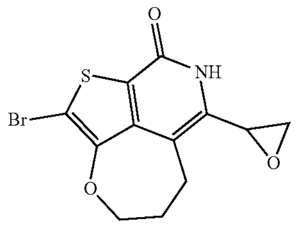 [SMILES: O=c1[nH]c(C2CO2)c2c3c(c(Br)sc13)OCCC2]

A mixture of sodium hydride (26 mg, 636.6 umol, 2 eq, 60% purity) and trimethylsulfonium iodide (195 mg, 954.9 umol) in DMSO (5 mL) was stirred for 1 h at r.t. Then a solution of bromo-5-oxo-12-oxa-3-thia-6-azatricyclo[6.4.1.$0^{4,13}$]trideca-1,4(13),7-triene-7-carbaldehyde (100 mg, 318.3 umol) in DMSO (10 mL) was added in portions. It was stirred for another 3 h at r.t. Upon the completion, the mixture was poured into water and extracted with DCM. The organic layers were combined, washed with brine, dried over anhydrous sodium sulfate, filtered and the filtrate was concentrated in vacuum to give 2-bromo-7-(oxiran-2-yl)-12-oxa-3-thia-6-azatricyclo[6.4.1.$0^{4,13}$]trideca-1,4(13),7-trien-5-one (70 mg). MS obsd. ($ESI^+$): m/z 328.3 $[(M+H)^+]$.

Step B: 1-bromo-5-(1-hydroxy-2-methoxyethyl)-4,6,7,8-tetrahydro-3H-9-oxa-2-thia-4-azabenzo[cd]azulen-3-one

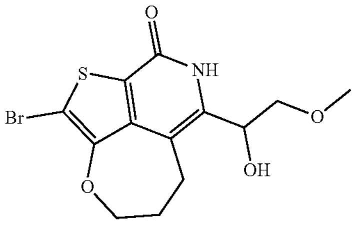 [SMILES: COCC(O)c1[nH]c(=O)c2sc(Br)c3c2c1CCCO3]

A mixture of 2-bromo-7-(oxiran-2-yl)-12-oxa-3-thia-6-azatricyclo[6.4.1.$0^{4,13}$]trideca-1,4(13),7-trien-5-one (140 mg, 426.6 umol), NaOMe (5 M, 10 mL), and DMSO (10 mL) was stirred for 3 h at r.t. Upon the completion, the mixture was poured into water and extracted with. The organic layers were combined, washed with brine, dried over anhydrous sodium sulfate, filtered and the filtrate was concentrated in vacuum, the residue was purified by reverse phase chromatography (eluted with MeCN in water from 0% to 30%, 0.5% FA in water) to give 2-bromo-7-(1-hydroxy-2-methoxy-ethyl)-12-oxa-3-thia-6-azatricyclo[6.4.1.$0^{4,13}$]trideca-1,4(13),7-trien-5-one (80 mg) as an off-white solid. MS obsd. ($ESI^+$): m/z 360.0 $[(M+H)^+]$.

Step C: 1-bromo-5-(1-chloro-2-methoxyethyl)-4,6,7,8-tetrahydro-3H-9-oxa-2-thia-4-azabenzo[cd]azulen-3-one

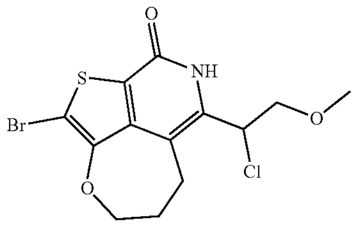 [SMILES: COCC(Cl)c1[nH]c(=O)c2sc(Br)c3c2c1CCCO3]

Thionyl chloride (105.69 mg, 888.3 umol) was added to a solution of 2-bromo-7-(1-hydroxy-2-methoxy-ethyl)-12-oxa-3-thia-6-azatricyclo[6.4.1.$0^{4,13}$]trideca-1,4(13),7-trien-5-one (32 mg, 88.8 umol) in DCM (6 mL) at 0° C. The mixture was warmed to r.t. and stirred for 2 h. Upon the completion, the mixture was washed with brine, dried over anhydrous sodium sulfate, filtered and the filtrate was concentrated in vacuum to give 2-bromo-7-(1-chloro-2-methoxy-ethyl)-12-oxa-3-thia-6-azatricyclo[6.4.1.$0^{4,13}$]trideca-1,4(13),7-trien-5-one (18 mg) as a yellow solid. MS obsd. ($ESI^+$): m/z 378.0 $[(M+H)^+]$.

Step D: 1-bromo-5-(2-methoxy-1-(1H-pyrazol-1-yl)ethyl)-4,6,7,8-tetrahydro-3H-9-oxa-2-thia-4-azabenzo[cd]azulen-3-one

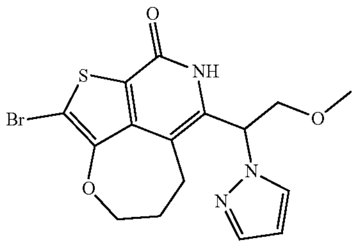 [SMILES: COCC(c1[nH]c(=O)c2sc(Br)c3c2c1CCCO3)n1cccn1]

A mixture of 2-bromo-7-(1-chloro-2-methoxy-ethyl)-12-oxa-3-thia-6-azatricyclo[6.4.1.$0^{4,13}$]trideca-1,4(13),7-trien-5-one (44 mg, 116.2 umol), potassium iodide (97 mg, 581.0 umol), 1H-pyrazole (330 mg, 4.85 mmol), potassium carbonate (110.0 mg, 795.9 umol) and $CH_3CN$ (20 mL) was stirred for 16 h at rt. Upon the completion, the mixture was concentrated, diluted with water, extracted with DCM. The organic layers were combined, washed with brine, dried over anhydrous sodium sulfate, filtered and the filtrate was concentrated in vacuum, the residue was purified by reverse phase chromatography (eluted with MeCN in water from 0% to 30%, 0.5% FA in water) to give 2-bromo-7-(2-methoxy-1-pyrazol-1-yl-ethyl)-12-oxa-3-thia-6-azatricyclo[6.4.1.$0^{4,13}$]trideca-1,4(13),7-trien-5-one (20 mg) as a white solid. MS obsd. ($ESI^+$): m/z 410.4 $[(M+H)^+]$.

Step E: 5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one

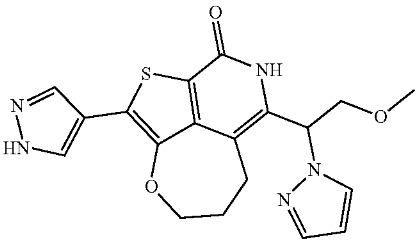 [SMILES: COCC(c1[nH]c(=O)c2sc(-c3cn[nH]c3)c3c2c1CCCO3)n1cccn1]

The mixture of 2-bromo-7-(2-methoxy-1-pyrazol-1-yl-ethyl)-12-oxa-3-thia-6-azatricyclo[6.4.1.$0^{4,13}$]trideca-1,4(13),7-trien-5-one (28 mg, 68.2 umol), 1H-pyrazol-4-ylboronic acid (16 mg, 136.5 umol), sodium carbonate (29 mg, 273.0 umol, 4 eq), Xphos (10 mg, 20.5 umol), Pd(dppf)$Cl_2$ (15 mg, 20.5 umol) in 1,4-dioxane:$H_2O$=5:1 (6 mL) was purged with argon 3 times. Then it was stirred at 105° C. under M.W. for 1 h. Upon the completion, the resulting mixture was cooled to room temperature, concentrated in vacuum. The crude product was purified by silica gel column chromatography (eluted with DCM:MeOH=10:1) at first and then purified by reverse phase chromatography (eluted with MeCN in water from 0% to 25%, 0.5% FA in water) to give 7-(2-methoxy-1-pyrazol-1-yl-ethyl)-2-(1H-pyrazol-4-yl)-12-oxa-3-thia-6-azatricyclo[6.4.1.$0^{4,13}$]trideca-1,4(13),7-trien-5-one (6.8 mg) as an off-white solid. MS obsd. ($ESI^+$): m/z 398.1 $[(M+H)^+]$. This racemic product underwent SFC chiral resolution to give (S)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one and (R)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one. The absolute stereochemistry was randomly assigned for these two compounds.

The compounds were prepared in a similar manner as Examples 35 and 36 and through chiral resolution.

| Ex. No. | Structure | Name | MS obsd. ($ESI^+$): m/z $[(M + H)^+]$ |
| --- | --- | --- | --- |
| 37 | 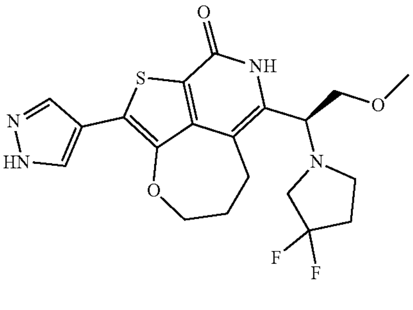 [SMILES: COC[C@H](c1[nH]c(=O)c2sc(-c3cn[nH]c3)c3c2c1CCCO3)N1CCC(F)(F)C1] | (S)-5-(1-(3,3-difluoropyrrolidin-1-yl)-2-methoxyethyl)-1-(1H-pyrazol-4-yl)-4,6,7,8-tetrahydro-3H-9-oxa-2-thia-4-azabenzo[cd]azulen-3-one# | 437 |

-continued

| Ex. No. | Structure | Name | MS obsd. (ESI+): m/z [(M + H)+] |
|---|---|---|---|
| 38 | 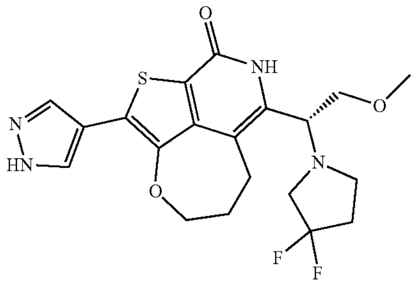 [SMILES: COC[C@@H](c1[nH]c(=O)c2sc(-c3cn[nH]c3)c3c2c1CCCO3)N1CCC(F)(F)C1] | (R)-5-(1-(3,3-difluoropyrrolidin-1-yl)-2-methoxyethyl)-1-(1H-pyrazol-4-yl)-4,6,7,8-tetrahydro-3H-9-oxa-2-thia-4-azabenzo[cd]azulen-3-one# | 437 |
| 39 | 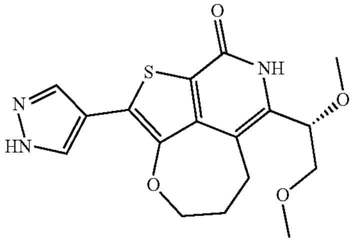 [SMILES: COC[C@@H](OC)c1[nH]c(=O)c2sc(-c3cn[nH]c3)c3c2c1CCCO3] | (S)-5-(1,2-dimethoxyethyl)-1-(1H-pyrazol-4-yl)-4,6,7,8-tetrahydro-3H-9-oxa-2-thia-4-azabenzo[cd]azulen-3-one# | 362 |
| 40 | 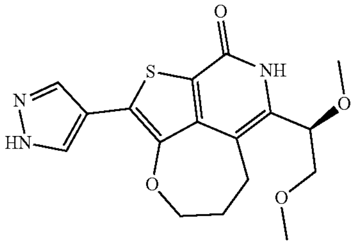 [SMILES: COC[C@H](OC)c1[nH]c(=O)c2sc(-c3cn[nH]c3)c3c2c1CCCO3] | (R)-5-(1,2-dimethoxyethyl)-1-(1H-pyrazol-4-yl)-4,6,7,8-tetrahydro-3H-9-oxa-2-thia-4-azabenzo[cd]azulen-3-one# | 362 |

#The absolute stereochemistry was randomly assigned.

The following compounds were prepared in a similar manner as Examples 26 and 27.

| Ex. No. | Structure | Name | MS obsd. (ESI+): m/z [(M + H)+] |
|---|---|---|---|
| 41 | 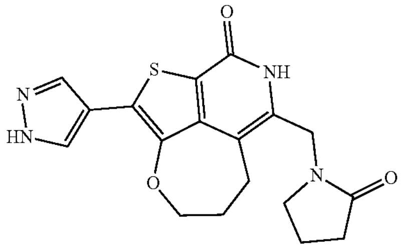 [SMILES: O=C1CCCN1Cc1[nH]c(=O)c2sc(-c3cn[nH]c3)c3c2c1CCCO3] | 5-((2-oxopyrrolidin-1-yl)methyl)-1-(1H-pyrazol-4-yl)-4,6,7,8-tetrahydro-3H-9-oxa-2-thia-4-azabenzo[cd]azulen-3-one | 371 |
| 42 | 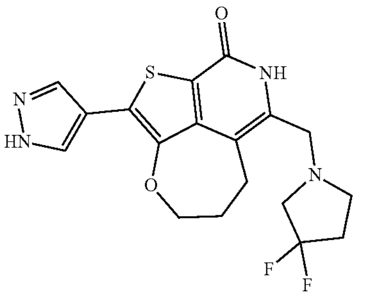 [SMILES: O=c1[nH]c(CN2CCC(F)(F)C2)c2c3c(c(-c4cn[nH]c4)sc13)OCCC2] | 5-((3,3-difluoropyrrolidin-1-yl)methyl)-1-(1H-pyrazol-4-yl)-4,6,7,8-tetrahydro-3H-9-oxa-2-thia-4-azabenzo[cd]azulen-3-one | 393 |

Example 43: 10,10-difluoro-7-methyl-2-(1H-pyrazol-4-yl)-12-oxa-3-thia-6-azatricyclo[6.4.1.$0^{4,13}$]trideca-1,4(13),7-trien-5-one

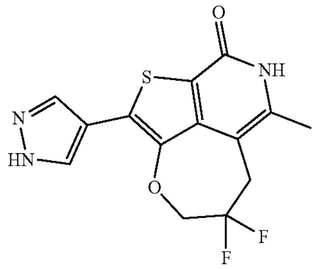 [SMILES: Cc1[nH]c(=O)c2sc(-c3cn[nH]c3)c3c2c1CC(F)(F)CO3]

Step A: 7-chloro-3-methoxy-5-methyl-4-vinylthieno[2,3-c]pyridine

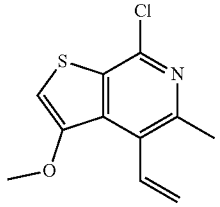

To a three-necked flask containing of methyl(triphenyl)phosphonium bromide (7.79 g, 21.80 mmol) in THF (100 mL) was added butyllithium (1.6 M, 15.0 mL) at −78° C. It was stirred at 0° C. for 1 h. And then, 7-chloro-3-methoxy-5-methyl-thieno[2,3-c]pyridine-4-carbaldehyde (3.29 g, 10.90 mmol) in THF (100 mL) was added to the mixture at −78° C. Then it was warmed to 0° C., and stirred at 0° C. for 2 h. Upon the completion, it was quenched with aq. $NH_4C1$, diluted with water, extracted with EtOAc. The organic layer was dried over anhydrous sodium sulfate, filtered and concentrated to give the residue. The residue was purified by flash column chromatography (eluted with PE:EtOAc=93:7) to give 7-chloro-3-methoxy-5-methyl-4-vinyl-thieno[2,3-c]pyridine (2.1 g) as white solid.

Step B: (S)-2-bromo-7-(hydroxymethyl)-8-((2-(trimethylsilyl)ethoxy)methyl)-4,5,7,8-tetrahydro-3-oxa-1-thia-5a,8-diazabenzo[cd]azulen-9(6H)-one

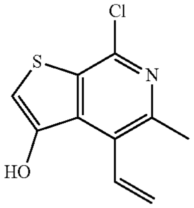

To a flask containing of 7-chloro-3-methoxy-5-methyl-4-vinyl-thieno[2,3-c]pyridine (2.1 g, 8.32 mmol) in dry DCM (50 mL) was slowly added tribromoborane (6.27 g, 25.03 mmol, 2.41 mL) at 0° C. Upon the completion, it was quenched with MeOH at 0° C. The mixture was stirred at 0° C. for 10 min. Then, it was concentrated to give the residue. It was diluted with EtOAc, washed with water. The organic layer was dried over anhydrous sodium sulfate, filtered and concentrated to give 7-chloro-5-methyl-4-vinyl-thieno[2,3-c]pyridin-3-ol (1.6 g) as yellow solid. MS obsd. ($ESI^+$): m/z 226.3 $[(M+H)^+]$, 228.3 $[(M+2+H)^+]$.

Step C: 3-(allyloxy)-7-chloro-5-methyl-4-vinylthieno[2,3-c]pyridine

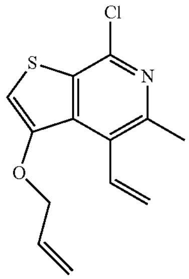 [SMILES: C=CCOc1csc2c(Cl)nc(C)c(C=C)c12]

To a flask containing of 7-chloro-5-methyl-4-vinyl-thieno[2,3-c]pyridin-3-ol (1.4 g, 5.83 mmol) in DMF (20 mL) was added potassium carbonate (2.42 g, 17.49 mmol) and 3-bromoprop-1-ene (705.4 mg, 5.83 mmol, 503.85 uL) at 0° C. And it was stirred at room temperature for 2 h. Upon the completion, It was diluted with EtOAc, washed with water. The organic layer was dried over anhydrous sodium sulfate, filtered and concentrated. The residue was purified by reverse phase chromatography (eluted with MeCN in water from 0% to 45%, 0.1% FA in water) to give 3-allyloxy-7-chloro-5-methyl-4-vinyl-thieno[2,3-c]pyridine (1.1 g) as yellow solid.

Step D: 5-chloro-7-methyl-12-oxa-3-thia-6-azatricyclo[6.4.1.$0^{4,13}$]trideca-1,4(13),5,7,9-pentaene

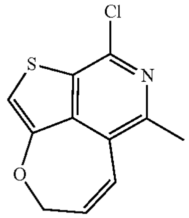

To a flask containing of 3-allyloxy-7-chloro-5-methyl-4-vinyl-thieno[2,3-c]pyridine (400 mg, 1.51 mmol) was added Hoveyda-Grubbs Catalyst 2nd Generation (142 mg, 225.8 umol) and dry DCM (300 mL). The mixture was stirred at 25° C. for 5 h under $N_2$ protection. Upon the completion, it was concentrated and purified by flash column chromatography (eluted with PE:EtOAc=94:6) to give 5-chloro-7-methyl-12-oxa-3-thia-6-azatricyclo[6.4.1.$0^{4,13}$]trideca-1,4(13),5,7,9-pentaene (290 mg) as white solid.

Step E: 5-chloro-7-methyl-12-oxa-3-thia-6-azatricyclo[6.4.1.$0^{4,13}$]trideca-1,4(13),5,7-tetraene-9,10-diol

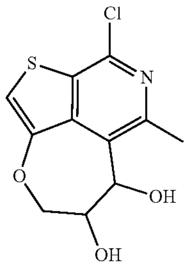 [SMILES: Cc1nc(Cl)c2scc3c2c1C(O)C(O)CO3]

To a flask containing of 5-chloro-7-methyl-12-oxa-3-thia-6-azatricyclo[6.4.1.$0^{4,13}$]trideca-1,4(13),5,7,9-pentaene (300 mg, 1.26 mmol) in tert-Butanol (30 mL) was added citric acid (485 mg, 2.52 mmol), 4-Methylmorpholine N-oxide (296 mg, 2.52 mmol) in $H_2O$ (30 mL) and potassium osmate(VI) dihydrate (23 mg, 63.1 umol) at room temperature. The mixture was stirred at 60° C. for 16 h. Upon the completion, the reaction mixture was quenched by addition of saturated $Na_2SO_3$ solution. It was stirred at room temperature for 20 min. Then it was extracted with DCM. The organic layer was dried over anhydrous sodium sulfate, filtered and concentrated. And then, it was purified by flash column chromatography (eluted with PE:EA=30:70) to give 5-chloro-7-methyl-12-oxa-3-thia-6-azatricyclo[6.4.1.$0^{4,13}$]trideca-1,4(13),5,7-tetraene-9,10-diol (245 mg) as a white solid. MS obsd. ($ESI^+$): m/z 272.3 [$(M+H)^+$], 274.3 [$(M+2+H)^+$].

Step F: 5-chloro-7-methyl-12-oxa-3-thia-6-azatricyclo[6.4.1.$0^{4,13}$]trideca-1,4(13),5,7-tetraen-10-one

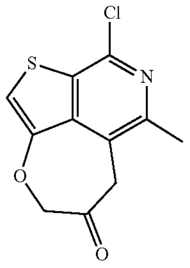 [SMILES: Cc1nc(Cl)c2scc3c2c1CC(=O)CO3]

To a three-necked flask containing of 5-chloro-7-methyl-12-oxa-3-thia-6-azatricyclo[6.4.1.$0^{4,13}$]trideca-1,4(13),5,7-tetraene-9,10-diol (230 mg, 846.5 umol) was added p-Toluenesulfonic acid (73 mg, 423.2 umol) in dry toluene (16 mL). The reaction mixture was heated under reflux for 4 h. Upon the completion, it was concentrated and purified by flash column chromatography (eluted with DCM:MeOH=100:1) to give 5-chloro-7-methyl-12-oxa-3-thia-6-azatricyclo[6.4.1.$0^{4,13}$]trideca-1,4(13),5,7-tetraen-10-one (175 mg) as light-yellow solid.

Step G: 5-chloro-10,10-difluoro-7-methyl-12-oxa-3-thia-6-azatricyclo[6.4.1.$0^{4,13}$]trideca-1,4 (13),5,7-tetraene

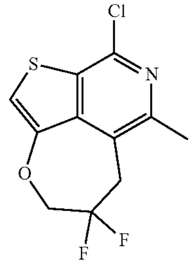 [SMILES: Cc1nc(Cl)c2scc3c2c1CC(F)(F)CO3]

To a plastic bottle containing of 5-chloro-7-methyl-12-oxa-3-thia-6-azatricyclo[6.4.1.$0^{4,13}$]trideca-1,4(13),5,7-tetraen-10-one (50 mg, 197.1 umol) in DCM (10 mL) was added morpholinosulfurtrifluoride (345 mg, 1.97 mmol) at room temperature. It was stirred at room temperature for 24 h. Upon the completion, it was neutralized with aq. $NaHCO_3$ to pH=8, extracted with DCM. The organic layer was dried over sodium sulfate, filtered and concentrated to give the residue. And then, it was purified by flash column chromatography (eluted with PE:EtOAc=20:1) to give 5-chloro-10,10-difluoro-7-methyl-12-oxa-3-thia-6-azatricyclo[6.4.1.$0^{4,13}$]trideca-1,4(13),5,7-tetraene (30 mg) as white solid. MS obsd. ($ESI^+$): m/z 276.3 [$(M+H)^+$], 278.3 [$(M+2+H)^+$].

Step H: 10,10-difluoro-7-methyl-12-oxa-3-thia-6-azatricyclo[6.4.1.$0^{4,13}$]trideca-1,4(13),7-trien-5-one

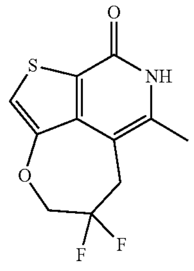 [SMILES: Cc1[nH]c(=O)c2scc3c2c1CC(F)(F)CO3]

To a flask containing of 5-chloro-10,10-difluoro-7-methyl-12-oxa-3-thia-6-azatricyclo[6.4.1.$0^{4,13}$]trideca-1,4 (13),5,7-tetraene (52 mg, 188.6 umol) in acetic acid (10 mL) was added ammonium acetate (140 mg, 1.81 mmol) and $H_2O$ (0.1 mL) at room temperature. Then, it was heated to 200° C. The reaction was stirred at 200° C. for 1 h. Upon the completion, it was cooled down to room temperature and concentrated to remove acetic acid. The residue was diluted with $H_2O$ and DCM, basified with ammonium hydroxide to pH=10. It was extracted with DCM:MeOH=10:1. The organic layer was dried over sodium sulfate, filtered and concentrated to give the solid. Then, it was recrystallized from PE:EA=30:1, filtered. The filter cake was collected to give 10,10-difluoro-7-methyl-12-oxa-3-thia-6-azatricyclo[6.4.1.$0^{4,13}$]trideca-1,4(13),7-trien-5-one (50 mg) as yellow solid. MS obsd. ($ESI^+$): m/z 258.4 [$(M+H)^+$].

Step I: 2-bromo-10,10-difluoro-7-methyl-12-oxa-3-thia-6-azatricyclo[6.4.1.$0^{4,13}$]trideca-1,4(13),7-trien-5-one

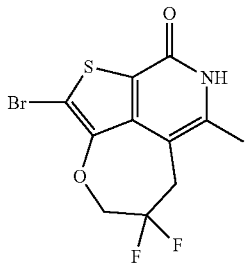 [SMILES: Cc1[nH]c(=O)c2sc(Br)c3c2c1CC(F)(F)CO3]

To a flask containing of 10,10-difluoro-7-methyl-12-oxa-3-thia-6-azatricyclo[6.4.1.$0^{4,13}$]trideca-1,4(13),7-trien-5-one (50 mg, 194.4 umol) in DCM (10 mL) was added pyridinium tribromide (311 mg, 971.8 umol) at 0° C. The reaction mixture was stirred at 25° C. for 24 h. Upon the completion, it was diluted with DCM, quenched by saturated $Na_2SO_3$ solution, washed with aq.$NaHCO_3$, brine. The organic layer was dried over sodium sulfate, filtered and concentrated to give the crude product. It was recrystallized from PE:EA=5:1 to give 2-bromo-10,10-difluoro-7-methyl-12-oxa-3-thia-6-azatricyclo[6.4.1.$0^{4,13}$]trideca-1,4(13),7-trien-5-one (50 mg) as yellow solid. MS obsd. (ESI$^+$): m/z 336.3 [(M+H)$^+$], 338.3 [(M+2+H)$^+$].

Step J: 10,10-difluoro-7-methyl-2-(1H-pyrazol-4-yl)-12-oxa-3-thia-6-azatricyclo[6.4.1.$0^{4,13}$]trideca-1,4(13),7-trien-5-one

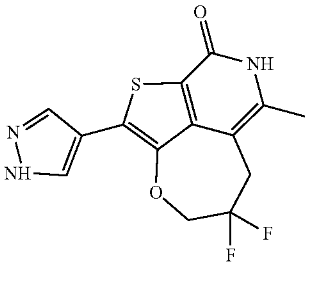 [SMILES: Cc1[nH]c(=O)c2sc(-c3cn[nH]c3)c3c2c1CC(F)(F)CO3]

To 2-bromo-10,10-difluoro-7-methyl-12-oxa-3-thia-6-azatricyclo[6.4.1.$0^{4,13}$]trideca-1,4 (13),7-trien-5-one (45 mg, 133.9 umol), 4-(4,4,5,5-tetramethyl-1,3,2-dioxaborolan-2-yl)-1H-pyrazole (52.0 mg, 267.7 umol), dicyclohexyl-[2-(2,4,6-triisopropylphenyl)phenyl]phosphane (19 mg, 40.2 umol), sodium carbonate (43 mg, 401.6 umol), [1,1'-Bis(diphenylphosphino)ferrocene]dichloropalladium(II) (19.6 mg, 26.8 umol) was added water (1.6 mL) and 1,4-dioxane (8 mL). And then, it was degassed by bubbling $N_2$ for 2 min. Then the reaction was sealed in a tube and it was stirred at 105° C. for 2.5 h in a microwave reactor, monitored by LCMS. Upon the completion, it was diluted with DCM, washed with water. The organic layer was dried over sodium sulfate, filtered and concentrated to give the residue. It was purified by flash column chromatography (eluted with DCM:MeOH=80:1) to give a crude product. Then, it was purified again by reverse phase chromatography (eluted with MeCN in water from 0% to 36%, 0.1% FA in water) to give 10,10-difluoro-7-methyl-2-(1H-pyrazol-4-yl)-12-oxa-3-thia-6-azatricyclo[6.4.1.$0^{4,13}$]trideca-1,4(13),7-trien-5-one (18 mg) as a white solid. MS obsd. (ESI$^+$): m/z 324 [(M+H)$^+$]. $^1$H NMR (400 MHz, DMSO) δ ppm: 13.28 (s, 1H), 11.50 (s, 1H), 8.21-7.92 (m, 2H), 4.55-4.48 (t, J=27.2 Hz, 2H), 3.51-3.44 (t, J=31.2 Hz, 2H), 2.23 (s, 3H).

Example 44: 7-(azetidin-1-ylmethyl)-10,10-difluoro-2-(1H-pyrazol-4-yl)-12-oxa-3-thia-6-azatricyclo[6.4.1.$0^{4,13}$]trideca-1,4(13),7-trien-5-one

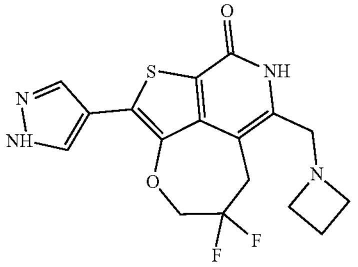 [SMILES: O=c1[nH]c(CN2CCC2)c2c3c(c(-c4cn[nH]c4)sc13)OCC(F)(F)C2]

Step A: 10,10-difluoro-5-oxo-12-oxa-3-thia-6-azatricyclo[6.4.1.$0^{4,13}$]trideca-1,4(13),7-triene-7-carbaldehyde

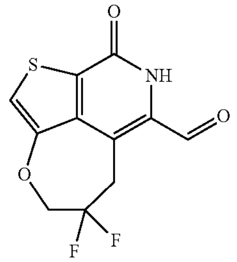 [SMILES: O=Cc1[nH]c(=O)c2scc3c2c1CC(F)(F)CO3]

To a flask containing of 10,10-difluoro-7-methyl-12-oxa-3-thia-6-azatricyclo[6.4.1.$0^{4,13}$]trideca-1,4(13),7-trien-5-one (75 mg, 291.5 umol) was added selenium dioxide (308 mg, 2.77 mmol) at room temperature. Then the reaction was stirred at 130° C. for 6.5 h. Upon the completion, it was diluted with water, extracted with EtOAc. The organic layer was dried over anhydrous sodium sulfate, filtered and concentrated to give crude. It was first purified by C18 column (eluted with 0.1% FA in water, water:MeCN=50:50) to remove 1-Methyl-2-pyrrolidinone. And then it was concentrated to give the residue which was purified twice by flash column chromatography (eluted with DCM:MeOH=30:1) and purified by silica Prep-TLC (eluted with DCM: MeOH=20:1) to give 10,10-difluoro-5-oxo-12-oxa-3-thia-6-azatricyclo[6.4.1.$0^{4,13}$]trideca-1,4(13),7-triene-7-carbaldehyde (24 mg) as yellow solid. MS obsd. (ESI$^+$): m/z 272 [(M+H)$^+$].

Step B: 2-bromo-10,10-difluoro-5-oxo-12-oxa-3-thia-6-azatricyclo[6.4.1.0$^{4,13}$]trideca-1,4(13),7-triene-7-carbaldehyde

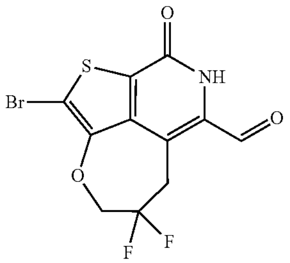 [SMILES: O=Cc1[nH]c(=O)c2sc(Br)c3c2c1CC(F)(F)CO3]

To a flask containing of 10,10-difluoro-5-oxo-12-oxa-3-thia-6-azatricyclo[6.4.1.0$^{4,13}$]trideca-1,4(13),7-triene-7-carbaldehyde (60 mg, 221.2 umol) in AcOH (6 mL) was added liquid bromide (590 mg, 3.69 mmol, 189.45 uL) at 0° C. Then it was stirred at room temperature for 3 h. Upon the completion, it was diluted with DCM, and then added to saturated sodium sulfite solution, extracted with DCM: MeOH=10:1. The organic layer was dried over sodium sulfate, filtered and then concentrated to give 2-bromo-10,10-difluoro-5-oxo-12-oxa-3-thia-6-azatricyclo[6.4.1.0$^{4,13}$]trideca-1,4(13),7-triene-7-carbaldehyde (60 mg) as yellow solid. MS obsd. (ESI$^+$): m/z 350 [(M+H)$^+$], 352 [(M+2+H)$^+$].

Step C: 7-(azetidin-1-ylmethyl)-2-bromo-10,10-difluoro-12-oxa-3-thia-6-azatricyclo[6.4.1.0$^{4,13}$]trideca-1,4(13),7-trien-5-one

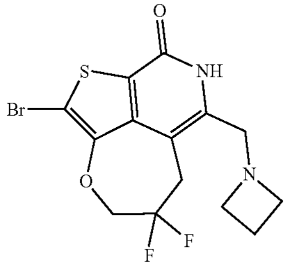 [SMILES: O=c1[nH]c(CN2CCC2)c2c3c(c(Br)sc13)OCC(F)(F)C2]

To a flask containing of 2-bromo-10,10-difluoro-5-oxo-12-oxa-3-thia-6-azatricyclo[6.4.1.0$^{4,13}$]trideca-1,4(13),7-triene-7-carbaldehyde (60 mg, 171.4 umol) in 1,2-dichloroethane (8.5 mL) was added azetidine (39 mg, 685.4 umol) at 20° C. The mixture was stirred at 20° C. for 1.5 h. Then, sodium cyanoboranuide (24 mg, 377 umol) was added to the mixture. The reaction was stirred at 20° C. for 15 h. Upon the completion, it was quenched with aq. $NaHCO_3$ at 0° C., extracted with DCM. The organic layer was dried over sodium sulfate, filtered and concentrated to give the crude. It was purified by silica Prep-TLC (eluted with DCM: MeOH=20:1) to give 7-(azetidin-1-ylmethyl)-2-bromo-10,10-difluoro-12-oxa-3-thia-6-azatricyclo[6.4.1.0$^{4,13}$]trideca-1,4(13),7-trien-5-one (38 mg) as yellow solid. MS obsd. (ESI$^+$): m/z 391 [(M+H)$^+$], 393 [(M+2+H)$^+$].

Step D: 7-(azetidin-1-ylmethyl)-10,10-difluoro-2-(1H-pyrazol-4-yl)-12-oxa-3-thia-6-azatricyclo[6.4.1.0$^{4}$,1$^{1}$]trideca-1,4(13),7-trien-5-one

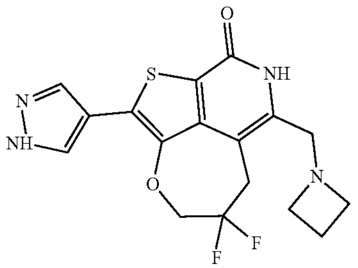 [SMILES: O=c1[nH]c(CN2CCC2)c2c3c(c(-c4cn[nH]c4)sc13)OCC(F)(F)C2]

To 7-(azetidin-1-ylmethyl)-2-bromo-10,10-difluoro-12-oxa-3-thia-6-azatricyclo[6.4.1.0$^{4,13}$]trideca-1,4(13),7-trien-5-one (44 mg, 102.2 umol), 1H-pyrazol-4-ylboronic acid (35 mg, 306.7 umol), Xphos (39 mg, 81.8 umol), [1,1'-Bis (diphenylphosphino) ferrocene]dichloropalladium(II) (37.4 mg, 51.1 umol), disodium carbonate (44 mg, 409.0 umol) was added 1,4-dioxane:$H_2O$=5:1 (3 mL) at room temperature. And then it was degassed by bubbling $N_2$ for 2 min. Then the reaction was sealed in a tube and it was stirred at 105° C. for 1.5 h in a microwave reactor. Upon the completion, the reaction was diluted with water, extracted with DCM. The organic layer was dried over sodium sulfate, filtered and concentrated to give the residue. It was purified twice by flash column chromatography (eluted with DCM: MeOH=10:1) and then purified the third time by C18 column (eluted with 0.1% FA in water, water:MeCN=80:20) to give 7-(azetidin-1-ylmethyl)-10,10-difluoro-2-(1H-pyrazol-4-yl)-12-oxa-3-thia-6-azatricyclo[6.4.1.0$^{4,13}$]trideca-1,4(13),7-trien-5-one (9 mg) as white solid. MS obsd. (ESI$^+$): m/z 379 [(M+H)$^+$]. $^1$H NMR (400 MHz, DMSO) δ ppm: 8.09 (s, 2H), 4.57-4.50 (t, J=27.2 Hz, 2H), 3.70-3.53 (m, 6H), 3.23-3.19 (t, J=14 Hz, 2H), 2.01-1.95 (m, 2H).

The following compound was prepared in a similar manner as that illustrated in Example 28 from corresponding bromide through Suzuki reaction.

| Compound No. | Compound Structure | Compound Name | MS obsd. (ESI$^+$): m/z [(M + H)$^+$] |
|---|---|---|---|
| 45 | 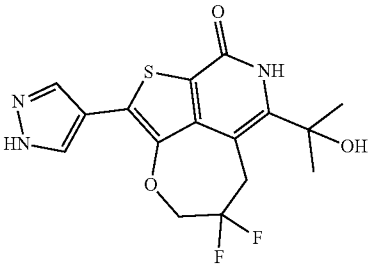 [SMILES: CC(C)(O)c1[nH]c(=O)c2sc(-c3cn[nH]c3)c3c2c1CC(F)(F)CO3] | 10,10-difluoro-7-(1-hydroxy-1-methyl-ethyl)-2-(1H-pyrazol-4-yl)-12-oxa-3-thia-6-aza tricyclo[6.4.1.0$^{4,13}$] trideca-1,4(13),7-trien-5-one | 368 |

Example 46: (R)-2-(1H-pyrazol-4-yl)-7-(1-pyrazol-1-ylethyl)-12-oxa-3-thia-6-azatricyclo[6.4.1.0$^{4,13}$]trideca-1, 4(13), 7-trien-5-one

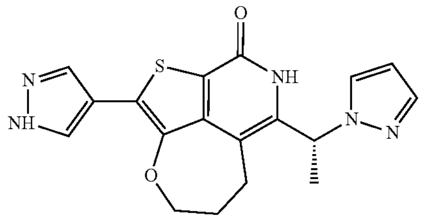 [SMILES: C[C@H](c1[nH]c(=O)c2sc(-c3cn[nH]c3)c3c2c1CCCO3)n1cccn1]

Example 47: (S)-2-(1H-pyrazol-4-yl)-7-(1-pyrazol-1-ylethyl)-12-oxa-3-thia-6-azatricyclo[6.4.1.0$^{4,13}$]trideca-1, 4(13), 7-trien-5-one

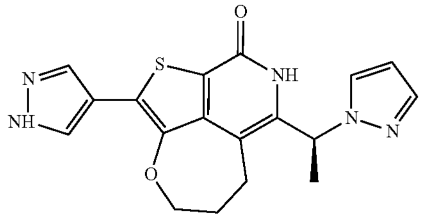 [SMILES: C[C@@H](c1[nH]c(=O)c2sc(-c3cn[nH]c3)c3c2c1CCCO3)n1cccn1]

Step A: methyl 3-amino-4-hydroxy-thiophene-2-carboxylate

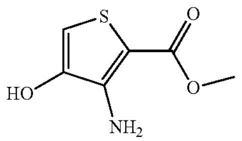

To a solution of methyl 4-hydroxy-3-nitro-thiophene-2-carboxylate (10.41 g, 49.17 mmol, 1.0 eq.) in $CH_3COOH$ (300.0 mL) was added iron powder (27.49 g, 491.70 mmol, 10.0 eq.). The mixture was stirred at 60° C. for 2 hr. LC-MS indicated complete conversion. The solvent was removed under reduced pressure. The residue was extracted with EA, and the combined organic layers were washed with brine, dried over anhydrous sodium sulfate and concentrated in vacuum. The residue was purified by flash chromatography on silica (MeOH/DCM, gradient 0-10%) to give methyl 3-amino-4-hydroxy-thiophene-2-carboxylate (7.40 g) as a light-yellow solid. MS obsd. ($ESI^+$): m/z 174.0 [$(M+H)^+$].

Step B: methyl 3-amino-4-pent-4-enoxy-thiophene-2-carboxylate

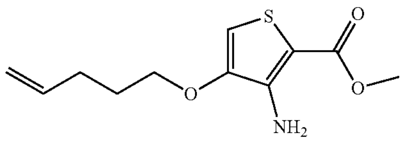 [SMILES: C=CCCCOc1csc(C(=O)OC)c1N]

To a solution of methyl 3-amino-4-hydroxy-thiophene-2-carboxylate (10.0 g, 57.57 mmol, 1.0 eq.) and 5-bromopent-1-ene (14.73 g, 97.86 mmol, 1.7 eq.) in DMF (200.0 mL) was added $K_2CO_3$ (12.04 g, 86.35 mmol, 1.5 eq.). The mixture was stirred at 80° C. for 2 hr. LC-MS indicated complete conversion. The solvent was removed in vacuum. The residue was extracted with EA, and the combined organic layers were washed with brine, dried over anhydrous sodium sulfate and concentrated in vacuum. The residue was purified by flash chromatography on silica (EA/PE, gradient 0-3%) to give methyl 3-amino-4-pent-4-enoxy-thiophene-2-carboxylate (12.50 g) as a yellow solid. MS obsd. ($ESI^+$): m/z 242.1 [$(M+H)^+$].

Step C: methyl 3-iodo-4-pent-4-enoxy-thiophene-2-carboxylate

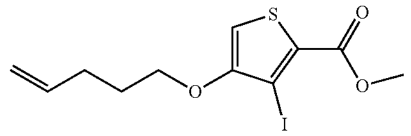 [SMILES: C=CCCCOc1csc(C(=O)OC)c1I]

To a solution of methyl 3-amino-4-pent-4-enoxy-thiophene-2-carboxylate (11.30 g, 45.42 mmol, 1.0 eq.) and $CH_2I_2$ (24.59 g, 90.85 mmol, 2.0 eq.) in MeCN (22.0 mL) was added amylnitrite (8.06 g, 68.14 mmol, 1.5 eq.). The mixture was stirred at 60° C. for 2 hr. LC-MS indicated complete conversion. The solvent was removed in vacuum. The reaction mixture was extracted with EA, and the combined organic layers were washed with brine, dried over anhydrous sodium sulfate and concentrated in vacuum. The residue was purified by flash chromatography on silica (EA/PE, gradient 0-3%) to give methyl 3-iodo-4-pent-4-enoxy-thiophene-2-carboxylate (5.28 g) as a yellow oil. MS obsd. ($ESI^+$): m/z 353.0 [$(M+H)^+$].

Step D: methyl 5-methylene-3,4-dihydro-2H-thieno[3,4-b]oxepine-6-carboxylate

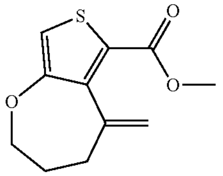

To a solution of methyl 3-iodo-4-pent-4-enoxy-thiophene-2-carboxylate (10.40 g, 28.94 mmol, 1.0 eq.) in DMF (200.0 mL) was added $Pd(PPh_3)_4$ (5.07 g, 4.34 mmol, 0.15 eq.) and $K_2CO_3$ (6.05 g, 43.41 mmol, 1.5 eq.). The reaction flask was evacuated and backed filled with nitrogen atmosphere. Then the mixture was stirred at 100° C. for 3 hr. LC-MS indicated complete conversion. The solvent was removed under reduced pressure. The residue was extracted with EA, and the combined organic layers were washed with brine, dried over anhydrous sodium sulfate and concentrated in vacuum. The residue was purified by flash chromatography on silica (EA/PE, gradient 0-3%) to give methyl 5-methylene-3,4-dihydro-2H-thieno[3,4-b]oxepine-6-carboxylate (3.40 g) as a light-yellow solid. MS obsd. ($ESI^+$): m/z 225.1 [$(M+H)^+$].

Step E: 5-methylene-3,4-dihydro-2H-thieno[3,4-b]oxepine-6-carboxylic acid

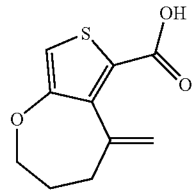

To a solution of methyl 5-methylene-3-dihydro-2-thieno[3,4-b]oxepine-6-carboxylate (3.23 g, 14.13 mmol, 1.0 eq.) in a mixed solvents of $H_2O$ (20.0 mL) and MeOH (60.0 mL) was added LiOH (512 mg, 21.19 mmol, 1.0 eq.). The mixture was stirred at 80° C. for 3 hr. LC-MS indicated complete conversion. The solvent was removed in vacuum. The residue was adjusted to pH=2 with 1M aqueous HCl, and extracted with EA. The combined organic layers were washed with brine, dried over anhydrous sodium sulfate and concentrated in vacuum to give crude 5-methylene-3,4-dihydro-2H-thieno[3,4-b]oxepine-6-carboxylic acid (2.97 g) as a white solid which was used directly in the next step without further purification. MS obsd. ($ESI^+$): m/z 211.1 $[(M+H)^+]$.

Step F: 5-oxo-3,4-dihydro-2H-thieno[3,4-b]oxepine-6-carboxylic acid

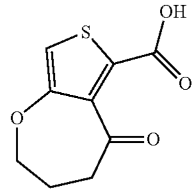 [SMILES: O=C(O)c1scc2c1C(=O)CCCO2]

To a solution of 5-methylene-3,4-dihydro-2H-thieno[3,4-b]oxepine-6-carboxylic acid (2.91 g, 13.70 mmol, 1.0 eq.) and $RuCl_3$ (62 mg, 0.27 mmol, 0.02 eq.) in MeCN (90.0 mL) was added a solution of $NaIO_4$ (8.00 g, 37.0 mmol, 2.7 eq.) and $H_2SO_4$ (2.71 g, 27.40 mmol, 2.0 eq.) in $H_2O$ (90.0 mL) at 0° C. The mixture was stirred at 0° C. for 0.5 h. LC-MS indicated complete conversion. The resulting mixture was extracted with EA, and the combined organic layers were washed with brine, dried over anhydrous sodium sulfate and concentrated in vacuum to give crude 5-oxo-3,4-dihydro-2H-thieno[3,4-b]oxepine-6-carboxylic acid (2.92 g) as a yellow solid which was used directly in the next step without further purification. MS obsd. ($ESI^+$): m/z 213.1 $[(M+H)^+]$.

Step G: ethyl 2-[(2,4-dimethoxyphenyl)methyl-(5-oxo-3,4-dihydro-2H-thieno[3,4-b]oxepine-6-carbonyl)amino]acetate

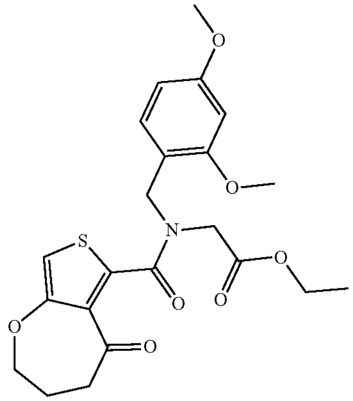 [SMILES: CCOC(=O)CN(Cc1ccc(OC)cc1OC)C(=O)c1scc2c1C(=O)CCCO2]

To a solution of 5-oxo-3,4-dihydro-2H-thieno[3,4-b]oxepine-6-carboxylic acid (2.42 g, 10.26 mmol, 1.0 eq.), ethyl 2-[(2,4-dimethoxyphenyl)methylamino]acetate (3.22 g, 12.32 mmol, 1.0 eq.) and HATU (5.91 g, 15.39 mmol, 1.5 eq.) in DMF (65.0 mL) was added DIPEA (2.68 g, 20.53 mmol, 2.0 eq.) at 0° C. The mixture was stirred at RT for 1 h. LC-MS indicated complete conversion. The resulting mixture was quenched with water at 0° C., extracted with EA, and the combined organic layers were washed with brine, dried over anhydrous sodium sulfate and concentrated in vacuum. The residue was purified by flash chromatography on silica (EA/PE, gradient 0-50%) to give ethyl 2-[(2,4-dimethoxyphenyl)methyl-(5-oxo-3,4-dihydro-2H-thieno[3,4-b]oxepine-6-carbonyl)-amino]acetate (4.00 g) as a yellow oil. MS obsd. ($ESI^+$): m/z 447.2 $[(M+H)^+]$.

Step H: Ethyl 6-[(2,4-dimethoxyphenyl)methyl]-5-oxo-12-oxa-3-thia-6-azatricyclo[$6.4.1.0^{4,13}$]trideca-1, 4(13), 7-triene-7-carboxylate

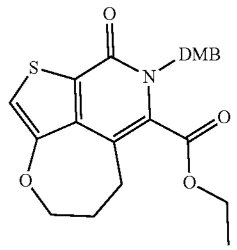

To a solution of ethyl 2-[(2,4-dimethoxyphenyl)methyl-(5-oxo-3,4-dihydro-2H-thieno[3,4-b]oxepine-6-carbonyl)amino]acetate (3.50 g, 7.83 mmol, 1.0 eq.) in DMF (35.0 mL) was added NaH (313 mg, 7.83 mmol, purity 60%, 1.0 eq.) at 0° C. The mixture was stirred at RT for 2 hr. LC-MS indicated complete conversion. The resulting mixture was added into the aqueous citric acid (30.0%) at 0° C. The mixture was extracted with EA, and the combined organic layers were washed with brine, dried over anhydrous sodium sulfate and concentrated in vacuum. The residue was purified by flash chromatography on silica (EA/PE, gradient 0-50%) to give ethyl 6-[(2,4-dimethoxyphenyl)methyl]-5- oxo-12-oxa-3-thia-6-azatricyclo[6.4.1.$0^{4,13}$]trideca-1,4(13),7-triene-7-carboxylate (2.15 g) as a yellow solid. MS obsd. ($ESI^+$): m/z 430.1 [$(M+H)^+$].

Step I: Ethyl 5-oxo-12-oxa-3-thia-6-azatricyclo[6.4.1.$0^{4,13}$]trideca-1,4(13),7-triene-7-carboxylate

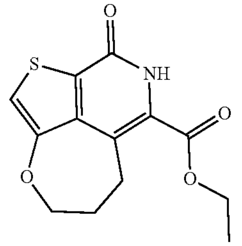 [SMILES: CCOC(=O)c1[nH]c(=O)c2scc3c2c1CCCO3]

A solution of ethyl 6-[(2,4-dimethoxyphenyl)methyl]-5-oxo-12-oxa-3-thia-6-azatricyclo[6.4.1.$0^{4,13}$]trideca-1,4(13),7-triene-7-carboxylate (2.15 g, 5.01 mmol, 1.0 eq.) in 4M HCl/dioxane (68.0 mL, 272.0 mmol, 54.0 eq.) was stirred at 80° C. for 3 hr. LC-MS indicated complete conversion. The solvent was removed in vacuum. The mixture was extracted with EA, and the combined organic layers were washed with brine, dried over anhydrous sodium sulfate and concentrated in vacuum. The residue was purified by flash chromatography on silica (EA/DCM, gradient 0-5%) to give ethyl 5-oxo-12-oxa-3-thia-6-azatricyclo[6.4.1.$0^{4,13}$]trideca-1,4(13), 7-triene-7-carboxylate (1.10 g, 3.94 mmol, 78.6% yield, 100.0% purity) as a white solid. MS obsd. ($ESI^+$): m/z 280.0 [$(M+H)^+$].

Step J: Ethyl 2-bromo-5-oxo-12-oxa-3-thia-6-azatricyclo[6.4.1.$0^{4,13}$]trideca-1, 4(13), 7-triene-7-carboxylate

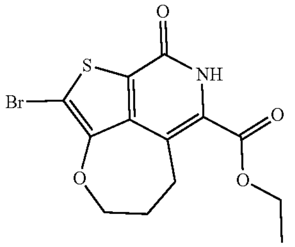 [SMILES: CCOC(=O)c1[nH]c(=O)c2sc(Br)c3c2c1CCCO3]

To a solution of ethyl 5-oxo-12-oxa-3-thia-6-azatricyclo[6.4.1.$0^{4,13}$]trideca-1,4(13),7-triene-7-carboxylate (1.13 g, 3.85 mmol, 1.0 eq.) in DMF (85.0 mL) was added NBS (822 mg, 4.62 mmol, 1.2 eq.) at 0° C. The mixture was stirred at RT for 2 hr. LC-MS indicated complete conversion. The resulting mixture was extracted with EA, and the combined organic layers were washed with brine, dried over anhydrous sodium sulfate and concentrated in vacuum. The residue was purified by flash chromatography on silica (MeOH/DCM, gradient 0-5%) to give ethyl 2-bromo-5-oxo-12-oxa-3-thia-6-azatricyclo[6.4.1.$0^{4,13}$]trideca-1,4(13),7-triene-7-carboxylate (791 mg) as a white solid. MS obsd. ($ESI^+$): m/z 357.9 [$(M+H)^+$].

Step K: 2-bromo-7-(hydroxymethyl)-12-oxa-3-thia-6-azatricyclo[6.4.1.$0^{4,13}$]trideca-1,4(13),7-trien-5-one

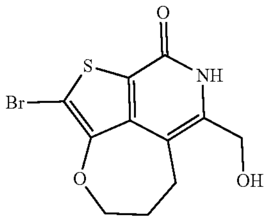 [SMILES: O=c1[nH]c(CO)c2c3c(c(Br)sc13)OCCC2]

To a solution of ethyl 2-bromo-5-oxo-12-oxa-3-thia-6-azatricyclo[6.4.1.$0^{4,13}$]trideca-1,4(13),7-triene-7-carboxylate (1.97 g, 5.50 mmol, 1.0 eq.) in DCM (250 mL) was added Diisobutylaluminum hydride (10.51 g, 22.0 mmol, 4.0 eq.) at −60° C. The mixture was stirred at −60° C. for 1 h. Then the mixture was stirred at RT overnight. LC-MS indicated complete conversion. The reaction mixture was quenched with water, extracted with DCM, and the combined organic layers were washed with brine, dried over anhydrous sodium sulfate and concentrated in vacuum. The residue was purified by flash chromatography on silica (MeOH/DCM, gradient 0-30%) to give crude 2-bromo-7-(hydroxymethyl)-12-oxa-3-thia-6-azatricyclo[6.4.1.$0^{4,13}$]trideca-1,4(13),7-trien-5-one (667 mg) as a yellow solid which was used directly in the next step without further purification. MS obsd. ($ESI^+$): m/z 317.2[$(M+H)^+$].

Step L: 2-bromo-5-oxo-12-oxa-3-thia-6-azatricyclo[6.4.1.$0^{4,13}$]trideca-1, 4(13), 7-triene-7-carbaldehyde

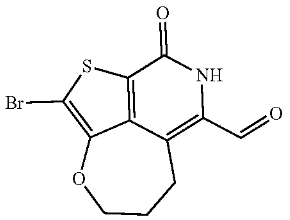 [SMILES: O=Cc1[nH]c(=O)c2sc(Br)c3c2c1CCCO3]

To a solution of 2-bromo-7-(hydroxymethyl)-12-oxa-3-thia-6-azatricyclo[6.4.1.$0^{4,13}$]trideca-1,4(13),7-trien-5-one (1.70 g, 5.38 mmol, 1.0 eq.) in DCM (150.0 mL) was added Dess-Martin Periodinane (4.56 g, 10.75 mmol, 2.0 eq.). The mixture was stirred at RT for 2 hr. LC-MS indicated complete conversion. The resulting mixture was quenched with water, extracted with DCM, and the combined organic layers were washed with brine, dried over anhydrous sodium sulfate and concentrated in vacuum. The residue was purified by flash chromatography on silica (MeOH/DCM, gradient 0-30%) to give 2-bromo-5-oxo-12-oxa-3-thia-6-azatricyclo[6.4.1.$0^{4,13}$]trideca-1,4(13),7-triene-7-carbaldehyde (368 mg) as a yellow solid. MS obsd. ($ESI^+$): m/z 313.1, 315.1 [$(M+H)^+$].

Step M: 2-bromo-7-(1-hydroxyethyl)-12-oxa-3-thia-6-azatricyclo[6.4.1.$0^{4,13}$]trideca-1,4(13),7-trien-5-one

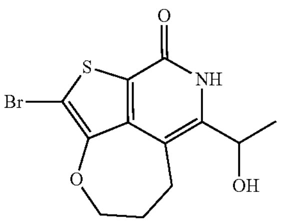 [SMILES: CC(O)c1[nH]c(=O)c2sc(Br)c3c2c1CCCO3]

To a solution of 2-bromo-5-oxo-12-oxa-3-thia-6-azatricyclo[6.4.1.$0^{4,13}$]trideca-1,4(13),7-triene-7-carbaldehyde (580 mg, 1.85 mmol, 1.0 eq.) in THF (50.0 mL) was added MeMgBr (2.20 g, 18.46 mmol, 10.0 eq.) slowly at 0° C. The mixture was stirred at 0° C. for 1 hr. LC-MS indicated complete conversion. The reaction mixture was quenched with saturated $NH_4Cl$ solution, extracted with EA, and the combined organic layers were washed with brine, dried over anhydrous sodium sulfate and concentrated in vacuum to give crude 2-bromo-7-(1-hydroxyethyl)-12-oxa-3-thia-6-azatricyclo[6.4.1.$0^{4,13}$]trideca-1,4(13),7-trien-5-one (470 mg) as a brown solid which was used directly in the next step without further purification. MS obsd. ($ESI^+$): m/z 330.0, 332.0 $[(M+H)^+]$.

Step N: 2-bromo-7-(1-chloroethyl)-12-oxa-3-thia-6-azatricyclo[6.4.1.$0^{4,13}$]trideca-1,4(13),7-trien-5-one

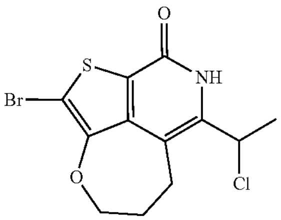 [SMILES: CC(Cl)c1[nH]c(=O)c2sc(Br)c3c2c1CCCO3]

To a solution of 2-bromo-7-(1-hydroxyethyl)-12-oxa-3-thia-6-azatricyclo[6.4.1.$0^{4,13}$]trideca-1,4(13),7-trien-5-one (360 mg, 1.09 mmol, 1.0 eq.) in DCM (50.0 mL) was added $SOCl_2$ (13.34 g, 109.00 mmol, 100 eq.) at ° C. The mixture was stirred at RT for 2 hr. LC-MS indicated complete conversion. The solvent was removed under reduced pressure. The residue was extracted with EA, and the combined organic layers were washed with brine, dried over anhydrous sodium sulfate and concentrated in vacuum to give crude 2-bromo-7-(1-chloroethyl)-12-oxa-3-thia-6-azatricyclo [6.4.1.$0^{4,13}$]trideca-1,4(13),7-trien-5-one (390 mg) as a white solid which was used directly in the next step without further purification. MS obsd. ($ESI^+$): m/z 347.9, 349.9 $[(M+H)^+]$.

Step O: 2-bromo-7-(1-pyrazol-1-ylethyl)-12-oxa-3-thia-6-azatricyclo[6.4.1.$0^{4,13}$]trideca-1,4(13),7-trien-5-one

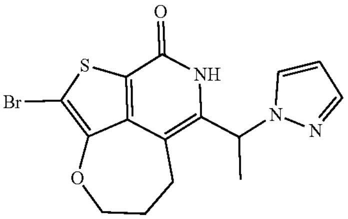 [SMILES: CC(c1[nH]c(=O)c2sc(Br)c3c2c1CCCO3)n1cccn1]

To a solution of 2-bromo-7-(1-chloroethyl)-12-oxa-3-thia-6-azatricyclo[6.4.1.$0^{4,13}$]trideca-1,4(13),7-trien-5-one (150 mg, 0.43 mmol, 1.0 eq.), 1H-pyrazole (75 mg, 1.08 mmol, 2.5 eq.) and $K_2CO_3$ (224 mg, 1.62 mmol, 3.8 eq.) in ACN (15.0 mL) was added KI (79 mg, 0.47 mmol, 1.1 eq.). The mixture was stirred at RT for 16 hr. LC-MS indicated complete conversion. The solvent was removed under reduced pressure. The resulting mixture was extracted with EA, and the combined organic layers were washed with brine, dried over anhydrous sodium sulfate and concentrated in vacuum. The residue was purified by flash chromatography on silica (MeOH/DCM, gradient 0-5%) to give 2-bromo-7-(1-pyrazol-1-ylethyl)-12-oxa-3-thia-6-azatricyclo[6.4.1.$0^4$ $1^3$]trideca-1, 4(13), 7-trien-5-one (110 mg) as a white solid. MS obsd. ($ESI^+$): m/z 380.0, 382.0 $[(M+H)^+]$.

Step P: 2-(1H-pyrazol-4-yl)-7-(1-pyrazol-1-ylethyl)-12-oxa-3-thia-6-azatricyclo[6.4.1.$0^{4,13}$]trideca-1, 4(13), 7-trien-5-one

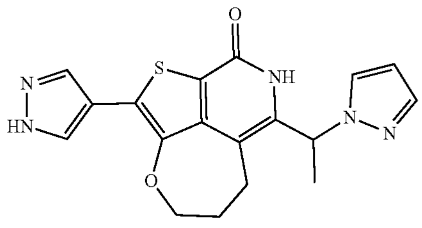 [SMILES: CC(c1[nH]c(=O)c2sc(-c3cn[nH]c3)c3c2c1CCCO3)n1cccn1]

To a solution of 2-bromo-7-(1-pyrazol-1-ylethyl)-12-oxa-3-thia-6-azatricyclo[6.4.1.$0^{4,13}$]trideca-1, 4(13), 7-trien-5-one (100 mg, 0.26 mmol, 1.0 eq.) and 1H-pyrazol-4-ylboronic acid (60 mg, 0.53 mmol, 2.0 eq.) in a mixed solvents of $H_2O$ (2.5 mL) and DMF (5.0 mL) was added Xphos (38 mg, 0.08 mmol, 0.3 eq.), $Na_2CO_3$ (84 mg, 0.08 mmol, 3.0 eq.) and $Pd(dppf)Cl_2$ (65 mg, 0.08 mmol, 0.3 eq.). The mixture was irradiated on a microwave reactor at 100° C. for 2 hr under nitrogen atmosphere. LC-MS indicated complete conversion. The solvent was removed under reduced pressure. The resulting mixture was extracted with EA, and the combined organic layers were washed with brine, dried over anhydrous sodium sulfate and concentrated in vacuum. The residue was purified by flash chromatography on silica (MeOH/DCM, gradient 0-5%) to give 2-(1H-pyrazol-4-yl)-7-(1-pyrazol-1-ylethyl)-12-oxa-3-thia-6-azatricyclo [6.4.1.$0^{4,13}$]trideca-1,4(13),7-trien-5-one (42 mg) as a white solid. MS obsd. ($ESI^+$): m/z 368.1 $[(M+H)^+]$.

The racemic product was resolved with chiral SFC to give (R)-2-(1H-pyrazol-4-yl)-7-(1-pyrazol-1-ylethyl)-12-oxa-3-thia-6-azatricyclo[6.4.1.$0^{4,13}$]trideca-1, 4(13), 7-trien-5-one as a white solid.

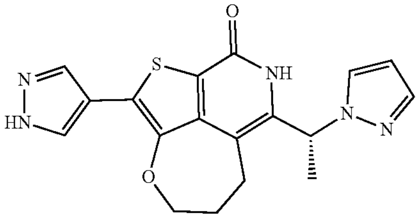 [SMILES: C[C@H](c1[nH]c(=O)c2sc(-c3cn[nH]c3)c3c2c1CCCO3)n1cccn1]

SFC condition: column-AD-H, column size-0.46 cm I.D.*15 cm L, injection—2 ul, mobile phase-HEP: EtOH (0.1% DEA) (60:40), flow rate-0.5 ml, wave length-UV 254 nm, T–25° C., solution of EtOH. MS obsd. ($ESI^+$): m/z 368.1 [$(M+H)^+$]. $^1H$ NMR (400 MHz, DMSO) δ ppm: 13.17 (s, 1H), 10.74 (s, 1H), 8.04 (s, 1H), 7.98 (d, J=2.4 Hz, 2H), 7.55 (d, J=1.9 Hz, 1H), 6.32 (t, J=2.1 Hz, 1H), 5.91-5.96 (m, 1H), 4.26-4.37 (m, 2H), 3.04-3.11 (m, 1H), 2.94-3.01 (m, 1H), 2.07-2.15 (m, 2H), 1.84 (d, J=7.1 Hz, 3H); and (S)-2-(1H-pyrazol-4-yl)-7-(1-pyrazol-1-ylethyl)-12-oxa-3-thia-6-azatricyclo[6.4.1.$0^{4,13}$]trideca-1, 4(13), 7-trien-5-one as a white solid.

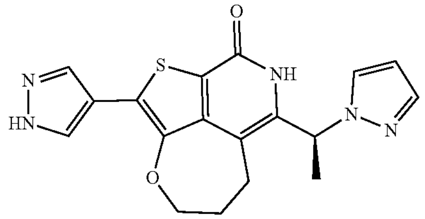 [SMILES: C[C@@H](c1[nH]c(=O)c2sc(-c3cn[nH]c3)c3c2c1CCCO3)n1cccn1]

SFC condition: column-AD-H, column size-0.46 cm I.D.*15 cm L, injection—2 ul, mobile phase-HEP: EtOH (0.1% DEA) (60:40), flow rate-0.5 ml, wave length-UV 254 nm, T–25° C., solution of EtOH. MS obsd. ($ESI^+$): m/z 368.1 [$(M+H)^+$]. $^1H$ NMR (400 MHz, DMSO-d6) δ ppm: 13.17 (s, 1H), 10.74 (s, 1H), 8.18 (s, 1H), 7.98 (s, 1H), 7.89 (s, 1H), 7.55 (d, J=1.9 Hz, 1H), 6.32 (t, J=2.1 Hz, 1H), 5.91-5.96 (i, 1H), 4.26-4.37 (m, 2H), 3.04-3.11 (m, 1H), 2.94-3.01 (m, 1H), 2.07-2.15 (m, 2H), 1.84 (d, J=7.1 Hz, 3H). The absolute stereochemistry of these two compounds was randomly assigned.

The following compounds were prepared in a similar manner as that illustrated in Examples 26 and 27.

| Compound No. | Compound Structure | Compound Name | MS obsd. ($ESI^+$): m/z [$(M + H)^+$] |
|---|---|---|---|
| Example 48 | 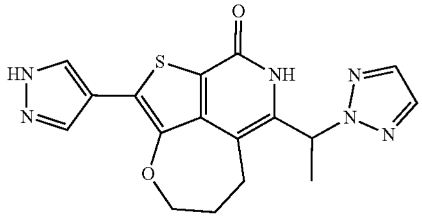 [SMILES: CC(c1[nH]c(=O)c2sc(-c3cn[nH]c3)c3c2c1CCCO3)n1nccn1] | 2-(1H-pyrazol-4-yl)-7-[1-(triazol-2-yl)ethyl]-12-oxa-3-thia-6-azatricyclo[6.4.1.$0^{4,13}$] trideca-1,4(13),7-trien-5-one (racemic) | 369 |
| Example 49 | 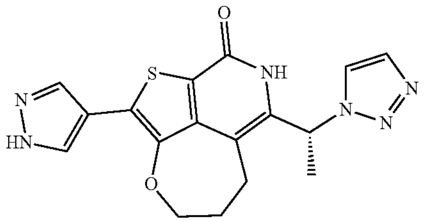 [SMILES: C[C@H](c1[nH]c(=O)c2sc(-c3cn[nH]c3)c3c2c1CCCO3)n1ccnn1] | (R)-5-(1-(1H-1,2,3-triazol-1-yl)ethyl)-1-(1H-pyrazol-4-yl)-4,6,7,8-tetrahydro-3H-9-oxa-2-thia-4-azabenzo[cd]azulen-3-one# | 369 |
| Example 50 | 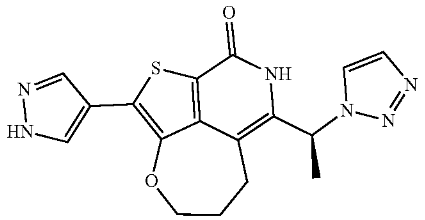 [SMILES: C[C@@H](c1[nH]c(=O)c2sc(-c3cn[nH]c3)c3c2c1CCCO3)n1ccnn1] | (S)-5-(1H-(1,2,3-triazol-1-yl)ethyl)-1-(1H-pyrazol-4-yl)-4,6,7,8-tetrahydro-3H-9-oxa-2-thia-4-azabenzo[cd]azulen-3-one# | 369 |

#The absolute stereochemistry was randomly assigned.

Example 51: 2-(1H-pyrazol-4-yl)-7-(pyrrolidine-1-carbonyl)-12-oxa-3-thia-6-azatricyclo[6.4.1.$0^4$,13]-trideca-1,4(13),7-trien-5-one

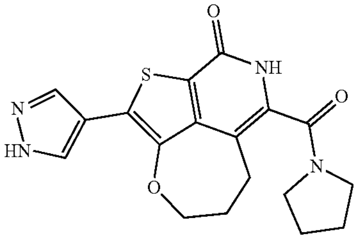 [SMILES: O=C(c1[nH]c(=O)c2sc(-c3cn[nH]c3)c3c2c1CCCO3)N1CCCC1]

Step A: 2-bromo-7-(pyrrolidine-1-carbonyl)-12-oxa-3-thia-6-azatricyclo[6.4.1.$0^{4,13}$]trideca-1,4(13),7-trien-5-one

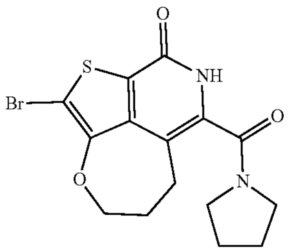 [SMILES: O=C(c1[nH]c(=O)c2sc(Br)c3c2c1CCCO3)N1CCCC1]

Ethyl 2-bromo-5-oxo-12-oxa-3-thia-6-azatricyclo[6.4.1.$0^{4,13}$]trideca-1,4(13),7-triene-7-carboxylate (50 mg, 0.14 mmol, 1 eq.) was dissolved in Pyrrolidine (1.5 mL) at room temperature. The mixture was stirred at 80° C. for 2 hr. LCMS showed the reaction was complete. The resulting mixture was concentrated, extracted with EA and H2O. Organic layers was combined, washed with brine, dried over anhydrous sodium sulfate, filtered and the filtrate was concentrated in vacuum, the residue was purified by column chromatography ($SiO_2$, DCM:MeOH=50:1 to 10:1) to give 2-bromo-7-(pyrrolidine-1-carbonyl)-12-oxa-3-thia-6-azatricyclo[6.4.1.$0^{4,13}$]trideca-1,4(13),7-trien-5-one (47 mg) as a white solid. MS obsd. ($ESI^+$): m/z 383.0, 385.0 [$(M+H)^+$].

Step B: 2-(1H-pyrazol-4-yl)-7-(pyrrolidine-1-carbonyl)-12-oxa-3-thia-6-azatricyclo[6.4.1.$0^4$,$1^1$]-trideca-1,4(13),7-trien-5-one

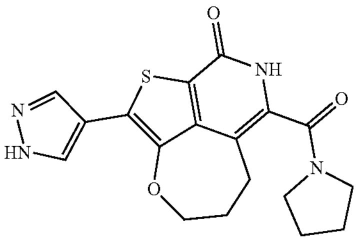 [SMILES: O=C(c1[nH]c(=O)c2sc(-c3cn[nH]c3)c3c2c1CCCO3)N1CCCC1]

To a solution of 2-bromo-7-(pyrrolidine-1-carbonyl)-12-oxa-3-thia-6-azatricyclo[6.4.1.$0^{4,13}$]-trideca-1,4(13),7-trien-5-one (42 mg, 0.11 mmol, 1.0 eq.) in a mixed solvents of DMF (3.0 mL) and $H_2O$ (0.6 mL) was added 1H-pyrazol-4-ylboronic acid (24 mg, 0.22 mmol, 2.0 eq.), Pd(dppf)$Cl_2$ (18 mg, 0.02 mmol, 0.2 eq.), X-Phos (16 mg, 0.03 mmol, 0.3 eq.), $NaHCO_3$ (9 mg, 0.33 mmol, 3.0 eq.) under $N_2$ at room temperature. The mixture was irradiated on a microwave reactor at 105° C. for 1.5 h. LCMS showed the reaction was complete. The resulting mixture was concentrated, extracted with EA. Organic layers was combined, washed with brine, dried over anhydrous sodium sulfate, filtered and the filtrate was concentrated in vacuum, the residue was purified by column chromatography ($SiO_2$, DCM:MeOH=50:1 to 10:1) to give the crude product which was further purified by prep-HPLC. The eluent was concentrated under reduced pressure at 50° C. to remove the organic solvent. The residual aqueous solution was lyophilized to give 2-(1H-pyrazol-4-yl)-7-(pyrrolidine-1-carbonyl)-12-oxa-3-thia-6-azatricyclo-[6.4.1.$0^{4,13}$]-trideca-1,4(13),7-trien-5-one (20 mg) as a white solid. MS obsd. ($ESI^+$): m/z 371.1 [$(M+H)^+$]. $^1$H NMR (400 MHz, DMSO) S ppm: 13.17 (s, 1H), 11.67 (s, 1H), 8.19 (s, 1H), 7.90 (s, 1H), 4.36 (t, J=5.6 Hz, 2H), 3.44-3.43 (m, 2H), 3.29-3.23 (m, 2H), 2.51-2.50 (m, 2H), 2.12-2.10 (m, 2H), 1.89-1.83 (m, 4H).

Example 52: 7-(morpholine-4-carbonyl)-2-(1H-pyrazol-4-yl)-12-oxa-3-thia-6-azatricyclo[6.4.1.$0^4$,13]-trideca-1,4(13),7-trien-5-one

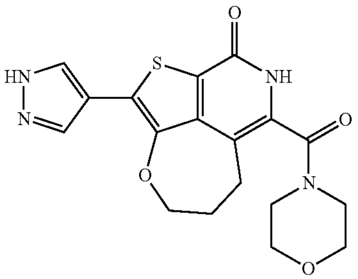 [SMILES: O=C(c1[nH]c(=O)c2sc(-c3cn[nH]c3)c3c2c1CCCO3)N1CCOCC1]

Step A: 2-bromo-7-(morpholine-4-carbonyl)-12-oxa-3-thia-6-azatricyclo[6.4.1.$0^{4,13}$]trideca-1,4(13),7-trien-5-one

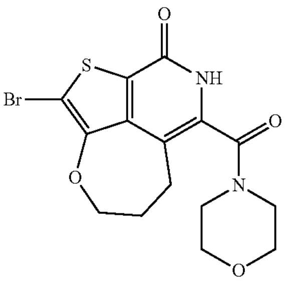 [SMILES: O=C(c1[nH]c(=O)c2sc(Br)c3c2c1CCCO3)N1CCOCC1]

A suspension of ethyl 2-bromo-5-oxo-12-oxa-3-thia-6-azatricyclo[6.4.1.$0^{4,13}$]trideca-1,4(13),7-triene-7-carboxylate (50 mg, 0.14 mmol, 1.0 eq.) in morpholino (2.0 mL) was heated to 100° C. for 2 h. LCMS showed the reaction was complete. The reaction mixture was extracted with EA, the organic layers were dried over anhydrous sodium sulfate and concentrated. The residue was purified with flash chromatography (MeOH/DCM, gradient 0-40%) to afford 7-(morpholine-4-carbonyl)-2-(1H-pyrazol-4-yl)-12-oxa-3-thia-6-azatricyclo[6.4.1.$0^{4,13}$]trideca-1,4(13),7-trien-5-one (28 mg) as a yellow solid. MS obsd. ($ESI^+$): m/z 399.0, 401.0 $[(M+H)^+]$.

Step B: 7-(morpholine-4-carbonyl)-2-(1H-pyrazol-4-yl)-12-oxa-3-thia-6-azatricyclo[6.4.1.$0^{4,13}$]-trideca-1,4(13),7-trien-5-one

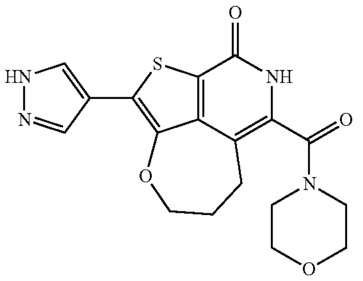 [SMILES: O=C(c1[nH]c(=O)c2sc(-c3cn[nH]c3)c3c2c1CCCO3)N1CCOCC1]

A suspension of 1H-pyrazol-4-ylboronic acid (16 mg, 0.13 mmol, 2.0 eq.), 2-bromo-7-(morpholine-4-carbonyl)-12-oxa-3-thia-6-azatricyclo[6.4.1.$0^{4,13}$]trideca-1,4(13),7-trien-5-one (28 mg, 0.07 mmol, 1.0 eq.), $NaHCO_3$ (17 mg, 0.20 mmol, 3.0 eq.), Xphos (10 mg, 0.02 mmol, 0.3 eq.), $Pd(dppf)_2Cl_2$ (11 mg, 0.01 mmol, 0.2 eq.) in a mixed solvents of DMF (0.5 mL) and $H_2O$ (0.1 mL) was irradiated on a microwave reactor at 105° C. for 1.5 h under nitrogen atmosphere. LCMS showed that complete conversion. The solvent was removed. The residue was extracted with EA, dried over $Na_2SO_4$ and concentrated. The residue was purified by flash column chromatography (EA/PE, gradient 0-70%) to afford 7-(morpholine-4-carbonyl)-2-(1H-pyrazol-4-yl)-12-oxa-3-thia-6-azatricyclo[6.4.1.$0^{4,13}$]-trideca-1,4(13),7-trien-5-one (3 mg) as a white solid. MS obsd. ($ESI^+$): m/z 399.0, 401.0 $[(M+H)^+]$. $^1H$ NMR (400 MHz, DMSO) δ ppm: 13.17 (s, 1H), 11.74 (s, 1H), 8.19 (s, 1H), 7.91 (s, 1H), 4.34-4.36 (m, 2H), 3.35-3.69 (m, 6H), 3.26-3.28 (m, 2H), 2.73-2.76 (m, 2H), 2.09-2.15 (m, 2H).

Example 53: 5-(3-hydroxyazetidine-1-carbonyl)-1-(1H-pyrazol-4-yl)-4,6,7,8-tetrahydro-3H-9-oxa-2-thia-4-azabenzo[cd]azulen-3-one

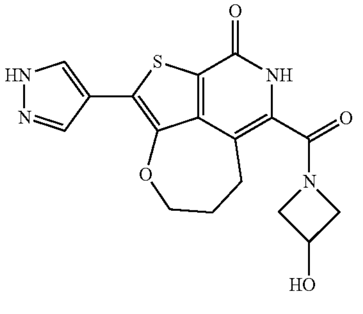 [SMILES: O=C(c1[nH]c(=O)c2sc(-c3cn[nH]c3)c3c2c1CCCO3)N1CC(O)C1]

Step A: (1-bromo-5-(3-hydroxyazetidine-1-carbonyl)-4,6,7,8-tetrahydro-3H-9-oxa-2-thia-4-aza benzo[cd]azulen-3-one

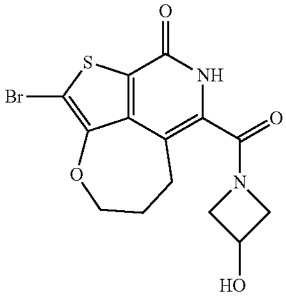 [SMILES: O=C(c1[nH]c(=O)c2sc(Br)c3c2c1CCCO3)N1CC(O)C1]

To a solution of azetidin-3-ol (363 mg, 3.32 mmol, 25.0 eq.) and ethyl 2-bromo-5-oxo-12-oxa-3-thia-6-azatricyclo[6.4.1.$0^{4,13}$]trideca-1,4(13),7-triene-7-carboxylate (50 mg, 0.13 mmol, 1.0 eq.) was dissolved in DBU (1.01 g, 6.63 mmol, 50.0 eq.). The mixture was stirred at 80'C for 1 h. LCMS showed the reaction was complete. The resulting mixture was extracted with EA. The combined organic layers were washed with brine, dried over anhydrous sodium sulfate and concentrated. The residue was purified by flash chromatography (MeOH/DCM, gradient 0-10%) to give (1-bromo-5-(3-hydroxyazetidine-1-carbonyl)-4,6,7,8-tetrahydro-3H-9-oxa-2-thia-4-azabenzo[cd]-azulen-3-one (42 mg) as a white solid. MS obsd. ($ESI^+$): m/z 386 $[(M+H)^+]$.

Step B: 5-(3-hydroxyazetidine-1-carbonyl)-1-(1H-pyrazol-4-yl)-4,6,7,8-tetrahydro-3H-9-oxa-2-thia-4-azabenzo[cd]azulen-3-one

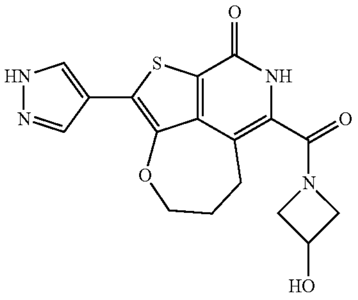 [SMILES: O=C(c1[nH]c(=O)c2sc(-c3cn[nH]c3)c3c2c1CCCO3)N1CC(O)C1]

To a solution of 2-bromo-7-(3-hydroxyazetidine-1-carbonyl)-12-oxa-3-thia-6-azatricyclo-[6.4.1.$0^{4,13}$]trideca-1,4(13),7-trien-5-one (34 mg, 0.08 mmol, 1.0 eq.), 1H-pyrazol-4-ylboronic acid (9 mg, 0.08 mmol, 1.0 eq.), $K_2CO_3$ (34 mg, 0.24 mmol, 3 eq.), $Pd(dppf)Cl_2$ (13 mg, 0.02 mmol, 0.2 eq.) and Xphos (12 mg, 0.02 mmol, 0.3 eq.) in DMF (2.5 mL) was added $H_2O$ (0.5 mL), The reaction mixture was irradiated on a microwave reactor at 120° C. for 1 h. LCMS showed the reaction was complete. The resulting mixture was extracted with EA. The combined organic layers were washed with brine, dried over anhydrous sodium sulfate and concentrated. The residue was purified by prep-HPLC to give 5-(3-hydroxyazetidine-1-carbonyl)-1-(1H-pyrazol-4-yl)-4,6,7,8-tetrahydro-3H-9-oxa-2-thia-4-azabenzo[cd]azulen-3-one (5 mg) as a brown solid. MS obsd. ($ESI^+$): m/z 373.1 $[(M+H)^+]$. $^1H$ NMR (400 MHz, DMSO) δ ppm 13.16

(s, 1H), 11.58 (s, 1H), 8.14 (s, H), 7.94 (s, H), 5.85 (d, J=5.9 Hz, 1H), 4.53 (d, J=5.8 Hz, 1H), 4.35 (t, J=5.7 Hz, 2H), 4.18-4.27 (m, 1H), 4.13 (t, J=8.28 Hz, 1H), 3.76 (m, 2H), 2.83-2.85 (m, 2H), 2.23-2.03 (m, 2H).

Example 54: 7-amino-2-(1H-pyrazol-4-yl)-12-oxa-3-thia-6-azatricyclo[6.4.1.0$^{4,13}$]trideca-1,4(13),7-trien-5-one

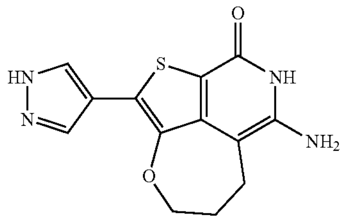 [SMILES: Nc1[nH]c(=O)c2sc(-c3cn[nH]c3)c3c2c1CCCO3]

Step A: 5-oxo-12-oxa-3-thia-6-azatricyclo[6.4.1.0$^{4,13}$]trideca-1,4(13),7-triene-7-carboxylic acid

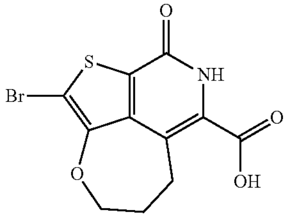 [SMILES: O=C(O)c1[nH]c(=O)c2sc(Br)c3c2c1CCCO3]

To a solution of ethyl 5-oxo-12-oxa-3-thia-6-azatricyclo[6.4.1.0$^{4,13}$]trideca-1,4(13),7-triene-7-carboxylate (776 mg, 2.17 mmol, 1.0 eq.) in MeOH (15.0 mL) was added NaOH (221 mg, 5.51 mmol, 2.0 eq.) and $H_2O$ (5.0 mL). The mixture was stirred at 60° C. for 4 h. LCMS indicated complete conversion. The mixture was acided with 3M aqueous HCl. The solid formed was collected and dried to afford 5-oxo-12-oxa-3-thia-6-azatricyclo[6.4.1.0$^{4,13}$]-trideca-1,4(13),7-triene-7-carboxylic acid (610 mg) as a white solid. MS obsd. (ESI$^+$): m/z 330.0, 332.0 [(M+H)$^+$].

Step B: Tert-butyl-N-(5-oxo-12-oxa-3-thia-6-azatricyclo[6.4.1.0$^{4,13}$]trideca-1,4(13),7-trien-7-yl)carbamate

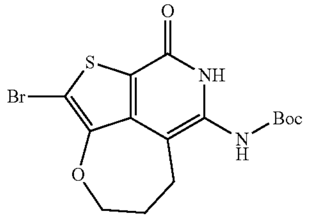 [SMILES: CC(C)(C)OC(=O)Nc1[nH]c(=O)c2sc(Br)c3c2c1CCCO3]

To a solution of 5-oxo-12-oxa-3-thia-6-azatricyclo[6.4.1.0$^{4,13}$]trideca-1,4(13),7-triene-7-carboxylic acid (100 mg, 0.30 mmol, 1.0 eq.) and DPPA (442 mg, 1.82 mmol, 4.0 eq.) in a mixed solvents of MeCN (45.0 mL) and t-BuOH (45.0 mL) was added $Et_3N$ (368 mg, 3.63 mmol, 6.0 eq.) dropwise at rt. The mixture was stirred at 80° C. for 72 h. LCMS indicated 80% conversion and. The mixture was extracted with EA, dried over $Na_2SO_4$, concentrated to afford tert-butyl-N-(5-oxo-12-oxa-3-thia-6-azatricyclo[6.4.1.0$^{4,13}$]trideca-1,4(13),7-trien-7-yl)carbamate (70 mg) as a yellow oil. MS obsd. (ESI$^+$): m/z 401.1, 403.1 [(M+H)$^+$].

Step C: 7-amino-2-bromo-12-oxa-3-thia-6-azatricyclo[6.4.1.0$^{4,13}$]trideca-1,4(13),7-trien-5-one

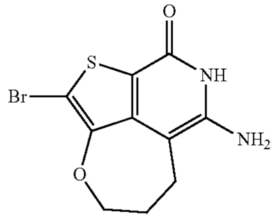 [SMILES: Nc1[nH]c(=O)c2sc(Br)c3c2c1CCCO3]

To a solution of tert-butyl N-(2-bromo-5-oxo-12-oxa-3-thia-6-azatricyclo[6.4.1.0$^{4,13}$]trideca-1,4(13),7-trien-7-yl) carbamate (75 mg, 0.18 mmol, 1.0 eq.) in EA (5.0 mL) was added HCl (4 M in 1,4-dioxane, 1.0 mL, excess) at rt. The mixture was stirred at 60° C. for 3 hr. LC-MS showed the reaction was completed. The solvent was removed in vacuum and the residue was treated with saturated aqueous $K_2CO_3$, diluted with $H_2O$, and extracted with EA. The combined organic extracts were washed with saturated aqueous NaCl (20 mL), dried ($Na_2SO_4$), and concentrated in vacuo. The crude residue was purified by flash chromatography ($SiO_2$, PE:EA=50:1 to 1:1) to give 7-amino-2-bromo-12-oxa-3-thia-6-azatricyclo[6.4.1.0$^{4,13}$]trideca-1,4(13),7-trien-5-one (50 mg) as a white solid. MS obsd. (ESI$^+$): m/z 301.0, 303.0 [(M+H)$^+$].

Step D: 7-amino-2-(1H-pyrazol-4-yl)-12-oxa-3-thia-6-azatricyclo[6.4.1.0$^{4,13}$]trideca-1,4(13),7-trien-5-one

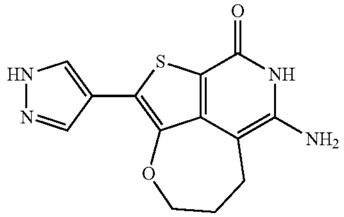 [SMILES: Nc1[nH]c(=O)c2sc(-c3cn[nH]c3)c3c2c1CCCO3]

To a solution of 7-amino-2-bromo-12-oxa-3-thia-6-azatricyclo[6.4.1.0$^{4,13}$]trideca-1,4(13),7-trien-5-one (50 mg, 0.16 mmol, 1.0 eq.) in a mixed solvents of DMF (10.0 mL) and $H_2O$ (5.0 mL) was added 1H-pyrazol-4-ylboronic acid (35 mg, 0.32 mmol, 2.0 eq.), $Na_2CO_3$ (50 mg, 0.47 mmol, 3.0 eq.), Pd(dppf)$Cl_2$ (26 mg, 0.03 mmol, 0.2 eq.) and X-Phos (21 mg, 0.05 mmol, 0.3 eq.) under $N_2$ at room temperature. The mixture was irradiated on a microwave reactor at 110° C. for 1.5 h. LCMS showed the reaction was complete. The resulting mixture was concentrated, extracted with EA. Organic layers was combined, washed with brine, dried over anhydrous sodium sulfate, filtered and the filtrate was concentrated in vacuum, the residue was purified by column chromatography ($SiO_2$, PE:EA=50:1 to 1:1) to give the crude product. The crude product was further purified by prep-HPLC to give amino-2-(1H-pyrazol-4-yl)-12-oxa-3-thia-6-azatricyclo[6.4.1.$0^{4,13}$]trideca-1,4(13),7-trien-5-one (5 mg) as the yellow solid. MS obsd. ($ESI^+$): m/z 289.0 $[(M+H)^+]$. $^1H$ NMR (400 MHz, DMSO) δ ppm: 13.06 (s, 1H), 10.72 (s, 1H), 8.14-7.80 (m, 2H), 5.40 (s, 2H), 4.27 (t, J=5.2 Hz, 2H), 2.64 (t, J=6.0 Hz, 2H), 2.14-2.10 (m, 2H).

Example 55: 5-(cyclobutoxymethyl)-1-(1H-pyrazol-4-yl)-4,6,7,8-tetrahydro-3H-9-oxa-2-thia-4-azabenzo[cd]azulen-3-one

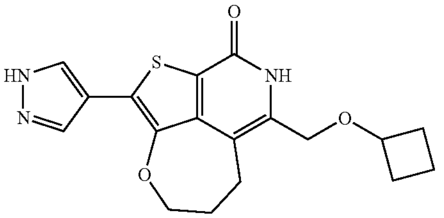 [SMILES: O=c1[nH]c(COC2CCC2)c2c3c(c(-c4cn[nH]c4)sc13)OCCC2]

Step A: 1-bromo-5-(chloromethyl)-4,6,7,8-tetrahydro-3H-9-oxa-2-thia-4-azabenzo[cd]azulen-3-one

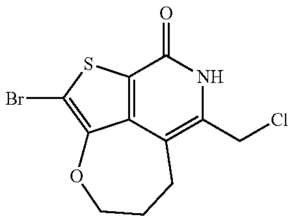 [SMILES: O=c1[nH]c(CCl)c2c3c(c(Br)sc13)OCCC2]

To a solution of 2-bromo-7-(hydroxymethyl)-12-oxa-3-thia-6-azatricyclo[6.4.1.$0^{4,13}$]trideca-1,4(13),7-trien-5-one (55 mg, 0.17 mmol, 1.0 eq.) in DCM (5.0 mL) was added $SOCl_2$ (207 mg, 1.74 mmol, 10.0 eq.). The mixture was stirred at rt for 2 h. LCMS showed the reaction was complete. The solvent was removed under reduced pressure to give 1-bromo-5-(chloromethyl)-4,6,7,8-tetrahydro-3H-9-oxa-2-thia-4-azabenzo[cd]azulen-3-one (54 mg) as a light-yellow solid which was used directly in the next step without further purification. MS obsd. ($ESI^+$): m/z 333.9, 335.9 $[(M+H)^+]$ Step B: 1-bromo-5-(cyclobutoxymethyl)-4,6,7,8-tetrahydro-3H-9-oxa-2-thia-4-azabenzo[cd]azulen-3-one

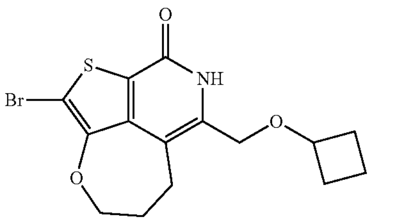 [SMILES: O=c1[nH]c(COC2CCC2)c2c3c(c(Br)sc13)OCCC2]

To a solution of cyclobutanol (111 mg, 1.53 mmol, 10.0 eq.) in DMF (3.0 mL) at rt was added NaH (7 mg, 0.18 mmol, 1.2 eq.) and stirred for 20 mins, 2-bromo-7-(chloromethyl)-12-oxa-3-thia-6-azatricyclo[6.4.1.$0^{4,13}$]trideca-1,4(13),7-trien-5-one (54 mg, 0.15 mmol, 1.0 eq.) was added to it. The mixture was stirred at rt for 2 h. LCMS showed the reaction was complete. The resulting mixture was extracted with EA. The combined organic layers were washed with brine, dried over anhydrous sodium sulfate and concentrated. The residue was purified by flash chromatography (EA/PE, gradient 0-50%) to give 1-bromo-5-(cyclobutoxymethyl)-4,6,7,8-tetrahydro-3H-9-oxa-2-thia-4-aza-benzo[cd]azulen-3-one (26 mg) as a light yellow solid. MS obsd. ($ESI^+$): m/z 370.0, 372.0 $[(M+H)^+]$.

Step C: 5-(cyclobutoxymethyl)-1-(1H-pyrazol-4-yl)-4,6,7,8-tetrahydro-3H-9-oxa-2-thia-4-azaben-zo[cd]azulen-3-one

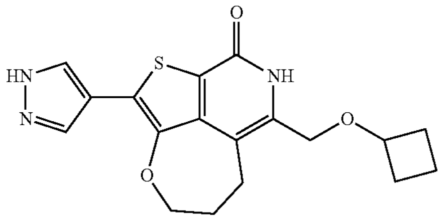 [SMILES: O=c1[nH]c(COC2CCC2)c2c3c(c(-c4cn[nH]c4)sc13)OCCC2]

To a solution of 2-bromo-7-(cyclobutoxymethyl)-12-oxa-3-thia-6-azatricyclo[6.4.1.$0^4$,1]-trideca-1,4(13),7-trien-5-one (26 mg, 0.07 mmol, 1.0 eq.), 1H-pyrazol-4-ylboronic acid (16 mg, 0.14 mmol, 2.0 eq.), Xphos (33 mg, 0.07 mmol, 1.0 eq.), $Na_2CO_3$ (9 mg, 0.07 mmol, 1.0 eq.), $Pd(dppf)Cl_2$ (57 mg, 0.07 mmol, 1.0 eq.) in DMF (2.0 mL) was added $H_2O$ (1.0 mL). The mixture was irradiated on a microwave reactor at 105° C. for 1.5 h under nitrogen atmosphere. LCMS showed the reaction was complete. The resulting mixture was extracted with EA, the combined organic layers were washed with brine, dried over anhydrous sodium sulfate and concentrated. The residue was purified by flash chromatography (MeOH/DCM, gradient 0-3%) to give 5-(cyclobutoxymethyl)-1-(1H-pyrazol-4-yl)-4,6,7,8-tetrahydro-3H-9-oxa-2-thia-4-azabenzo-[cd]azulen-3-one (11 mg) as a light yellow solid. MS obsd. ($ESI^+$): m/z 358.1 $[(M+H)^+]$. $^1H$ NMR (400 MHz, DMSO) δ ppm 13.15 (s, 1H), 11.33 (s, 1H), 8.17 (s, 1H), 7.90 (s, 1H), 4.32 (t, J=5.72 Hz, 4H), 4.30 (s, 1H), 3.95-4.03 (m, 1H), 2.90-2.93 (m, 2H), 2.02-2.13 (m, 4H), 1.85-1.87 (m, 2H), 1.60-1.63 (m, 1H), 1.40-1.45 (m, 1H).

Example 56: N-methyl-N-(3-oxo-1-(1H-pyrazol-4-yl)-4,6,7,8-tetrahydro-3H-9-oxa-2-thia-4-azabenzo[cd]azulen-5-yl)acetamide

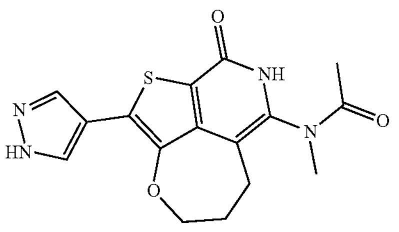 [SMILES: CC(=O)N(C)c1[nH]c(=O)c2sc(-c3cn[nH]c3)c3c2c1CCCO3]

Step A: ethyl3-chloro-7,8-dihydro-6H-9-oxa-2-thia-4-azabenzo[cd]azulene-5-carboxylate

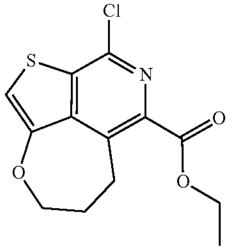 [SMILES: CCOC(=O)c1nc(Cl)c2scc3c2c1CCCO3]

A solution of ethyl 5-oxo-12-oxa-3-thia-6-azatricyclo[6.4.1.0$^{4,13}$]trideca-1,4(13),7-tri-ene-7-carboxylate (300 mg, 1.07 mmol, 1.0 eq.) in $POCl_3$ (15.0 mL) was stirred at 100° C. for 1 h. LCMS showed the reaction was complete. The resulting mixture was added to water slowly, and extracted with EA, the combined organic layers were washed with brine, dried over anhydrous sodium sulfate and concentrated. The residue was purified by flash chromatography (EA/PE, gradient 0-15%) to give ethyl 3-chloro-7,8-dihydro-6H-9-oxa-2-thia-4-azabenzo[cd]azulene-5-carboxylate (304 mg) as a white solid. MS obsd. (ESI$^+$): m/z 298.0 [(M+H)$^+$].

Step B: Ethyl1-bromo-3-chloro-7,8-dihydro-6H-9-oxa-2-thia-4-azabenzo[cd]azulene-5-carboxylate

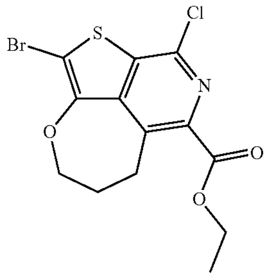 [SMILES: CCOC(=O)c1nc(Cl)c2sc(Br)c3c2c1CCCO3]

To a solution of ethyl 5-chloro-12-oxa-3-thia-6-azatricyclo[6.4.1.0$^{4,13}$]trideca-1,4(13),5,7-tetraene-7-carboxylate (100 mg, 0.32 mmol, 1 eq.) in DMF (5.0 mL) was added NBS (68 mg, 0.38 mmol, 1.2 eq.). The mixture was stirred at rt for 2 h. LCMS showed the reaction was complete. The resulting mixture was added to water slowly and was extracted with EA, the combined organic layers were washed with brine, dried over anhydrous sodium sulfate and concentrated. The residue was purified by flash chromatography (MeOH/DCM, gradient 0-3%) to give ethyl 2-bromo-5-chloro-12-oxa-3-thia-6-azatricyclo[6.4.1.0$^{4,13}$]trideca-1,4(13),5,7-tetraene-7-carboxylate (120 mg) as a white solid. MS obsd. (ESI$^+$): m/z 378.2 [(M+H)$^+$].

Step C: 1-bromo-3-chloro-7,8-dihydro-6H-9-oxa-2-thia-4-azabenzo[cd]azulene-5-carboxylic acid

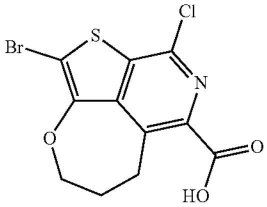 [SMILES: O=C(O)c1nc(Cl)c2sc(Br)c3c2c1CCCO3]

To a solution of ethyl 2-bromo-5-chloro-12-oxa-3-thia-6-azatricyclo[6.4.1.0$^{4,13}$]trideca-1,4(13),5,7-tetraene-7-carboxylate (120 mg, 0.30 mmol, 1.0 eq.) in a mixed solvents of MeOH (6.0 mL) and $H_2O$ (2.0 mL) was added NaOH (24 mg, 0.61 mmol, 2.0 eq.). The mixture was stirred at 80° C. for 2 h. LCMS showed the reaction was complete. The mixture was extracted with EA, the water phase was collected and acided with 1.2 M HCl. The solid formed was collected and dried by lyophilization to give the 2-bromo-5-chloro-12-oxa-3-thia-6-azatricyclo[6.4.1.0$^{4,13}$]trideca-1,4(13),5,7-tetraene-7-carboxylic acid (95 mg) as a white solid which was used directly in the next step without further purification. MS obsd. (ESI$^+$): m/z 257.2 [(M+H)$^+$].

Step D: Tert-butyl(1-bromo-3-chloro-7,8-dihydro-6H-9-oxa-2-thia-4-azabenzo[cd]azulen-5-yl)carbamate

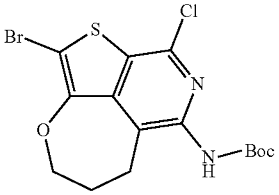 [SMILES: CC(C)(C)OC(=O)Nc1nc(Cl)c2sc(Br)c3c2c1CCCO3]

To a solution of 2-bromo-5-chloro-12-oxa-3-thia-6-azatricyclo[6.4.1.0$^{4,13}$]trideca-1,4(13), 5,7-tetraene-7-carboxylic acid (100 mg, 0.29 mmol, 1.0 eq.), DPPA (210 mg, 0.86 mmol, 3.0 eq.) in a mixed solvents of t-BuOH (10.0 mL) and MeCN (10.0 mL) was added $Et_3N$ (175 mg, 1.73 mmol, 6.0 eq.) dropwise at RT under nitrogen atmosphere. The mixture was stirred at 80° C. for 16 h. LCMS indicated 71.0% conversion. The resulting mixture was extracted with EA, the combined organic layers were washed with brine, dried over anhydrous sodium sulfate and concentrated. The residue was purified by flash chromatography (EA/PE, gradient 0-25%) to give tert-butyl N-(5-oxo-12-oxa-3-thia-6-azatricyclo[6.4.1.0$^{4,13}$]trideca-1,4(13),7-trien-7-yl)carbamate (115 mg) as a light-yellow solid. MS obsd. (ESI$^+$): m/z 419 [(M+H)$^+$].

Step E: Tert-butyl(1-bromo-3-chloro-7,8-dihydro-6H-9-oxa-2-thia-4-azabenzo[cd]azulen-5-yl) (methyl)carbamate

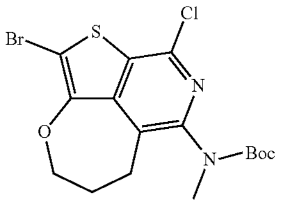 [SMILES: CN(C(=O)OC(C)(C)C)c1nc(Cl)c2sc(Br)c3c2c1CCCO3]

To a solution of tert-butyl N-(2-bromo-5-chloro-12-oxa-3-thia-6-azatricyclo[6.4.1.$0^{4,13}$]-trideca-1,4(13),5,7-tetraen-7-yl)carbamate (115 mg, 0.25 mmol, 1.0 eq.) in DMF (5.0 mL) was added NaH (14 mg, 0.37 mmol, 60.0% purity, 1.5 eq.) and stirred for 20 mins. MeI (70 mg, 0.49 mmol, 2.0 eq.) was added to it, and the mixture was stirred at rt for 2 h. LCMS showed the reaction was complete. The resulting mixture was extracted with EA. The combined organic layers were washed with brine, dried over anhydrous sodium sulfate and concentrated. The residue was purified by flash chromatography (EA/PE, gradient 0-15%) to give tert-butyl (1-bromo-3-chloro-7,8-dihydro-6H-9-oxa-2-thia-4-azabenzo[cd]azulen-5-yl)(methyl)carbamate (84 mg) as a white solid. MS obsd. ($ESI^+$): m/z 377.2, 379.2 [$(M-56+H)^+$].

Step F: 1-bromo-3-chloro-N-methyl-7,8-dihydro-6H-9-oxa-2-thia-4-azabenzo[cd]azulen-5-amine

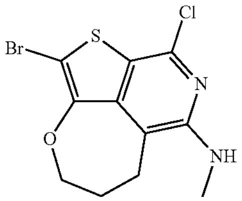 [SMILES: CNc1nc(Cl)c2sc(Br)c3c2c1CCCO3]

To a solution of tert-butyl N-(2-bromo-5-chloro-12-oxa-3-thia-6-azatricyclo[6.4.1.$0^{4,13}$]tri-deca-1,4(13),7-trien-7-yl)-N-methyl-carbamate (84 mg, 0.19 mmol, 1.0 eq.) in EA (3.0 mL) was added 4M HCl-dioxane (1.5 mL) at RT. The mixture was stirred at rt for 12 h. LCMS showed the reaction was complete. The solvent was removed under reduced pressure. The residue was based with saturated aqueous $NaHCO_3$ solution. The resulting mixture was extracted with EA. The combined organic layers were washed with brine, dried over anhydrous sodium sulfate and concentrated. The residue was purified by flash chromatography (EA/PE, gradient 0-25%) to give 2-bromo-5-chloro-N-methyl-12-oxa-3-thia-6-azatricyclo[6.4.1.$0^{4,13}$]trideca-1,4(13),7-trien-7-amine (64 mg) as a white solid. MS obsd. ($ESI^+$): m/z 333.0, 335.0 [$(M+H)^+$].

Step G: N-(1-bromo-3-chloro-7,8-dihydro-6H-9-oxa-2-thia-4-azabenzo[cd]azulen-5-yl)-N-methylacetamide

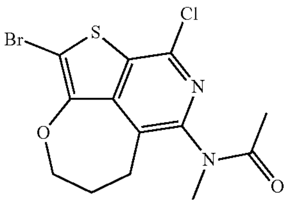 [SMILES: CC(=O)N(C)c1nc(Cl)c2sc(Br)c3c2c1CCCO3]

A solution of 2-bromo-5-chloro-N-methyl-12-oxa-3-thia-6-azatricyclo[6.4.1.$0^{4,13}$]tri-deca-1,4(13),5,7-tetraen-7-amine (64 mg, 0.18 mmol, 1.0 eq.) in acetyl acetate (93 mg, 0.91 mmol,) was heated at 70° C. for 4 h. LCMS showed the reaction was complete. The solvent was removed by evaporation. The residue was purified by flash chromatography (EA/PE, gradient 0-15%) to give N-(2-bromo-5-chloro-12-oxa-3-thia-6-azatricyclo[6.4.1.$0^{4,13}$]trideca-1,4(13),5,7-tetraen-7-yl)-N-methyl-acetamide (50 mg) as a light-yellow solid. MS obsd, ($ESI^+$): m/z 375.1, 377.1 [$(M+H)^+$].

Step H: N-(1-bromo-3-oxo-4,6,7,8-tetrahydro-3H-9-oxa-2-thia-4-azabenzo[cd]azulen-5-yl)-N-methylacetamide

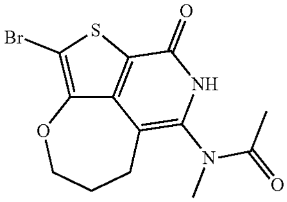 [SMILES: CC(=O)N(C)c1[nH]c(=O)c2sc(Br)c3c2c1CCCO3]

To a solution of N-(2-bromo-5-chloro-12-oxa-3-thia-6-azatricyclo[6.4.1.$0^{4,13}$]trideca-1,4 (13),5,7-tetraen-7-yl)-N-methyl-acetamide (20 mg, 0.05 mmol, 1.0 eq.) in acetic acid (3.0 mL) was added $H_2O$ (0.5 mg, 0.03 mmol, 0.5 eq.) and ammonium acetate (21 mg, 0.25 mmol, 5.0 eq.) at 25° C. The mixture was irradiated on a microwave reactor at 200° C. for 2 h. LCMS showed the reaction was complete. The solvent was removed by evaporation. The residue was purified by flash chromatography (EA/PE, gradient 0-50%) to give N-(2-bromo-5-oxo-12-oxa-3-thia-6-azatricyclo [6.4.1.$0^{4,13}$]trideca-1,4(13),7-trien-7-yl)-N-methyl-acetamide (15 mg) as a white solid. MS obsd, ($ESI^+$): m/z 357.2, 359.2 [$(M+H)^+$].

Step I: N-methyl-N-(3-oxo-1-(1H-pyrazol-4-yl)-4,6,7,8-tetrahydro-3H-9-oxa-2-thia-4-azabenzo[cd]azulen-5-yl)acetamide

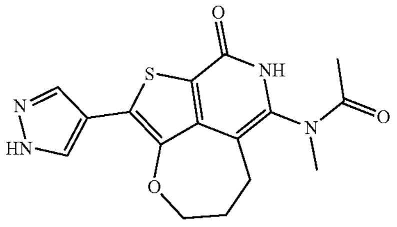 [SMILES: CC(=O)N(C)c1[nH]c(=O)c2sc(-c3cn[nH]c3)c3c2c1CCCO3]

To a solution of N-(2-bromo-5-oxo-12-oxa-3-thia-6-azatricyclo[6.4.1.$0^{4,13}$]trideca-1,4(13), 7-trien-7-yl)-N-methylacetamide (30 mg, 0.08 mmol, 1.0 eq.), 1H-pyrazol-4-ylboronic acid (19 mg, 0.17 mmol, 2.0 eq.), Xphos (40 mg, 0.08 mmol, 1.0 eq.), $Na_2CO_3$ (11 mg, 0.08 mmol, 1.0 eq.), Pd(dppf)$Cl_2$ (69 mg, 0.08 mmol, 1.0 eq.) in DMF (1.0 mL) was added $H_2O$ (2.0 mL). Then the mixture was irradiated on a microwave reactor at 105° C. for 1.5 h under nitrogen atmosphere. LCMS showed the reaction was complete. The resulting mixture was extracted with EA. The combined organic layers were washed with brine, dried over anhydrous sodium sulfate and concentrated. The residue was purified by pre-HPLC to give N-methyl-N-[5-oxo-2-(1H-pyrazol-4-yl)-12-oxa-3-thia-6-azatricyclo[6.4.1.$0^{4,13}$]trideca-1,4(13), 7-trien-7-yl]acetamide (11 mg) as a white solid. MS obsd. ($ESI^+$): m/z 345.1 [$(M+H)^+$]. $^1H$ NMR (400 MHz, DMSO) δ ppm 13.23 (s, 1H), 8.43 (s, 1H), 8.05 (s, 2H), 4.36 (t, J=5.5 Hz, 2H), 3.04 (s, 3H), 2.73 (t, J=5.8 Hz, 2H), 2.10-2.14 (m, 2H), 1.83 (s, 3H).

Example 57: (S)-5-(2-hydroxybutan-2-yl)-1-(1H-pyrazol-4-yl)-4,6,7,8-tetrahydro-3H-9-oxa-2-thia-4-azabenzo[cd]azulen-3-one

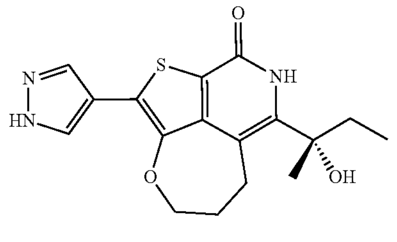 [SMILES: CC[C@](C)(O)c1[nH]c(=O)c2sc(-c3cn[nH]c3)c3c2c1CCCO3]

Example 58: (R)-5-(2-hydroxybutan-2-yl)-1-(1H-pyrazol-4-yl)-4,6,7,8-tetrahydro-3H-9-oxa-2-thia-4-azabenzo[cd]azulen-3-one

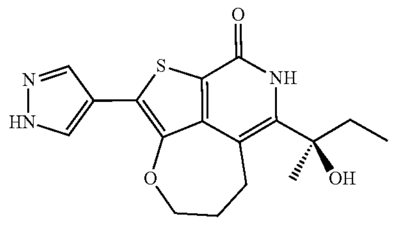 [SMILES: CC[C@@](C)(O)c1[nH]c(=O)c2sc(-c3cn[nH]c3)c3c2c1CCCO3]

Step A: 2-bromo-7-(1-hydroxy-1-methyl-propyl)-12-oxa-3-thia-6-azatricyclo[6.4.1.$0^{4,13}$]trideca-1,4(13),7-trien-5-one

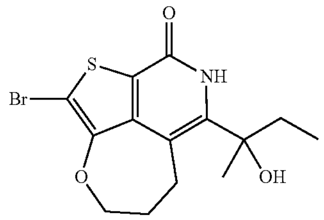 [SMILES: CCC(C)(O)c1[nH]c(=O)c2sc(Br)c3c2c1CCCO3]

To a solution of 7-acetyl-2-bromo-12-oxa-3-thia-6-azatricyclo[6.4.1.$0^{4,13}$]trideca-1,4(13),7-trien-5-one (100 mg, 304.7 umol) in dry THF (20 mL) at 0° C., ethyl magnesium bromide (1 M, 1.52 mL) was added to the mixture at 0° C. After the addition, the mixture was stirred at 25° C. for 2 h. Upon the completion, it was cooled to 0° C. and saturated $NH_4Cl$ (20 mL) was added at 0° C. The resulting mixture was extracted with EtOAc. The combined organic phase was dried over anhydrous sodium sulfate, filtered and concentrated to give a residue. It was purified by flash column chromatography (eluting with 0-10% MeOH in DCM) to give 2-bromo-7-(1-hydroxy-1-methyl-propyl)-12-oxa-3-thia-6-azatricyclo[6.4.1.$0^{4,13}$]trideca-1,4(13),7-trien-5-one (30 mg) as a yellow solid. MS obsd. ($ESI^+$): m/z 358.2 $[M+H]^+$, 360.2 $[M+2+H]^+$.

Step B: 7-(1-hydroxy-1-methyl-propyl)-2-(1-tritylpyrazol-4-yl)-12-oxa-3-thia-6-azatricyclo[64.1.$0^{4,13}$]trideca-1,4(13),7-trien-5-one

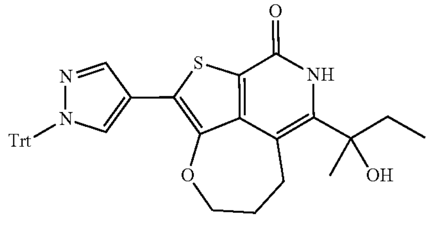

To a solution of 2-bromo-7-(1-hydroxy-1-methyl-propyl)-12-oxa-3-thia-6-azatricyclo[6.4.1.$0^{4,13}$]trideca-1,4(13),7-trien-5-one (100 mg, 279.1 umol) in dioxane:$H_2O$=5:1 (13 mL) was added 4-(4,4,5,5-tetramethyl-1,3,2-dioxaborolan-2-yl)-1-trityl-pyrazole (183 mg, 418.7 umol), sodium carbonate (60 mg, 558.3 umol), Xphos (40 mg, 83.7 umol), Pd(dppf)$Cl_2$ (62 mg, 83.7 umol). The reaction was stirred at 105° C. for 2.3 h under microwave. Upon the completion, it was cooled to 25° C., diluted with $H_2O$. The resulting mixture was extracted with EtOAc. The combined organic phase were dried over anhydrous sodium sulfate, filtered and concentrated to give a residue. It was purified by flash column chromatography (eluting with 0-10% MeOH in DCM) to give 7-(1-hydroxy-1-methyl-propyl)-2-(1-tritylpyrazol-4-yl)-12-oxa-3-thia-6-azatricyclo[6.4.1.$0^{4,13}$]trideca-1,4(13),7-trien-5-one (120 mg) as yellow oil. MS obsd. ($ESI^+$): m/z 588.7 $[M+H]^+$.

Step C: 5-(2-hydroxybutan-2-yl)-1-(1H-pyrazol-4-yl)-4,6,7,8-tetrahydro-3H-9-oxa-2-thia-4-azabenzo[cd]azulen-3-one

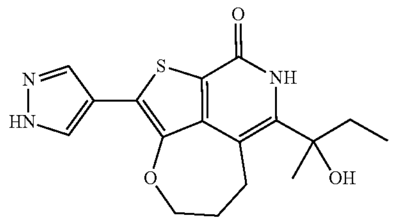 [SMILES: CCC(C)(O)c1[nH]c(=O)c2sc(-c3cn[nH]c3)c3c2c1CCCO3]

To a solution of 7-(1-hydroxy-1-methyl-propyl)-2-(1-tritylpyrazol-4-yl)-12-oxa-3-thia-6-azatricyclo[6.4.1.0$^{4,13}$]trideca-1,4(13),7-trien-5-one (240 mg, 408.4 umol) in DCM (10 mL) was added TFA (233 mg, 2.04 mmol) at 0° C. The reaction was stirred at 25° C. for 2 h. LCMS showed about 84% conversion, then it was cooled to 0° C., saturated $NaHCO_3$ was added carefully at 0° C., adjusted the PH=8. The resulting mixture was extracted with DCM. The combined organic phase was dried over anhydrous sodium sulfate, filtered and concentrated to give a residue. It was purified by flash column chromatography (eluting with 0-10% MeOH in DCM) to give 5-(2-hydroxybutan-2-yl)-1-(1H-pyrazol-4-yl)-4,6,7,8-tetrahydro-3H-9-oxa-2-thia-4-azabenzo[cd]azulen-3-one (75 mg) as white solid. MS obsd. ($ESI^+$): m/z 346.4 $[M+H]^+$.

(S)-5-(2-hydroxybutan-2-yl)-1-(1H-pyrazol-4-yl)-4,6,7,8-tetrahydro-3H-9-oxa-2-thia-4-azabenzo[cd]azulen-3-one and (R)-5-(2-hydroxybutan-2-yl)-1-(1H-pyrazol-4-yl)-4,6,7,8-tetrahydro-3H-9-oxa-2-thia-4-azabenzo[cd]azulen-3-one

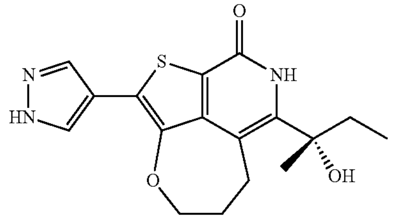

-continued

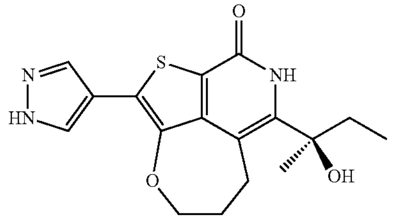

The enantiomers of 5-(2-hydroxybutan-2-yl)-1-(1H-pyrazol-4-yl)-4,6,7,8-tetraydro-3H-9-oxa-2-thia-4-azabenzo[cd]azulen-3-one7-(1-hydroxy-1-methyl-propyl)-2-(1-tritylpyrazol-4-yl)-12-oxa-3-thia-6-azatricyclo[6.4.1.0$^{4,13}$]trideca-1,4(13),7-trien-5-one (27 mg) were separated by chiral HPLC using the method as below: (Column: AD-H, Column size: 0.46 cm I.D.×15 cm L, Injection: 2 ul, Mobile phase: HEP:ETOH (0.1% DEA)=60:40, Flow rate: 0.5 ml, Wave length: UV 254 nm, Temperature: 25° C.) to give 7-[(1S)-1-hydroxy-1-methyl-propyl]-2-(1H-pyrazol-4-yl)-12-oxa-3-thia-6-azatricyclo[6.4.1.0$^{4,13}$]trideca-1,4(13),7-trien-5-one (9 mg) as a white solid. MS obsd. ($ESI^+$): m/z 346.1 $[M+H]^+$. $^1$H NMR (400 MHz, DMSO-d6) δ ppm: 13.18 (s, 1H), 9.70 (s, 1H), 8.19 (s, 1H), 7.90 (s, 1H), 5.98 (s, 1H), 4.32-4.28 (m, 2H), 3.10-2.92 (m, 2H), 2.20-2.05 (m, 2H), 1.95-1.80 (m, 1H), 1.75-1.60 (m, 1H), 1.56 (s, 3H), 0.78 (t, J=10.2 Hz, 3H). 7-[(1R)-1-hydroxy-1-methyl-propyl]-2-(1H-pyrazol-4-yl)-12-oxa-3-thia-6-azatricyclo[6.4.1.0$^{4,13}$]trideca-1,4(13),7-trien-5-one (8 mg) as a white solid. MS obsd. ($ESI^+$): m/z 346.2 $[M+H]^+$. $^1$H NMR (400 MHz, DMSO-d6) δ ppm: 13.18 (s, 1H), 9.70 (s, 1H), 8.19 (s, 1H), 7.90 (s, 1H), 5.98 (s, 1H), 4.32-4.26 (m, 2H), 3.10-2.92 (m, 2H), 2.20-2.05 (m, 2H), 1.95-1.80 (m, 1H), 1.75-1.60 (m, 1H), 1.56 (s, 3H), 0.78 (t, J=10.2 Hz, 3H). The absolute stereochemistry of these two compounds was randomly assigned.

The following compounds were prepared in a similar manner as that illustrated in Example 57 and 58.

| Ex. No. | Structure | Name | MS Obsd. ($ESI^+$): m/z $[(M + H)^+]$ |
|---|---|---|---|
| 59 | 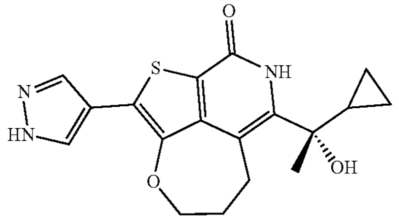 [SMILES: C[C@@](O)(c1[nH]c(=O)c2sc(-c3cn[nH]c3)c3c2c1CCCO3)C1CC1] | (S)-5-(1-cyclopropyl-1-hydroxyethyl)-1-(1H-pyrazol-4-yl)-4,6,7,8-tetrahydro-3H-9-oxa-2-thia-4-azabenzo[cd]azulen-3-one# | 358 |

-continued

| Ex. No. | Structure | Name | MS Obsd. (ESI$^+$): m/z [(M + H)$^+$] |
|---|---|---|---|
| 60 | 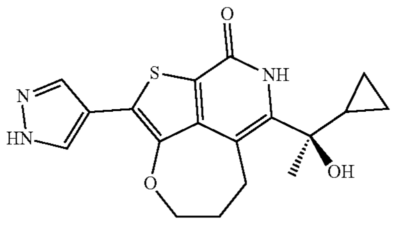 [SMILES: C[C@](O)(c1[nH]c(=O)c2sc(-c3cn[nH]c3)c3c2c1CCCO3)C1CC1] | (R)-5-(1-cyclopropyl-1-hydroxyethyl)-1-(1H-pyrazol-4-yl)-4,6,7,8-tetrahydro-3H-9-oxa-2-thia-4-azabenzo[cd]azulen-3-one# | 358 |
| 61 | 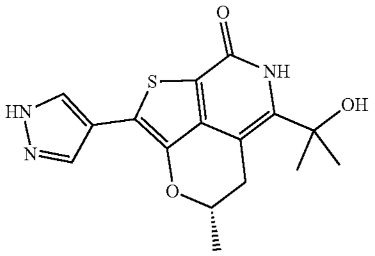 [SMILES: C[C@H]1Cc2c(C(C)(C)O)[nH]c(=O)c3sc(-c4cn[nH]c4)c(c23)O1] | (S)-6-(2-hydroxypropan-2-yl)-4-methyl-2-(1H-pyrazol-4-yl)-5,7-dihydro-3-oxa-1-thia-7-azaacenaphthylen-8(4H)-one# | 332 |
| 62 | 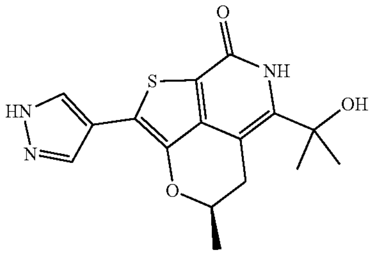 [SMILES: C[C@@H]1Cc2c(C(C)(C)O)[nH]c(=O)c3sc(-c4cn[nH]c4)c(c23)O1] | (R)-6-(2-hydroxypropan-2-yl)-4-methyl-2-(1H-pyrazol-4-yl)-5,7-dihydro-3-oxa-1-thia-7-azaacenaphthylen-8(4H)-one# | 332 |

#The absolute stereochemistry was randomly assigned.

The following compounds were prepared in a similar manner as that illustrated in Examples 26 and 27.

| Ex. No. | Structure | Name | MS Obsd. (ESI$^+$): m/z [(M + H)$^+$] |
|---|---|---|---|
| 63 | 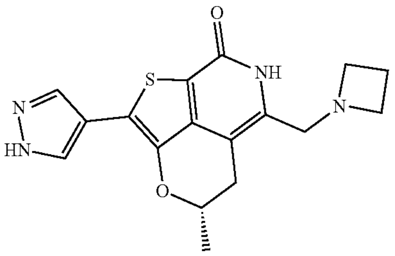 [SMILES: C[C@H]1Cc2c(CN3CCC3)[nH]c(=O)c3sc(-c4cn[nH]c4)c(c23)O1] | (S)-6-(azetidin-1-ylmethyl)-4-methyl-2-(1H-pyrazol-4-yl)-5,7-dihydro-3-oxa-1-thia-7-azaacenaphthylen-8(4H)-one# | 343 |
| 64 | 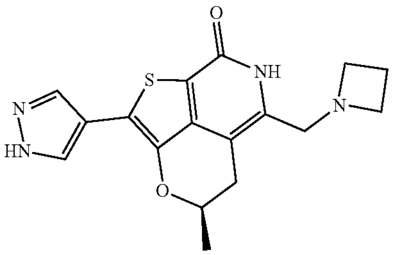 [SMILES: C[C@@H]1Cc2c(CN3CCC3)[nH]c(=O)c3sc(-c4cn[nH]c4)c(c23)O1] | (R)-6-(azetidin-1-ylmethyl)-4-methyl-2-(1H-pyrazol-4-yl)-5,7-dihydro-3-oxa-1-thia-7-azaacenaphthylen-8(4H)-one# | 343 |

-continued

| Ex. No. | Structure | Name | MS Obsd. (ESI+): m/z [(M + H)+] |
|---|---|---|---|
| 65 | 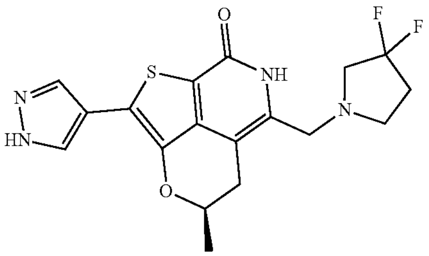 [SMILES: C[C@@H]1Cc2c(CN3CCC(F)(F)C3)[nH]c(=O)c3sc(-c4cn[nH]c4)c(c23)O1] | (R)-6-((3,3-difluoropyrrolidin-1-yl)methyl)-4-methyl-2-(1H-pyrazol-4-yl)-5,7-dihydro-3-oxa-1-thia-7-azaacenaphthylen-8(4H)-one# | 393 |
| 66 | 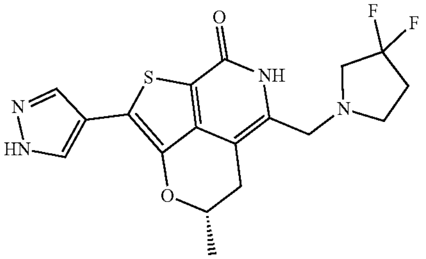 [SMILES: C[C@H]1Cc2c(CN3CCC(F)(F)C3)[nH]c(=O)c3sc(-c4cn[nH]c4)c(c23)O1] | (S)-6-((3,3-difluoropyrrolidin-1-yl)methyl)-4-methyl-2-(1H-pyrazol-4-yl)-5,7-dihydro-3-oxa-1-thia-7-azaacenaphthylen-8(4H)-one# | 393 |
| 67 | 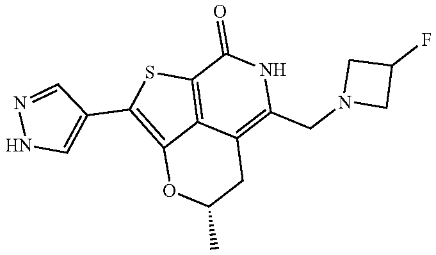 [SMILES: C[C@H]1Cc2c(CN3CC(F)C3)[nH]c(=O)c3sc(-c4cn[nH]c4)c(c23)O1] | (R)-6-((3-fluoroazetidin-1-yl)methyl)-4-methyl-2-(1H-pyrazol-4-yl)-5,7-dihydro-3-oxa-1-thia-7-azaacenaphthylen-8(4H)-one# | 361 |
| 68 | 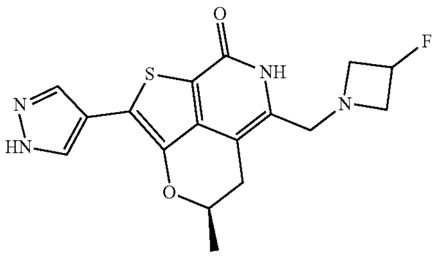 [SMILES: C[C@@H]1Cc2c(CN3CC(F)C3)[nH]c(=O)c3sc(-c4cn[nH]c4)c(c23)O1] | (S)-6-((3-fluoroazetidin-1-yl)methyl)-4-methyl-2-(1H-pyrazol-4-yl)-5,7-dihydro-3-oxa-1-thia-7-azaacenaphthylen-8(4H)-one# | 361 |
| 69 | 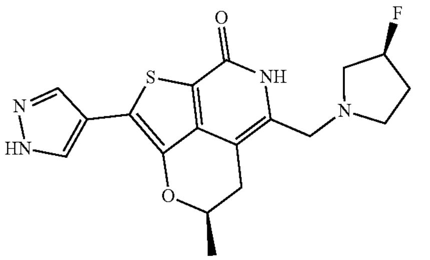 [SMILES: C[C@@H]1Cc2c(CN3CC[C@H](F)C3)[nH]c(=O)c3sc(-c4cn[nH]c4)c(c23)O1] | (S)-6-(((S)-3-fluoropyrrolidin-1-yl)methyl)-4-methyl-2-(1H-pyrazol-4-yl)-5,7-dihydro-3-oxa-1-thia-7-azaacenaphthylen-8(4H)-one# | 375 |

-continued

| Ex. No. | Structure | Name | MS Obsd. (ESI+): m/z [(M + H)+] |
|---|---|---|---|
| 70 | 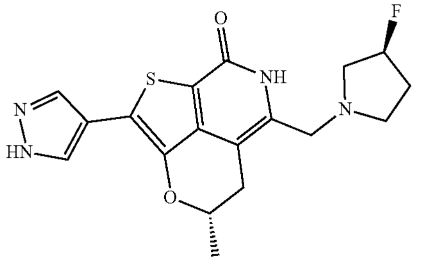 [SMILES: C[C@H]1Cc2c(CN3CC[C@H](F)C3)[nH]c(=O)c3sc(-c4cn[nH]c4)c(c23)O1] | (R)-6-(((S)-3-fluoropyrrolidin-1-yl)methyl)-4-methyl-2-(1H-pyrazol-4-yl)-5,7-dihydro-3-oxa-1-thia-7-azaacenaphthylen-8(4H)-one# | 375 |

#The absolute stereochemistry was randomly assigned.

The following compounds were prepared in a similar manner as that illustrated in Example 57 and 58.

| Ex. No. | Structure | Name | MS obsd. (ESI+): m/z [(M + H)+] |
|---|---|---|---|
| 71 | 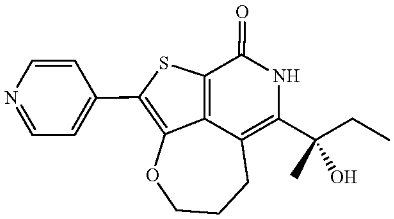 [SMILES: CC[C@](C)(O)c1[nH]c(=O)c2sc(-c3ccncc3)c3c2c1CCCO3] | (S)-5-(2-hydroxybutan-2-yl)-1-(pyridin-4-yl)-4,6,7,8-tetrahydro-3H-9-oxa-2-thia-4-azabenzo[cd]azulen-3-one# | 357 |
| 72 | 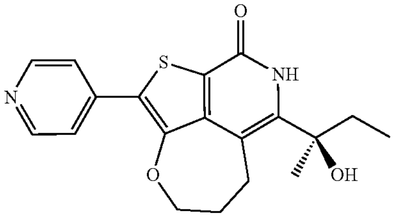 [SMILES: CC[C@@](C)(O)c1[nH]c(=O)c2sc(-c3ccncc3)c3c2c1CCCO3] | (R)-5-(2-hydroxybutan-2-yl)-1-(pyridin-4-yl)-4,6,7,8-tetrahydro-3H-9-oxa-2-thia-4-azabenzo[cd]azulen-3-one# | 357 |
| 73 | 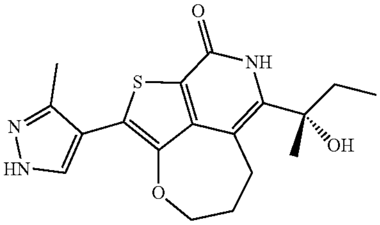 [SMILES: CC[C@](C)(O)c1[nH]c(=O)c2sc(-c3c[nH]nc3C)c3c2c1CCCO3] | (S)-5-(2-hydroxybutan-2-yl)-1-(3-methyl-1H-pyrazol-4-yl)-4,6,7,8-tetrahydro-3H-9-oxa-2-thia-4-azabenzo[cd]azulen-3-one# | 360 |
| 74 | 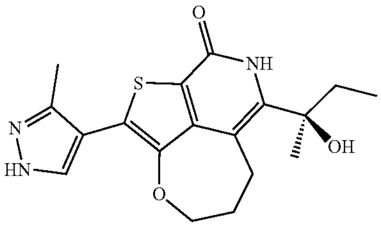 [SMILES: CC[C@@](C)(O)c1[nH]c(=O)c2sc(-c3c[nH]nc3C)c3c2c1CCCO3] | (R)-5-(2-hydroxybutan-2-yl)-1-(3-methyl-1H-pyrazol-4-yl)-4,6,7,8-tetrahydro-3H-9-oxa-2-thia-4-azabenzo[cd]azulen-3-one# | 360 |

#The absolute stereochemistry was randomly assigned.

Example 75: 2-(3-oxo-1-(1H-pyrazol-4-yl)-4,6,7,8-tetrahydro-3H-9-oxa-2-thia-4-azabenzo[cd]azulen-5-yl)acetonitrile

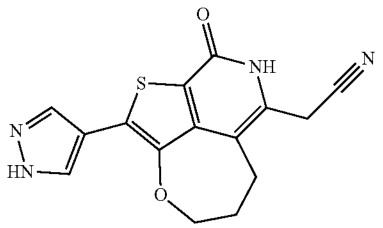 [SMILES: N#CCc1[nH]c(=O)c2sc(-c3cn[nH]c3)c3c2c1CCCO3]

Step A: 2-(1-bromo-3-oxo-4,6,7,8-tetrahydro-3H-9-oxa-2-thia-4-azabenzo[cd]azulen-5-yl)acetonitrile

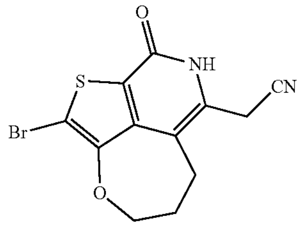 [SMILES: N#CCc1[nH]c(=O)c2sc(Br)c3c2c1CCCO3]

To a solution of Bromo-5-(chloromethyl)-4,6,7,8-tetrahydro-3H-9-oxa-2-thia-4-azabenzo[cd]azulen-3-one (150 mg, 0.448 mmol) in DMSO (10 mL), NaCN (24 mg, 0.448 mmol) was added. After the addition, the mixture was stirred at 60° C. for 1 h. The reaction mixture was cooled down to room temperature, diluted with water, extracted with ethyl acetate, the combined ethyl acetate layer was further washed with water. The organic layer was dried over anhydrous magnesium sulfate and concentrated and the resultant product was purified by prep-TLC (eluting with 10% MeOH in DCM) to give 2-(1-bromo-3-oxo-4,6,7,8-tetrahydro-3H-9-oxa-2-thia-4-azabenzo[cd]azulen-5-yl)acetonitrile (130 mg) as a white solid. MS obsd. (ESI$^+$): m/z 325.3 [(M+H)$^+$], 327.3 [(M+2+H)$^+$].

Step B: 2-(3-oxo-1-(1H-pyrazol-4-yl)-4,6,7,8-tetrahydro-3H-9-oxa-2-thia-4-azabenzo[cd]azulen-5-yl) acetonitrile

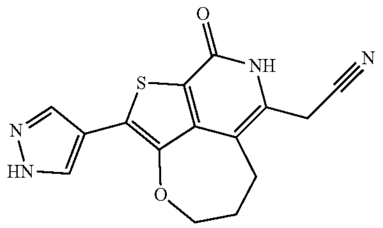 [SMILES: N#CCc1[nH]c(=O)c2sc(-c3cn[nH]c3)c3c2c1CCCO3]

To a solution of 2-(1-bromo-3-oxo-4,6,7,8-tetrahydro-3H-9-oxa-2-thia-4-azabenzo[cd]azulen-5-yl)acetonitrile (130 mg, 0.4 mmol) in dioxane:$H_2O$=5/1 (10 mL) was added $Na_2CO_3$ (43 mg, 0.4 mmol), Pd(dppf)$Cl_2$ (29 mg, 0.04 mmol), X-phos (95 mg, 0.08 mmol) and the suspension was degassed with $N_2$ for 3 min. Then the mixture was sealed in a tube and heated to 110° C. with microwave for 1 h under $N_2$. The mixture was added $H_2O$ and extracted with ethyl acetate. The organic layer was dried and concentrated in vacuum and the residue was purified by prep-TLC (eluting with 10% MeOH in DCM) to give 2-(3-oxo-1-(1H-pyrazol-4-yl)-4,6,7,8-tetrahydro-3H-9-oxa-2-thia-4-azabenzo[cd]azulen-5-yl)acetonitrile (65 mg) as a light-yellow solid. MS obsd. (ESI$^+$): m/z 313.1 [(M+H)$^+$]. $^1$H NMR (400 MHz, DMSO-d6) δ ppm: 13.17 (s, 1H), 11.59 (s, 1H), 8.20 (s, 1H), 7.91 (s, 1H), 4.34 (t, J=5.2 Hz, 2H), 3.97 (s, 2H), 2.92 (t, J=5.6 Hz, 2H), 2.17 (t, J=5.6 Hz, 2H).

Example 76: methyl 2-(3-oxo-1-(1H-pyrazol-4-yl)-4,6,7,8-tetrahydro-3H-9-oxa-2-thia-4-azabenzo[cd]azulen-5-yl)acetate

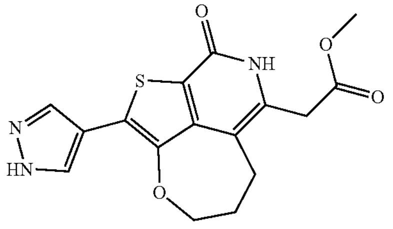 [SMILES: COC(=O)Cc1[nH]c(=O)c2sc(-c3cn[nH]c3)c3c2c1CCCO3]

The mixture of 2-(3-oxo-1-(1H-pyrazol-4-yl)-4,6,7,8-tetrahydro-3H-9-oxa-2-thia-4-azabenzo[cd]azulen-5-yl)acetonitrile (60 mg, 192.1 umol) in 4 M HCl/MeOH (5 mL) was stirred at 60° C. for 2 h. Then the mixture was concentrated under reduced pressure, the residue was poured into saturated $NaHCO_3$ solution, extracted with EtOAc and the combined organic layer was washed with brine, dried over anhydrous sodium sulfate, filtered and concentrated to give the crude product which was purified by prep-TLC (eluting with 10% MeOH in DCM) to give methyl 2-(3-oxo-1-(1H-pyrazol-4-yl)-4,6,7,8-tetrahydro-3H-9-oxa-2-thia-4-azabenzo[cd]azulen-5-yl)acetate (35 mg) as a light-yellow solid. MS obsd. (ESI$^+$): m/z 346.1 [(M+H)$^+$]. $^1$H NMR (400 MHz, DMSO-d6) δ ppm: 13.15 (s, 1H), 11.37 (s, 1H), 8.18 (s, 1H), 7.89 (s, 1H), 4.31 (t, J=5.2 Hz, 2H), 3.76 (s, 2H), 3.66 (s, 3H), 2.80-2.77 (m, 2H), 2.13-2.07 (m, 2H).

Example 77: 5-(2-hydroxy-2-methylpropyl)-1-(1H-pyrazol-4-yl)-4,6,7,8-tetrahydro-3H-9-oxa-2-thia-4-azabenzo[cd]azulen-3-one

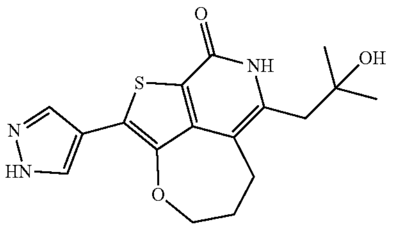 [SMILES: CC(C)(O)Cc1[nH]c(=O)c2sc(-c3cn[nH]c3)c3c2c1CCCO3]

To a solution of methyl 2-(3-oxo-1-(1H-pyrazol-4-yl)-4,6,7,8-tetrahydro-3H-9-oxa-2-thia-4-azabenzo[cd]azulen-5-yl)acetate (72 mg, 183 umol, 88% purity) in THF (10 mL) was slowly added MeLi (1.6 M, 0.9 mL) under ice bath. After addition, the reaction was stirred at 60° C. for 1 h. The reaction mixture was slowly poured into saturated aqueous $NH_4Cl$ solution under ice bath. Then, it was extracted by DCM. The organic layer was dried by $Na_2SO_4$, filtered and concentrated to give the crude product, which was purified by prep-TLC plate (7% MeOH in DCM) and then C18 column (eluting with 0-30% MeCN in water, 0.1% FA) to give the product 5-(2-hydroxy-2-methylpropyl)-1-(1H-pyrazol-4-yl)-4,6,7,8-tetrahydro-3H-9-oxa-2-thia-4-azabenzo[cd]azulen-3-one (2.9 mg) as a light-yellow solid. MS obsd. ($ESI^+$): m/z 346.3 $[(M+H)^+]$. $^1H$ NMR (400 MHz, DMSO-d6) δ ppm: 13.19 (s, 1H), 10.72 (s, 1H), 8.03 (brs, 2H), 4.66 (s, 1H), 4.31 (t, J=6.4 Hz, 2H), 2.93-2.90 (m, 2H), 2.71 (s, 2H), 2.10-2.07 (m, 2H), 1.16 (s, 6H).

The following compounds were prepared in a similar manner as that illustrated in Examples 26 and 27.

| Ex. No. | Structure | Name | MS obsd. ($ESI^+$): m/z $[(M + H)^+]$ |
|---|---|---|---|
| 78 | 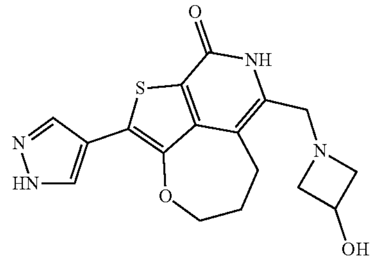 [SMILES: O=c1[nH]c(CN2CC(O)C2)c2c3c(c(-c4cn[nH]c4)sc13)OCCC2] | 7-[(3-hydroxyazetidin-1-yl)methyl]-2-(1H-pyrazol-4-yl)-12-oxa-3-thia-6-azatricyclo[6.4.1.0$^{4,13}$]trideca-1,4(13),7-trien-5-one | 359 |
| 79 | 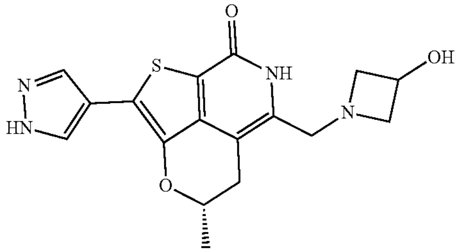 [SMILES: C[C@H]1Cc2c(CN3CC(O)C3)[nH]c(=O)c3sc(-c4cn[nH]c4)c(c23)O1] | (S)-6-((3-hydroxyazetidin-1-yl)methyl)-4-methyl-2-(1H-pyrazol-4-yl)-5,7-dihydro-3-oxa-1-thia-7-azaacenaphthylen-8(4H)-one# | 359 |
| 80 | 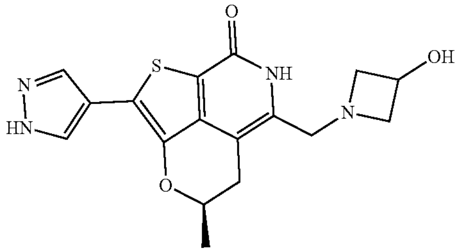 [SMILES: C[C@@H]1Cc2c(CN3CC(O)C3)[nH]c(=O)c3sc(-c4cn[nH]c4)c(c23)O1] | (R)-6-((3-hydroxyazetidin-1-yl)methyl)-4-methyl-2-(1H-pyrazol-4-yl)-5,7-dihydro-3-oxa-1-thia-7-azaacenaphthylen-8(4H)-one# | 359 |
| 81 | 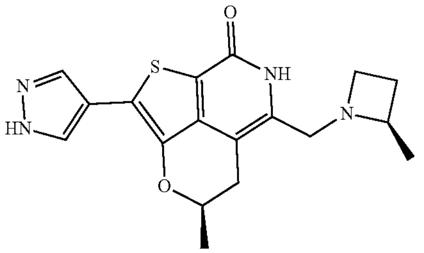 [SMILES: C[C@@H]1Cc2c(CN3CC[C@H]3C)[nH]c(=O)c3sc(-c4cn[nH]c4)c(c23)O1] | (R)-4-methyl-6-(((R)-2-methylazetidin-1-yl)methyl)-2-(1H-pyrazol-4-yl)-5,7-dihydro-3-oxa-1-thia-7-azaacenaphthylen-8(4H)-one# | 357 |
| 82 | 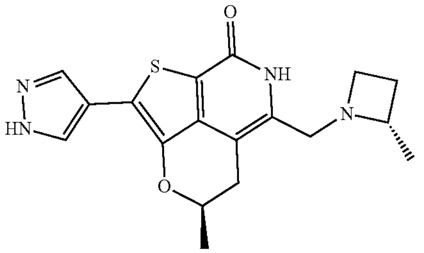 [SMILES: C[C@@H]1Cc2c(CN3CC[C@@H]3C)[nH]c(=O)c3sc(-c4cn[nH]c4)c(c23)O1] | (R)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one# | 357 |

-continued

| Ex. No. | Structure | Name | MS obsd. ($ESI^+$): m/z $[(M + H)^+]$ |
|---|---|---|---|
| 83 | 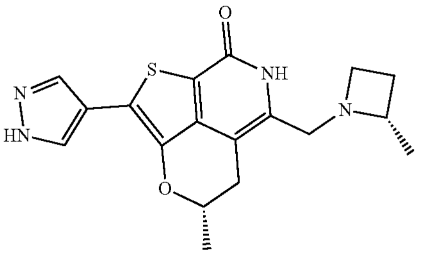 [SMILES: C[C@H]1Cc2c(CN3CC[C@@H]3C)[nH]c(=O)c3sc(-c4cn[nH]c4)c(c23)O1] | (S)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one[#] | 357 |
| 84 | 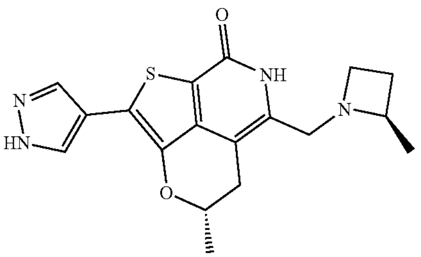 [SMILES: C[C@@H]1CCN1Cc1[nH]c(=O)c2sc(-c3cn[nH]c3)c3c2c1C[C@H](C)O3] | (S)-4-methyl-6-(((R)-2-methylazetidin-1-yl)methyl)-2-(1H-pyrazol-4-yl)-5,7-dihydro-3-oxa-1-thia-7-azaacenaphthylen-8(4H)-one[#] | 357 |

[#]The absolute stereochemistry was randomly assigned.

Example 85: 5-(1-hydroxycyclopentyl)-1-(1H-pyrazol-4-yl)-4,6,7,8-tetrahydro-3H-9-oxa-2-thia-4-azabenzo[cd]azulen-3-one

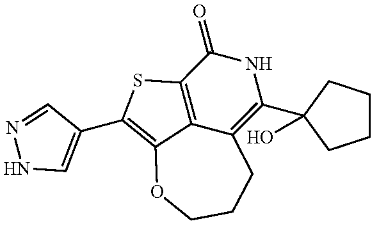 [SMILES: O=c1[nH]c(C2(O)CCCC2)c2c3c(c(-c4cn[nH]c4)sc13)OCCC2]

Step A: 5-oxo-12-oxa-3-thia-6-azatricyclo[6.4.1.$0^{4,13}$]trideca-1,4(13),7-triene-7-carbaldehyde

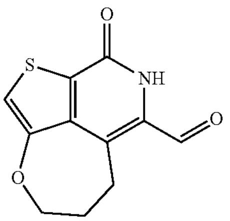 [SMILES: O=Cc1[nH]c(=O)c2scc3c2c1CCCO3]

To a solution of 7-methyl-12-oxa-3-thia-6-azatricyclo [6.4.1.$0^{4,13}$]trideca-1,4(13),7-trien-5-one (220 mg, 994.2 umol) in 1,4-dioxane (70 mL), selenium dioxide (441 mg, 3.98 mmol) was added at 25° C. After addition, the mixture was stirred at 100° C. for 16 h. The reaction mixture was filtered and concentrated under vacuum to give crude product. Then crude product was purified by flash column chromatography (eluting with 0-2% MeOH in DCM) to afford 5-oxo-12-oxa-3-thia-6-azatricyclo[6.4.1.$0^{4,13}$]trideca-1,4(13),7-triene-7-carbaldehyde (130 mg) as a yellow solid. MS obsd. ($ESI^+$): m/z 236.2 $[M+H]^+$.

Step B: 7-(1-hydroxypent-4-enyl)-12-oxa-3-thia-6-azatricyclo[6.4.1.$0^{4,13}$]trideca-1,4(13),7-trien-5-one

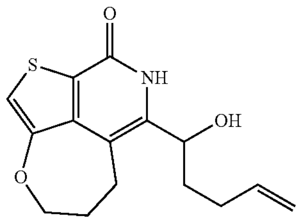 [SMILES: C=CCCC(O)c1[nH]c(=O)c2scc3c2c1CCCO3]

To a solution of 5-oxo-12-oxa-3-thia-6-azatricyclo [6.4.1.$0^{4,13}$]trideca-1,4(13),7-triene-7-carbaldehyde (100 mg, 425.1 umol) in THF (10 mL) was slowly added allylmagnesium bromide (0.5 M, 8.50 mL) at 0° C. After addition, the mixture was stirred for 2 h at 0° C. The reaction mixture was slowly poured into saturated aqueous $NH_4Cl$ solution in an ice bath. Then, it was extracted with EtOAc. The organic layer was dried and filtered and concentrated to give the crude product. It was purified by flash column chromatography (eluting with 0-3% MeOH in DCM) to afford 7-(1-hydroxypent-4-enyl)-12-oxa-3-thia-6-azatricyclo[6.4.1.$0^{4,13}$]trideca-1,4(13),7-trien-5-one (90 mg) as a yellow solid. MS obsd. ($ESI^+$): m/z 292.2 $[M+H]^+$.

Step C: 7-pent-4-enoyl-12-oxa-3-thia-6-azatricyclo[6.4.1.$0^{4,13}$]trideca-1,4(13),7-trien-5-one

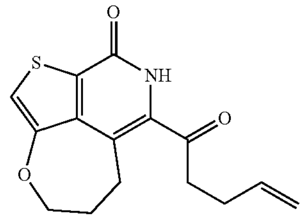 [SMILES: C=CCCC(=O)c1[nH]c(=O)c2scc3c2c1CCCO3]

To a solution of 7-(1-hydroxypent-4-enyl)-12-oxa-3-thia-6-azatricyclo[6.4.1.$0^{4,13}$]trideca-1,4(13),7-trien-5-one (190 mg, 652.1 umol) in DCM (12 mL) was slowly added Dess-Martin Periodinane (276 mg, 652.1 umol) at 0° C. After addition, the reaction was stirred for 3 h at rt. The reaction was quenched with saturated aqueous $Na_2S203$ solution, and neutralized with aqueous $NaHCO_3$ solution at 0° C. The mixture was extracted with DCM. Then it was dried, filter, concentrated and purified by flash column chromatography (eluting with 0-35% EtOAc in PE) to afford 7-pent-4-enoyl-12-oxa-3-thia-6-azatricyclo[6.4.1.$0^{4,13}$]trideca-1,4(13),7-trien-5-one (150 mg) as a white solid. MS obsd. ($ESI^+$): m/z 290.2 $[M+H]^+$.

Step D: 7-(1-hydroxy-1-vinyl-pent-4-enyl)-12-oxa-3-thia-6-azatricyclo[6.4.1.$0^{4,13}$]trideca-1,4(13),7-trien-5-one

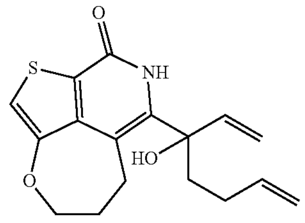 [SMILES: C=CCCC(O)(C=C)c1[nH]c(=O)c2scc3c2c1CCCO3]

To a solution of 7-pent-4-enoyl-12-oxa-3-thia-6-azatricyclo[6.4.1.$0^{4,13}$]trideca-1,4(13),7-trien-5-one (210 mg, 725.8 umol) in THF (25 mL) was slowly added vinylmagnesium bromide (1 M, 4 mL) at 0° C. After addition, the mixture was stirred at rt for 4 h. The reaction mixture was slowly poured into saturated aqueous $NH_4Cl$ solution in an ice bath. Then, The mixture was extracted with EtOAc, dried over $Na_2SO_4$, filtered and concentrated to give the crude product, which was purified by flash column chromatography (eluting with 0-35% EtOAc in PE) to afford 7-(1-hydroxy-1-vinyl-pent-4-enyl)-12-oxa-3-thia-6-azatricyclo[6.4.1.$0^{4,13}$]trideca-1,4(13),7-trien-5-one (150 mg) as a light yellow oil. MS obsd. ($ESI^+$): m/z 318.2 $[M+H]^+$.

Step E: 7-(1-hydroxycyclopent-3-en-1-yl)-12-oxa-3-thia-6-azatricyclo[6.4.1.$0^{4,13}$]trideca-1,4(13),7-trien-5-one

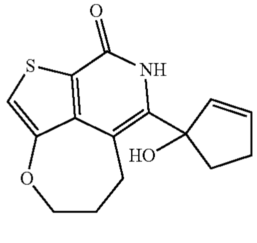 [SMILES: O=c1[nH]c(C2(O)C=CCC2)c2c3c(csc13)OCCC2]

To a flask containing of 7-(1-hydroxy-1-vinyl-pent-4-enyl)-12-oxa-3-thia-6-azatricyclo[6.4.1.$0^{4,13}$]trideca-1,4(13),7-trien-5-one (110 mg, 346.6 umol) was added Hoveyda-Grubbs Catalyst 2nd Generation (33 mg, 52.0 umol) in dry DCM (26 mL). The mixture was stirred at rt for 3 h under $N_2$ protection. The mixture was concentrated and purified by flash column chromatography (eluting with 0-7% MeOH in DCM) to afford 7-(1-hydroxycyclopent-3-en-1-yl)-12-oxa-3-thia-6-azatricyclo[6.4.1.$0^{4,13}$]trideca-1,4(13),7-trien-5-one (75 mg) as a brown solid. MS obsd. ($ESI^+$): m/z 290.2 [$(M+H)^+$].

Step F: 7-(1-hydroxycyclopentyl)-12-oxa-3-thia-6-azatricyclo[6.4.1.$0^{4,13}$]trideca-1,4(13),7-trien-5-one

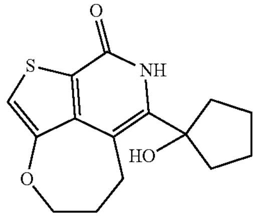 [SMILES: O=c1[nH]c(C2(O)CCCC2)c2c3c(csc13)OCCC2]

To a solution of 7-(1-hydroxycyclopent-2-en-1-yl)-12-oxa-3-thia-6-azatricyclo[6.4.1.$0^{4,13}$]trideca-1,4(13),7-trien-5-one (150 mg, 518.4 umol) in EtOAc (25 mL) was added Pd/C (20% wt, 30 mg) at rt under $N_2$ atmosphere. Then, the mixture was stirred at rt under $H_2$ for 36 h. The reaction mixture was filtered, and the filtrate was concentrated to afford 7-(1-hydroxycyclopentyl)-12-oxa-3-thia-6-azatricyclo[6.4.1.$0^{4,13}$]trideca-1,4(13),7-trien-5-one (146 mg) as a brown solid. MS obsd. ($ESI^+$): m/z 292.2 $[M+H]^+$.

Step G: 2-bromo-7-(1-hydroxycyclopentyl)-12-oxa-3-thia-6-azatricyclo[6.4.1.$0^{4,13}$]trideca-1,4(13),7-trien-5-one

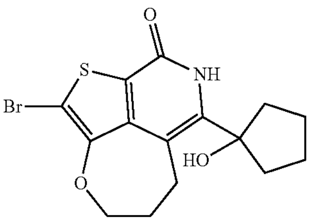 [SMILES: O=c1[nH]c(C2(O)CCCC2)c2c3c(c(Br)sc13)OCCC2]

To a solution of 7-(1-hydroxycyclopentyl)-12-oxa-3-thia-6-azatricyclo[6.4.1.0$^{4,13}$]trideca-1,4(13),7-trien-5-one (65 mg, 223.1 umol) in THF (18 mL) was added NBS (55 mg, 312.3 umol) at 0° C. After addition, the reaction was stirred at rt for 5 h. The reaction was quenched with saturated $Na_2SO_3$ solution (5 mL), extracted with EtOAc (15 mL×3), dried over anhydrous sodium sulfate, filtered and the filtrate was concentrated in vacuum to afford crude product which was purified by flash column chromatography (eluting with 0-5% MeOH in DCM) to afford 2-bromo-7-(1-hydroxycyclopentyl)-12-oxa-3-thia-6-azatricyclo[6.4.1.0$^{4,13}$]trideca-1,4(13),7-trien-5-one (58 mg) as a white solid. MS obsd. ($ESI^+$): m/z 370.2 $[M+H]^+$, 372.2 $[M+2+H]^+$.

Step H: 5-(1-hydroxycyclopentyl)-1-(1-trityl-1H-pyrazol-4-yl)-4,6,7,8-tetrahydro-3H-9-oxa-2-thia-4-azabenzo[cd]azulen-3-one

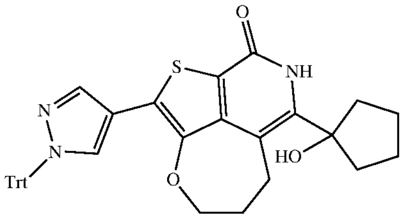

To a solution of (1-tritylpyrazol-4-yl)boronic acid (143 mg, 405.1 umol) in 1,4-dioxane:$H_2O$=5:1 (4 mL) was added 2-bromo-7-(1-hydroxycyclopentyl)-12-oxa-3-thia-6-azatricyclo[6.4.1.0$^{4,13}$]trideca-1,4(13),7-trien-5-one (50 mg, 135.0 umol), Pd(dppf)$Cl_2$ (20 mg, 27.0 umol), $Na_2CO_3$ (43 mg, 405.1 umol), Xphos (26 mg, 54.0 umol). The reaction was stirred at 105° C. for 1 h under microwave irradiation. The reaction mixture was filtered, concentrated to give the crude product. The crude product was purified by flash column chromatography (eluting with 0-4% MeOH in DCM) to afford 7-(1-hydroxycyclopentyl)-2-(1-tritylpyrazol-4-yl)-12-oxa-3-thia-6-azatricyclo[6.4.1.0$^{4,13}$]trideca-1,4(13),7-trien-5-one (40 mg) as a white solid. MS obsd. ($ESI^+$): m/z 600.5 $[M+H]^+$.

Step I: 5-(1-hydroxycyclopentyl)-1-(1H-pyrazol-4-yl)-4,6,7,8-tetrahydro-3H-9-oxa-2-thia-4-azabenzo[cd]azulen-3-one

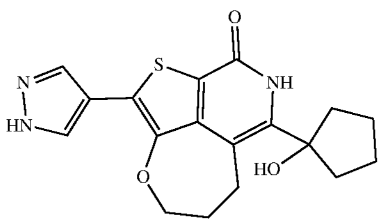 [SMILES: O=c1[nH]c(C2(O)CCCC2)c2c3c(c(-c4cn[nH]c4)sc13)OCCC2]

A mixture of 7-(1-hydroxycyclopentyl)-2-(1-tritylpyrazol-4-yl)-12-oxa-3-thia-6-azatricyclo[6.4.1.0$^{4,13}$]trideca-1,4(13),7-trien-5-one (20 mg, 33.35 umol), 2,2,2-trifluoroacetic acid (740 mg, 6.49 mmol, 0.2 mL) and DCM (10 mL) was stirred for 30 min at rt. The mixture was adjusted to pH=8 with saturated $NaHCO_3$ solution carefully at 0° C. The mixture was extracted with DCM:MeOH=10:1, dried over anhydrous sodium sulfate, filtered and the filtrate was concentrated in vacuum. Then it was purified by reverse column chromatography (eluting with 0-25% $CH_3CN$ in water (0.1% FA in water)) to afford 7-(1-hydroxycyclopentyl)-2-(1H-pyrazol-4-yl)-12-oxa-3-thia-6-azatricyclo[6.4.1.0$^{4,13}$]trideca-1,4(13),7-trien-5-one (5 mg) as a white solid. MS obsd. ($ESI^+$): m/z 358.1 $[M+H]^+$. $^1H$ NMR (400 MHz, DMSO-d6) δ ppm: 13.23 (s, 1H), 9.80 (s, 1H), 8.03 (brs, 2H), 5.86 (s, 1H), 4.30 (t, J=6.7 Hz, 2H), 2.97-2.83 (m, 2H), 2.14-2.02 (m, 4H), 1.96-1.83 (m, 6H).

Biological Assays

CDC7 Kinase Biochemical Assay Protocol:

Full length human CDC7 protein co-expressed with DBF4 was purchased from SignalChem (China). CDC7 kinase activity was determined with PDKtide (SignalChem) as a substrate and by measuring ADP production using the ADP-Glo™ Kinase Assay kit (Promega) following the manufacturers instructions. The kinase reaction was performed using the following conditions: Buffer: 40 mM Tris pH 7.5, 20 mM $MgCl_2$, 0.1 mg/ml BSA and 50 uM DTT. Final reaction mix contained 0.1 nM CDC7/DBF4, 1 uM ATP and 10 uM PDKtide. The kinase reaction time was 4 h. The ADP-Glo signal was measured using an EnVision plate reader (PerkinELmer).

Percent inhibition of CDC7 kinase activity was calculated based on the following formula:

$$\text{Inhibition}(\%) = 100\% \times \left(1 - \frac{S_{Sample} - S_{Low\,Ctrl}}{S_{High\,Ctrl} - S_{Low\,Ctrl}}\right)$$

$S_{sample}$: the signal of compounds $S_{High\ Ctrl}$: the signal of high control (DMSO)

$S_{Low\ Ctrl}$: the signal of low control (positive control CDC7 inhibitor)

Phosphorylated MCM2 MSD Electrochemiluminescence Assay

The effect of CDC7 inhibitors on cellular phosphorylation of the CDC7 substrate MCM2 was determined using the following protocol:

A total of 40,000 colo205 cells in 100 uL culture medium (1640 medium+10% Fetal bovine serum+1% Penicillin-Streptomycin) were plated in 96-well cell culture plates and allowed to attach for 6 hours. 3-fold serial dilutions of test compounds were prepared in completed PBS at 25×final concentration and 4 uL of each were added to the cells and incubated for 20 hours at 37° C., 5% $CO_2$. Each concentration was tested in duplicate. After the 20 h incubation, cells were washed with 150 uL PBS and lysed with 40 uL MSD lysis buffer (obtained from Meso Scale Diagnostics) supplied with 1×complete ULTRA cocktail inhibitor (obtained from Roche). To detect phosphorylation of MCM2 S53, 30 μL of capture antibody solution (obtained from Abnova, catalog number H00004171-MO1, 1:500) was added to each well of MULTI-ARRAY 96-well High Bind Plate, and incubated overnight. The antibody solution was removed, wells blocked with BSA solution and plates washed, followed by addition of 30 ul of cell lysate per well. After 2 h incubation, plates were washed. 30 μL of 1×detection antibody solution (obtained from Abcam, catalog number ab109133, 1:1000) was then added to each well and incubate for 1 hour. Plates were washed and 30 μL of 1×secondary antibody solution (obtained from MSD, catalog number R32AB-1, 1:5000) was added to each well and incubate for 1 hour. Plates were washed and 150 L of 1×Read Buffer T was added to each well of the MSD plate. The electrochemiluminescence signal was measured on a MESO SECTOR S600 plate reader. The percentage of remaining phosphorylated MCM2 signal was calculated following the equation below.

$$\% \text{ Inhibition} = 100 \times \frac{R_{HC} - R_{cpds}}{R_{HC} - R_{LC}}$$

HC (high control): Cells treated with DMSO
Cpds: Cells treated with test compounds
LC (low control): Cells treated with positive control CDC7 inhibitor

TABLE A

| CDC7 Kinase Inhibition | |
|---|---|
| Cmpd. No. | CDC7 ADP-Glo PDKtide $IC_{50}$ |
| 1. | A |
| 2. | A |
| 3. | B |
| 4. | A |
| 5. | A |
| 6. | B |
| 7. | A |
| 8. | A |
| 9. | A |
| 10. | B |
| 11. | A |
| 12. | A |
| 13. | A |
| 14. | B |
| 15. | B |
| 16. | C |
| 17. | B |
| 18. | A |
| 19. | A |
| 20. | A |
| 21. | A |
| 22. | A |
| 23. | A |
| 24. | A |
| 25. | A |
| 26. | A |
| 27. | A |
| 28. | A |
| 29. | A |
| 30. | A |
| 31. | A |
| 32. | A |
| 33. | A |
| 34. | A |
| 35. | A |
| 36. | A |
| 37. | B |
| 38. | B |
| 39. | A |
| 40. | A |
| 41. | A |
| 42. | A |
| 43. | A |
| 44. | A |
| 45. | A |
| 46. | A |
| 47. | A |
| 48. | A |
| 49. | A |
| 50. | A |
| 51. | B |
| 52. | B |
| 53. | B |
| 54. | A |
| 55. | A |
| 56. | A |
| 57. | A |

TABLE A-continued

| CDC7 Kinase Inhibition | |
|---|---|
| Cmpd. No. | CDC7 ADP-Glo PDKtide $IC_{50}$ |
| 58. | A |
| 59. | A |
| 60. | A |
| 61. | A |
| 62. | A |
| 63. | A |
| 64. | A |
| 65. | A |
| 66. | A |
| 67. | A |
| 68. | A |
| 69. | A |
| 70. | A |
| 71. | A |
| 72. | A |
| 73. | C |
| 74. | C |
| 75. | A |
| 76. | A |
| 77. | A |
| 78. | A |
| 79. | A |
| 80. | A |
| 81. | A |
| 82. | A |
| 83. | A |
| 84. | A |
| 85. | A |

A denotes $IC_{50} < 1$ nM;
B denotes 1 nM $\leq IC_{50} <$ 10 nM;
C denotes $IC_{50} \geq 10$ nM.

TABLE B

| Electrochemiluminescence assay | |
|---|---|
| Cmpd. No. | pMCM2-S53 MSD Colo205 $IC_{50}$ |
| 1 | B |
| 5 | A |
| 7 | B |
| 8 | B |
| 13 | A |
| 24 | B |
| 28 | A |
| 30 | A |
| 31 | A |
| 44 | A |
| 46 | B |
| 47 | A |
| 51 | C |
| 54 | C |
| 55 | A |
| 57 | A |
| 58 | A |

A denotes $IC_{50} < 100$ nM;
B denotes 100 nM $\leq IC_{50} <$ 1000 nM;
C denotes $IC_{50} \geq 1000$ nM.

What is claimed is:

1. A compound of Formula (I):

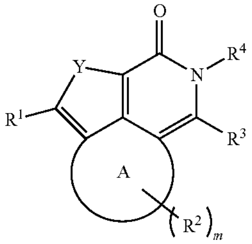

or a pharmaceutically acceptable salt thereof, wherein:

$R^1$ is a 5-10 membered heteroaryl, optionally substituted with 1-3 substituents independently selected from the group consisting of C1-C6 alkyl, amino, halogen, hydroxy, cyano, C1-C6 haloalkyl, C1-C6 alkoxy, and C3-C6 cycloalkyl;

Y is —S— or —S(═O)—;

Ring A is a C5-C7 cycloalkyl or 5-7 membered heterocyclyl;

each $R^2$ is independently selected from the group consisting of hydrogen, halogen, hydroxy, cyano, C1-C6 haloalkyl, C1-C6 hydroxyalkyl, C1-C6 alkoxy, —$NR^B R^C$, C1-C6 alkoxyalkyl, —C(═O) NH-5-10 membered heteroaryl, 4-6 membered heterocyclyl, 5-10 membered heteroaryl, C1-C6 alkyl optionally substituted with 1-3 independently selected $R^A$, and C3-C6 cycloalkyl optionally substituted with hydroxyl; or two $R^2$ together with the atom to which they are attached, join together to form an oxo group; a C3-C6 cycloalkyl optionally substituted with 1-3 substituents independently selected from halogen, cyano, C1-C6 alkyl, and C1-C6 alkoxy; or a 3-6 membered heterocyclyl optionally substituted with 1-3 substituents independently selected from halogen, cyano, C1-C6 alkyl, and C1-C6 alkoxy;

$R^3$ is selected from hydrogen and C0-C6 alkyl optionally substituted with 1-4 substituents independently selected from:

(i) hydroxyl;

(ii) cyano;

(iii) halogen;

(iv) C3-C6 cycloalkoxy;

(v) C(═O) ORF;

(vi) C1-C6 alkoxy;

(vii) 4-10 membered heterocyclyloxy optionally substituted with 1-3 independently selected halogens;

(viii) —$NR^B R^C$;

(ix) C3-C6 cycloalkyl optionally substituted with 1-3 groups independently selected from hydroxyl, cyano, halogen, C1-C6 alkoxy, C1-C6 haloalkoxy, —$NR^B R^C$, 3-6 membered heterocyclyloxy, and 3-6 membered heterocyclyl optionally substituted with 1-3 $C_1$-$C_6$ alkoxy;

(x) 3 to 10 membered heterocyclyl optionally substituted with 1-4 substituents independently selected from halogen, hydroxyl, C1-C6 hydroxyalkyl, C1-C6 alkoxy, C1-C6 haloalkyl, —$NR^B R^C$, C1-C6 alkyl optionally substituted with 1-3 substituents independently selected from halogen, C1-C6 alkoxy, and C3-C6 cycloalkoxy, and C3-C6 cycloalkyl optionally substituted with halogen or hydroxyl;

(xi) 5-6 membered heteroaryl optionally substituted with 1-3 substituents independently selected from cyano, hydroxyl, C1-C6 alkyl, C1-C6 alkoxy, C3-C6 cycloalkyl, and 4-10 membered heterocyclyl, wherein said C3-C6 cycloalkyl is optionally substituted with 1-2 substituents independently selected from cyano and hydroxyl, and said 4-10 membered heterocyclyl is optionally substituted with 1-3 independently selected $R^A$; and (xii) —C(═O)—X; wherein X is —$NR^B R^C$, C1-C6 alkyl, 5-6 membered heteroaryl, —NH-5-6 membered heteroaryl, —ORE, or 3-6 membered heterocyclyl optionally substituted with hydroxyl;

each $R^A$ and $R^E$ are independently halogen, cyano, hydroxyl, C1-C6 alkoxy, C1-C6 alkyl, C1-C6 haloalkyl, C1-C6 hydroxyalkyl, C1-C6 alkylamino, 4-6 membered heterocyclyl, or C3-C6 cycloalkyl;

each $R^B$ and $R^C$ are independently hydrogen, C1-C6 alkyl, C1-C6 haloalkyl, —C(═O)—C1-C6 alkyl, —(C1-C6 alkylene)$_p$-C3-C8 cycloalkyl optionally substituted with C1-C6 alkyl, cyano, halogen, hydroxyl, or C3-C6 cycloalkyl; 3 to 6 membered heterocyclyl optionally substituted with C1-C6 alkyl; —C(═O)O—C1-C6 alkyl; or benzyl optionally substituted with C1-C6 alkoxy; or $R^B$ and $R^C$ together with the atom to which they are attached, join together to form a 4-10 membered heterocyclyl optionally substituted with 1-3 substituents independently selected from halogen, hydroxyl, cyano, C1-C6 alkyl, —$NR^F R^G$, C3-C6 cycloalkoxy, C1-C6 haloalkoxy, and C1-C6 alkoxy;

each p is independently 0 or 1;

m is 0, 1, 2, 3, or 4;

$R^4$ is hydrogen or C1-C6 alkyl; and each $R^F$ and $R^G$ are independently hydrogen or C1-C6 alkyl.

2. The compound of claim 1, wherein Y is —S—.

3. The compound of claim 1, wherein Ring A is a 5-7 membered heterocyclyl.

4. The compound of claim 1, wherein Ring A includes one oxygen atom.

5. The compound of claim 1, wherein:

a) $R^1$ is an unsubstituted 5-10 membered heteroaryl;

b) $R^1$ is an unsubstituted 5-6 membered heteroaryl;

c) $R^1$ is pyrazole;

d) $R^1$ is

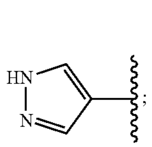

e) $R^1$ is pyridine;

f) $R^1$ is

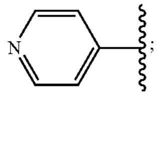 [SMILES: *c1ccncc1]

g) $R^1$ is pyrimidine; or h) $R^1$ is

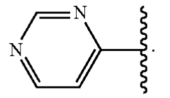

6. The compound of claim 1, wherein:

i) each $R^2$ is independently —C(═O)NH-5-10 membered heteroaryl;

j) each $R^2$ is independently 4-6 membered heterocyclyl;

k) each $R^2$ is independently 5-10 membered heteroaryl;

l) each $R^2$ is independently C3-C6 cycloalkyl optionally substituted with hydroxyl;

m) each $R^2$ is independently C1-C6 alkyl optionally substituted with 1-3 independently selected $R^A$; or n) each $R^2$ is independently C1-C6 alkyl substituted with 1-3 independently selected $R^A$.

7. The compound of claim 1, wherein two $R^2$ together with the atom to which they are attached, join together to form a 3-6 membered heterocyclyl optionally substituted with 1-3 substituents independently selected from halogen, cyano, C1-C6 alkyl, and C1-C6 alkoxy.

8. The compound of claim 1, wherein $R^3$ is C1-C6 alkyl optionally substituted with 1-3 substituents independently selected from hydroxyl, cyano, C1-C6 alkoxy, C3-C6 cycloalkoxy and C3-C6 cycloalkyl.

9. The compound of claim 1, wherein $R^3$ is C1-C6 alkyl substituted with azetidine, pyrrolidine or piperidine; each optionally substituted with C1-C6 alkyl, hydroxyl, or halogen.

10. The compound of claim 1, wherein $R^3$ is:

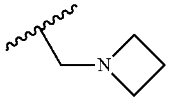
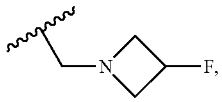
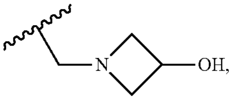
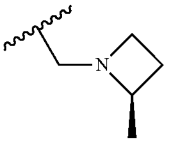
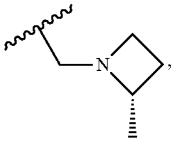
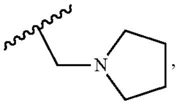
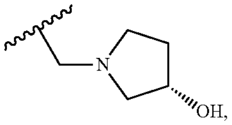
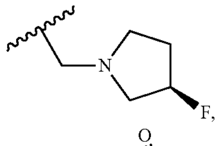
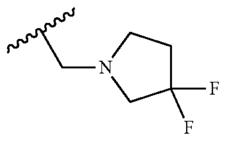
or
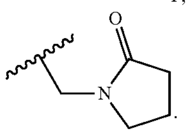

11. The compound of claim 1, wherein:

o) $R^4$ is C1-C6 alkyl;

p) $R^4$ is methyl; or q) $R^4$ is hydrogen.

12. A method for treating cancer in a subject in need thereof, comprising:

(a) determining if the cancer is associated with a dysregulation of a CDC7 gene, a CDC7 kinase, or expression or activity or level of any of the same; and (b) if the cancer is determined to be associated with a dysregulation of a CDC7 gene, a CDC7 kinase, or expression or activity or level of any of the same, administering to the subject an effective amount of a compound of claim 1 or a pharmaceutically acceptable salt thereof.

13. The method of claim 12, wherein the step of determining if the cancer in the subject is a CDC7-associated cancer includes performing an assay to detect dysregulation in a CDC7 gene, a CDC7 kinase protein, or expression or activity or level of any of the same in a sample from the subject.

14. The method of claim 12, further comprising obtaining a sample from the subject.

15. The method of claim 14, wherein the sample is a biopsy sample.

16. The method of claim 12, further comprising administering an additional therapy or therapeutic agent to the subject.

17. The method of claim 16, wherein the additional therapy or therapeutic agent is selected from radiotherapy, cytotoxic chemotherapeutics, kinase targeted-therapeutics, apoptosis modulators, signal transduction inhibitors, immune-targeted therapies and angiogenesis-targeted therapies.

18. The method of claim 16, wherein the compound of claim 1 or a pharmaceutically acceptable salt or solvate thereof and the additional therapeutic agent are administered simultaneously as separate dosages.

19. The method of claim 16, wherein the compound of claim 1 or a pharmaceutically acceptable salt thereof and the additional therapeutic agent are administered as separate dosages sequentially in any order.

20. A compound, wherein the compound is selected from:

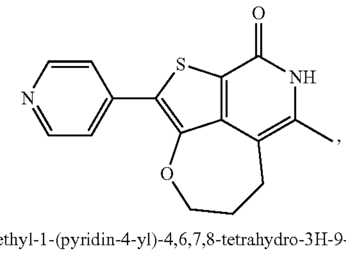

5-methyl-1-(pyridin-4-yl)-4,6,7,8-tetrahydro-3H-9-oxa-2-thia-4-azabenzo[cd]azulen-3-one: Scheme

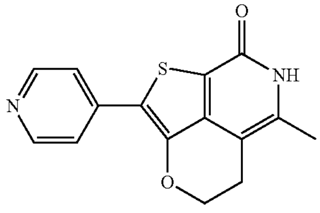

6-methyl-2-(pyridin-4-yl)-5,7-dihydro-3-oxa-1-thia-7-azaacenaphthylen-8(4H)-one

-continued

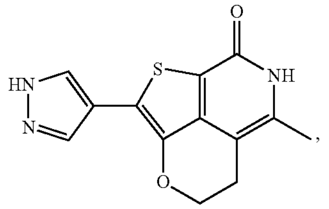

6-methyl-2-(1H-pyrazol-4-yl)-5,7-dihydro-3-oxa-1-thia-7-azaacenaphthylen-8(4H)-one

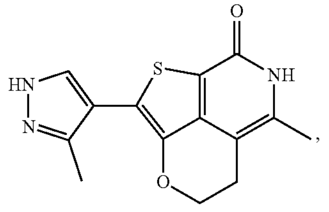

6-methyl-2-(3-methyl-1H-pyrazol-4-yl)-5,7-dihydro-3-oxa-1-thia-7-azaacenaphthylen-8(4H)-one

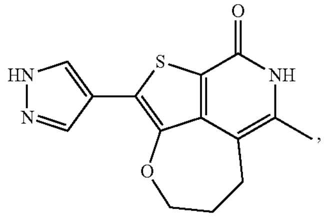

5-methyl-1-(1H-pyrazol-4-yl)-4,6,7,8-tetrahydro-3H-9-oxa-2-thia-4-azabenzo[cd]azulen-3-one

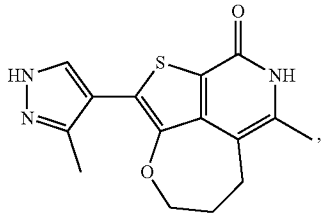

5-methyl-1-(3-methyl-1H-pyrazol-4-yl)-4,6,7,8-tetrahydro-3H-9-oxa-2-thia-4-azabenzo[cd]azulen-3-one

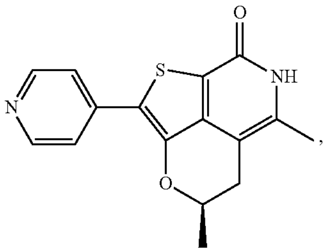

(R)-4,6-dimethyl-2-(pyridin-4-yl)-5,7-dihydro-3-oxa-1-thia-7-azaacenaphthylen-8(4H)-one

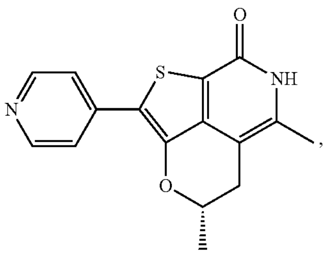

(S)-4,6-dimethyl-2-(pyridin-4-yl)-5,7-dihydro-3-oxa-1-thia-7-azaacenaphthylen-8(4H)-one -continued

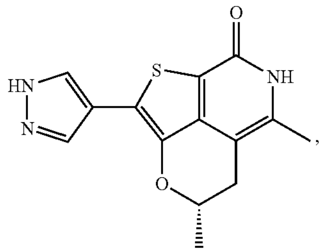

4,6-dimethyl-2-(1H-pyrazol-4-yl)-5,7-dihydro-3-oxa-1-thia-7-azaacenaphthylen-8(4H)-one

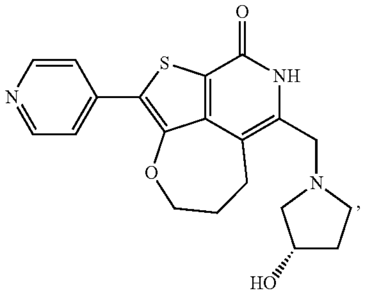

(S)-5-((3-hydroxypyrrolidin-1-yl)methyl)-1-(pyridin-4-yl)-4,6,7,8-tetrahydro-3H-9-oxa-2-thia-4-azabenzo[cd]azulen-3-one

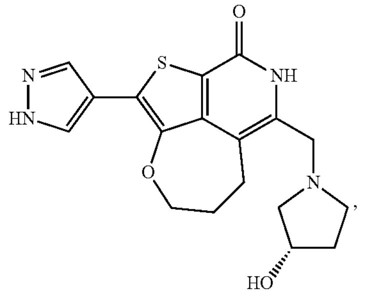

(S)-5-((3-hydroxypyrrolidin-1-yl)methyl)-1-(1H-pyrazol-4-yl)-4,6,7,8-tetrahydro-3H-9-oxa-2-thia-4-azabenzo[cd]azulen-3-one

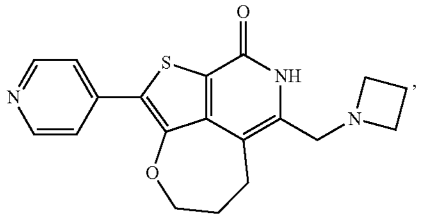

5-(azetidin-1-ylmethyl)-1-(pyridin-4-yl)-4,6,7,8-tetrahydro-3H-9-oxa-2-thia-4-azabenzo[cd]azulen-3-one

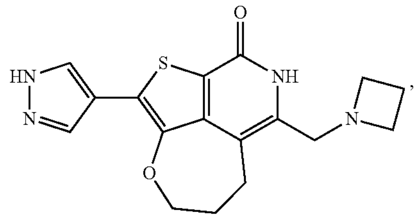

5-(azetidin-1-ylmethyl)-1-(1H-pyrazol-4-yl)-4,6,7,8-tetrahydro-3H-9-oxa-2-thia-4-azabenzo[cd]azulen-3-one -continued

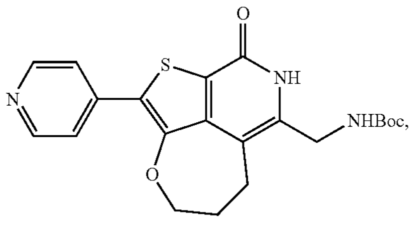

Tert-butyl ((3-oxo-1-(pyridin-4-yl)-4,6,7,8-tetrahydro-3H-9-oxa-2-thia-4-azabenzo[cd]azulen-5-yl)methyl)carbamate

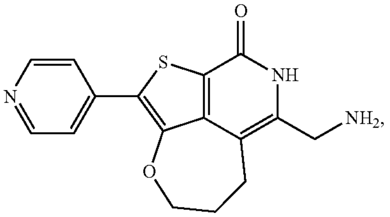

5-(aminomethyl)-1-(pyridin-4-yl)-4,6,7,8-tetrahydro-3H-9-oxa-2-thia-4-azabenzo[cd]azulen-3-one

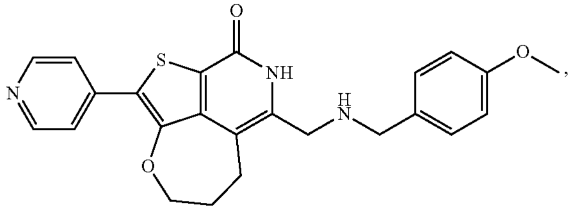

5-(((4-methoxybenzyl)amino)methyl)-1-(pyridin-4-yl)-4,6,7,8-tetrahydro-3H-9-oxa-2-thia-4-azabenzo[cd]azulen-3-one

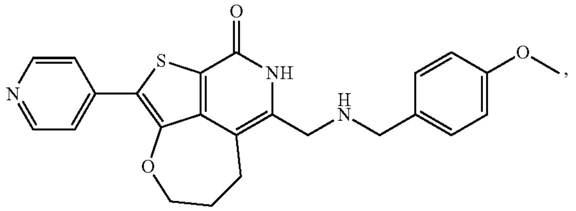

5-(((4-methoxybenzyl)amino)methyl)-1-(pyridin-4-yl)-4,6,7,8-tetrahydro-3H-9-oxa-2-thia-4-azabenzo[cd]azulen-3-one

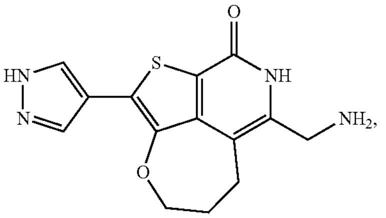

7-(aminomethyl)-2-(1H-pyrazol-4-yl)-12-oxa-3-thia-6-azatricyclo[6.4.1.04,13]trideca-1,4(13),7-trien-5-one

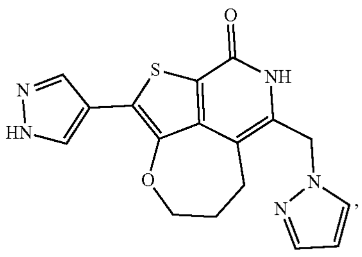

2-(1H-pyrazol-4-yl)-7-(pyrazol-1-ylmethyl)-12-oxa-3-thia-6-azatricyclo[6.4.1.$0^{4,13}$]trideca-1,4(13),7-trien-5-one -continued

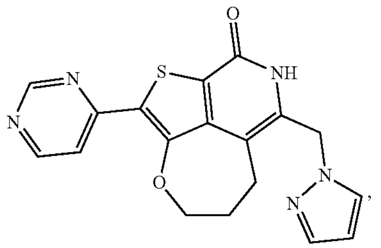

7-(pyrazol-1-ylmethyl)-2-pyrimidin-4-yl-12-oxa-3-thia-6-azatricyclo[6.4.1.04,13]trideca-1,4(13),7-trien-5-one

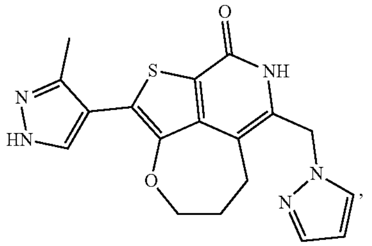

2-(3-methyl-1H-pyrazol-4-yl)-7-(pyrazol-1-ylmethyl)-12-oxa-3-thia-6-azatricyclo[6.4.1.$0^{4,13}$]trideca-1,4(13),7-trien-5-one

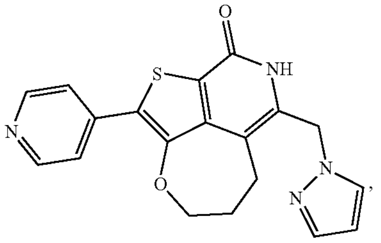

7-(pyrazol-1-ylmethyl)-2-(4-pyridyl)-12-oxa-3-thia-6-azatricyclo[6.4.1.$0^{4,13}$]trideca-1,4(13),7-trien-5-one

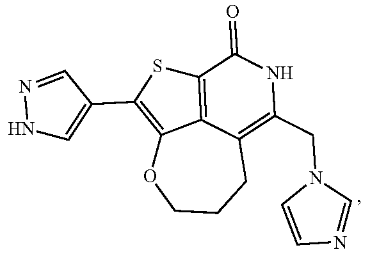

7-(imidazol-1-ylmethyl)-2-(1H-pyrazol-4-yl)-12-oxa-3-thia-6-azatricyclo[6.4.1.$0^{4,13}$]trideca-1,4(13),7-trien-5-one

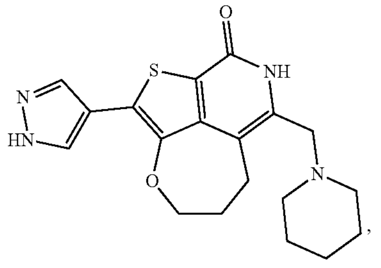

5-(piperidin-1-ylmethyl)-1-(1H-pyrazol-4-yl)-4,6,7,8-tetrahydro-3H-9-oxa-2-thia-4-azabenzo[cd]azulen-3-one -continued

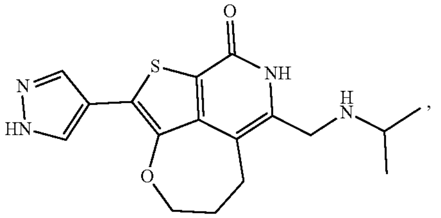

5-((isopropylamino)methyl)-1-(1H-pyrazol-4-yl)-4,6,7,8-tetrahydro-3H-9-oxa-2-thia-4-azabenzo[cd]azulen-3-one

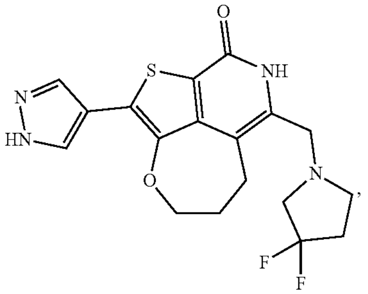

7-[(3,3-difluoropyrrolidin-1-yl)methyl]-2-(1H-pyrazol-4-yl)-12-oxa-3-thia-6-azatricyclo[6.4.1.0$^{4,13}$]trideca-1,4(13),7-trien-5-one

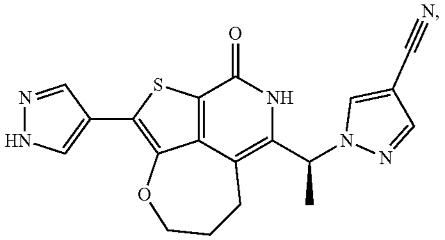

(S)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile

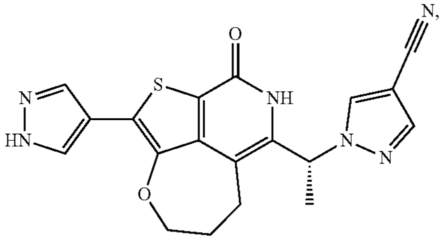

(R)-1-(1-(3-oxo-1-(1H-pyrazol-4-yl)-4,6,7,8-tetrahydro-3H-9-oxa-2-thia-4-azabenzo[cd]azulen-5-yl)ethyl)-1H-pyrazole-4-carbonitrile

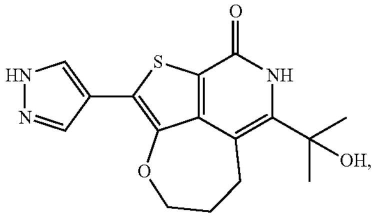

5-(2-hydroxypropan-2-yl)-1-(1H-pyrazol-4-yl)-4,6,7,8-tetrahydro-3H-9-oxa-2-thia-4-azabenzo[cd]azulen-3-one -continued

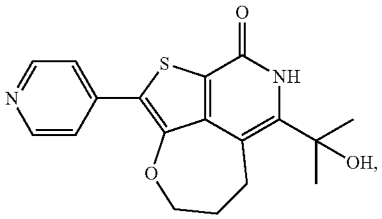

5-(2-hydroxypropan-2-yl)-1-(pyridin-4-yl)-4,6,7,8-tetrahydro-3H-9-oxa-2-thia-4-azabenzo[cd]azulen-3-one

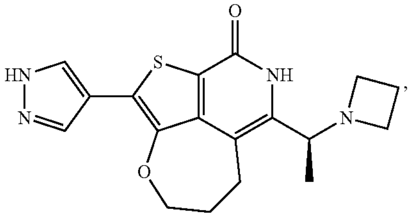

(S)-5-(1-(azetidin-1-yl)ethyl)-1-(1H-pyrazol-4-yl)-4,6,7,8-tetrahydro-3H-9-oxa-2-thia-4-azabenzo[cd]azulen-3-one

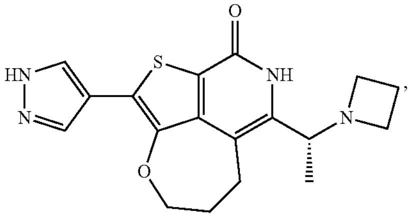

(R)-5-(1-(azetidin-1-yl)ethyl)-1-(1H-pyrazol-4-yl)-4,6,7,8-tetrahydro-3H-9-oxa-2-thia-4-azabenzo[cd]azulen-3-one

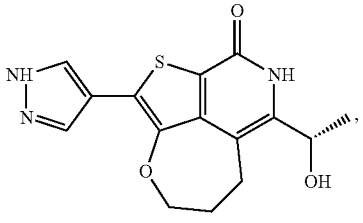

(S)-5-(1-hydroxyethyl)-1-(1H-pyrazol-4-yl)-4,6,7,8-tetrahydro-3H-9-oxa-2-thia-4-azabenzo[cd]azulen-3-one

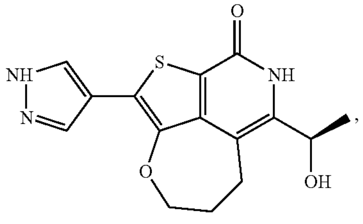

(R)-5-(1-hydroxyethyl)-1-(1H-pyrazol-4-yl)-4,6,7,8-tetrahydro-3H-9-oxa-2-thia-4-azabenzo[cd]azulen-3-one

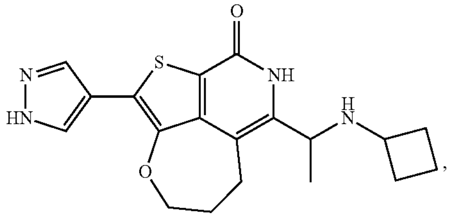

5-(1-(cyclobutylamino)ethyl)-1-(1H-pyrazol-4-yl)-4,6,7,8-tetrahydro-3H-9-oxa-2-thia-4-azabenzo[cd]azulen-3-one -continued

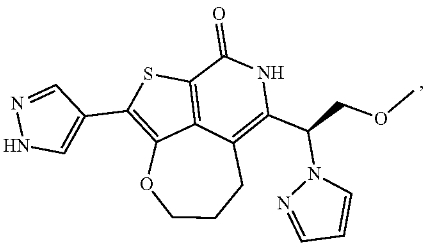

(S)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one

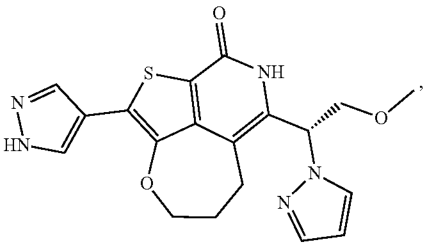

(R)-5-(2-methoxy-1-(1H-pyrazol-1-yl)ethyl)-1-(1H-pyrazol-4-yl)-4,6,7,8-tetrahydro-3H-9-oxa-2-thia-4-azabenzo[cd]azulen-3-one

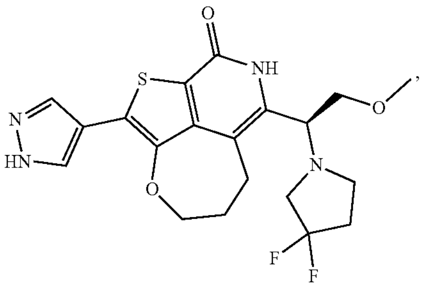

(S)-5-(1-(3,3-difluoropyrrolidin-1-yl)-2-methoxyethyl)-1-(1H-pyrazol-4-yl)-4,6,7,8-tetrahydro-3H-9-oxa-2-thia-4-azabenzo[cd]azulen-3-one

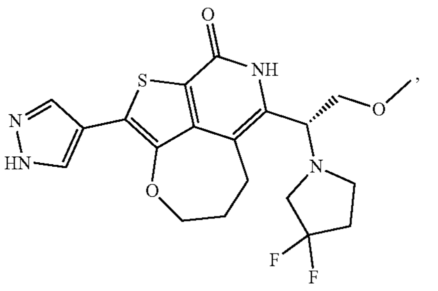

(R)-5-(1-(3,3-difluoropyrrolidin-1-yl)-2-methoxyethyl)-1-(1H-pyrazol-4-yl)-4,6,7,8-tetrahydro-3H-9-oxa-2-thia-4-azabenzo[cd]azulen-3-one

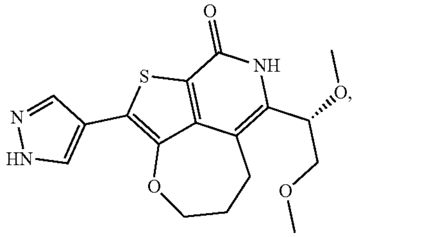

(S)-5-(1,2-dimethoxyethyl)-1-(1H-pyrazol-4-yl)-4,6,7,8-tetrahydro-3H-9-oxa-2-thia-4-azabenzo[cd]azulen-3-one -continued

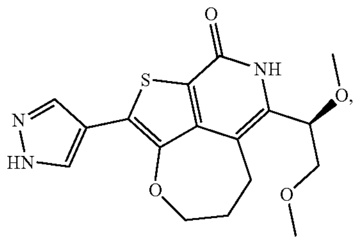

(S)-5-(1,2-dimethoxyethyl)-1-(1H-pyrazol-4-yl)-4,6,7,8-tetrahydro-3H-9-oxa-2-thia-4-azabenzo[cd]azulen-3-one

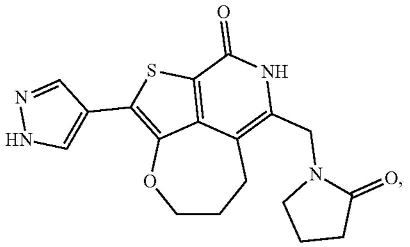

5-((2-oxopyrrolidin-1-yl)methyl)-1-(1H-pyrazol-4-yl)-4,6,7,8-tetrahydro-3H-9-oxa-2-thia-4-azabenzo[cd]azulen-3-one

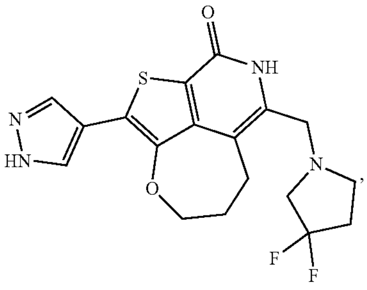

5-((3,3-difluoropyrrolidin-1-yl)methyl)-1-(1H-pyrazol-4-yl)-4,6,7,8-tetrahydro-3H-9-oxa-2-thia-4-azabenzo[cd]azulen-3-one

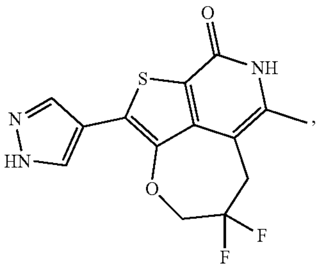

10,10-difluoro-7-methyl-2-(1H-pyrazol-4-yl)-12-oxa-3-thia-6-azatricyclo [6.4.1.$0^{4,13}$] trideca-1,4(13),7-trien-5-one

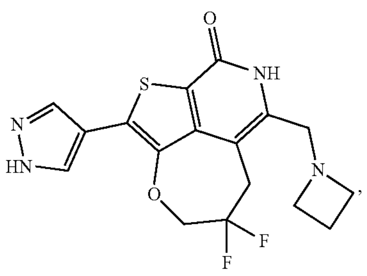

7-(azetidin-1-ylmethyl)-10,10-difluoro-2-(1H-pyrazol-4-yl)-12-oxa-3-thia-6-azatricyclo [6.4.1.$0^{4,13}$] trideca-1,4(13),7-trien-5-one -continued

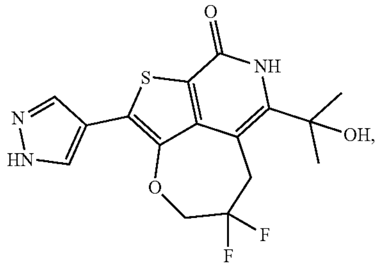

10,10-difluoro-7-(1-hydroxy-1-methyl-ethyl)-2-(1H-pyrazol-4-yl)-12-oxa-3-thia-6-azatricyclo [6.4.1.$0^{4,13}$] trideca-1,4(13),7-trien-5-one

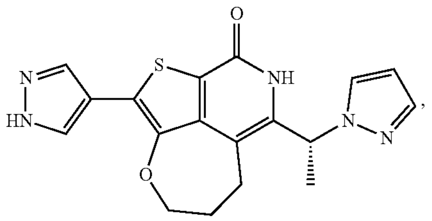

(R)-2-(1H-pyrazol-4-yl)-7-(1-pyrazol-1-ylethyl)-12-oxa-3-thia-6-azatricyclo [6.4.1.04, 13] trideca-l, 4(13), 7-trien-5-one

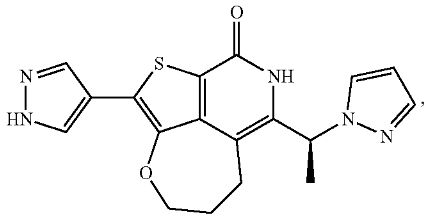

(S)-2-(1H-pyrazol-4-yl)-7-(1-pyrazol-1-ylethyl)-12-oxa-3-thia-6-azatricyclo [6.4.1.$0^{4, 13}$] trideca-l, 4(13), 7-trien-5-one

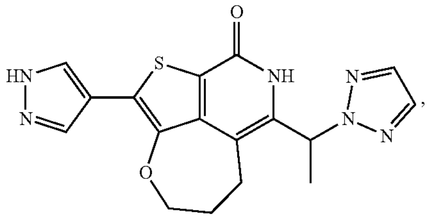

2-(1H-pyrazol-4-yl)-7-[1-(triazol-2-yl)ethyl]-12-oxa-3-thia-6-azatricyclo[6.4.1.$0^{4, 13}$] trideca-l,4(13),7-trien-5-one

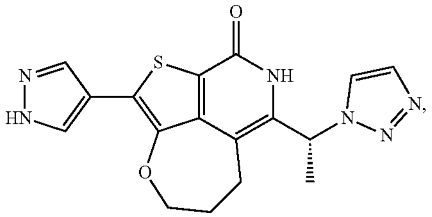

(R)-5-(1-(1H-1,2,3-triazol-1-yl)ethyl)-1-(1H-pyrazol-4-yl)-4,6,7,8-tetrahydro-3H-9-oxa-2-thia-4-azabenzo[cd]azulen-3-one

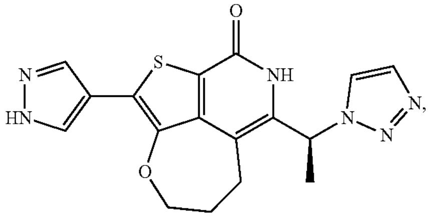

(S)-5-(1-(1H-1,2,3-triazol-1-yl)ethyl)-1-(1H-pyrazol-4-yl)-4,6,7,8-tetrahydro-3H-9-oxa-2-thia-4-azabenzo[cd]azulen-3-one -continued

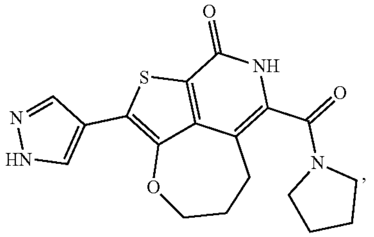

2-(1H-pyrazol-4-yl)-7-(pyrrolidine-1-carbonyl)-12-oxa-3-thia-6-azatricyclo[6.4.1.$0^{4,13}$]-trideca-1,4(13),7-trien-5-one

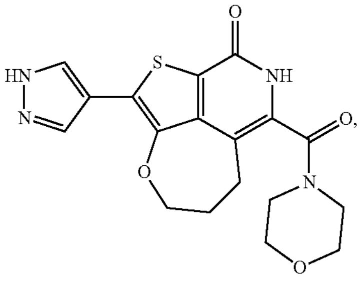

7-(morpholine-4-carbonyl)-2-(1H-pyrazol-4-yl)-12-oxa-3-thia-6-azatricyclo[6.4.$10^{4,13}$]-trideca-1,4(13),7-trien-5-one

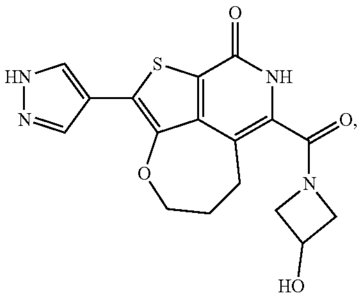

5-(3-hydroxyazetidine-1-carbonyl)-1-(1H-pyrazol-4-yl)-4,6,7,8-tetrahydro-3H-9-oxa-2-thia-4-azabenzo[cd]azulen-3-one

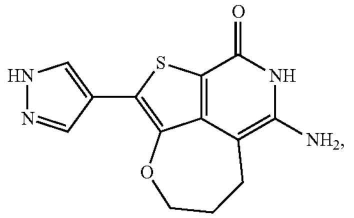

7-amino-2-(1H-pyrazol-4-yl)-12-oxa-3-thia-6-azatricyclo[6.4.1.$0^{4'13}$]trideca-1,4(13),7-trien-5-one

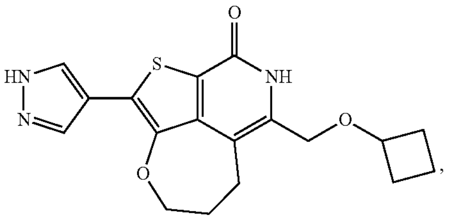

5 -(cyclobutoxymethyl)-1-(1H-pyrazol-4-yl)-4,6,7,8-tetrahydro-3H-9-oxa-2-thia-4-azaben -zo[cd]azulen-3-one -continued

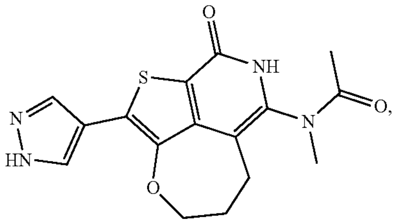
,

N-methyl-N-(3-oxo-1-(1H-pyrazol-4-yl)-4,6,7,8-tetrahydro-3H-9-oxa-2-thia-4-azabenzo[c d]azulen-5-yl)acetamide

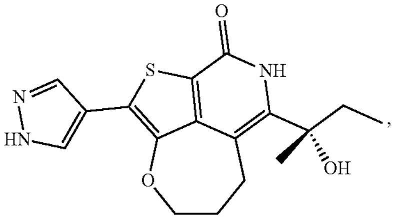
, (S)-5-(2-hydroxybutan-2-yl)-1-(1H-pyrazol-4-yl)-4,6,7,8-tetrahydro-3H-9-oxa-2-thia-4-azabenzo[cd]azulen-3-0ne

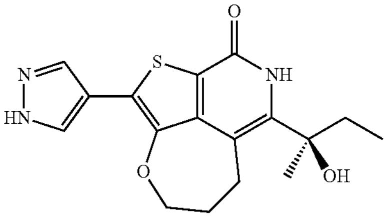
, (R)-5-(2-hydroxybutan-2-yl)-1-(1H-pyrazol-4-yl)-4, 6, 7, 8-tetrahydro-3H-9-oxa-2-thia-4-azabenzo[cd]azulen-3-one

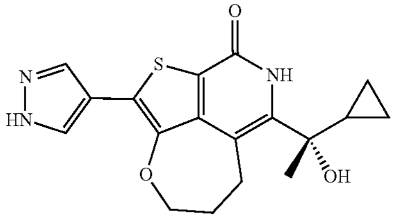
, (S)-5-(1-cyclopropyl-1-hydroxyethyl)-1-(1H-pyrazol-4-yl)-4, 6, 7, 8-tetrahydro-3H-9-oxa-2-thia-4-azabenzo[cd]azulen-3-one

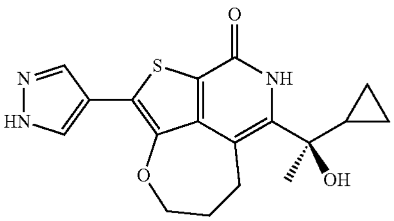
, (R)-5-(1-cyclopropyl-1-hydroxyethyl)-1-(1H-pyrazol-4-yl)-4, 6, 7, 8-tetrahydro-3H-9-oxa-2-thia-4-azabenzo[cd]azulen-3-one -continued

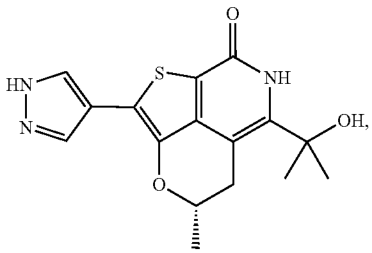
, (S)-6-(2-hydroxypropan-2-yl)-4-methyl-2-(1H-pyrazol-4-yl)-5 ,7-dihydro-3-oxa-1-thia-7-azaacenaphthylen-8(4H)-one

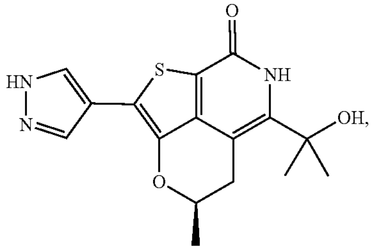
, (S)-6-(2-hydroxypropan-2-yl)-4-methyl-2-(1H-pyrazol-4-yl)-5 ,7-dihydro-3-oxa-1-thia-7-azaacenaphthylen-8(4H)-one

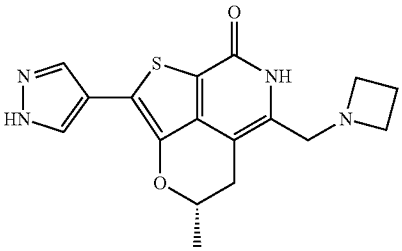
, (S)-6-(azetidin-1-ylmethyl)-4-methyl-2-(1H-pyrazol-4-yl)-5, 7-dihydro-3-oxa-1-thia-7-azaacenaphthylen-8(4H)-one

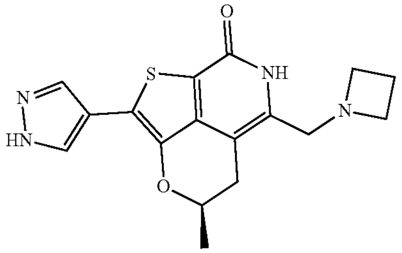
, (R)-6-(azetidin-1-ylmethyl)-4-methyl-2-(1H-pyrazol-4-yl)-5, 7-dihydro-3-oxa-1-thia-7-azaacenaphthylen-8(4H)-one -continued

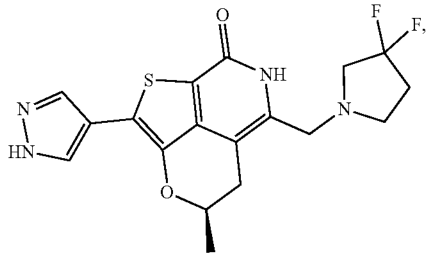

(R)-6-((3, 3-difluoropyrrolidin-1-yl)methyl)-4-methyl-2-(1H-pyrazol-4-yl)-5, 7-dihydro-3-oxa-1-thia-7-azaacenaphthylen-8(4H)-one

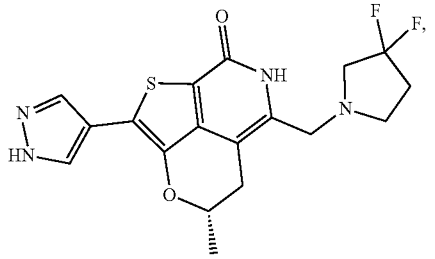

(S)-6-((3, 3-difluoropyrrolidin-1-yl)methyl)-4-methyl-2-(1H-pyrazol-4-yl)-5, 7-dihydro-3-oxa-1-thia-7-azaacenaphthylen-8(4H)-one

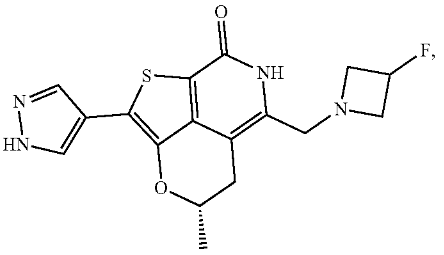

(R)-6-((3-fluoroazetidin-1-yl)methyl)-4-methyl-2-(1H-pyrazol-4-yl)-5, 7-dihydro-3-oxa-1-thia-7-azaacenaphthylen-8(4H)-one

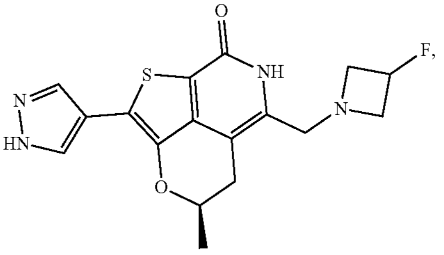

(S)-6-((3-fluoroazetidin-1-yl)methyl)-4-methyl-2-(1H-pyrazol-4-yl)-5, 7-dihydro-3-oxa-1-thia-7-azaacenaphthylen-8(4H)-one -continued

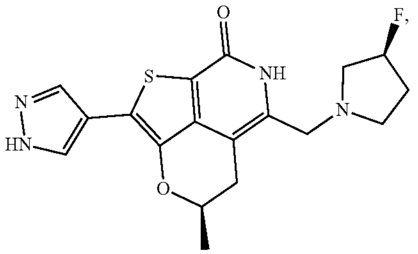

(S)-6-(((S)-3-fluoropyrrolidin-1-yl)methyl)-4-methyl-2-(1H-pyrazol-4-yl)-5, 7-dihydro-3-oxa-1-thia-7-azaacenaphthylen-8(4H)-one

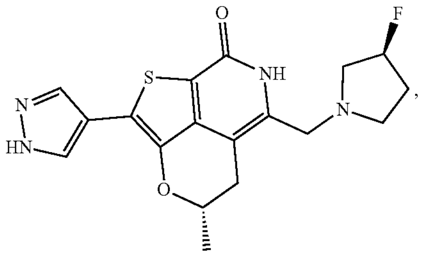

(R)-6-(((S)-3-fluoropyrrolidin-1-yl)methyl)-4-methyl-2-(1H-pyrazol-4-yl)-5, 7-dihydro-3-oxa-1-thia-7-azaacenaphthylen-8(4H)-one

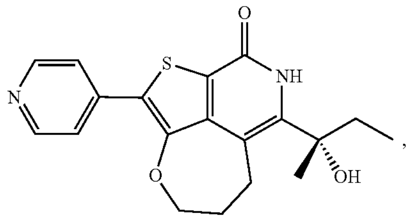

(S)-5-(2-hydroxybutan-2-yl)-1-(pyridin-4-yl)-4, 6, 7, 8-tetrahydro-3H-9-oxa-2-thia-4-azabenzo[cd]azulen-3-one

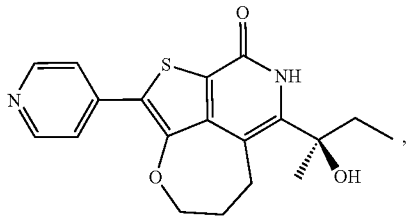

(R)-5-(2-hydroxybutan-2-yl)-1-(pyridin-4-yl)-4, 6, 7, 8-tetrahydro-3H-9-oxa-2-thia-4-azabenzo[cd]azulen-3-one

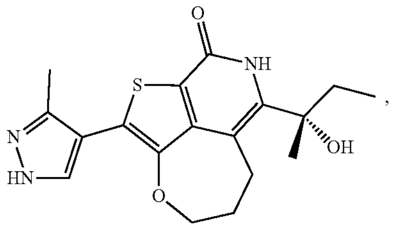

(S)-5-(2-hydroxybutan-2-yl)-1-(3-methyl-1H-pyrazol-4-yl)-4, 6, 7, 8-tetrahydro-3H-9-oxa-2-thia-4-azabenzo[cd]azulen-3-one

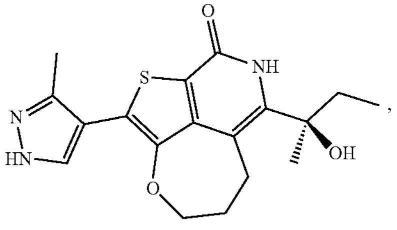

(R)-5-(2-hydroxybutan-2-yl)-1-(3-methyl-1H-pyrazol-4-yl)-4, 6, 7, 8-tetrahydro-3H-9-oxa-2-thia-4-azabenzo[cd]azulen-3-one

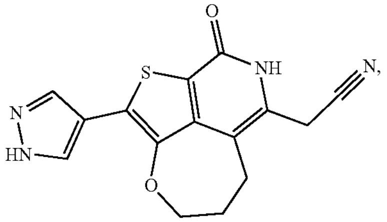

2-(3-oxo-1-(1H-pyrazol-4-yl)-4, 6, 7, 8-tetrahydro-3H-9-oxa-2-thia-4-azabenzo[cd]azulen-5- yl)acetonitrile

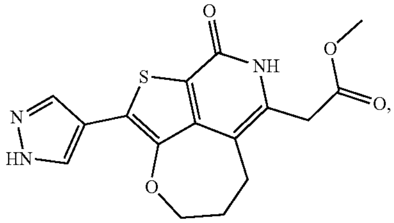

methyl 2-(3-oxo-1-(1H-pyrazol- 4-yl)-4, 6, 7, 8-tetrahydro-3H-9-oxa-2-thia-4-azabenzo[cd]azulen-5-yl)acetate

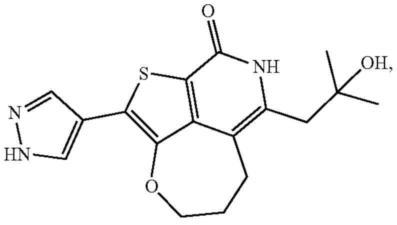

5-(2-hydroxy-2-methylpropyl)-1-(1H-pyrazol-4-yl)-4, 6, 7, 8-tetrahydro-3H-9-oxa-2-thia-4-azabenzo[cd]azulen-3-one

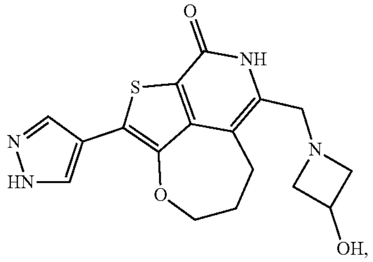

7-[(3-hydroxyazetidin-1-yl) methyl]-2-(1H-pyrazol-4-yl)-12-oxa-3-thia-6-azatricyclo [6.4.1.0$^{4,13}$]trideca-1, 4(13), 7-trien-5-one

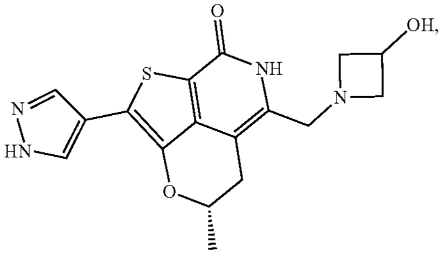

(S)-6-((3-hydroxyazetidin-1-yl)methyl)-4-methyl-2-(1H-pyrazol-4-yl)-5, 7-dihydro-3-oxa-1-thia-7-azaacenaphthylen-8(4H)-one

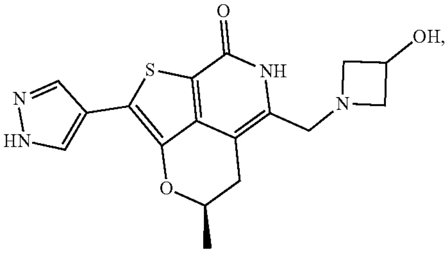

(R)-6-((3-hydroxyazetidin-1-yl)methyl)-4-methyl-2-(1H-pyrazol-4-yl)-5, 7-dihydro-3-oxa-1-thia-7-azaacenaphthylen-8(4H)-one

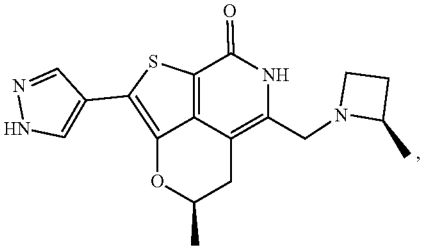

(R)-4-methyl-6-(((R)-2-methylazetidin-1-yl)methyl)-2-(1H-pyrazol-4-yl)-5, 7-dihydro-3-oxa-1-thia-7-azaacenaphthylen-8(4H)-one -continued

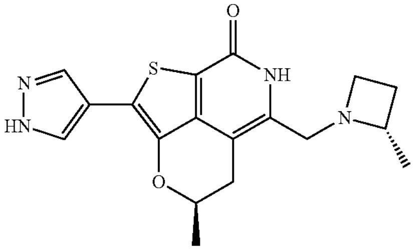

, (R)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one

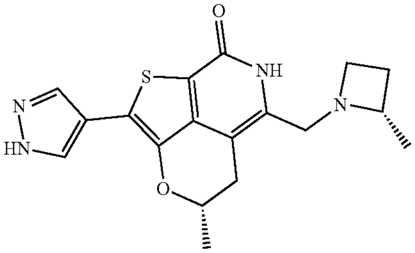

, (S)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one -continued

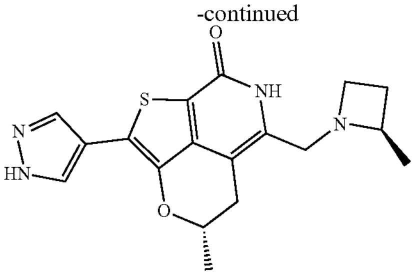

, and (S)-4-methyl-6-(((S)-2-methylazetidin-1-yl)methyl)-2-(1H-pyrazol-4-yl)-5,7-dihydro-3-oxa-1-thia-7-azaacenaphthylen-8(4H)-one

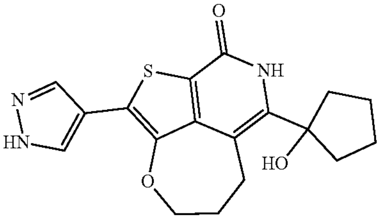

, 5-(1-hydroxycyclopentyl)-1-(1H-pyrazol-4-yl)-4, 6, 7, 8-tetrahydro-3H-9-oxa-2-thia-4-azabenzo[cd]azulen-3-one or a pharmaceutically acceptable salt thereof.

* * * * *